US010130714B2

United States Patent
Wong et al.

(10) Patent No.: US 10,130,714 B2
(45) Date of Patent: Nov. 20, 2018

(54) ENHANCED ANTI-INFLUENZA AGENTS CONJUGATED WITH ANTI-INFLAMMATORY ACTIVITY

(71) Applicant: Academia Sinica, Taipei (TW)

(72) Inventors: Chi-Huey Wong, Rancho Sante Fe, CA (US); Jim-Min Fang, Taipei (TW); Kung-Cheng Liu, Taipei (TW); Jia-Tsrong Jan, Taipei (TW); Yih-Shyun E. Cheng, Taipei (TW); Ting-Jen R. Cheng, Taipei (TW)

(73) Assignee: ACADEMIA SINICA, Taipei (TW)

( * ) Notice: Subject to any disclaimer, the term of this patent is extended or adjusted under 35 U.S.C. 154(b) by 65 days.

(21) Appl. No.: 13/836,356

(22) Filed: Mar. 15, 2013

(65) Prior Publication Data

US 2013/0274229 A1    Oct. 17, 2013

Related U.S. Application Data

(60) Provisional application No. 61/624,250, filed on Apr. 14, 2012.

(51) Int. Cl.
*A61K 31/351* (2006.01)
*C07D 309/28* (2006.01)
*A61K 47/55* (2017.01)
*A61K 47/48* (2006.01)

(52) U.S. Cl.
CPC .......... *A61K 47/481* (2013.01); *A61K 31/351* (2013.01); *A61K 47/55* (2017.08); *C07D 309/28* (2013.01)

(58) Field of Classification Search
CPC .... A61K 47/481; A61K 47/55; A61K 31/351; C07D 309/28
See application file for complete search history.

(56) References Cited

U.S. PATENT DOCUMENTS

| | | | |
|---|---|---|---|
| 3,773,919 | A | 11/1973 | Boswell et al. |
| 3,896,111 | A | 7/1975 | Kupchan et al. |
| 4,137,230 | A | 1/1979 | Hashimoto et al. |
| 4,151,042 | A | 4/1979 | Higashide et al. |
| 4,248,870 | A | 2/1981 | Miyashita et al. |
| 4,256,746 | A | 3/1981 | Miyashita et al. |
| 4,260,608 | A | 4/1981 | Miyashita et al. |
| 4,265,814 | A | 5/1981 | Hashimoto et al. |
| 4,270,537 | A | 6/1981 | Romaine |
| 4,294,757 | A | 10/1981 | Asai |
| 4,307,016 | A | 12/1981 | Asai et al. |
| 4,308,268 | A | 12/1981 | Miyashita et al. |
| 4,308,269 | A | 12/1981 | Miyashita et al. |
| 4,309,428 | A | 1/1982 | Miyashita et al. |
| 4,313,946 | A | 2/1982 | Powell et al. |
| 4,315,929 | A | 2/1982 | Freedman et al. |
| 4,317,821 | A | 3/1982 | Miyashita et al. |
| 4,322,348 | A | 3/1982 | Asai et al. |
| 4,331,598 | A | 5/1982 | Hasegawa et al. |
| RE30,985 | E | 6/1982 | Cartaya |
| 4,361,650 | A | 11/1982 | Asai et al. |
| 4,362,663 | A | 12/1982 | Kida et al. |
| 4,364,866 | A | 12/1982 | Asai et al. |
| 4,371,533 | A | 2/1983 | Akimoto et al. |
| 4,376,110 | A | 3/1983 | David et al. |
| 4,419,446 | A | 12/1983 | Howley et al. |
| 4,424,219 | A | 1/1984 | Hashimoto et al. |
| 4,450,254 | A | 5/1984 | Isley et al. |
| 4,560,655 | A | 12/1985 | Baker |
| 4,596,556 | A | 6/1986 | Morrow et al. |
| 4,596,792 | A | 6/1986 | Vyas |
| 4,599,230 | A | 7/1986 | Milich et al. |
| 4,599,231 | A | 7/1986 | Milich et al. |
| 4,601,903 | A | 7/1986 | Frasch |
| 4,601,978 | A | 7/1986 | Karin |
| 4,657,866 | A | 4/1987 | Kumar |
| 4,676,980 | A | 6/1987 | Segal et al. |
| 4,741,900 | A | 5/1988 | Alvarez et al. |

(Continued)

FOREIGN PATENT DOCUMENTS

| | | |
|---|---|---|
| EP | 404097 | 12/1990 |
| EP | 0341735 B1 | 9/1992 |

(Continued)

OTHER PUBLICATIONS

Koshihara et al. 1984, Biochimica et biophysica acta, 792(1), pp. 92-97.*

Andrews et al., Synthesis and influenza virus sialidase inhibitory activity of analogues of 4-Guanidino-Neu5Ac2en (Zanamivir) modified in the glycerol side-chain. Eur J Med Chem. Jul.-Aug. 1999;34(7-8):563-74.

Baz et al., Emergence of oseltamivir-resistant pandemic H1N1 virus during prophylaxis. N Engl J Med. Dec. 3, 2009;361(23):2296-7. doi: 10.1056/NEJMc0910060. Epub Nov. 11, 2009.

Carter, A rationale for using steroids in the treatment of severe cases of H5N1 avian influenza. J Med Microbiol. Jul. 2007;56(Pt 7):875-83.

(Continued)

*Primary Examiner* — Kara R McMillian
(74) *Attorney, Agent, or Firm* — Duane Morris LLP

(57) ABSTRACT

Novel dual-targeted, bifunctional anti-influenza drugs formed by conjugation with anti-inflammatory agents are disclosed. Exemplary drugs according to the invention include caffeic acid (CA)-bearing zanamivir (ZA) conjugates ZA-7-CA (1), ZA-7-CA-amide (7) and ZA-7-Nap (43) for simultaneous inhibition of influenza virus neuraminidase and suppression of proinflammatory cytokines. Synthetic methods for preparation of these enhanced anti-influenza conjugate drugs are provided. The synthetic bifunctional ZA conjugates act synergistically towards protection of mice lethally infected by H1N1 or H5N1 influenza viruses. The efficacy of ZA-7-CA, ZA-7-CA-amide and ZA-7-Nap conjugates is much greater than the combination therapy of ZA with anti-inflammatory agents.

6 Claims, 29 Drawing Sheets

(56) References Cited

U.S. PATENT DOCUMENTS

| | | |
|---|---|---|
| 4,767,704 A | 8/1988 | Cleveland et al. |
| 4,790,824 A | 12/1988 | Morrow et al. |
| 4,816,567 A | 3/1989 | Cabilly et al. |
| 4,849,222 A | 7/1989 | Broaddus |
| 4,886,499 A | 12/1989 | Cirelli et al. |
| 4,927,762 A | 5/1990 | Darfler |
| 4,940,460 A | 7/1990 | Casey et al. |
| 4,941,880 A | 7/1990 | Burns |
| 4,965,199 A | 10/1990 | Capon et al. |
| 4,970,198 A | 11/1990 | Lee et al. |
| 4,975,278 A | 12/1990 | Senter et al. |
| 5,004,697 A | 4/1991 | Pardridge |
| 5,015,235 A | 5/1991 | Crossman |
| 5,053,394 A | 10/1991 | Ellestad et al. |
| 5,061,620 A | 10/1991 | Tsukamoto et al. |
| 5,064,413 A | 11/1991 | McKinnon et al. |
| 5,075,109 A | 12/1991 | Tice et al. |
| 5,079,233 A | 1/1992 | Lee |
| 5,100,669 A | 3/1992 | Hyon et al. |
| 5,112,596 A | 5/1992 | Malfroy-Camine |
| 5,122,469 A | 6/1992 | Mather et al. |
| 5,141,496 A | 8/1992 | Dalto et al. |
| 5,190,521 A | 3/1993 | Hubbard et al. |
| 5,208,020 A | 5/1993 | Chari et al. |
| 5,229,275 A | 7/1993 | Goroff |
| 5,264,365 A | 11/1993 | Georgiou et al. |
| 5,268,164 A | 12/1993 | Kozarich et al. |
| 5,312,335 A | 5/1994 | McKinnon et al. |
| 5,326,856 A | 7/1994 | Coughlin et al. |
| 5,328,483 A | 7/1994 | Jacoby |
| 5,334,144 A | 8/1994 | Alchas et al. |
| 5,339,163 A | 8/1994 | Homma et al. |
| 5,362,852 A | 11/1994 | Geoghegan |
| 5,369,017 A | 11/1994 | Wong et al. |
| 5,374,541 A | 12/1994 | Wong et al. |
| 5,383,851 A | 1/1995 | McKinnon, Jr. et al. |
| 5,395,541 A | 3/1995 | Carpenter et al. |
| 5,416,064 A | 5/1995 | Chari et al. |
| 5,417,662 A | 5/1995 | Hjertman et al. |
| 5,466,220 A | 11/1995 | Brenneman |
| 5,480,381 A | 1/1996 | Weston |
| 5,500,362 A | 3/1996 | Robinson et al. |
| 5,503,627 A | 4/1996 | McKinnon et al. |
| 5,506,206 A | 4/1996 | Kozarich et al. |
| 5,508,192 A | 4/1996 | Georgiou et al. |
| 5,518,725 A | 5/1996 | Daynes et al. |
| 5,520,639 A | 5/1996 | Peterson et al. |
| 5,527,288 A | 6/1996 | Gross et al. |
| 5,545,806 A | 8/1996 | Lonberg et al. |
| 5,545,807 A | 8/1996 | Surani et al. |
| 5,565,332 A | 10/1996 | Hoogenboom et al. |
| 5,567,610 A | 10/1996 | Borrebaeck et al. |
| 5,569,189 A | 10/1996 | Parsons |
| 5,569,825 A | 10/1996 | Lonberg et al. |
| 5,571,894 A | 11/1996 | Wels et al. |
| 5,580,717 A | 12/1996 | Dower et al. |
| 5,585,089 A | 12/1996 | Queen et al. |
| 5,587,458 A | 12/1996 | King et al. |
| 5,591,669 A | 1/1997 | Krimpenfort et al. |
| 5,591,828 A | 1/1997 | Bosslet et al. |
| 5,599,302 A | 2/1997 | Lilley et al. |
| 5,606,040 A | 2/1997 | McGahren et al. |
| 5,624,821 A | 4/1997 | Winter et al. |
| 5,625,126 A | 4/1997 | Lonberg et al. |
| 5,633,425 A | 5/1997 | Lonberg et al. |
| 5,635,483 A | 6/1997 | Pettit et al. |
| 5,639,635 A | 6/1997 | Joly et al. |
| 5,641,870 A | 6/1997 | Rinderknecht et al. |
| 5,643,577 A | 7/1997 | Pang et al. |
| 5,648,237 A | 7/1997 | Carter |
| 5,648,260 A | 7/1997 | Winter et al. |
| 5,649,912 A | 7/1997 | Peterson |
| 5,661,016 A | 8/1997 | Lonberg et al. |
| 5,663,149 A | 9/1997 | Pettit et al. |
| 5,674,988 A | 10/1997 | Sabesan |
| 5,677,180 A | 10/1997 | Robinson et al. |
| 5,686,416 A | 11/1997 | Kozarich et al. |
| 5,690,938 A | 11/1997 | Ermak et al. |
| 5,693,762 A | 12/1997 | Queen et al. |
| 5,704,911 A | 1/1998 | Parsons |
| 5,712,374 A | 1/1998 | Kuntsman et al. |
| 5,714,374 A | 2/1998 | Arnold et al. |
| 5,714,586 A | 2/1998 | Kunstman et al. |
| 5,731,168 A | 3/1998 | Cater et al. |
| 5,733,743 A | 3/1998 | Johnson et al. |
| 5,736,137 A | 4/1998 | Anderson et al. |
| 5,739,116 A | 4/1998 | Hamann et al. |
| 5,767,285 A | 6/1998 | Hamann et al. |
| 5,770,701 A | 6/1998 | McGahren et al. |
| 5,773,001 A | 6/1998 | Hamann et al. |
| 5,780,588 A | 7/1998 | Pettit et al. |
| 5,814,344 A | 9/1998 | Tice et al. |
| 5,820,883 A | 10/1998 | Tice et al. |
| 5,821,337 A | 10/1998 | Carter et al. |
| 5,837,234 A | 11/1998 | Gentile et al. |
| 5,840,523 A | 11/1998 | Simmons et al. |
| 5,849,716 A | 12/1998 | Akimoto |
| 5,853,763 A | 12/1998 | Tice et al. |
| 5,869,046 A | 2/1999 | Presta et al. |
| 5,877,296 A | 3/1999 | Hamann et al. |
| 5,893,397 A | 4/1999 | Peterson et al. |
| 5,993,412 A | 11/1999 | Deily et al. |
| 6,004,940 A | 12/1999 | Marasco et al. |
| 6,027,888 A | 2/2000 | Georgiou et al. |
| 6,083,715 A | 7/2000 | Georgiou et al. |
| 6,111,132 A | 8/2000 | Kim et al. |
| 6,143,724 A | 11/2000 | Ohira et al. |
| 6,210,670 B1 | 4/2001 | Berg |
| 6,265,150 B1 | 7/2001 | Terstappen et al. |
| 6,329,173 B1 | 12/2001 | Marasco et al. |
| 6,340,702 B1 | 1/2002 | Honda et al. |
| 6,399,071 B1 | 6/2002 | Duthaler |
| 6,455,571 B1 | 9/2002 | Maring et al. |
| 6,506,564 B1 | 1/2003 | Mirkin et al. |
| 6,528,286 B1 | 3/2003 | Ryll |
| 6,548,476 B1 | 4/2003 | Wu et al. |
| 6,680,054 B1 | 1/2004 | Reece et al. |
| 6,696,304 B1 | 2/2004 | Davies |
| 6,703,019 B1 | 3/2004 | Malfroy-Camine |
| 6,824,780 B1 | 11/2004 | Devaux et al. |
| 6,855,551 B2 | 2/2005 | Bawendi et al. |
| 6,873,914 B2 | 3/2005 | Winfield et al. |
| 6,984,630 B1 | 1/2006 | Descamps et al. |
| 6,994,966 B2 | 2/2006 | Dukler |
| 7,019,288 B2 | 3/2006 | Becker |
| 7,090,973 B1 | 8/2006 | Breton |
| 7,151,164 B2 | 12/2006 | Hansen et al. |
| 7,157,433 B2 | 1/2007 | Mercep et al. |
| 7,205,333 B2 | 4/2007 | Wu et al. |
| 7,488,491 B2 | 2/2009 | Tsjui et al. |
| 7,498,298 B2 | 3/2009 | Doronina et al. |
| 7,854,934 B2 | 12/2010 | Danishefsky |
| 7,888,337 B2 | 2/2011 | Wong et al. |
| 7,923,013 B2 | 4/2011 | Tsuji et al. |
| 7,928,077 B2 | 4/2011 | Wong et al. |
| 7,943,330 B2 | 5/2011 | Wong et al. |
| 7,960,139 B2 | 6/2011 | Sawa et al. |
| 7,977,097 B1 | 7/2011 | Gay et al. |
| 8,022,043 B2 | 9/2011 | Porcelli |
| 8,088,387 B2 | 1/2012 | Steeves et al. |
| 8,101,179 B2 | 1/2012 | Numazaki et al. |
| 8,268,969 B2 | 9/2012 | Wong et al. |
| 8,383,554 B2 | 2/2013 | Wong et al. |
| 8,507,660 B2 | 8/2013 | Wong et al. |
| 8,680,020 B2 | 3/2014 | Wong et al. |
| 8,716,465 B2 | 5/2014 | Rossi et al. |
| 8,802,438 B2 | 8/2014 | Rossi et al. |
| 8,815,941 B2 | 8/2014 | Withers |
| 8,883,506 B2 | 11/2014 | Rossi et al. |
| 8,906,832 B2 | 12/2014 | Wong et al. |
| 8,907,111 B2 | 12/2014 | Withers |
| 9,187,552 B2 | 11/2015 | Stadheim |
| 9,221,859 B2 | 12/2015 | Withers |
| 9,382,284 B2 | 7/2016 | Withers |

(56) References Cited

U.S. PATENT DOCUMENTS

| | | |
|---|---|---|
| 9,434,786 B2 | 9/2016 | Wang |
| 9,759,726 B2 | 9/2017 | Wong et al. |
| 9,803,177 B2 | 10/2017 | Rossi et al. |
| 9,914,956 B2 | 3/2018 | Wong et al. |
| 2002/0025313 A1 | 2/2002 | Micklus et al. |
| 2002/0038086 A1 | 3/2002 | Hynynen et al. |
| 2002/0065259 A1 | 5/2002 | Schatzberg et al. |
| 2003/0073713 A1 | 4/2003 | Schoenhard |
| 2003/0083299 A1 | 5/2003 | Ferguson |
| 2003/0104402 A1 | 6/2003 | Zauderer et al. |
| 2003/0118592 A1 | 6/2003 | Ledbetter et al. |
| 2003/0129186 A1 | 7/2003 | Beliveau et al. |
| 2003/0162695 A1 | 8/2003 | Schatzberg et al. |
| 2003/0175884 A1 | 9/2003 | Umana et al. |
| 2003/0219433 A1 | 11/2003 | Hansen et al. |
| 2004/0072290 A1 | 4/2004 | Umana et al. |
| 2004/0086423 A1 | 5/2004 | Wohlstadter |
| 2004/0131692 A1 | 7/2004 | Kreuter et al. |
| 2004/0137557 A1 | 7/2004 | DeFrees et al. |
| 2004/0204354 A1 | 10/2004 | Nelson et al. |
| 2004/0259142 A1 | 12/2004 | Chai et al. |
| 2005/0085413 A1 | 4/2005 | Jin et al. |
| 2005/0089473 A1 | 4/2005 | Black et al. |
| 2005/0106108 A1 | 5/2005 | Hansen et al. |
| 2005/0123546 A1 | 6/2005 | Umana et al. |
| 2005/0124533 A1 | 6/2005 | Schatzberg et al. |
| 2005/0221337 A1 | 10/2005 | Seeberger et al. |
| 2005/0221397 A1 | 10/2005 | Saito |
| 2005/0255491 A1 | 11/2005 | Lee |
| 2006/0019256 A1 | 1/2006 | Clarke et al. |
| 2006/0073122 A1 | 4/2006 | Koezuka et al. |
| 2006/0073161 A1 | 4/2006 | Breton |
| 2006/0211856 A1 | 9/2006 | Tsuji et al. |
| 2006/0286140 A1 | 12/2006 | Wickstrom et al. |
| 2006/0286637 A1 | 12/2006 | Hamilton |
| 2007/0059769 A1 | 3/2007 | Blixt et al. |
| 2007/0065949 A1 | 3/2007 | Hutchens |
| 2007/0207090 A1 | 9/2007 | Giudice |
| 2007/0213278 A1 | 9/2007 | Wong et al. |
| 2007/0219351 A1 | 9/2007 | Fiume et al. |
| 2007/0224189 A1 | 9/2007 | Lazar et al. |
| 2007/0238871 A1 | 10/2007 | Tsuji et al. |
| 2008/0070324 A1 | 3/2008 | Floyd |
| 2008/0220988 A1 | 9/2008 | Zhou |
| 2008/0260774 A1 | 10/2008 | Wong et al. |
| 2009/0035179 A1 | 2/2009 | Rakow et al. |
| 2009/0081255 A1 | 3/2009 | Bublot et al. |
| 2009/0123439 A1 | 5/2009 | Yun et al. |
| 2009/0285837 A1 | 11/2009 | Kao et al. |
| 2009/0298797 A1 | 12/2009 | Zheng et al. |
| 2009/0317837 A1 | 12/2009 | Wong et al. |
| 2010/0009339 A1 | 1/2010 | Bovin et al. |
| 2010/0022026 A1 | 1/2010 | Rump et al. |
| 2010/0047827 A1 | 2/2010 | Laine et al. |
| 2010/0047828 A1 | 2/2010 | Sorenson et al. |
| 2010/0068806 A1 | 3/2010 | Laine et al. |
| 2010/0112195 A1 | 5/2010 | Kodas et al. |
| 2010/0113397 A1 | 5/2010 | Wong et al. |
| 2010/0136009 A1 | 6/2010 | Papkoff et al. |
| 2010/0136042 A1 | 6/2010 | Wong et al. |
| 2010/0173323 A1 | 7/2010 | Strome |
| 2011/0086408 A1 | 4/2011 | Power |
| 2011/0104188 A1 | 5/2011 | Tashiro et al. |
| 2011/0124116 A1 | 5/2011 | Wohlstadter et al. |
| 2011/0137570 A1 | 6/2011 | Lapadula et al. |
| 2011/0237459 A1 | 9/2011 | Nova et al. |
| 2011/0263828 A1 | 10/2011 | Wong et al. |
| 2012/0046346 A1 | 2/2012 | Rossi et al. |
| 2012/0171201 A1 | 7/2012 | Sapra |
| 2012/0178705 A1 | 7/2012 | Liang et al. |
| 2012/0178802 A1 | 7/2012 | Withers et al. |
| 2012/0226024 A1 | 9/2012 | Wang et al. |
| 2012/0294859 A1 | 11/2012 | Goletz et al. |
| 2012/0322864 A1 | 12/2012 | Rossi et al. |
| 2012/0322865 A1 | 12/2012 | Rossi et al. |
| 2012/0328646 A1 | 12/2012 | Wong et al. |
| 2013/0189258 A1 | 7/2013 | Rother et al. |
| 2013/0196356 A1 | 8/2013 | Jackson et al. |
| 2013/0230886 A1 | 9/2013 | Votsmeier et al. |
| 2013/0295104 A1 | 11/2013 | Deckert et al. |
| 2013/0337018 A1 | 12/2013 | Fox |
| 2014/0051127 A1 | 2/2014 | Wong et al. |
| 2014/0086916 A1 | 3/2014 | Zha |
| 2014/0127241 A1 | 5/2014 | Leuschner et al. |
| 2014/0178365 A1 | 6/2014 | Ghaderi et al. |
| 2014/0302028 A1 | 10/2014 | Zha |
| 2014/0308746 A1 | 10/2014 | Rossi et al. |
| 2015/0087814 A1 | 3/2015 | Wang |
| 2015/0160217 A1 | 6/2015 | Wong et al. |
| 2015/0225766 A1 | 8/2015 | Wong et al. |
| 2015/0309041 A1 | 10/2015 | Wong et al. |
| 2015/0344544 A1 | 12/2015 | Wong et al. |
| 2015/0344551 A1 | 12/2015 | Wong et al. |
| 2015/0344559 A1 | 12/2015 | Wong et al. |
| 2015/0344585 A1 | 12/2015 | Wong et al. |
| 2015/0344587 A1 | 12/2015 | Wong et al. |
| 2016/0009803 A1 | 1/2016 | Rother et al. |
| 2016/0102151 A1 | 4/2016 | Wong et al. |
| 2016/0215061 A1 | 7/2016 | Shaeen |
| 2016/0274121 A1 | 9/2016 | Wong et al. |
| 2016/0280794 A1 | 9/2016 | Wong et al. |
| 2016/0289340 A1 | 10/2016 | Wong et al. |
| 2017/0275389 A1 | 9/2017 | Wong et al. |
| 2017/0283878 A1 | 10/2017 | Wong et al. |

FOREIGN PATENT DOCUMENTS

| | | |
|---|---|---|
| EP | 0425235 B1 | 9/1996 |
| EP | 1208909 A2 | 5/2002 |
| EP | 1391213 A1 | 2/2004 |
| EP | 2123271 | 11/2009 |
| EP | 2187217 A1 | 5/2010 |
| JP | 05-222085 | 8/1993 |
| JP | 05-507068 | 10/1993 |
| JP | 05-339283 A | 12/1993 |
| JP | 11-343295 A | 12/1999 |
| JP | 2005-06008 | 5/2000 |
| WO | WO 87/00195 A1 | 1/1987 |
| WO | WO 90/03430 A1 | 4/1990 |
| WO | WO 91/00360 A1 | 1/1991 |
| WO | WO 91/10741 A1 | 7/1991 |
| WO | WO 92/00373 A1 | 1/1992 |
| WO | WO 92/006691 | 4/1992 |
| WO | WO 92/09690 A2 | 6/1992 |
| WO | WO 93/01161 A1 | 1/1993 |
| WO | WO 93/06213 A1 | 4/1993 |
| WO | WO 93/07861 A1 | 4/1993 |
| WO | WO 93/08829 A1 | 5/1993 |
| WO | WO 93/09764 * | 5/1993 |
| WO | WO 93/16185 A2 | 8/1993 |
| WO | WO 93/021232 A1 | 10/1993 |
| WO | WO 94/04690 A1 | 3/1994 |
| WO | WO 94/11026 | 5/1994 |
| WO | WO 94/29351 | 12/1994 |
| WO | WO 95/11010 A1 | 4/1995 |
| WO | WO 96/07754 A1 | 3/1996 |
| WO | WO 96/16673 A1 | 6/1996 |
| WO | WO 96/33735 A1 | 10/1996 |
| WO | WO 96/34096 A1 | 10/1996 |
| WO | WO 97/05267 A2 | 2/1997 |
| WO | WO 97/013537 | 4/1997 |
| WO | WO 97/17852 A1 | 5/1997 |
| WO | WO 97/037705 | 10/1997 |
| WO | WO 98/00558 A1 | 1/1998 |
| WO | WO 98/02463 A1 | 1/1998 |
| WO | WO 98/24893 A2 | 6/1998 |
| WO | WO 99/034850 | 7/1999 |
| WO | WO 99/49019 A2 | 9/1999 |
| WO | WO 99/051642 | 10/1999 |
| WO | WO 99/057134 A1 | 11/1999 |
| WO | WO 01/42505 A2 | 6/2001 |
| WO | WO 01/86001 A1 | 11/2001 |
| WO | WO 02/088172 | 11/2002 |
| WO | WO 03/040104 A1 * | 5/2003 |

(56) References Cited

FOREIGN PATENT DOCUMENTS

| | | |
|---|---|---|
| WO | WO 03/68821 A2 | 8/2003 |
| WO | WO 03/077945 A1 | 9/2003 |
| WO | WO 2004/035607 A2 | 4/2004 |
| WO | WO 2004/056312 A2 | 7/2004 |
| WO | WO 2004/063351 | 7/2004 |
| WO | WO 2004/103404 A1 | 12/2004 |
| WO | WO 2005/030258 A2 | 4/2005 |
| WO | WO 2005/044859 | 5/2005 |
| WO | WO 2005/088310 A2 | 9/2005 |
| WO | WO 2005/103081 A2 | 11/2005 |
| WO | WO 2006/055925 A2 | 5/2006 |
| WO | WO 2006/064983 A1 | 6/2006 |
| WO | WO 2006/106959 | 10/2006 |
| WO | WO 2006/126069 A2 | 11/2006 |
| WO | WO 2006/130458 A2 | 12/2006 |
| WO | WO 2007/078873 A1 | 7/2007 |
| WO | WO 2007/0133855 | 11/2007 |
| WO | WO 2007/146847 A2 | 12/2007 |
| WO | WO 2008-020596 A2 | 2/2008 |
| WO | WO 2008/087260 A1 | 7/2008 |
| WO | WO 2008/118013 | 10/2008 |
| WO | WO 2008/133801 A1 | 11/2008 |
| WO | WO 2008/0133857 A1 | 11/2008 |
| WO | WO 2009/029888 A3 | 3/2009 |
| WO | WO 2010/006315 A2 | 1/2010 |
| WO | WO 2010/009271 A1 | 1/2010 |
| WO | WO 2010/011703 | 1/2010 |
| WO | WO 2011/005756 A1 | 1/2011 |
| WO | WO 2011/006237 A1 | 1/2011 |
| WO | WO 2011/031236 A1 | 3/2011 |
| WO | WO 2011/074621 A1 | 6/2011 |
| WO | WO 2011/089004 A1 | 7/2011 |
| WO | WO 2011/130332 | 10/2011 |
| WO | WO 2011/143262 A2 | 11/2011 |
| WO | WO 2011/0145957 A1 | 11/2011 |
| WO | WO 2012/082635 A1 | 6/2012 |
| WO | WO 2012/094540 A2 | 7/2012 |
| WO | WO 2013/011347 A1 | 1/2013 |
| WO | WO 2013/012066 | 1/2013 |
| WO | WO 2013/120066 A1 | 8/2013 |
| WO | WO 2013/130603 A1 | 9/2013 |
| WO | WO 2013/152034 A1 | 10/2013 |
| WO | WO 2013/155375 A1 | 10/2013 |
| WO | WO 2013/181585 A2 | 12/2013 |
| WO | WO 2014/031498 | 2/2014 |
| WO | WO 2014/031762 A1 | 2/2014 |
| WO | WO 2014/078373 A1 | 5/2014 |
| WO | WO 2014/210397 A1 | 12/2014 |
| WO | WO 2014/210564 | 12/2014 |
| WO | WO 2015/026484 A1 | 2/2015 |
| WO | WO 2015/035337 A1 | 3/2015 |
| WO | WO 2015/038963 A1 | 3/2015 |
| WO | WO 2015/184008 | 12/2015 |
| WO | WO 2016/040369 A2 | 3/2016 |
| WO | WO 2016-118090 A1 | 7/2016 |

OTHER PUBLICATIONS

Chandler et al., Synthesis of the potent influenza neuraminidase inhibitor 5-guanidino Neu5Ac2en. X-Ray molecular structure of 5-acetamindo-4amino-2,6-anahydro-3,4,5-tryoxy-D-erythoro-L-gluco-nononic acid. J Chem Soc Perkin Trans 1. 1995;:1173-1180.
Chiang et al., Ethyl caffeate suppresses NF-kappaB activation and its downstream inflammatory mediators, iNOS, COX-2, and PGE2 in vitro or in mouse skin. Br J Pharmacol. Oct. 2005;146(3):352-63.
De Jong et al., Fatal outcome of human influenza A (H5N1) is associated with high viral load and hypercytokinemia. Nat Med. Oct. 2006;12(10) 1203-7. Epub Sep. 10, 2006.
Fedson, Confronting the next influenza pandemic with anti-inflammatory and immunomodulatory agents: why they are needed and how they might work. Influenza Other Respi Viruses. Jul. 2009;3(4):129-42. doi: 10.1111/j.1750-2659.2009.00090.x.
Geiler et al., Comparison of pro-inflammatory cytokine expression and cellular signal transduction in human macrophages infected with different influenza A viruses. Med Microbiol Immunol. Feb. 2011;200(1):53-60. doi: 10.1007/s00430-010-0173-y. Epub Sep. 24, 2010.
Govorkova et al, Combination chemotherapy for influenza. Viruses. Aug. 2010;2(8):1510-29. doi: 10.3390/v2081510. Epub Jul. 27, 2010.
Honda et al., Synthesis and anti-influenza virus activity of 7-O-alkylated derivatives related to zanamivir. Bioorg Med Chem Lett. Aug. 5, 2002;12(15):1925-8.
Kale et al., Detection of intact influenza viruses using biotinylated biantennary S-sialosides. J Am Chem Soc. Jul. 2, 2008;130(26):8169-71. doi: 10.1021/ja800842v. Epub Jun. 5, 2008.
Kruis et al., Low dose balsalazide (1.5 g twice daily) and mesalazine (0.5 g three times daily) maintained remission of ulcerative colitis but high dose balsalazide (3.0 g twice daily) was superior in preventing relapses. Gut. Dec. 2001;49(6):783-9.
Liu et al., Enhanced anti-influenza agents conjugated with anti-inflammatory activity. J Med Chem. Oct. 11, 2012;55(19):8493-501. doi: 10.1021/jm3009844. Epub Sep. 20, 2012.
Liu et al., Synthesis and anti-influenza activities of carboxyl alkoxyalkyl esters of 4-guanidino-Neu5Ac2en (zanamivir). Bioorg Med Chem Lett. Sep. 1, 2007;17(17):4851-4. Epub Jun. 20, 2007.
Michaluart et al., Inhibitory effects of caffeic acid phenethyl ester on the activity and expression of cyclooxygenase-2 in human oral epithelial cells and in a rat model of inflammation. Cancer Res. May 15, 1999;59(10):2347-52.
Morphy et al., Designed multiple ligands. An emerging drug discovery paradigm. J Med Chem. Oct. 20, 2005;48(21):6523-43.
Morphy et al., From magic bullets to designed multiple ligands. Drug Discov Today. Aug. 1, 2004;9(15):641-51.
Natarajan et al, Caffeic acid phenethyl ester is a potent and specific inhibitor of activation of nuclear transcription factor NF-kappa B. Proc Natl Acad Sci USA. Aug. 20, 1996;93(17):9090-5.
Ottolini et al., Combination anti-inflammatory and antiviral therapy of influenza in a cotton rat model. Pediatr. Pulmonol. 2003:36;290-4.
Peiris et al., Re-emergence of fatal human influenza A subtype H5N1disease. Lancet. Feb. 21, 2004;363(9409):617-9.
Salomon et al., Inhibition of the cytokine response does not protect against lethal H5N1 influenza infection. Proc Natl Acad Sci U S A. Jul. 24, 2007;104(30):12479-81. Epub Jul. 17, 2007.
Varghese et al., Three-dimensional structure of the complex of 4-guanidino-Neu5Ac2en and influenza virus neuraminidase. Protein Sci. Jun. 1995;4(6):1081-7.
Woo et al. Cytokine profiles induced by the novel swine-origin influenza A/H1N1 virus: implications for treatment strategies. J Infect Dis. Feb. 1, 2010;201(3):346-53.
Yamashita et al., CS-8958, a prodrug of the new neuraminidase inhibitor R-125489, shows long-acting anti-influenza virus activity. Antimicrob Agents Chemother. Jan. 2009;53(1):186-92. doi: 10.1128/AAC.00333-08. Epub Oct. 27, 2008.
Ying et al., One-bead-one-inhibitor-one-substrate screening of neuraminidase activity. Chembiochem. Oct. 2005;6(10):1857-65.
Yuen et al., Human infection by avian influenza A H5N1. Hong Kong Med J. Jun. 2005;11(3):189-99.
Zheng et al., Delayed antiviral plus immunomodulator treatment still reduces mortality in mice infected by high inoculum of influenza A/H5N1 virus. Proc Natl Acad Sci U S A. Jun. 10, 2008;105(23):8091-6. doi:10.1073/pnas.0711942105. Epub Jun. 3, 2008.
Zimmermann et al., Multi-target therapeutics: when the whole is greater than the sum of the parts. Drug Discov Today. Jan. 2007;12(1-2):34-42. Epub Nov. 28, 2006.
Liu et al., Intramolecular ion-pair prodrugs of zanamivir and guanidino-oseltamivir. Bioorganic & Medicinal Chemistry. Jun. 2011;19(16):4796-4802.
Supplementary European Search Report in European Application No. EP 13775664.9, dated Oct. 27, 2015, in 7 pages.
Abrahmsén et al, "Analysis of signals for secretion in the staphylococcal protein A gene," EMBO J., Dec. 30, 1985, 4(13B):3901-3906.

(56) References Cited

OTHER PUBLICATIONS

Altschul SF et al., "Basic local alignment search tool", *J Mol Biol.* Oct. 5, 1990;215(3):403-10.
Altschul SF, et al., "Gapped BLAST and PSI-BLAST: a new generation of protein database search programs", *Nucleic Acids Res.* Sep. 1, 1997;25(17):3389-402.
Anderson et al., "Stimulation of Natural Killer T Cells by Glycolipids", *Molecules*, May 2013, 18(12), 15662-15688.
Arié et al., "Chaperone function of FkpA, a heat shock prolyl isomerase, in the periplasm of *Escherichia coli*," *Mol. Microbiol.*, Jan. 2001, 39(1):199-210.
Bachmann, *Cellular and Molecular Biology*, vol. 2, Chapter 72: Derivations and Genotypes of Some Mutant Derivatives of *Escherichia coli* K-12, Neidhardt et al., eds., 1987, pp. 1190-1219, American Society for Microbiology, Washington, D.C.
Baldwin et al., "Monoclonal antibodies in cancer treatment," *Lancet*, Mar. 15, 1986, 327(8481):603-605.
Barbas et al., "Assembly of combinatorial antibody libraries on phage surfaces: the gene III site," *Proc. Natl. Acad. Sci. U.S.A.*, Sep. 15, 1991, 88(18):7978-7982.
Barbas et al., "In vitro evolution of a neutralizing human antibody to human immunodeficiency virus type 1 to enhance affinity and broaden strain cross-reactivity," *Proc. Nat. Acad. Sci. U.S.A.*, Apr. 26, 1994, 91(9):3809-3813.
Barbas et al., "Semisynthetic combinatorial antibody libraries: a chemical solution to the diversity problem," *Proc. Natl. Acad. Sci. U.S.A.*, May 15, 1992, 89(10):4457-4461.
Barnes et al., "Methods for growth of cultured cells in serum-five medium," *Anal. Biochem.*, Mar. 1, 1980, 102(2):255-270.
Baselga J, et al., "Phase II study of weekly intravenous recombinant humanized anti-p185HER2 monoclonal antibody in patients with HER2/neu-overexpressing metastatic breast cancer", *J Clin Oncol.* Mar. 1996;14(3):737-44.
Bass et al., "Hormone phage: an enrichment method for variant proteins with altered binding properties," *Proteins*, 1990, 8(4):309-314.
Beck A., "Biosimilar, biobetter and next generation therapeutic antibodies" *MAbs.* Mar.-Apr. 2011;3(2):107-10. Epub Mar. 1, 2011.
Berra et al., "Correlation between ganglioside distribution and histological grading of human astrocytomas," *Int. J. Cancer*, Sep. 15, 1985, 36(3):363-366.
Birklé et al., "Role of tumor-associated gangliosides in cancer progression," *Biochimie*, Mar.-Apr. 2003, 85(3-4):455-463.
Bobo et al., "Convection-enhanced delivery of macromolecules in the brain," *Proc. Natl. Acad. Sci. U.S.A.*, Mar. 15, 1994, 91(6) 2076-2080.
Boerner et al., "Production of antigen-specific human monoclonal antibodies from in vitro-primed human splenocytes," *J. Immunol.*, Jul. 1, 1991, 147(1):86-95.
Bothmann et al., "The periplasmic *Escherichia coli* peptidylprolyl cis,trans-isomerase FkpA. I. Increased functional expression of antibody fragments with and without cis-prolines," *J. Biol. Chem.*, Jun. 2, 2000, 275(22):17100-17105.
Brennan et al., "Preparation of bispecific antibodies by chemical recombination of monoclonal immunoglobulin $G_1$ fragments," *Science*, Jul. 5, 1985, 229(4708):81-83.
Brimble et al., "The cell surface glycosphingolipids SSEA-3 and SSEA-4 are not essential for human ESC pluripotency," *Stem Cells*, Jan. 2007, 25(1):54-62.
Brodeur et al., *Monoclonal Antibody Production Techniques and Applications*, Chapter 4: Mouse-Human Myeloma Partners for the Production of Heterohybridomas, Schook, ed., 1987, pp. 51-63, Marcel Dekker, Inc., New York.
Brüggemann et al., "Designer mice: the production of human antibody repertoires in transgenic animals," *Year in Immunol.*, 1993, 7:33-40.
Capel PJ et al., "Heterogeneity of human IgG Fc receptors" *Immunomethods.* Feb. 1994;4(1):25-34.
Carter et al., "High level *Escherichia coli* expression and production of a bivalent humanized antibody fragment," *Nature Biotechnology*, Feb. 1992, 10(2):163-167.
Carter et al., "Humanization of an anti-p185$^{HER2}$ antibody for human cancer therapy," *Proc. Natl. Acad. Sci. U.S.A.*, May 15, 1992, 89(10):4285-4289.
Carter PJ. "Potent antibody therapeutics by design" *Nat Rev Immunol.* May 2006;6(5):343-357.
Chang et al., "Expression of Globo H and SSEA3 in breast cancer stem cells and the involvement of fucosyl transferases 1 and 2 in Globo H synthesis," *Proc. Natl. Acad. Sci. U.S.A.*, Aug. 19, 2008, 105(33):11667-11672.
Chen et al., "Chaperone activity of DsbC," *J. Bio. Chem.*, Jul. 9. 1999, 274(28):19601-19605.
Chen et al., "Selection and analysis of an optimized anti-VEGF antibody: crystal structure of an affinity-matured Fab in complex with antigen," *J. Mol. Biol.*, Nov. 5, 1999, 293(4):865-881.
Chen et al., "Selective killing of transformed cells by cyclin/cyclin-dependent kinase 2 antagonists," *Proc. Natl. Acad. Sci. U.S.A.*, Apr. 13, 1999, 96(8):4325-4329.
Chothia et al., "Canonical structures for the hypervariable regions of immunoglobulins," *J. Mol. Biol.*, Aug. 20, 1987, 196(4):901-917.
Clackson et al., "Making antibody fragments using phage display libraries," *Nature*, Aug. 15, 1991, 352(6336):624-628.
Clark EA et al., "Structure, function, and genetics of human B cell-associated surface molecules" *Adv Cancer Res.* 1989;52:81-149.
Clynes R, et al., "Fc receptors are required in passive and active immunity to melanoma" *Proc Natl Acad Sci U S A.* Jan. 20, 1998;95(2):652-6.
Cunningham et al., "High-resolution epitope mapping of hGH-receptor interactions by alanine-scanning mutagenesis," *Science*, Jun. 2, 1989, 244(4908):1081-1085.
Daëron, "Fc receptor biology," *Annu. Rev. Immunol.*, 1997, 15:203-234.
De Haas et al., "Fcγ receptors of phagocytes," *J. Lab. Clin. Med.*, Oct. 1995, 126(4):330-341.
Durrant et al., "Immunology in the clinic review series; focus on cancer: glycolipids as targets for tumour immunotherapy," *Clin. Exp. Immunol.*, Feb. 2012, 167(2):206-215.
Embleton et al., "In-cell PCR from mRNA: amplifying and linking the rearranged immunoglobulin heavy and light chain V-genes within single cells," *Nucl. Acids Res.*, Aug. 11, 1992, 20(15):3831-3837.
Engels et al., "Gene synthesis [new synthetic methods (77)]," *Angew. Chem. Int. Ed. Engl.*, Jun. 1989, 28(6):716-734.
Fellouse et al., "Synthetic antibodies from a four-amino-acid code: a dominant role for tyrosine in antigen recognition," *Proc. Natl. Acad. Sci. U.S.A.*, Aug. 24, 2004, 101(34):12467-12472.
Fishwild et al., "High-avidity human IgGK monoclonal antibodies from a novel strain of minilocus transgenic mice," *Nature Biotechnol.*, Jul. 1996, 14(7):845-851.
Fredman et al., "Expression of gangliosides GD3 and 3'-isoLM1 in autopsy brains from patients with malignant tumors," *J. Neurochem.*, Jan. 1993, 60(1):99-105.
Fredman et al., "Potential ganglioside antigens associated with human gliomas," *Neurol. Res.*, Jun. 1986, 8(2):123-126.
Fredman et al., "Sialyllactotetraosylceramide, a ganglioside marker for human malignant gliomas," *J. Neurochem.*, Mar. 1988, 50(3):912-919.
Fujita M et al., "A novel disaccharide substrate having 1,2-oxazoline moiety for detection of transglycosylating activity of endoglycosidases" *Biochim Biophys Acta.* Sep. 3, 2001;1528(1):9-14.
Galfrè et al., "Preparation of monoclonal antibodies: strategies and procedures," *Methods Enzymol.*, 1981, 73(Pt B):3-46.
Gazzano-Santoro et al., "A non-radioactive complement-dependent cytotoxicity assay for anti-CD20 nonclonal antibody," *J. Immunol. Methods*, Mar. 28, 1997, 202(2): 163-171.
GenBank accession No. AAA24922.1, "endoglycosidase F [Elizabethkingia meningoseptica]," May 27, 2008.
GenBank accession No. AAA24923.1, "endoglycosidase, partial [Elizabethkingia meningoseptica]," Jun. 8, 1993.

(56) References Cited

OTHER PUBLICATIONS

GenBank accession No. AAA24924.1.1, "endoglycosidase, partial [Elizabethkingia meningoseptica]," Jun. 7, 1993.
GenBank accession No. AAA26738.1, "endo-beta-N-acetylglucosaminidase H [*Streptomyces plicatus*]," Apr. 26, 1993.
GenBank accession No. J05449.1, "F.meningosepticum peptide-N-4-(N-acetyl-beta-D-glucosaminyl) asparagine amidase (PNGase F) mRNA, complete cds," Jan. 16, 1996.
GenBank accession No. YP_212855.1, "Putative exported alpha-L-fucosidase protein [Bacteroides fragilis NCTC 9343]," Mar. 2, 2014.
Gill et al., "Direct brain infusion of glial cell line-derived neurotrophic factor in Parkinson disease," *Nature Med.*, May 2003, 9(5):589-595 and Addendum from Apr. 2006, 12(4):479.
Goding, *Monoclonal Antibodies: Principles and Practice 2nd ed., Chapter 3: Production of Monoclonal Antibodies*, 1986, pp. 59-103, Academic Press, London.
Goochee CF et al., "The oligosaccharides of glycoproteins: bioprocess factors affecting oligosaccharide structure and their effect on glycoprotein properties", *Biotechnology*(N Y). Dec. 1991;9(12):1347-55.
Gottschling et al., "*Stage-specific embryonic antigen-4* is expressed in basaloid lung cancer and associated with poor prognosis," *Eur. Respir. J.*, Mar. 2013, 41(3):656-663.
Graham et al., "Characteristics of a human cell line transformed by DNA from human adenovirus type 5," *J. Gen. Virol.*, Jul. 1977, 36(1):59-72.
Gram et al., "In vitro selection and affinity maturation of antibodies from a naive combinatorial immunoglobulin library," *Proc. Natl. Acad. Sci. U.S.A.*, Apr. 15, 1992, 89(8):3576-3580.
Green, "Targeting targeted therapy," *N. Engl. J. Med.*, May 20, 2004, 350(21):2191-2193.
Griffiths et al., "Human anti-self antibodies with high specificity from phage display libraries," *EMBO J.*, Feb. 1993, 12(2):725-734.
Gruber et al., "Efficient tumor cell lysis mediated by a bispecific single chain antibody expressed in *Escherichia coli,*" *J. Immunol.*, Jun. 1, 1994, 152(11):5368-5374.
Guss et al., "Structure of the IgG-binding regions of streptococcal protein G," *EMBO J.*, Jul. 1986, 5(7):1567-1575.
Guyer et al., "Immunoglobulin binding by mouse intestinal epithelial cell receptors," *J. Immunol.*, Aug. 1976, 117(2):587-593.
Hakomori et al., "Glycosphingolipid antigens and cancer therapy," *Chem. Biol.*, Feb. 1997, 4(2):97-104.
Hakomori, "Glycosylation defining cancer malignancy: new wine in an old bottle," *Proc. Natl. Acad. Sci. U.S.A.*, Aug. 6, 2002, 99(16):10231-10233.
Hara et al., "Overproduction of penicillin-binding protein 7 suppresses thermosensitive growth defect at low osmolarity due to an spr mutation of *Escherichia coli,*" *Microbial Drug Resistance*, Spring 1996, 2(1):63-72.
Harris, "Production of humanized monoclonal antibodies for in vivo imaging and therapy," *Biochem. Soc. Transactions*, Nov. 1995, 23(4):1035-1038.
Hata, K. et al., "Limited Inhibitory Effects of Oseltamivir and Zanamivir on Human Sialidases," Antimicrobial Agents and Chemotherapy, vol. 52, No. 10, Oct. 2008, in 8 pages.
Hawkins et al., "Selection of phage antibodies by binding affinity. Mimicking affinity maturation," *J. Mol. Biol.*, 1992, 226(3):889-896.
Heyman, "Complement and Fc-receptors in regulation of the antibody response," *Immunol. Lett.*, Dec. 1996, 54(2-3):195-199.
Hinman et al., "Preparation and characterization of monoclonal antibody conjugates of the calicheamicins: a novel and potent family of antitumor antibiotics," *Cancer Res.*, Jul. 15, 1993, 53(14):3336-3342.
Hogrefe et al., "A bacteriophage lambda vector for the cloning and expression of immunoglobulin Fab fragments on the surface of filamentous phage," *Gene*, Jun. 15, 1993, 128(1):119-126.
Holliger et al., "'Diabodies': small bivalent and bispecific antibody fragments," *Proc. Natl. Acad. Sci. U.S.A.*, Jul. 15, 1993, 90(14):6444-6448.

Honegger et al., "Yet another numbering scheme for immunoglobulin variable domains: an automatic modeling and analysis tool," *J. Mol. Biol.*, Jun. 8, 2001, 309:657-670.
Hoogenboom et al., "By-passing immunisation. Human antibodies from synthetic repertoires of germline $V_H$ gene segments rearranged in vitro," *J. Mol. Biol.*, Sep. 20, 1992, 227(2):381-388.
Hoogenboom et al., "Multi-subunit proteins on the surface of filamentous phage: methodologies for displaying antibody (Fab) heavy and light chains," *Nucl. Acids Res.*, Aug. 11, 1991 19(15):4133-4137.
Huang et al., "Carbohydrate-based vaccines with a glycolipid adjuvant for breast cancer," *Proc. Natl. Acad. Sci. U.S.A.*, Feb. 12, 2013, 110(7):2517-2522.
Hung et al., "Investigation of SSEA-4 binding protein in breast cancer cells," *J. Am. Chem. Soc.*, Apr. 24, 2013, 135(16):5934-5937.
Hurle et al., "Protein engineering techniques for antibody humanization," *Curr. Opin. Biotechnol.*, Aug. 1994, 5(4):428-433.
Inouye et al., "Single-step purification of $F(ab')_{2\mu}$ fragments of mouse monoclonal antibodies (immunoglobulins M) by hydrophobic interaction high-performance liquid chromatography using TSKgel Ether-5PW," *J. Biochem. Biophys. Methods*, Feb. 1993, 26(1):27-39.
Jackson et al., "In vitro antibody maturation: Improvement of a high affinity, neutralizing antibody against IL-1β," *J. Immunol.*, Apr. 1, 1995, 154(7):3310-3319.
Jakobovits et al., "Analysis of homozygous mutant chimeric mice: deletion of the immunoglobulin heavy-chain joining region blocks B-cell development and antibody production," *Proc. Natl. Acad. Sci. U.S.A.*, Mar. 15, 1993, 90(6):2551-2555.
Jakobovits et al., "Germ-line transmission and expression of a human-derived yeast artificial chromosome," *Nature*, Mar. 18, 1993, 362(6417):255-258.
Jenkins N, Curling EM., "Glycosylation of recombinant proteins: problems and prospects", *Enzyme Microb Technol.* May 1994;16(5):354-64.
Jones et al., "Rapid PCR-cloning of full-length mouse immunoglobulin variable regions," *Nature Biotechnol.*, Jan. 1991, 9(1):88-89.
Jones et al., "Replacing the complementarity-determining regions in a human antibody with those from a mouse," *Nature*, May 29-Jun. 4, 1986, 321(6069):522-525.
Jones, "Analysis of polypeptides and proteins," *Adv. Drug Delivery Rev.*, Jan.-Apr. 1993, 10(1):29-90.
Kam et al., "Carbon nanotubes as multifunctional biological transporters and near-infrared agents for selective cancer cell destruction," *Proc. Natl. Acad. Sci. U.S.A.*, Aug. 16, 2005, 102(33):11600-11605.
Kaneko et al., "Anti-inflammatory activity of immunoglobulin G resulting from Fc sialylation," *Science*, Aug. 4, 2006, 313(5787):670-673.
Kannagi et al., "New globoseries glycosphingolipids in human teratocarcinoma reactive with the monoclonal antibody directed to a developmentally regulated antigen, stage-specific embryonic antigen 3," *J. Biol. Chem.*, Jul. 25, 1983, 258(14):8934-8942.
Kannagi et al., "Stage-specific embryonic antigens (SSEA-3 and -4) are epitopes of a unique globo-series ganglioside isolated from human teratocarcinoma cells, "*EMBO J.*, 1983, 2(12):2355-2361.
Karlin S. et al., "Methods for assessing the statistical significance of molecular sequence features by using general scoring schemes", *Proc Natl Acad Sci USA.* Mar. 1990;87(6):2264-8.
Kato et al., "GMab-1, a high-affinity anti-3'-isoLM1/3'6'-isoLD1 IgG monoclonal antibody, raised in lacto-series ganglioside-defective knockout mice," *Biochem. Biophys. Res. Commun.*, Jan. 1, 2010, 391(1):750-755.
Kim et al., "Localization of the site of the murine IgG1 molecule that is involved in binding to the murine intestinal Fc receptor," *Eur. J. Immunol.*, 1994, 24:2429-2434.
Köhler et al., "Continuous cultures of fused cells secreting antibody of predefined specificity," *Nature*, Aug. 7, 1975, 256(5517):495-497.
Kontermann, "Intrabodies as therapeutic agents," *Methods*, Oct. 2004, 34(2):163-170.

(56) References Cited

OTHER PUBLICATIONS

Kostelny et al., "Formation of a bispecific antibody by the use of leucine zippers," *J. Immunol.*, Mar. 1, 1992, 148(5):1547-1553.
Kozbor, "A human hybrid myeloma for production of human monoclonal antibodies," *J. Immunol.*, Dec. 1984, 133(6):3001-3005.
Kriegler M et al., "A novel form of NF/cachectin is a cell surface cytotoxic transmembrane protein: ramifications for the complex physiology of TNF" *Cell.* Apr. 8, 1988;53(1):45-53.
Kudo et al., "Up-regulation of a set of glycosyltransferase genes in human colorectal cancer," *Lab. Invest.*, Jul. 1998, 78(7):797-811.
Lau et al., "N-Glycans in cancer progression," *Glycobiology*, Oct. 2008, 18(10):750-760.
Lee et al., "Bivalent antibody phage display mimics natural immunoglobulin," *J. Immunol. Methods*, Jan. 2004, 284(1-2):119-132.
Lee et al., "High-affinity human antibodies from phage-displayed synthetic Fab libraries with a single framework scaffold," *J. Mol. Biol.*, Jul. 23, 2004, 340(5):1073-1093.
Lefranc et al., "IMGT, The international ImMunoGeneTics database," *Nucleic Acids Res.*, Jan. 1, 1999, 27(1):209-212.
Lehninger, *Biochemistry: The Molecular Basis of Cell Structure and Function*, 2nd ed., 1975, pp. 73-75, Worth Publishers, New York.
Leung et al., "A method for random mutagenesis of a defined DNA segment using a modified polymerase chain reaction," *Technique—A Journal of Methods in Cell and Molecular Biology*, Aug. 1989, 1(1):11-15.
Lindmark et al., "Binding of immunoglobulins to protein A and immunoglobulin levels in mammalian sera," *J. Immunol. Meth.*, Aug. 12, 1983, 62(1):1-13.
Liu C, et al., "Expansion of spleen myeloid suppressor cells represses NK cell cytotoxicity in tumor-bearing host" *Blood.* May 15, 2007;109(10):4336-42. Epub Jan. 23, 2007.
Liu et al., "Eradication of large colon tumor xenografts by targeted delivery of maytansinoids," *Proc. Natl., Acad. Sci. U.S.A.*, Aug. 6, 1996, 93(16):8618-8623.
LoBuglio et al., "Mouse/human chimeric monoclonal antibody in man: kinetics and immune response," *Proc. Natl. Acad. Sci. U.S.A.*, Jun. 1989, 86(11):4220-4224.
Lode et al., "Targeted therapy with a novel enediyene antibiotic calicheamicin $\Theta^I_1$ effectively suppresses growth and dissemination of liver metastases in a syngeneic model of murine neuroblastoma," *Cancer Res.*, Jul. 15, 1998, 58(14):2925-2928.
Lonberg et al., "Antigen-specific human antibodies from mice comprising four distinct genetic modifications," *Nature*, Apr. 28, 1994, 368(6474):856-859.
Lonberg et al., "Human antibodies from transgenic mice," *Int. Rev. Immunol.*, 1995, 13(1):65-93.
Louis et al., "The 2007 WHO classification of tumours of the central nervous system," *Acta. Neuropathol.*, Aug. 2007, 114(2):97-109.
Lu et al., "Single chain anti-c-Met antibody conjugated nanoparticles for in vivo tumor-targeted imaging and drug delivery," *Biomaterials*, Apr. 2011, 32(12):3265-3274.
MacFarlane GT, et al., "Formation of glycoprotein degrading enzymes by Bacteroides fragilis" *FEMS Microbiol Lett.* Jan. 15, 1991;61(2-3):289-93.
Mandler et al., "Immunoconjugates of geldanamycin and anti-HER2 monoclonal antibodies: antiproliferative activity on human breast carcinoma cell lines," *J. Nat. Cancer Inst.*, Oct. 4, 2000, 92(19):1573-1581.
Mandler et al., "Modifications in synthesis strategy improve the yield and efficacy of geldanamycin-herceptin immunoconjugates," *Bioconjugate Chem.*, Jul.-Aug. 2002, 13(4):786-791.
Mandler et al., "Synthesis and evaluation of antiproliferative activity of a geldanamycin-Herceptin™ immunoconjugate," *Bioorganic & Med. Chem. Letters*, May 15, 2000, 10(10):1025-1028.
Månsson et al., "Characterization of new gangliosides of the lactotetraose series in murine xenografts of a human glioma cell line," *FEBS Lett.*, May 26, 1986, 201(1):109-113.
Marasco et al., "Design, intracellular expression, and activity of a human anti-human innumodeficiency virus type 1 gp120 single-chain antibody," *Proc. Natl. Acad. Sci. U.S.A.*, Aug. 15, 1993, 90(16):7889-7893.
Marasco, "Intrabodies: turning the humoral immune system outside in for intracellular immunization," *Gene Therapy*, Jan. 1997, 4(1):11-15.
Marks et al., "By-passing immunization Human antibodies from V-gene libraries displayed on phage," *J. Mol. Biol.*, Dec. 5, 1991, 222(3):581-597.
Marks et al., "By-passing immunization: Building high affinity human antibodies by chain shuffling," *Nature Biotechnology*, Jul. 1992, 10(7):779-783.
Mather et al., "Culture of testicular cells in hormone-supplemented serum-free medium," *Annals N.Y. Acad. Sci.*, 1982, 383:44-68.
Mather, "Establishment and characterization of two distinct mouse testicular epithelial cell lines," *Biol. Reprod.*, Aug. 1980, 23(1):243-252.
Matsuda et al., "Structure and physical map of 64 variable segments in the 3' 0.8-megabase region of the human immunoglobulin heavy-chain locus," *Nature Genet.*, Jan. 1993, 3(1):88-94.
McCafferty et al., "Phage antibodies: Filamentous phage displaying antibody variable domains," *Nature*, Dec. 6, 1990, 348:552-554.
McKimm-Breschkin, J. et al., "Neuraminidase Sequence Analysis and Susceptibilities of Influenza Virus Clinical Isolates to Zanamivir and Oseltamivir," Antimicrobial Agents and Chemotherapy, vol. 47, No. 7, Jul. 2003, in 10 pages.
Meezan et al., "Comparative studies on the carbohydrate-containing membrane components of normal and virus-transformed mouse fibroblasts: II: Separation of glycoproteins and glycopeptides by Sephadex chromatography," *Biochemistry*, Jun. 1969, 8(6):2518-2524.
Meyer, "Malignant gliomas in adults," *N. Engl. J. Med.*, Oct. 23, 2008, 359(17):1850.
Mimura et al., "Role of oligosaccharide residues of IgG1-Fc in FcγRIIb binding," *J. Biol. Chem.*, Dec. 7, 2001, 276(49):45539-45547.
Mishima et al., "Growth suppression of intracranial xenografted glioblastomas overexpressing mutant epidermal growth factor receptors by systemic administration of monoclonal antibody (mAb) 806, a novel monoclonal antibody directed to the receptor," *Cancer Res.*, Jul. 15, 2001, 61(14):5349-5354.
Morelle, W. et al., "The Mass Spectrometric Analysis of Glycoproteins and their Glycan Sturctures", *Review in Current Analytical Chemistry*, vol. 1, No. 1 (2005), pp. 29-57.
Mori K, et al., "Non-fucosylated therapeutic antibodies: the next generation of therapeutic antibodies" *Cytotechnology.* Dec. 2007;55(2-3):109-14. Epub Oct. 31, 2007.
Morimoto et al., "Single-step purification of F(ab')₂ fragments of mouse monoclonal antibodies (immunoglobulins G1) by hydrophobic interaction high performance liquid chromatography using TSKgel Phenyl-5PW," *J. Biochem. Biophys. Meth.*, Mar. 1992, 24(1-2):107-117.
Morrison et al., "Chimeric human antibody molecules: mouse antigen-binding domains with human constant region domains," *Proc. Natl. Acad. Sci. U.S.A.*, Nov. 1984, 81(21):6851-6855.
Morrison, "Immunology. Success in specification," *Nature*, Apr. 28, 1994, 368(6474):812-813.
Munson et al., "Ligand: a versatile computerized approach for characterization of ligand-binding systems," *Anal. Biochem.*, Sep. 1, 1980, 107(1):220-239.
Neuberger et al., "Recombinant antibodies possessing novel effector functions," *Nature*, Dec. 13-19, 1984, 312(5995):604-608.
Neuberger, "Generating high-avidity human Mabs in mice," *Nature Biotechnol.*, Jul. 1996, 14(7):826.
Nicolaou et al., "Calicheamicin $\Theta^I_1$: A rationally designed molecule with extremely potent and selective DNA cleaving properties and apoptosis inducing activity," *Angew. Chem. Intl. Ed. Engl.*, Feb. 1, 1994, 33(2):183-186.
Niculescu-Duvaz et al., "Antibody-directed enzyme prodrug therapy (ADEPT): A review," *Adv. Drg. Del. Rev.*, Jul. 7, 1997, 26(2-3):151-172.

(56) References Cited

OTHER PUBLICATIONS

Noto et al., "CD44 and SSEA-4 positive cells in an oral cancer cell line HSC-4 possess cancer stem-like cell characteristics," *Oral Oncol.*, Aug. 2013, 49(8):787-795.
Orlandi et al., "Cloning immunoglobulin variable domains for expression by the polymerase chain reaction," *Proc. Natl. Acad. Sci. U.S.A.*, May 1989, 86(10):3833-3837.
Ørum et al., "Efficient method for constructing comprehensive murine Fab antibody libraries displayed on phage." *Nucleic Acids Res.*, Sep. 25, 1993, 21(19):4491-4498.
Papanastassiou et al., "The potential for efficacy of the modified (ICP 34.5⁻) herpes simplex virus HSV1716 following intratumoural injection into human malignant glioma: a proof of principle study," *Gene Therapy*, Mar. 2002, 9(6):398-406.
Pearlman et al., *Peptide and Protein Drug Delivery*, Chapter 6: Analysis of Protein Drugs, Lee, ed., 1991, pp. 247-301, Marcel Dekker Publishing, New York.
Peipp et al., "Antibody fucosylation differentially impacts cytotoxicity mediated by NK and PMN effector cells," *Blood*, 2008, 112(6):2390-2399.
Plückthun, "Mono- and bivalent antibody fragments produced in *Escherichia coli*: Engineering, folding and antigen binding," *Immunol. Rev.*, Dec. 1992, 130:151-188.
Plückthun, *Handbook of Experimental Pharmacology*, vol. 113: The Pharacology of Monoclonal Antibodies, Chapter 11: Antibodies from Escherichia coli, Rosenberg et al., eds., 1994, pp. 269-315, Springer-Verlag, Berlin.
Presta et al., "Humanization of an antibody directed against IgE," *J. Immunol.*, Sep. 1, 1993, 151(5):2623-2632.
Presta et al., "Humanization of an anti-vascular endothelial growth factor monoclonal antibody for the therapy of solid tumors and other disorders," *Cancer Res.*, Oct. 15, 1997, 57(20):4593-4599.
Presta, "Antibody engineering," *Curr. Opin. Biotechnol.*, Aug. 1992, 3(4):394-398.
Presta, "Antibody engineering," *Curr. Opin. Struct. Biol.*, Aug. 1992, 2(4):593-596.
Proba et al., "Functional antibody single-chain fragments from the cytoplasm of *Escherichia coli*: influence of thioredoxin reductase (TrxB)," *Gene*, Jul. 4, 1995, 159(2):203-207.
Puigbò P, Guzmán E, Romeu A, Garcia-Vallvé S. OPTIMIZER: a web server for optimizing the codon usage of DNA sequences. *Nucleic Acids Res.* Jul. 2007;35(Web Server issue):W126-31. Epub Apr. 16, 2007.
Ramm et al., "The periplasmic *Escherichia coli* peptidylprolyl cis,trans-isomerase FkpA. II. Isomerase-independent chaperone activity in vitro," *J. Biol. Chem.*, Jun. 2, 2000, 275(22):17106-17113.
Ravetch et al., "Divergent roles for Fc receptors and complement in vivo," *Ann. Rev. Immunol.*, 1998, 16:421-432.
Ravetch et al., "Fc receptors," *Annu. Rev. Immunol.*, 1991, 9:457-492.
Reyes et al., "Expression of human β-interferon cDNA under the control of a thymidine kinase promoter from herpes simplex virus," *Nature*, Jun. 17, 1982, 297(5867):598-601.
Riechmann et al., "Reshaping human antibodies for therapy," *Nature*, Mar. 24, 1988, 332(6162):323-327.
Roguska et al., "Humanization of murine monoclonal antibodies through variable domain resurfacing," *Proc. Natl. Acad. Sci. U.S.A.*, Feb. 1, 1994, 91(3):968-973.
Roos et al., "Specific inhibition of the classical complement pathway by C1q-binding peptides," *J. Immunol.*, Dec. 15, 2001, 167(12):7052-7059.
Rowland et al, "Drug localisation and growth inhibition studies of vindesine-monoclonal anti-CEA conjugates in a human tumour xenograft," *Cancer Immunol. Immunother.*, 1986, 21(3):183-187.
Ruiz et al., "IMGT, the international ImMunoGeneTics database," *Nucl. Acids Res.*, Jan. 1, 2000, 28(1):219-221.
Saito et al., "Expression of globo-series gangliosides in human renal cell carcinoma," *Jpn. J. Cancer Res.*, Jul. 1997, 88(7):652-659.

Saito et al., "Human α2,3-sialyltransferase (ST3Gal II) is a stage-specific embryonic antigen-4 synthase," *J. Biol. Chem.*, Jul. 18, 2003, 278(29):26474-26479.
Sastry et al., "Cloning of the immunological repertoire in *Escherichia coli* for generation of monoclonal catalytic antibodies: construction of a heavy chain variable region-specific cDNA library," *Proc. Natl. Acad. Sci. U.S.A.*, Aug. 1989, 86(15):5728-5732.
Schenkel-Brunner, *Human Blood Groups*, Chapter 8: P System, 1995, pp. 211-234, Springer-Verlag, Vienna.
Schier et al., "Identification of functional and structural amino-acid residues by parsimonious mutagenesis," *Gene*, Mar. 9, 1996, 169(2):147-155.
Sell, "Cancer-associated carbohydrates identified by monoclonal antibodies," *Hum. Pathol.*, Oct. 1990, 21(10):1003-1019.
Shalaby et al., "Development of humanized bispecific antibodies reactive with cytotoxic lymphocytes and tumor cells overexpressing the HER2 protooncogene," *J. Exp. Med.*, Jan. 1, 1992, 175(1):217-225.
Shields et al., "High resolution mapping of the binding site on human IgG1 for FcγRI, FcγRII, FcγRIII, and FcRn and design of IgG1 variants with improved binding to the FcγR," *J. Biol. Chem.*, Mar. 2, 2001, 276(9):6591-6604.
Shields et al., "Lack of fucose on human IgG1 N-linked oligosaccharide improves binding to human FcγRIII antibody-dependent cellular toxicity," *J. Biol. Chem.*, Jul. 26, 2002, 277(30):26733-26740.
Shinkawa et al., "The absence of fucose but not the presence of galactose or bisecting N-acetylglucosamine of human IgG1 complex-type oligosaccharides shows the critical role of enhancing antibody-dependent cellular cytotoxicity," *J. Biol. Chem.*, Jan. 31, 2003, 278(5):3466-3473.
Sidhu et al., "Phage-displayed antibody libraries of synthetic heavy chain complementarity determining regions," *J. Mol. Biol.*, Apr. 23, 2004, 338(2):299-310.
Siebenlist et al., "*E. coli* RNA polymerase interacts homologously with two different promoters," *Cell*, Jun. 1980, 20(2):269-281.
Simmons et al., "Expression of full-length immunoglobulins in *Escherichia coli*: Rapid and efficient production of aglycosylated antibodies," *J. Immunol. Methods*, May 1, 2002, 263(1-2):133-147.
Sims et al., "A humanized CD18 antibody can block function without cell destruction," *J. Immunol.*, Aug. 15, 1993, 151(4):2296-2308.
Skerra, "Bacterial expression of immunoglobulin fragments," *Curr. Opinion in Immunol.*, Apr. 1993, 5(2):256-262.
Slamon DJ, et al., "Human breast cancer: correlation of relapse and survival with amplification of the HER-2/neu oncogene" *Science*. Jan. 9, 1987; 235(4785):177-82.
Smith RA et al., "The active form of tumor necrosis factor is a trimer" *J Biol Chem.* May 25, 1987;262(15):6951-4.
Smyth MJ, et al., "CD4+CD25+ T regulatory cells suppress NK cell-mediated immunotherapy of cancer" *J Immunol.* Feb. 1, 2006;176(3):1582-7.
Suresh et al., "Bispecific monoclonal antibodies from hybrid hybridomas," *Methods in Enzymology*, 1986, 121:210-228.
Suzuki E, et al., "A nonfucosylated anti-HER2 antibody augments antibody-dependent cellular cytotoxicity in breast cancer patients" *Clin Cancer Res.* Mar. 15, 2007;13(6):1875-82.
Svennerholm et al., "Human brain gangliosides: Developmental changes from early fetal stage to advanced age," *Biochim. Biophys. Acta*, Sep. 25, 1989, 1005(2): 109-117.
Syrigos et al., "Antibody directed enzyme prodrug therapy (ADEPT): a review of the experimental and clinical considerations," *Anticancer Research*, Jan.-Feb. 1999, 19(1A):605-614.
Takeda et al., "Construction of chimaeric processed immunoglobulin genes containing mouse variable and human constant region sequences," *Nature*, Apr. 4-10, 1985, 314(6010):452-454.
Taylor-Papadimitriou et al., "Exploiting altered glycosylation patterns in cancer: Progress and challenges in diagnosis and therapy," *Trends Biotechnol.*, Jun. 1994, 12(6):227-233.
Thorpe, (1985) "Antibody Carriers of Cytotoxic Agents in Cancer Therapy: A Review," in *Monoclonal Antibodies '84: Biological and Clinical Applications*, A. Pinchera et al. (ed.s), pp. 475-506.

(56) References Cited

OTHER PUBLICATIONS

Tomlinson et al., "The repertoire of human germline $V_H$ sequences reveals about fifty groups of $V_H$ segments with different hypervariable loops," *J. Mol. Biol.*, Oct. 5, 1992, 227(3):776-798.

Traunecker et al., "Bispecific single chain molecules (Janusins) target cytotoxic lymphocytes on HIV infected cells," *EMBO J.*, Dec. 1991, 10(12):3655-3659.

Traylor et al., "Gangliosides of human cerebral astrocytomas," *J. Neurochem.*, Jan. 1980, 34(1):126-131.

Tsai TI, et al., "Effective sugar nucleotide regeneration for the large-scale enzymatic synthesis of Globo H and SSEA4" *J Am Chem Soc.* Oct. 2, 2013;135(39):14831-9, Epub Sep. 17, 2013.

Tutt et al., "Trispecific F(ab')₃ derivatives that use cooperative signaling via the TCR/CD3 complex and CD2 to activate and redirect resting cytotoxic T cells," *J. Immunol.*, Jul. 1, 1991, 147(1):60-69.

Tyagarajan K et al., "Exoglycosidase purity and linkage specificity: assessment using oligosaccharide substrates and high-pH anion-exchange chromatography with pulsed amperometric detection" *Glycobiology.* Jan. 1996;6(1):83-93.

Urlaub et al., "Isolation of Chinese hamster cell mutants deficient in dihydrofolate reductase activity." *Proc. Natl. Acad. Sci. U.S.A.*, Jul. 1980, 77(7):4216-4220.

Valentine MA, et al., "Phosphorylation of the CD20 phosphoprotein in resting B lymphocytes. Regulation by protein kinase C" *J Biol Chem.* Jul. 5, 1989;264(19):11282-7.

van Beek et al., "Increased sialic acid density in surface glycoprotein of transformed and malignant cells—a general phenomenon?" *Cancer Res.*, Nov. 1973, 33(11):2913-2922.

Van Meir et al., "Exciting new advances in neuro-oncology: the avenue to a cure for malignant glioma," *CA Cancer J. Clin.*, May-Jun. 2010, 60(3):166-193.

Van Slambrouck et al., "Clustering of monosialyl-Gb5 initiates downstream signalling events leading to invasion of MCF-7 breast cancer cells," *Biochem. J.*, Feb. 1, 2007, 401(3):689-699.

Vaswani et al., "Humanized antibodies as potential therapeutic drugs," *Ann. Allergy, Asthma Immunol.*, Aug. 1998, 81(2):105-116, 119.

Verhoeyen et al., "Reshaping human antibodies: grafting an antilysozyme activity," *Science*, Mar. 25, 1988, 239(4847):1534-1536.

Vermeer AW et al., "The thermal stability of immunoglobulin: unfolding and aggregation of a multi-domain protein" *Biophys J.* Jan. 2000;78(1):394-404.

Wang et al., "Glycan microarray of Globo H and related structures for quantitative analysis of breast cancer," *Proc. Natl. Acad. Sci. U.S.A.*, Aug. 19, 2008, 105(33):11661-11666.

Ward et al., "Binding activities of a repertoire of single immunoglobulin variable domains secreted from *Escherichia coli*," *Nature*, Oct. 12, 1989, 341(6242):544-546.

Waterhouse et al., "Combinatorial infection and in vivo recombination: a strategy for making large phage antibody repertoires," *Nuc. Acids Res.*, May 11, 1993, 21(9):2265-2266.

Wikstrand et al., "Monoclonal antibody therapy of human gliomas: Current status and future approaches," *Cancer Metastasis Rev.*, 1999, 18(4):451-464.

Williams et al., "Cloning and sequencing of human immunoglobulin V lambda gene segments." *Eur. J. Immunol.*, Jul. 1993, 23(7):1456-1461.

Winter et al., "Making antibodies by phage display technology," *Annu. Rev. Immunol.*, 1994, 12:433-455.

Woof et al., "Human antibody-Fc receptor interactions illuminated by crystal structures," *Nat. Rev. Immunol.*, Feb. 2004, 4(2):89-99.

Yansura et al., "Nucleotide sequence selection for increased expression of heterologous genes in *Escherichia coli*," *Methods: A Companion to Methods in Enzymol.*, Aug. 1992, 4(2):151-158.

Ye et al., "Stage-specific embryonic antigen 4 expression in epithelial ovarian carcinoma," *Int. J. Gynecol. Cancer*, Aug. 2010, 20(6):958-964.

Yelton et al., "Affinity maturation of the BR96 anti-carcinoma antibody by codon-based mutagenesis." *J. Immunol.*, Aug. 15, 1995, 155(4):1994-2004.

Yu et al., "Anti-GD2 antibody with GM-CSF, interleukin-2, and isotretinoin for neuroblastoma," *N. Engl. J. Med.*, Sep. 30, 2010, 363(14):1324-1334.

Zapata et al., "Engineering linear F(ab')₂ fragments for efficient production in *Escherichia coli* and enhanced antiproliferative activity," *Protein Eng.*, Oct. 1995, 8(10):1057-1062.

Zarei et al., "Separation and identification of GM1b pathway Neu5Ac- and Neu5Gc gangliosides by on-line nanoHPLC-QToF MS and tandem MS: toward glycolipidomics screening of animal cell lines," *Glycobiology*, Jan. 2010, 20(1):118-126.

Zhang et al., "Selection of tumor antigens as targets for immune attack using immunohistochemistry: I. Focus on gangliosides," *Int. J. Cancer*, Sep. 26, 1997, 73(1):42-49.

European Search Report issued in connection with corresponding European Patent Application No. 15181446.4, dated Dec. 7, 2015, 10 pages.

International Search Report and Written Opinion issued for International application No. PCT/US2015/032738, dated Oct. 20, 2015, 15 pages.

International Search Report and Written Opinion issued for International application No. PCT/US2015/032744, dated Oct. 2, 2015, 12 pages.

International Search Report and Written Opinion issued for International application No. PCT/US2015/032740, dated Oct. 26, 2015, 13 pages.

International Search Report and Written Opinion issued for International application No. PCT/US2015/032737, dated Oct. 1, 2015, 13 pages.

International Search Report and Written Opinion issued for International application No. PCT/US2015/032745, dated Oct. 8, 2015, 13 pages.

International Search Report issued for International application No. PCT/US2015/049014, dated Dec. 14, 2015, 3 pages.

Simon JF MacDonald, et al, *Potent and Long-Acting Dimeric Inhibitors of Influenza Virus Neuraminidase Are Effective at a Once-Weekly Dosing Regimen*; Antimicrobial Agents and Chemotherapy, American Society for Microbiology, Dec. 2004, pp. 4542-4549, vol. 48, No. 12.

Pedro Michaluart, et al., *Inhibitory Effects of Caffeic Acid Phenethyl Ester on the Activity and Expression of Cyclooxygenase-2 in Human Oral Epithelial Cells and in a Rat Model of Inflammation*, Cancer Research 59, 2347-2352, May 15, 1999.

U.S. Appl. No. 15/005,930, filed Jan. 25, 2016, Wong et al.
U.S. Appl. No. 15/011,543, filed Jan. 30, 2016, Wong et al.
U.S. Appl. No. 15/011,544, filed Jan. 30, 2016, Wong et al.
U.S. Appl. No. 15/173,496, filed Jun. 3, 2016, Wong et al.

Abbas et al., "Functional diversity of helper T lymphocytes," *Nature*, Oct. 31, 1996, 383(6603):787-793.

Achtman, M., Epidemic Spread and Antigenic Variability of Neisseria Meningitidis, Trends Microbial 1995, 3, 186-192.

Adam et al., "Proteomic profiling of mechanistically distinct enzyme classes using a common chemotype," *Nat. Biotechnol.*, Aug. 2002, 20(8):805-809.

Agard, N. et al., A Strain-Promoted [3+2]Azide-Alkyne Cycloaddition for Covalent Modification of Biomolecules in Living Systems, J. Am. Chem. Soc. 2004, 126, 15046-15047.

Ahmadi, T. S. et al., Shape-Controlled Synthesis of Colloidal Platinum Nanoparticles, Science, 272, 1924 (1996).

Ahmed et al.,Structural Characterization of Anti-Inflammatory Immunoglobulin G Fc Proteins, K Mol Biol (2014) 426, 3166-3179.

Altevogt, Peter et al., Different Patterns of Lectin Binding and Cell Surface Sialylation Detected on Related High- and Low-Metastatic Tumor Lines, Cancer Res. 43, 5138-5144, 1983.

Amin, M. N. et al. Synthetic glycopeptides reveal the glycan specificity of HIV-neutralizing antibodies. Nat. Chem. Biol. 9, 521-526, (2013.

Angata et al., "Chemical diversity in the sialic acids and related α-keto acids: an evolutionary perspective," *Chem. Rev.*, Feb. 2002, 102(2):439-469.

(56) References Cited

OTHER PUBLICATIONS

Anthony, Robert et al., Recapitulation of IVIG Anti-Inflammatory Activity with a Recombinant IgG Fc, Science Apr. 18, 2008. 320:373-376.
Arase et al., "NK1.1+ CD4+ CD8− thymocytes with specific lymphokine secretion," Eur. J. Immunol., Jan. 1993, 23(1):307-310.
Aspeslagh et al., "Galactose-modified iNKT cell agonists stabilized by an induced fit of CD1d prevent tumour metastasis," EMBO J., Jun. 1, 2011, 30(11):2294-2305.
Astronomo, R. D. & Burton, D.R. Carbohydrate vaccines: developing sweet solutions to sticky situations? Nat. Rev. Drug. Discov. 9, 308-324, (2010.
Bacilieri, Magdalena et al., Ligand-Based Drug Design Methodologies in Drug Discovery Process: An Overview, Current Drug Discovery Technologies, vol. 3 (3), Sep. 2006, p. 155-165.
Bai, Dan et al., Exploring Forster Electronic Energy Transfer in a Decoupled Anthracenyl-based Borondipyrromethene (Bodipy) Dyad, Physical Chemistry Chemical Physics (2012), 14(13), 4447-4456.
Bailey, Ryan et al., Real-Time Multicolor DNA Detection with Chemoresponsive Diffraction Gratings and Nanoparticle Probes, J. Am Chem. Soc., 2003, 125, 13541-13547.
Banchereau et al., "Dendritic cells and the control of immunity," Nature, Mar. 19, 1998, 392(6673):245-252.
Bardotti, Angela et al., Size Determination of Bacterial Capsular Oligosaccharides Used to Prepare Conjugated Vaccines Against Neisseria Meningitidis Groups Y and W135, Vaccine 2005, 23, 1887-1899.
Barouch, D. H. Challenges in the development of an HIV-I vaccine. Nature 455, 613-619, (2008).
Barry, C.S. et al., 'Naked' and Hydrated Confirmers of the Conserved Core Pentasaccharide of N-Linked Glycoproteins and Its Building Blocks, Journal of the American Chemical Society, 2013, vol. 135(45), p. 16895-16903.
Basak et al., In Vitro Elucidation of Substrate Specificity and Bioassay of Proprotein Convertase 4 Using Intramolecularly Quenched Fluorogenic Peptides, Biochem. J. Jun. 1, 2004, 380(pt 2): 505-514.
Baskin, J.M.; Amacher, S. L.; Bertozzi, C.R."In vivo imaging of membraneassociated glycans in developing zebrafish." Science 2008, 320, 664-667.
Bassell, G.J. et al., Single mRNAs Visualized by Ultrastructural in Situ Hybridization are Principally Localized at Actin Filament Intersections in Fibroblasts, J. Cell Biol., 126, 863-876 (1994.
Beckman et al., Antibody constructs in cancer therapy: protein engineering strategies to improve exposure in solid tumors, cancer, 109(2): 170-179 (2007).
Bendayan, Moise, Possibilities of False Immunocytochemical Results Generated by the Use of Momoclonal Antibodies: The Example of the Anti-Proinsulin Antibody, J. Histochem. Cytochem, 43: 881-886, (1995).
Bennett, Clay et al., Chemoenzymatic Approaches to Glycoprotein Synthesis, Chem. Soc. Rev. 2007, 36:1227-1238.
Berge, Steven et al. J. Pharmaceutical Sciences (1977) 66: 1-19.
Best, M. D. "Click chemistry and bioorthogonal reactions: unprecedented selectivity in the labeling of biological molecules." Biochemistry 2009, 48, 6571-6584.
Bertozzi, CR et al., Glycans in Cancer and Inflammation—Potential for Therapeutics and Diagnostics, Nat Rev Drug Discovery, 2005, 4, 477-488.
Bigi et al., "Human sialidase NEU4 long and short are extrinsic proteins bound to outer mitochondrial membrane and the endoplasmic reticulum, respectively," Glycobiology, Feb. 2010, 20(2):148-157.
Blixt, O. et al. Printed covalent glycan array for ligand profiling of diverse glycan binding proteins. Proc. Natl. Acad. Sci. U.S. A. 101, 17033-17038, (2004.
Boens, N. et al., "Fluorescent indicators based on BODIPY." Chem. Soc. Rev. 2012, 41, 1130-1172.
Borg et al., "CD1d-lipid-antigen recognition by the semi-invariant NKT T-cell receptor," Nature, Jul. 5, 2007, 448(7149):44-49.

Bosmann et al., "Enzyme activity in invasive tumors of human breast and colon," Proc. Natl. Acad. Sci. USA, May 1974, 71(5):1833-1837.
Bost, Kenneth et al., Antibodies Against a Peptide Sequence Within The HIV Envelope Protein Crossreacts With Human Interleukin-2, Immunol. Invest., 17: 577-586 (1988).
Boyer, David et al., Photothermal Imaging of Nanometer-Sized Metal Particles Among Scatterers, Science, 2002, 297, 1160-116 3.
Braun-Howland et al., Development of a Rapid Method for Detecting Bacterial Cell In Situ Using 16S rRNA-Targeted Probes, Biotechniques, 13, 928-931 (1992).
Bricard et al., "Enrichment of human CD4+ Vα24/Vβ11 invariant NKT cells in intrahepatic malignant tumors," J. Immunol., Apr. 15, 2009, 182(2):5140-5151.
Bruchez, Marcel et al. Semiconductor Nanocrystals as Fluorescent Biological Labels, Science 281:2013-2016, 1998.
Buchini et al., "Towards a new generation of specific Trypanosoma cruzi trans-sialidase inhibitors," Angew. Chem. Int. Ed. Engl., 2008, 47(14):2700-2703.
Burton, D.R., Mascola, J. R. Antibody responses to envelope glycoproteins in HIV-I infection. Nature Immunol. 16, 571-6, (2015).
Calarese, D. A. et al. Antibody domain exchange is an immunological solution to carbohydrate cluster recognition. Science 300, 2065-2071, (2003).
Cao, Y. C. et al., Nanoparticles with Raman Spectroscopic Fingerprints for DNA and RNA Detection, Science, 2002, 289, 1757-60.
Carlsson, Jan et al., Protein Thiolation and Reversible Protein-Protein Conjugation, Biochem J 173: 723-737 (1978).
Centers for Disease Control and Prevention (CDC), "Influenza activity—United States and worldwide, 2007-08 season" MMWR, Jun. 27, 2008, 57(25):692-697.
Cespedes et al., Mouse models in oncogenesis and cancer therapy, Clin Transl Oncl., 8(5): 318-329 (2006).
Chan, Warren et al., Quantum Dot Bioconjugates for Ultrasensitive Nonisotopic Detection, Science 281:2016-2018 (1998).
Chang, S. H. et al. Glycan array on aluminum oxide-coated glass slides through phosphonate chemistry. J. Am. Chem. Soc. 132, 13371-13380, (2010).
Chang et al., "Potent immune-modulating and anticancer effects of NKT cell stimulatory glycolipids," Proc. Natl. Acad. Sci. USA, Jun. 19, 2007, 104(25):10299-10304.
Chao, W.; Fang, X.; Nisaraporn, S.; Jian, S.; Qian, W. "Tuning the optical properties of BODIPY dye through Cu(I) catalyzed azide-alkyne cycloaddition (CuAAC) reaction." Sci. China Chemistry 2012, 55, 125-130.
Chari, Ravi et al., Immunoconjugates Containing Novel Maytansinoids: Promising Anticancer Drugs Cancer Research 52: 127-131 (1992).
Chauhan, D. P.; Saha, T.; Lahiri, M.; Talukdar, P. "BODIPY based 'click on' fluorogenic dyes: application in live cell imaging." Tetrahedron Lett. 2014, 55, 244-247.
Cheng, Peter et al., Oseltamivir- and Amandtadine-resistant Influenza Viruses A (H1N1), Emerg. Infect. Dis., Jun. 2009, 15(6): 966-968.
Cheung et al., Stage-specific embryonic antigen-3 (SSEA-3) and beta3GalT5 are cancer specific and significant markers for breast cancer stem cells, PNAS, Jan. 26, 2016, vol. 113, No. 4, pp. 960-965.
Chiari, M. et al., Advanced Polymers for Molecular Recognition and Sensing at the Interface. J Chromatography B, Apr. 15, 2008, 866(1-2):89-103.
Childs et al., Receptor-Binding Specificity of Pandemic Influenza A (H1N1) 2009 Virus Determined by Carbohydrate Microarray. Nat. Biotechnol. 2009, 27(9): 797-799.
Cho, Se-Heon et al., Sialyl-Tn Antigen Expression Occurs Early During Human Mammary Carcinogenesis and Is Associated with High Nuclear Grade and Aneuploidy, Cancer Res. 54, 6302-6305, 1994.
Chong et al., Influenza Virus Sialidase: Effect of Calcium on Steady-State Kinetic Parameters, Biochim. Biophys. Acta, Mar. 8, 1991, 1077(1): 65-71.
Chothia et al., "Domain association in immunoglobulin molecules. The packing of variable domains," J. Mol. Biol., Dec. 5, 1985, 186(3):651-663.

(56) References Cited

OTHER PUBLICATIONS

Codelli, J. A. et al., Second-Generation Difluorinated Cycloctynes for Copper-Free Click Chemistry, J. Am. Chem. Soc. 2008, 130, 11486-11493.
Cohen-Daniel et al., Emergance of Oseltamivir-Resistant Influenza A/H3N2 Virus with Altered Hemagglutination Pattern in Hematopoietic Stem Cell Transplant Recipient, J Clin Virol., Feb. 2009, 44(2):138-140.
Coligan et al., Current Protocols in Immunology, sections 2.5.1-2.6.7, 1991.
Collins et al., Crystal Structures of Oseltamivir-Resistant Influenza Virus Neuraminidase Mutants, Nature, Jun. 26, 2008, 453(7199):1258-1261.
Connor, Robert et al., Receptor Specifcity in Human, Avian, and Equine H2 and H3 Influenza Virus Isolates, Virology, 205: 17, 1994.
Cox et al., New Options for the Prevention of Influenza, N. Engl. J. Med. Oct. 28, 1999, 341(18): 1387-1388.
Cragg, M.S. et al., Complement-Mediated Lysis by Anti-CD20 mAb Correlates with Segregation into Lipid Rafts, Blood 101 (2003) 1045-1052.
Cragg, M.S. et al., Antibody Specificity Controls in Vivo Effector Mechanism of Anti-CD20 Reagents, Blood, 103 (2004) 2738-2743.
Craigo, J. K., Montelaro, R. C. Lessons in AIDS vaccine development learned from studies of equine infectious, anemia virus infection and immunity. Viruses 5, 2963-76, (2013).
Crispin et al., "Carbohydrate and domain architecture of an immature antibody glycoform exhibiting enhanced effector functions," J. Mol. Biol., Apr. 17, 2009, 387(5):1061-1066.
Cyranoski, Threat of Pandemic Brings Flu Drug Back to Life, Nat. Med. Sep. 2005, 11(9): 909.
Davies, JW et al., Streamlining Lead Discovery by Aligning in Silico and High-Throughput Screening, Curr Opin Chem Biol. Aug. 2006; 10(4):343-51.
Davodeau et al., "Close phenotypic and functional similarities between human and murine $\alpha\beta$ T cells expressing invariant TCR alpha-chains," J. Immunol., Jun. 15, 1997, 158(12):5603-5611.
de Almeida et al., "Thiacycloalkynes for copper-free click chemistry," Angew. Chem. Int. Ed. Engl., Mar. 5, 2012, 51(10):2443-2447.
Debets, M. F. et al., Bioconjugation with Strained Alkenes and Alkynes, Acc. Chem. Res. 2011, 44, 805-815.
Delente, Jacqubs, Glycosylation Revisited, Trends in Biotechnology 3, letters to editor, No. 9 (1985).
Dellabona et al., "An invariant V$\alpha$24-J$\alpha$Q/V$\beta$11 T cell receptor is expressed in all individuals by clonally expanded CD4$^-$8$^-$ T cells," J. Exp. Med., Sep. 1, 1994, 180(3):1171-1176.
Demchenko, A.V., Ed., Hanbook of Chemical Glycosylation: Advances in Stereoselectivity and Therapeutic Relevance (2008) WILEY-VCH. Chapter 1. General Aspects of the Glycosidic Bond Formation, in 28 pages.
Dennis, Carina, Cancer: Off by a whisker, Nature 442: 739-741 (2006).
De Paz, J. L., Horlacher, T. & Seeberger, P.H. Oligosaccharide microarrays to map interactions of carbohydrates in biological systems. Methods Enzymol. 415, 269-292, (2006).
Dhodapkar et al., "$\alpha$-Galactosyl ceramide-loaded dendritic cells for expansion of natural killer T cells" CAPLUS 145:354715 (2006).
Dhodapkar et al., "A reversible defect in natural killer T cell function characterizes the progression of premalignant to malignant multiple myeloma," J. Exp. Med., Jun. 16, 2003, 197(12):1667-1676.
Dohi, Taeko et al., Fucosyltransferase-Producing Sialyl Lea and Sialyl Lex Carbohydrate Antigen in Benign and Malignant Gastrointestinal Mucosa, Cancer 73, 1552, 1994.
Dohi, H. et al., Stereoselective Glycal Fluorophosphorlation: Synthesis of ADP-2-Fluoroheptose, an Inhibitor of the LPS Biosynthesis, Chem-Eur J 2008, 14, 9530-9539.
Dommerholt, Jan, Readily Accessible Bicyclononynes for Bioorthogonal Labeling and Three-Dimensional Imaging of Living Cells, Angew. Chem. Int. Ed. 2010, 49, 9422-9425.
Doores KJ, et al. A nonself sugar mimic of the HIV glycan shield shows enhanced antigenicity. Proc. Natl. Acad Sci. US.A. 107(40), 17107-17112, (2010).
Doores, K. J. & Burton, D.R. Variable Loop Glycan Dependency of the Broad and Potent HIV-I-Neutralizing Antibodies PG9 and PG16. J. Virol. 84, 10510-10521, (2010).
Doores, K. J. et al. Envelope glycans of immunodeficiency virions are almost entirely oligomannose antigens. Proc. Natl. Acad. Sci. U.S. A 107, 13800-13805, (2010).
Doronina, Svetlana et al., Development of Potent Monoclonal Antibody Auristatin Conjugates for Cancer Therapy, Nat Biotechnol 21(7): 778-784 (2003).
Dougan, Michael et al., Immune Therapy for Cancer, Annual Review of Immunology, 2009, 27, pp. 83-117.
Drugs of the future 25(7): 686 (2000).
Dubertret. Benoit et al., In Vivo Imaging of Quantum Dots Encapsulated in Phospholipid Micelles, Science 298:759-1762, 2002.
Duncan, AR; Winter, G, The binding Site for C1q on 1gG, Nature 322:738-40 (1988).
Dunn et al., Zanamivir: A Review of Its Use in Influenza, Drugs, Oct. 1999, 58(4):761-784.
Eberl et al., "Selective bystander proliferation of memory CD4$^+$ and CD8$^+$ T cells upon NK T or T cell activation," J. Immunol., Oct. 15, 2000, 165(8):4305-4311.
Eberl et al., "Selective induction of NK cell proliferation and cytotoxicity by activated NKT cells," Eur. J. Immunol., Apr. 2000, 30(4):985-992.
Eggink, D. et al. Lack of complex N-glycans on HIV-I envelope glycoproteins preserves protein conformation and entry function. Virology 401, 236-247, (2010).
Eisen, Michael et al., Binding of the Influenza A Virus to Cell-Surface Receptors: Structures of Five Hemagglutinin-Sialyloligosaccharide Complexes Determined by X-Ray Crystallography, Virology, 232:19, 1997.
Ellis J., et al., Evaluation of Four Real-Time PCR Assays for Detection of Influenza A9H1N1)v Viruses, Euro Surveill. 2009; 14(22), p. 1-3.
Evans, Michael et al., "Mechanism-based profiling of enzyme families," Chem. Rev., Aug. 2006, 106(8):3279-3301.
Evans, "The rise of azide-alkyne 1,3-dipolar 'click' cycloaddition and its application to polymer science and surface modification," Australian J. Chem., Jun. 2007, 60(6):384-395.
Extended European Search Report dated Jan. 5, 2016 in European Patent Application No. 13830785.5, in 10 pages.
Falkowska, E. et al. Broadly neutralizing HIV antibodies define a glycan-dependent epitope on the prefusion conformation of gp41 on cleaved envelope trimers. Immunity 40, 657-68, 2014.
Fan, Shu-Quan et al., Remarkable Transglycosylation Activity of Glycosynthase Mutants of Endo-D, an Endo-$\beta$-N-acetylglucosaminidase from Streptococcus pneumoniae, JBC vol. 287, No. 14, pp. 11272-11281, Mar. 30, 2012.
Fazio, F. et al., Synthesis of sugar arrays in microtiter plate. J. Am. Chem. Soc. 124, 14397-14402, (2002).
FDA Guidance for Industry for Container Closure Systems for Packaging Human Drugs and Biologics, May 1999.
Feizi, Ten, Carbohydrate Differentiation Antigens: Probable Ligands for Cell Adhesion Molecules,Trends Biochem. Sci. 16, 84-86.
Fernandez-Tejada, Alberto et al., Designing synthetic vaccines for HIV. Expert Rev. Vaccines 14, 815-31, 2015.
Fernandez-Megia et al., A Click Approach to Unprotected Glycodendrimers. Macromolecules 2006, vol. 39, pp. 2113-2120.
Fessner et al., Enzymes in Organic Synthesis, Short Enzymatic Synthesis of L-Fucose Analogs. Eur. J. Org. Chem 2000, p. 125-132.
Fiehn, Oliver, Combining Genomics, Metabolome Analysis, and Biochemical Modelling to Understand Metabolic Networks, Comparative and Functional Genomics 2:155-168, 2001.
Fraker, PJ et al., Protein and Cell Membrane Iodinations with a Sparingly Soluble Chloroamide, 1,3,4,6-tetrachloro-3a,6a-diphrenylglycoluril, Biochem. Biophys. Res. Commun. 80: 49-57 (1978).

(56) References Cited

OTHER PUBLICATIONS

Friscourt, F. et al., A Fluorogenic Probe for the Catalyst-Free Detection of Azide-Tagged Molecules, J. Am. Chem. Soc. 2012, 134, 18809-18815.
Friscourt et al., "Polar Dibenzocyclooctynes for Selective Labeling of Extracellular Glycoconjugates of Living Cells," *J. Am. Chem. Soc.*, Mar. 21, 2012, 134(11):5381-5389.
Fujimore, Kenji et al., A Modeling Analysis of Monoclonal Antibody Percolation Through Tumors: A Binding-Site Barrier, J Nuc Med. 31: 1191-1198 (1990).
Fujio, M. et al. "Structure-Based Discovery of Glycolipids for CD1d-Mediated NKT Cell Activation: Turning the Adjuvant versus Immunosuppression Activity." CAPLUS 145:240945 (2006).
Fujio, M. et al. "Structure-Based Discovery of Glycolipids for CD1d-Mediated NKT Cell Activation: Turning the Adjuvant versus Immunosuppression Activity." J. Am. Chem. Soc. (2006), vol. 128, pp. 9022-9023.
Fukui, S et al., Oligosaccharide microarrays for high-throughput detection and specificity assignments of carbohydrate-protein interactions. Nat. Biotechnol. 20, 1011-1017, (2002).
Gabius, HJ. Tumor Lectinology: at the intersection of carbohydrate chemistry, biochemistry, cell biology and oncology. Angew. Chem. Int. Ed. Engl. 27, 1267-1276.
Gamblin, SJ et al., The Structure and Receptor Binding Properties of the 1918 Influenza Hemagglutinin, Science, 303:1838, 2004.
Garces, F. et al. Structural evolution of glycan recognition by a family of potent HIV antibodies. Cell 159, 69-79, (2014).
Gaschen, B. et al. AIDS—Diversity Considerations in HIV-I vaccine selection. Science 296, 2354-2360, (2002).
GenBank accession No. WP_0080769537.1, published May 10, 2013.
GenBank accession No. WP_008767711.1, published May 10, 2013.
Geoghegan, Kieran et al., Site-Directed Conjugation of Nonpeptide Groups to Peptides and Proteins via Periodate Oxidation of a 2-amino Alcohol. Applications to Modification at N-Terminal Serine, Bioconjugate chem. 3:138-146 (1992).
Gerson et al., "ESR. Spectra and Structures of Radical Anions in the Dibenzo[a, e]cyclooxtene Series," *Helvetica Chinica Acta*, Jan. 1, 1976, 59(6): 2038-2048.
Giaccone, Giuseppe et al., "A phase I study of the natural killer T-cell ligand α-galactosylceramide (KRN7000) in patients with solid tumors," *Clin. Cancer Res.*, Dec. 2002, 8(12):3702-3709.
Go, E. P. et al. Characterization of glycosylation profiles of HIV-I transmitted/founder envelopes by mass spectrometry. J. Virol. 85, 8270-8284, (2011).
Go, E. P. et al. Comparative Analysis of the Glycosylation Profiles of Membrane-Anchored HIV-I Envelope Glycoprotein Trimers and Soluble gp140. J. Virol. 89, 8245-57, (2015).
Godefroy, S. et al., Effect of Skin Barrier Disruption on Immune Responses to Topically Applied Cross-Reacting Material, CRM197 of Diphtheria Toxin, Infect. Immun. 2005, 73, 4803.
Goldenthal et al., "Safety Evaluation of Vaccine Adjuvants: National Cooperative Vaccine Development Working Group," *AIDS Res. Hum. Retroviruses*, 1993, 9(Supp.1):S47-S51.
Golkowski et al., "Strategy for catch and release of azide-tagged biomolecules utilizing a photolabile strained alkyne construct," *Organic and Biomolecular Chemistry*, Jan. 1, 2012, 10(23):4496.
Gordon et al., "Reactivity of biarylazacyclooctynones in copper-free click chemistry," *J. Am. Chem. Soc.*, Jun. 6, 2012, 134(22): 9199-9208.
Graham, Duncan et al., Surface-Enhanced Resonance Raman Scattering as a Novel Method of DNA Discrimination, Angew. Chem., 2000, 112(6), 1103-1105.
Grandjean, C. et al., On the Preparation of Carbohydrate-Protein Conjugates Using the Traceless Staudinger Ligation, J Org Chem 2005, 70, 7123-7132.
Greenbaum et al., "Chemical approaches for functionally probing the proteome," *Mol. Cell. Proteomics*, 2002, 1:60-68.
Grubisha, D. S. et al., Femtomolar Detection of Prostate-Specific Antigen: An Immunoassay Based on Surface-Enhanced Raman Scattering and Immunogold labels, Anal. Chem. (2003), 75, 5936-5943.
Gulati et al., Deletions of Neuraminidase and Resistance to Oseltamivir May Be a Consequence of Restricted Receptor Specificity in Recent H3N2 Influenza Viruses. Virol. J. 2009, 6(22)L 1-15.
Gulland, Fire Cases of Spread of Oseltamivir Resistant Swine Flu Between Patients are Reported in Wales, BMJ, Nov. 23, 2009:339:b4975.
Ha, YA et al., X-Ray Structures of H5 Avian and H9 Swine Influenza Virus Hemagglutinins Bound to Avian and Human Receptor Analogs, Proc Natl Acad Sci USA, 98:11181-11186, 2001.
Ha, YA et al., X-Ray Structure of the Hemagglutinin of a Potential H3 Avian Progenitor of the 1968 Hong Kong Pandemic Influenza Virus, Virology, 309:209-218, 2003.
Hajishengallis, "Mucosal immunization with a bacterial protein antigen genetically coupled to cholera toxin A2/B subunits," *J. Immuol.*, May 1, 1995, 154(9):4322-4332.
Ham, Richard et al., Media and Growth Requirements, Meth. Enz 58, 44 (1979).
Hammerling et al., in: Monoclonal Antibodies and T-Cell Hybridomas 563-587, 1981.
Han, Junyan et al., 3- and 5-Functionalized BODIPYs via the Liebeskind-Srogl Reaction, Organic & Biomolecular Chemistry (2009), 7(1), 34-36.
Hanski, Christoph et al., Altered Glycosylation of the MUC-1 Protein Core Contributes to the Colon Carcinoma-Associated Increase of Mucin-Bound Sialyl-Lewis Expression, Cancer Res. 53, 4082-4088 (1993).
Hanski, C. et al., Characterization of the Major Sialyl-Lex-Poristive Mucins Present in Colon, Colon Carcinoma, and Sera of Patients with Colorectal Cancer, Cancer Res. 55, 928-933 (1995).
Hasegawa, Akira, et al., Synthesis of Sialyl Lewis X Ganglioside Analogues Containing Modified L-Fucose Residues, Carbohydr. Res. 1995, 274, 165-181.
Healthy Living, "10 Simple and Natural Ways to Boost Your Immune System," Published Jan. 31, 2014, downloaded from online, http://www.everydayhealth.com/columns/white-seeber-grogan-the-remedy-chicks/ten-simple-natural-ways-to-b . . . on Aug. 19, 2016.
Henglein, A. et al., Absorption Spectrum and Some Chemical Reactions of Colloidal Platinum in Aqueous Solution, J. Phys. Chem., 99, 14129 (1995).
Herner, A et al., A new family of bioorthogonally applicable fluorogenic labelst, Org. Biomol. Chem. 2013, 11, 3297-3306.
Hey, Thomas et al., Artificial, non-antibody binding proteins for pharmaceutical and industrial application, Trends in Biotechnology 23(10) 514-522 (2005).
Hirabayashi, J. et al., Oligosaccharide Microarrays for Glycomics, Trends in Biotechnology 21 (4): 141-143, 2003.
Holmskov, Uffe et al., Collectins: Collagenous C-Type Lectins of the Innate Immune Defense System, 1994, Immunol. Today, 15: 67.
Hotha, Srinivas et al., "Click Chemistry" Inspired Synthesis of Pseudo-Oligosaccharides and Amino Acid Glycoconjugates, J Org Chem 2006, 71, 364-367.
Horiya, S. et al., Recent strategies targeting HIV glycans in vaccine design. Nat. Chem. Biol. 10, 990-999, (2014).
Horn et al., Investigation into an Efficient Synthesis of 2,3-dehydro-N-acetyl Neuraminic Acid Leads to Three Decarboxylated Sialic Acid Dimers, Carbohdr. Res., Apr. 7, 2008, 343(5):936-940.
Howard et al., "Biological properties of interleukin 10," *Immunol. Today*, Jun. 1992, 13(6): 198-200.
Hsu et al., "Alkynyl sugar analogs for the labeling and visualization of glycoconjugates in cells," *Proc. Natl. Acad. Sci. USA*, Feb. 20, 2007, 104(8), 2614-2619.
Hsu, C, H. et al. Highly alpha-selective sialyl phosphate donors for efficient preparation of natural sialosides. Chem. Eur. J 16-6, 1754-1760, (2010).
Huang, Lijun et al., Iterative One-Pot Syntheses of Chitotetroses, Carbohydr. Res. 2006, 341, 1669-1679.
Huang et al., Recombinant immunotherpaeutics: current state and perspectives regarding the feasibility and market, Appl Microbiol Biotechnol, 87: 401-410. 2010.

(56) References Cited

OTHER PUBLICATIONS

Immunogenicity, Wikipedia p. 1-3. Downloaded on Aug. 16, 2016 from https://en.wikipedia.org/wiki/Immunogenicity. (2016).
International Search Report and Written Opinion issued for International application No. PCT/US2015/011748, dated Aug. 21, 2015, 17 pages.
International Search Report dated Jan. 13, 2012, from corresponding International Patent Application No. PCT/US2011/035982, 17 pages.
International Search Report dated Nov. 13, 2014, from corresponding International Patent Application No. PCT/US2014/054617, 10 pages.
International Search Report and Written Opinion in International Application No. PCT/US16/15858, dated Jun. 27, 2016, in 8 pages.
International Search Report issued for International application No. PCT/US15/22977, dated Jun. 22, 2015, 3 pages.
International Search Report issued for International application No. PCT/US15/40199, dated Mar. 2, 2016, 6 pages.
International Search Report issued for International application No. PCT/US2009/050754, dated Feb. 24, 2010, 10 pages.
International Search Report and Written Opinion in International Application No. PCT/US2017/021454, dated Jul. 31, 2017, 8 pages.
Isshiki et al., Cloning, Expression, and Characterization of a Novel UDP-galactose:b-N-Acetylglucosamine b1,3-Galactosyltransferase (b3Ga1-T5) Responsible for Synthesis of Type 1 Chain in Colorectal and Pancreatic Epithelia and Tumor Cells Derived Therefrom, The Journal of Biological Chemistry, Apr. 30, 1999, vol. 274, No. 18, pp. 12499-12507.
Ito, Akihiro et al., A Novel Ganglioside Isolated From Renal Cell Carcinoma, Biol Chem 2001, 276, 16695.
Jacobs et al., "Metabolic labeling of glycoproteins with chemical tags through unnatural sialic acid biosynthesis," *Methods Enzymol.*, 2000, 327:260-275.
Japanese Office Action dated Apr. 21, 2015, from Related Japanese Patent Application No. 2013-510261, 6 Pages.
Jayasena, Sumedha, Aptamers: An Emerging Class of Molecules That Rival Antibodies in Diagnostics, Clin. Chem. (1999), 45, 1628-1650.
Jewett, J.C.; Bertozzi, C.R., Cu-Free Click Cycloaddition Reactions in Chemical Biology, Chem. Soc. Rev. 2010, 39, 1272-1279.
Jewett, J.C.; Sletten, E. M.; Bertozzi, C.R., Rapid Cu-Free Click Chemistry with Readily Synthesized Biarylazacyclooctynones, J. Am. Chem. Soc. 2010, 132, 3688-3690.
Jewett et al., "Synthesis of a fluorogenic cyclooctyne activate by Cu-free click chemistry," *Org. Lett.*, Nov. 18, 2011, 13(22):5937-5939.
Jin, R. C. et al., Photoinduced Conversion of Silver Nanospheres to Nanoprisms, Science (2001), 294, 1901-1903.
Jobling, Michael et al., Fusion Proteins Containing the A2 Domain of Cholera Toxin Assemble With B Polypeptides of Cholera Toxin to Form Immunoreactive and Functional Holotoxin-Like Chimeras, Infect Immun., 60: 4915-24, 1992.
John, F. & Hendrickson, T. L. Synthesis of Truncated Analogues for Studying the Process of Glycosyl Phosphatidylinositol Modification. Org. Lett. 12, 2080-2083, (2010).
Jonges, M. et al., Dynamics of Antiviral-Resistant Influenza Viruses in the Netherlands, 2005-2008, Antiviral Res., Sep. 2009, 83(3): 290-297.
Jorgensen, Trond et al., Up-Regulation of the Oligosaccharide Sialyl Lewisx: A New Prognostic Parameter in Metastatic Prostate Cancer, Cancer Res. 55, 1817-1819, 1995.
Jose, Jiney et al., Energy transfer dyads based on Nile Red, Tetrahedron Letters (2009), 50(47), 6442-6445.
Joshi, Shantaran et al., Cell Surface Properties Associated with Malignancy of Metastatic Large Cell Lymphoma Cells, (1987) Cancer Res. 47, 3551-3557.
Joyce, J. G. et al. An oligosaccharide-based HIV-I 2G12 mimotope vaccine induces carbohydrate-specific antibodies that fail to neutralize HIV-I virions. Proc. Natl. Acad. Sci. U. S. A 105, 15684-15689, (2008).

Kakeji, Y. et al., Correlation Between Sialyl Tn Antigen and Lymphatic Metastasis in Patients with Borrmann Type IV Gastric Carcinoma, Brit. J. Cancer 71, 191-195, 1995.
Kalesh et al., "Peptide-based activity-based probes (ABPs) for target-specific profiling of protein tyrosine phosphatases (PTPs)," *Chem. Commun.*, Jan. 28, 2010, 46(4):589-591.
Kamkaew, A. et al., "BODIPY dyes in photodynamic therapy." Chem. Soc. Rev. 2013, 42, 77-88.
Kawakami et al., "Critical role of V$\alpha$14$^+$ natural killer T cells in the innate phase of host protection against *Streptococcus pneumoniae* infection," *Eur. J. Immunol.*, Dec. 2003, 33(12):3322-3330.
Kawano et al., "CD1d-restricted and TCR-mediated activation of V$_\alpha$14 NKT cells by glycosylceramides," *Science*, Nov. 28, 1997, 278(5343):1626-1629.
Kanie, Osmau et al., Orthogonal glycosylation strategy in synthesis of extended blood group B determinant. Tetrahedron Lett. 37, 4551-4554 (1996).
Kannappan, Ramaswamy et al., "Photoaffinity labeling of sialidase with a biotin-conjugated phenylaminodizairine derivative of 2,3-didehydro-2-deoxy-N-acetylneuraminic acid," *Biol. Pharm. Bull.*, Mar. 2008, 31(3):352-356.
Karlin, Samuel et al., Applications and Statistics for Multiple High-Scoring Segments in Molecular Sequences, Proc. Natl. Acad Sci. USA 90:5873-77, 1993.
Karmakar, M. et al., Current Trends in Research and Application of Microbial Cellulases, Research Journal of Microbiology, (2001) 6(1): 41-53.
Kermani, Pouneh et al., Production of ScFv Antibody Fragments Following Immunization with a Phage-Displayed Fusion Protein and Analysis of Reactivity to Surface-Exposed Epitopes of the Protein F of Pseudomonas Aeruginosa by Cytofluorometry, Hybridoma, 14(4):323-328 (1995).
Kidd et al., "Profiling serine hydrolase activities in complex proteomes," *Biochemistry*, Apr. 3, 2001, 40(13):4005-4015.
Kiick, K.L. et al., Identificationof an Expanded Set of Translationally Active Methionine Analogues in *Escherichia coli*, tetrahedron 56:9487, 2001.
Kim et al., High-Throughput Screening of Glycan-Binding Proteins Using Miniature Pig Kidney N-Glycan-Immobilized Beads, Chemistry & biology 15.3, p. 215-223 (2008).
Kim, Gap-Sue et al., AB Initio Study of Excited Electronic States and Vibronic Spectra of Phenyl Radical, Chem Phys. Lett., 2002, 3 5 2, 421.
Kimura et al., Design and Synthesis of Immobilized Tamiflu Analog on Resin for Affinity Chromatography, Tetrahedron Lett., Jul. 1, 2009, 50(26):3205-3208.
King, M. et al., New Tetramethlthiepinium (TMTI) for Copper-Free Click Chemistry, Chem. Commun. 2012, 48, 9308-9309.
Kitamura et al., "$\alpha$-galactosylceramide induces early B-cell activation through IL-4 production by NKT cells," *Cell. Immunol.*, Jan. 10, 2000, 199(1):37-42.
Klein, J. et al., "Isomaltines and their N-acyl derivatives, their preparation, and use of some acyl derivatives as surfactants or for preparation of hydrophilic polymers," CAPLUS 110:95711 (1989).
Kolb et al., "Click chemistry: diverse chemical function from a few good reactions," *Angew. Chem. Int. Ed. Engl.*, Jun. 1, 2001, 40(11):2004-2021.
Kolb et al., "The growing impact of click chemistry on drug discovery," *Drug Discov. Today*, Dec. 15, 2003, 8(24):1128-1137.
Komba S, et al. Synthesis and Bioloical Activities of Three Sulfated Sialyl Lex Ganglioside Analogues for Clarifying the Real Carbohydrate Ligand Structure of L-Selectin, Bioorg. Med. Chem. 1996, 4, 1833-1847.
Komori, Tatsuya et al., Study on Systematizing the Synthesis of the A-Series Ganglioside Glycans GT1a, GD1a, and GM1 Using the Newly Developed N-Troc-Protected GM3 and GalN Intermediates, Carbohydr. Res. 2009, 344, 1453.
Kong, L. et al. Expression-system-dependent modulation of HIV-I envelope glycoprotein antigenicity and immunogenicity. J. Mol. Biol. 403, 131-147, (2010).
Kos, "Regulation of adaptive immunity by natural killer cells," *Immunol. Res.*, 1998, 17(3):303-312.

(56) References Cited

OTHER PUBLICATIONS

Kotteas et al., Immunotherapy for pancreatic cancer, J cancer Res Clin Oncol, 142(8): 1795-1805, 2016.
Krise, Jeffrey et al., Prodrugs of Phosphates, Phosphonates, and Phosphinates, Adv. Drug Deliv. Rev. 1996, 19(2), 287-310.
Kubin, R. F. et al., Fluorescence Quantum Yields of Some Rhodamine Dyes, Luminescence 1982, 27, 455-462.
Kubler-Kielb, J. et al., A New Method for Conjugation of Carbohydrates to Proteins Using an Aminooxy-Thiol Heterbifunctional Linker, J Org Chem 2005, 70, 6987-6990.
Kwong, Peter et al., Rational Design of Vaccines to Elicit Broadly Neutralizing Antibodies to HIV-I. Cold Spring Harb.Perspect. Med. 1, 2011, 1-16.
Lantz et al., "An invariant T cell receptor $\alpha$ chain is used by a unique subset of major histocompatibility complex class I-specific $CD4^+$ and $CD4^-8^-$ T cells in mice and humans," *J. Exp. Med.*, Sep. 1, 1994, 180(3):1097-1106.
Lau, K. et al. Highly efficient chemoenzymatic synthesis of β1-4-linked galactosides with promiscuous bacterial β1-4-galactosyltransferases. Chem. Commun. 46, 6066-6068, (2010).
Le, Mai et al., Avian flu: Isolation of Drug-Resistant H5N1 Virus, Nature, Oct. 20, 2005, 437(7062):1108.
Lebens et al., Mucosal vaccines based on the use of cholera toxin B as immunogen and antigen carrier, *Dev. Biol. Stand.*, 1994, 82:215-227.
Le Droumaguet, C. et al., Fluorogenic Click Reaction., Chem. Soc. Rev. 2010, 39, 1233-1239.
Lederman et al., A single amino acid substitution in a common African allele of the CD4 molecule ablates binding of the monoclonal antibody, OKT4, Molecular Immunology, 28, 1171-1181 (1991).
Lee et al., Analogs of Cell Surface Carbohydrates. Synthesis of D-Galactose Derivatives Having an Ethynyl, Vinyl or Epoxy Residue at c-5. Carbohydrate Research 1988, vol. 176, pp. 59-72.
Lee et al., A new Solvent System for Efficient Synthesis of 1,2,3-Triazoles, Tetrahedron Lett., Jul. 17, 2006, 47(29):5105-5109.
Lee et al., An Efficient and Practical Method for the Synthesis of Mono-N-Protected α,ω-diaminoalkanes, Tetrahedron Lett., Apr. 2, 2001, 42(14):2709-2711.
Lee, H.K. et al. Reactivity-based one-pot synthesis of oligomannoses: defining antigens recognized by 2G12, a broadly neutralizing anti-HIV-I antibody. Angew. Chem. Int. Ed. 43, 1000-1003, (2004).
Lee et al., Immunogenicity Study of Globo H Analogues with Modification at the Reducing or Nonreducing end of the tumor antigen, J Am Chem Soc, 136: 16844-16853 (2014).
Lemieux, R. U. et al., Halide ion catalyzed glycosidation reactions. Syntheses of a-linked disaccharides. J Am. Chem. Soc. 97(14), 4056-62, (1975).
Lew et al., Discovery and Development of GS 4104 (oseltamivir): an Orally Active Influenza Neuraminidase Inhibitor, Curr Med Chem, Jun. 2000, 7(6):663-672.
Li et al., β-endorphin omission analogs: Dissociation of Immunoreactivity from other biological activities, Proc Natl Avad Sci USA, 77:3211-3214 (1980).
Li, Y. L. et al., Crystallization and Melting Behaviors of PPC-BS/PVA Blends, 19, 1557-1566, 2003.
Li, Henghui et al., MALDI-MS Analysis of Sialylated N-Glycan Linkage Isomers Using Solid-Phase Two Step Derivatization Method, Analytica Chimica Acta 924 (2016) 77-85.
Li et al., "Design of a potent CD1d-binding NKT cell ligand as a vaccine adjuvant," *Proc. Natl. Acad. Sci. USA*, Jul. 20, 2010, 107:13010-13015.
Li, J.; Hu, M.; Yao, S. Q. "Rapid synthesis, screening, and identification ofxanthone and xanthene-based fluorophores using click chemistry." Org. Lett. 2009, 11, 3008-3011.
Li, Lingling, et al., "Syntheses and spectral properties of functionalized, water-soluble BODIPY derivatives." J. Org. Chem. 2008, 73, 1963-1970.
Li, L. et al. Efficient chemoenzymatic synthesis of an N-glycan isomer library. Chem. Sci. 6, 5652-5661 (2015).

Liang et al., "Quantitative microarray analysis of intact glycolipid-CD1d interaction and correlation with cell-based cytokine production," *J. Am. Chem. Soc.*, Sep. 17, 2008, 130(37):12348-12354.
Liang, Chi-Hui et al., Iron Oxide/Gold Core/Shell Nanoparticles for Ultrasensitive Detection of Carbohydrate-Protein Interactions, Anal. Chem. 2009; 81, 7750-7756.
Liang, P.H. et al., Quantitative Analysis of Carbohydrate-Protein Interactions Using Glycan Microarrays: Determination of Surface and Solution Dissociation Constants, J. Amer. Chem. Sci. 2007, 129, 11177-11184.
Lin et al., A common glycan structure on immunoglobulin G for enhancement of effector functions, PNAS, Aug. 25, 2015, vol. 112, No. 34, p. 10611-10616.
Liu et al., "Activity-based protein profiling: the serine hydrolases," *Proc. Natl. Acad. Sci. USA*, Dec. 21, 1999, 96(26):14694-14699.
Lopes, J.F. et al., Simulataneous Chromatographic Separation of Enantiomers, Anomers and Structural Isomers of Some Biologically Relevant Monsaccharides. J. Chomatogr. A, (2008) 1188:34-42.
Lou, et al., Stage-specific embryonic antigent-4 as a potential therapeutic target in glioblastoma multiforms and other cancers. Proc Natl Acad Sci USA 2014, 111(7):2482-7.
Loudet, A.; Burgess, K. "BODIPY dyes and their derivatives: syntheses and spectroscopic properties." Chem. Rev. 2007, 107, 4891-4932.
Lu et al., "Design of a mechanism-based probe for neuraminidase to capture influenza viruses," *Angew. Chem. Int. Ed. Engl.*, Oct. 28, 2005, 44(42):6888-6892.
Lu, Guokai et al., Reactivity-Based One-Pot Synthesis of Immunosuppressive Glycolipids From the Caribbean Sponge Plakortis Simplex, J. Chem. 2009, 27, 2217-2222.
MacBeath, G. and Schreiber, S. L., Printing Proteins as Microarrays for High-Throughput Function Determination, Science, 289, 1760-1763, 2000.
Makino et al., Predominant expression of invariant $V_\alpha 14^+$ TCR $\alpha$ chain in $NK1.1^+$ T cell populations, *Int. Immunol.*, Jul. 1995, 7(7):1157-1161.
Mandal, M., Dudkin, V. Y., Geng, X. & Danishefsky, S. J. In pursuit of carbohydrate-based HIV vaccines, part I: The total synthesis of hybrid-type gp 120 fragments. Angew. Chem. Int. Ed. 43, 2557-2561, (2004).
Marcato et al., "Chapter 17: The Rocky Road from Cancer Stem Cell Discovery to Diagnostic Applicability," Cancer Stem Cells Theories and Practice, pp. 335-360, Mar. 22, 2011.
Massart, R., IEEE Transactions on Magnetics, 17, 1247 (1981).
Masuko, T. et al., Thiolation of Chitosan. Attachment of Proteins via Thioether Formation, Biomacromolecules 2005, 6, 880-884.
Matrosovich M, et al., The Surface Glycoproteins of H5 Influenza Viruses Isolated From Humans, Chickens, and Wild Aquatic Birds Have Distinguishable Properties, J. Virol. 1999, 73, 1146-1155.
Matz et al., "Fluorescent proteins from nonbioluminescent Anthozoa species," *Nat. Biotechnol.*, Oct. 1999, 17(10):969-973.
McKimm-Breschkin et al., "Tethered neuraminidase inhibitors that bind an influenza virus: a first step towards a diagnostic method for influenza," Angew. Chem. Int. Ed Engl., Jul. 14, 2003, 42(27):3118-3121.
McKimm-Breschkin, "Resistance of influenza viruses to neuraminidase inhibitors—a review," Antiviral Res., Jul. 2000, 47(1): 1-17.
Medelson et al., NKp46 O-glycan Sequences that are involved in the interaction with Hemagglutinin Type 1 of Influenza Virus. J. Virol. Feb. 10, 2010, 84(8):3789-3797.
McLellan, J. S. et al. Structure of HIV-I gp120 V1/V2 domain with broadly neutralizing antibody PG9. Nature 480, 336-343, 2011.
Milstein, C & Cuello, AC, Hybrid Hydridomas and their use in immunohistochemistry, Nature 305, 537-540, Oct. 1993.
Miyagi et al., "Mammalian sialidases: Physiological and pathological roles in cellular functions," *Glycobiology*, Jul. 2012, 22(7):880-896.
Miyagi et al., "Plasma membrane-associated sialidase as a crucial regulator of transmembrane signalling," *J. Biochem.*, Sep. 2008, 144(3):279-285.
Miyagi et al., "Sialidase and malignancy: a minireview," *Glycoconj. J.*, 2004, 20(3): 189-198.

(56) References Cited

OTHER PUBLICATIONS

Miyagi, "Aberrant expression of sialidase and cancer progression," *Proc. Jpn. Acad. Ser. B. Phys. Biol. Sci.*, 2008(10), 84:407-418.

Miyaji, E. N. et al., Induction of Neutralizing Antibodies Against Diphtheria Toxin by Priming with Recombinant *Mycobacterium bovis* BCG Expressing CRM197, a Mutant Diphtheria Toxin, Infect. Immun. 2001, 69, 869.

Miyamoto et al., "A synthetic glycolipid prevents autoimmune encephalomyelitis by inducing $T_H2$ bias of natural killer T cells," *Nature*, Oct. 4, 2001, 413(6855):531-534.

Monti et al., "Sialidases in vertebrates: a family of enzymes tailored for several cell functions," *Adv. Carbohydr. Chem. Biochem.*, 2010, 64:403-479.

Moody, M. D. et al., Array-based ELISAs for High-Throughput Analysis of Human Cytokines. Biotechniques (2001), 31, 186-194.

Moscona, "Global transmission of oseltamivir-resistant influenza," N Engl. J Med, Mar. 5, 2009, 360(10):953-956.

Moscona, Oseltamivir Resistance—Disabling Our Influenza Defenses, The New England Journal of Medicine, 2005, vol. 353, pp. 2633-2636.

Mosmann et al., "The expanding universe of T-cell subsets: Th1, Th2 and more," *Immunol. Today*, Mar. 1996, 17(3):138-146.

Mossong et al., "Emergence of oseltamivir-resistant influenza a H1N1 virus during the 2007-2008 winter season in Luxembourg: clinical characteristics and epidemiology," Antiviral Res., Oct. 2009, 84(1):91-94.

Mouquet, H. et al. Complex-type N-glycan recognition by potent broadly neutralizing HIV antibodies. Proc. Natl. Acad. Sci. U. S. A 109, E3268-E3277, (2012).

Murphy, C. I. et al. Enhanced expression, secretion, and large-scale purification of recombinant HIV-I gp 120 in insect cell using the baculovirus egt and p67 signal peptides. Protein Expres. Purif. 4, 349-357 (1993).

Muthana, S., Yu, H., Huang, S., and Chen, X. Chemoenzymatic synthesis of size-defined polysaccharides by sialyltransferase-catalyzed block transfer of oligosaccharides. J. Am. Chem. Soc. 129, 11918-11919, (2007).

Ni, Jing et al., Immunoassay Readout Method Using Extrinsic Raman Labels Adsorbed on Immunogold Colloids, Anal. Chem., 1999, 71(21), pp. 4903-4908.

Nieuwenhuis et al., "CD1d-dependent macrophage-mediated clearance of *Pseudomonas aeruginosa* from lung," *Nat. Med.*, Jun. 2002, 8(6):588-593.

Nielsen, U. B. et al., Multiplexed Sandwich Assays in Microarray Format, Journal Immunol. Meth. (2004), 290, 107-120.

Ning, X. et al., Visualizing Metabolically-Labeled Glycoconjugates of Living Cells by Copper-Free and Fast Huisgen Cycloadditions, J. Angew. Chem. Int. Ed. 2008, 47, 2253-2255.

Nowak, MW et al., Nicotinic Receptor Binding Site Probed With Unnatural Amino Acid Incorporation in Intact Cells, Science 268:439, 1995.

Novotný et al., "Structural invariants of antigen binding: comparison of immunoglobulin $V_L$-$V_H$ and $V_L$-$V_L$ domain dimers," *Proc. Natl. Acad. Sci. USA*, Jul. 1985, 82(14):4592-4596.

Office Action dated Dec. 3, 2013, from corresponding Chinese Patent Application No. 201180034218.3, 15 total pages.

Office Action dated Oct. 22, 2014, from corresponding Chinese Patent Application No. 201180034218.3, 16 total pages.

O'Garra, "Cytokines induce the development of functionally heterogeneous T helper cell subsets," *Immunity*, Mar. 1998, 8(3):275-283.

Okada, Yoshio et al. Changes in the Expression of Sialyl-Lewisx, a Hepatic Necroinflammation-Associated Carbohydrate Neoantigen, in Human Depatocellular Carcinomas, (1994) Cancer 73, 1811-1816.

Okamura et al., "Interleukin-18: a novel cytokine that augments both innate and acquired immunity," *Adv. Immunol.*, 1998, 70:281-312.

Olden, Kenneth et al., Carbohydrate Moieties of Glycoproteins: A Re-Evaluation of Their Function, Biochem et Biophys Acta 650:209-232 (1982).

Otsubo N, et al., An Efficient and Straightforward Synthesis of Sialyl Lex Glycolipid as a Potent Selectin Blocker[[1]], Carbohydr. Res. 1998, 306, 517-530.

Oyelaran, O. & Gildersleeve, J. C. Glycan arrays: recent advances and future challenges. Curr. Opin. Chem. Biol. 13, 406-413, (2009).

Pabst, M. et al., Glycan profiles of the 27 Nglycosylation sites of the HIV envelope protein CN54gp140. Biol. Chem. 393, 719-730, (2012).

Pacino, G. et al., Purification and Characterization of a Breast-Cancer-Associated Glycoprotein Not Expressed in Normal Breast and Identified by Monoclonal Antibody 83D4, Br. J. Cancer, 1991, 63, 390-398.

Pancera, M. et al. Crystal structure of PG16 and chimeric dissection with somatically related PG9: structure-function analysis of two quaternary-specific antibodies that effectively neutralize HIV-I. J. Virol. 84, 8098-8110, (2010).

Pancera, M. et al. Structural basis for diverse N-glycan recognition by HIV-I-neutralizing V1-V2-directed antibody PG16. Nat. Struct. Mol. Biol. 20, 804-813, (2013).

Parker, C. A.; Rees, W. T., Correction of Fluorescence Spectra and Measurement of Fluorescence Quantum Efficiency, Analyst 1960, 85, 587-600.

Parrish, M. L. et al., A Microarray Platform Comparison for Neuroscience Applications, J. Neurosci. Methods, 2004, 132, 57-68.

Patricelli et al., "Functional interrogation of the kinome using nucleotide acyl phosphates," *Biochemistry*, Jan. 16, 2007, 46(2):350-358.

Paulson, J. C., Blixt, 0. & Collins, B. E. Sweet spots in functional glycomics. Nat. Chem. Biol. 2, 238-248, (2006).

Peelle et al., "Characterization and use of green fluorescent proteins from *Renilla mulleri* and *Ptilosarcus guernyi* for the human cell display of functional peptides," *J. Protein Chem.*, Aug. 2001, 20(6):507-519.

Pejchal, R. et al. A potent and broad neutralizing antibody recognizes and penetrates the HIV glycan shield. Science 334, 1097-1103, (2011).

Pellicci et al., "Differential recognition of CD1d-α-galactosyl ceramide by the Vβ8.2 and Vβ7 semi-invariant NKT T-cell receptors," *Immunity*, Jul. 17, 2009, 31(1):47-59.

Perlmutter, R.M. et al., Subclass Restriction of Murine Anti-Carbohydrate Antibodies, Journal of Immunology 1978, 121, 566-572.

Pettit, George et al., Antineoplastic Agents. Part 189. The Absolute Configuration and Synthesis of Natural (–)-Dolastatin 10, J Am Chem Soc. 111:5463-5465 (1989).

Pettit, George et al., Dolastatins 23: Stereospecific Synthesis of Dolaisoleuine, J Chem Soc Perkin Trans. 15:853-858 (1996).

Pettit, George et al., Antineoplastic Agents 365. Dolastatin 10 SAR Probes, Anti-Cancer Drug Design 13:243-277 (1998).

Pettit, Robin et al., Specific Activities of Dolastatin 10 and Peptide Derivatives Against Cryptococcus Neoformans, Antimicrob Agents Chemother. 42:2961-2965 (1998).

Pettit, George et al., The Dolastatins; 18: Stereospecific Synthesis of Dolaproine, Synthesis, 719-725 (1996).

Piizi, G. and Hardinger, S., Stereochemistry: an Introduction, UCLA Chemistry 30A Presentation, Fall 2002, in 40 pages.

Poloukhtine et al., "Selective labeling of living cells by a photo-triggered click reaction," *J. Am. Chem. Soc.*, Nov. 4, 2009, 131(43):15769-15776.

Porcelli, S.A., "Preparation of α-galactosylceramide derivatives as modulators of immunity and autoimmunity," CAPLUS 147:440317 (2007).

Potier et al., "Fluorometric assay of neuraminidase with a sodium (4-methylumbelliferyl-alpha-D-N-acetylneuraminate) substrate," Anal. Biochem., Apr. 15, 1979, 94(2):287-296.

Pratt, M. R. & Bertozzi, C. R. Chemoselective ligation applied to the synthesis of a biantennary N-linked glycoform of CD52. J Am. Chem. Soc. 125, 6149-6159, (2003).

Prescher, J. A.; Bertozzi, C.R. "Chemistry in living systems." Nat. Chem. Biol. 2005, 1, 13-21.

(56) References Cited

OTHER PUBLICATIONS

Pritchard, L. K. et al. Structural Constraints Determine the Glycosylation of HIV-I Envelope Trimers. Cell Rep. 11, 1604-13, (2015).

Pritchard, Laura et al., Cell- and Protein-Directed Glycosylation of Native Cleaved HIV-I Envelope. J. Virol. 89, 8932-44, (2015).

Pshezhetsky, M. Potier, J. Biol. Chem. 1996, 271, 28359-28365. Association of N-acetylgalactosamine-6-sulfate sulfatase with the multienzyme lysosomal complex of betagalactosidase, cathepsin A, and neuraminidase. Possible implication for intralysosomal catabolism of keratan sulfate.

Qi, Jianjun et al., Developing visible fluorogenic 'clickon' dyes for cellular imaging, Bioconjugate Chem. 2011, 22, 1758-1762.

Rabbani, Said et al., Glycosyltransferases: An efficient tool for the enzymatic synthesis of oligosaccharides and derivatives as well as mimetics thereof Chimia 60, 23-27, (2006).

Raju et al., "Synthesis and evaluation of 3"- and 4"-deoxy and -fluoro analogs of the immunostimulatory glycolipid, KRN7000," *Bioorg. Med. Chem. Lett.*, 2009, 19:4122-4125.

Rana, G. Kucukayan-Dogu, E. Bengu "Growth of vertically aligned carbon nanotubes over self-ordered nano-porous alumina films and their surface properties" Applied Surface Science, 2012, 258 7112-7117.

Raska, M. et al. Glycosylation patterns of HIV-I gp120 depend on the type of expressing cells and affect antibody recognition. J. Biol. Chem. 285, 20860-20869, (2010).

Rillahan, C. D. & Paulson, J. C. Glycan microarrays for decoding the glycome. Annu. Rev. Biochem. 80, 797-823, (2011).

Ritamo, Ilja al., Comparison of the Glycosylation of in Vitro Generated Polyclonal Human lgG and Therapeutic Immunoglins, Mol Immunol. Feb. 2014; 57(2): 255-62.

Rogers, GN et al., Single Amino Acid Substitutions in Influenza Haemagglutinin Change Receptor Binding Specificity. Nature, 304:76, 1983.

Rogers, GN et al., Receptor Determinants of Human and Animal Influenza Virus Isolates: Differences in Receptor Specificity of the H3 Hemagglutinin Based on Species of Origin. Virology, 127:361, 1983.

Romagnani, "Induction of $T_H1$ and $T_H2$ responses: a key role for the 'natural' immune response?" Immunol. Today, Oct. 1992, 13(10):379-381.

Rosenstein, N.E. et al, Meningococcal Disease, N Engl J Med 2001, 344, 1378-1388.

Rostovtsev et al., "A stepwise Huisgen cycloaddition process catalyzed by copper(I) regioselective ligation of azides and terminal alkynes," *Angew. Chem. Int. Ed. Engl.*, Jul. 15, 2002, 41(41):2596-2599.

Roth, Jurgen et al., Reexpression of Poly(sialic Acid) Units of the Neural Cell Adhesion Molecule in Wilms Tumor, Proc. Natl. Acad. Sci. 85, 2999-3000, 1988.

Rudnick et al., Affinity and Avidity in Antibody-Based Tumor Targeting, Can Biotherp & Radoipharm, 24, 155-162 (2009).

Russell et al., "The structure of H5N1 avian influenza neuraminidase suggests new opportunities for drug design," Nature, Sep. 7, 2006, 443(7107):45-49.

Saito, Seiichi et al., Haptoglobin-β Chain Defined by Monoclonal Antibody RM2 as a Novel Serum Marker for Prostate Cancer, Int. J Cancer, 2008, 123(3), 633-640.

Saitoh, Osamu et al., Differential Glycosylation and Cell Surface Expression of Lysosomal Membrane Glycoproteins in Sublines of a Human Colon Cancer Exhibiting Distinct Metastatic Potentials, J. Biol. Chem. 267, 5700-5711, 1992.

Salisbury et al., "Activity-based probes for proteomic profiling of histone deacetylase complexes," *Proc. Natl. Acad. Sci. USA*, Jan. 23, 2007, 104(4):1171-1176.

Sanna, Peitro et al., Directed Selection of Recombinant Human Monoclonal Antibodies to Herpes Simplex Virus Glycoproteins From Phage Display Libraries, Proc. Natl. Acad. Sci., 92:6439 (1995).

Sarkar et al., "Disaccharide uptake and priming in animal cells: inhibition of sialyl Lewis X by acetylated Galβ1→4GlcNAcβ-O-naphthalenemethanol," *Proc. Natl. Acad. Sci. USA*, Apr. 11, 1995, 92(8):3323-3327.

Sauter, NK et al., Binding of Influenza Virus Hemagglutinin to Analogs of Its Cell-Surface Receptor, Sialic Acid: Analysis by Proton Nuclear Magnetic Resonance Spectroscopy and X-Ray Crystallography. Biochemistry, 31 :9609, 1992.

Sawa, M.; Hsu, T.-L.; Itoh,T.; Sugiyama, M. ; Hanson, S. R. ; Vogt, P. K.; Wong, C.-H. "Glycoproteomic probes for fluorescent imaging of fucosylated glycans in vivo." Proc. Nat. Acad. Sci. USA., 2006, 103, 12371-12376.

Sawada, Tetsuji et al., E-Selectin Binding by Pancreatic Tumor Cells is Inhibited by Cancer Sera, Int. J. Cancer 57, 901-907, 1994.

Sawada, Ritsuko et al., Differential E-Selectin-Dependent Adhesion Efficiency in Sublines of a Human Colon Cancer Exhibiting Distinct Metastatic Potentials, J. Biol. Chem. 269, 1425-1431, 1994.

Scanlan, C. N. et al., Exploiting the defensive sugars of HIV-I for drug and vaccine design. Nature 446, 1038-1045, (2007).

Schena, M. et al., Quantitative Monitoring of Gene Expression Patterns with a Complementary DNA Microarray, Science, 1995, 270:467-70.

Schengrund et al., "Localization of sialidase in the plasma membrane of rat liver cells," *J. Biol. Chem.*, May 10, 1972, 247(9):2742-2746.

Schmitz, U. et al., Phage Display: A Molecular Tool for the Generation of Antibodies—A Review, Placenta, 21 Suppl. A:S 106 (2000).

Schneider, M.C. et al., Interactions Between Neisseria Meningitidis and the Complement System, Trends Microbial 2007, 15, 233-240.

Schroder et al., The Peptides, vol. 1, p. 76-136, 1965.

Schug, Kevin et al., "Noncovalent binding between guanidinium and anionic groups: focus on biological- and synthetic-based arginine/guanidinium interactions with phosph[on]ate and sulf[on]ate residues," Chem. Rev., Jan. 2005, 105(1):67-113.

Schweitzer, Barry et al., Multiplexed Protein Profiling on Microarrays by Rolling-Circle Amplification, Nat. Biotechnol. (2002), 20, 359-365.

Scurr, D. J. et al. Surface characterization of carbohydrate microarrays. Langmuir 26, 17143-17155, (2010).

Serna, S. et al., Construction of N-Glycan Microarrays by Using Modular Synthesis and On-Chip Nanoscale Enzymatic Glycosylation. Chem. Eur. J 16, 13163-13175, (2010).

Severi et al., "Sialic acid utilization by bacterial pathogens," *Microbiology*, Sep. 2007, 153(Pt 9):2817-2822.

Seyrantepe et al., "Neu4, a novel human lysosomal lumen sialidase, confers normal phenotype to sialidosis and galactosialidosis cells," *J. Biol. Chem.*, Aug. 27, 2004, 279(35):37021-37029.

Sheu et al., "Surveillance for neuraminidase inhibitor resistance among human influenza A and B viruses circulating worldwide from 2004 to 2008," *Antimicrob. Agents Chemother.*, Sep. 2008, 52(9):3284-3292.

Shie, Jiun-Jie et al., "A concise and flexible synthesis of the potent anti-influenza agents tamiflu and tamiphosphor," Angew. Chem. Int. Ed Engl., 2008, 47(31):5788-5791.

Shie, Jiun-Jie et al., An Azido-BODIPY Probe for Glycosylation: Initiation of Strong Fluorescence Upon Triazole Formation, J. Am. Chem. Soc. 2014, 136, 9953-9961.

Shieh, Peyton et al., Fluorogenic Azidofluoresceins for Biological Imaging, J. Am. Chem. Soc. 2012, 134, 17428-17431.

Shivatare, S. S. et al. Efficient convergent synthesis of bi-, tri-, and tetra-antennary complex type N-glycans and their HIV-1 antigenicity. J. Am. Chem. Soc. 135, 15382-15391, (2013).

Shivatare, S. S. et al., Modular Synthesis of N-Glycans and Arrays for the Hetero-Ligand Binding Analysis of HIV Antibodies, Nature Chemistry, Mar. 7, 2016, vol. 8(4), p. 338-346.

Shriver, Zachary et al., Glycomics: a Pathway to a Class of New and Improved Therapeutics, Nat Rev Drug Disc, 2004, 3, 863-873.

Sieber et al., "Proteomic profiling of metalloprotease activities with cocktails of active-site probes," *Nat. Chem. Biol.*, May 2006, 2(5):274-281.

(56) References Cited

OTHER PUBLICATIONS

Sivakumar, Krishnamoorthy et al., "A fluorogenic 1,3-dipolar cycloaddition reaction of 3-azidocoumarins and acetylenes." Org. Lett. 2004,24, 4603-4606.
Skehel, John et al., Receptor Binding and Membrane Fusion in Virus Entry: The Influenza Hemagglutinin, Ann. Rev Biochem, 69:531, 2000.
Sletten et al., "Bioorthogonal Chemistry: Fishing for Selectivity in a Sea of Functionality," Angew. Che. Int. Ed. Engl., Aug. 27, 2009, 48(38):6974-6998.
Sok, Devin et al., SnapShot: Broadly Neutralizing Antibodies. Cell 155, 728-728, (2013).
Solomons, G. and Fryhle, C., Chapter 5 Titled, Stereochemistry: Chiral Molecules, p. 184-228, in "Organic Chemistry," 7th Edition, Wiley, Jun. 18, 2001.
Soriano del Amo, David et al. Chemoenzymatic synthesis of the sialyl Lewis X glycan and its derivatives. Carbohydr. Res. 345, 1107-13, (2010).
Spinosa, Maria Rita et al., The Neisseria Meningitidis Capsule is Important for Intracellular Survival in Huamn Cells, Infect Immun 2001, 75, 3594-3603.
Srinivasan, Quantitative et al., Biochemical Rationale for Differences in Transmissibility of 1918 Pandemic Influenza A Viruses, Proc. Natl. Acad. Sci., 105, 2800-2805, 2008.
Stein, K.E. et al., The Immune Response to an Isomaltohexosyl-Protein Conjugate, a Thymus-Dependent Analogue of Alpha(1 Replaced by 6) Dextran., J Immunol 1982, 128, 1350-1354.
Stein, K.E., Thymus-Independent and Thymus-Dependent Responses to Polysaccharide Antigens, J Infect Dis 1992, 165 Suppl 1, S49-52.
Stephens, David, Conquering the Meningococcus, FEALS Microbial Rev 2007, 31, 3-14.
Stephens, D.S. et al., Epidemic Meningitis, Meningococcaemia, and Neisseria Meningitidis, Lancet 2007, 369, 2196-2210.
Stephenson et al., "Neuraminidase inhibitor resistance after oseltamivir treatment of acute influenza A and B in children," Clin. Infect. Dis., Feb. 15, 2009, 48(4):389-396.
Stevanovic, Stefan, Identification of Tumour-Associated T-Cell Epitopes for Vaccine Development, Nat. Rev. Cancer, 2002, 2, 514-520.
Stevens, James et al., Structure of the Uncleaved Human H1 Hemagglutinin From the Extinct 1918 Influenza Virus, Science, 303:1866, 2004.
Stevens, James et al., Structure and Receptor Specificity of the Hemagglutinin From an H5N1 Influenza Virus, Science, 312:404, 2006.
Stevens et al., Glycan Microarry Analysis of the Hemagglutinins From Modern and Pandemic Influenza Viruses Reveals Different Receptor Specificities. Journal of Molecular Biology 355.5 (2006): 1143-1155.
Stickings, P. et al., nfect. Immun. 2008, 76, 1766.
Stockmann, H. et al., Development and Evaluation of New Cyclootynes for Cell Surface Glycan Imaging in Cancer Cells, J. Chem. Sci. 2011, 2, 932-936.
Streicher et al., "Building a successful structural motif into sialylmimetics-cyclohexenephosphonate monoesters as pseudo-sialosides with promising inhibitory properties," Bioorg. Med Chem., Feb. 15, 2006, 14(4):1047-1057.
Stubbs et al., "Synthesis and use of mechanism-based protein-profiling probes for retaining β-D-glucosaminidases facilitate identification of Pseudomonas aeruginosa NagZ," J. Am. Chem. Soc., Jan. 9, 2008, 130(1):327-335.
Su, G. Hahner, W. Zhou "Investigation of the pore formation in anodic aluminum oxide" J Mater. Chem. 2008, 18 5787-5795.
Sun, B., Srinibasan, B., Huang, X., Pre-activation-based one-pot synthesis of an alpha-(2,3)-sialylated core-fucosylated complex type bi-antennary N-glycan dodecasaccharide. Chem. Eur. J 14 (23), 7072-81, (2008).
Sutton, VR et al., Bcl-2 Prevents Apoptosis Induced by Perforin and Granzyme B, But Not That Mediated by Whole Cytotoxic Lymphocytes, J of Immunology 1997, 158(12), 5783.

Tahir et al., "Loss of IFN-γ production by invariant NK T cells in advanced cancer," J. Immunol., Oct. 1, 2001, 167(7):4046-4050.
Takakura, Yoshimitsu et al., Molecular cloning, expression and properties of an alpha/beta-Galactoside alpha 2,3-sialyltransferase from Vibrio sp. JT- FAJ-16. J. Biochem. 142, 403-412, (2007).
Takano, Ryo et al., Sialylation and Malignant Potential in Tumour Cell Glycosylation Mutants, Glycobiology 4, 665-674 (1994).
Taki, Takao et al., Glycolipids of Metastatic Tissue in Liver From Colon Cancer: Appearance of Sialylated Lex and Lex Lipids, J. Biochem. 103, 998-1003, 1998.
Talmadge et al., Murine models to evaluate novel and conventional therapeutic strategies for cancer, Am. J. Pathol, 170(3): 793-804 (2007).
Tanaka, Hiroshi et al., An Efficient Convergent Synthesis of GP1c Ganglioside Epitope, J Am Chem Soc. 2008, 130, 17244.
Tanaka, Katsunori et al., Synthesis of a Sialic Acid Containing Complex-Type N-Glycan on a Solid Support, Chemistry-an Asian Journal, 2009, vol. 4 (4), p. 574-580.
Taton, T. Andrew et al., Scanometric DNA Array Detection with Nanoparticle Probes, Science 289 (2000) 1757-1760.
Taton, T. Andrew et al., Two-Color Labeling of Oligonucleotide Arrays Via Size-Selective Scattering of Nanoparticle Probes, J. Am. Chem. Soc. (2001), 123, 5164-5165.
Telford et al., "The Aspergillus Fumigatus Sialidase is a 3'-Deoxy-D-galacto-2-nonulosonic Acid Hydrolase (KDNase)," The Journal of Biological Chemistry, 286(12), 10783-10792 (Mar. 25, 2011).
"The Human Protein Atlas", B3GALT5 URL:http://www.proteinatlas.org/ENSG00000183778-B3GALT5/cancer, Sep. 9, 2015.
Thurber, Greg et al., Antibody Tumor Penetration: Transport Opposed by Systemic and Antigen-Mediated Clearance, Adv Drug Deliv Rev, 60: 1421-1434, 2008.
Toba, et al., "Synthesis and biological evaluation of truncated α-glaactosylceramide derivatives focusing on cytokine induction profile," Bioorganic & Medicinal Chemistry 20(2012): 2850-2859.
Torres-Sanchez et al., "Synthesis and Biological Evaluation of Phophono Analogues of Capsular Polysaccharide Fragments From Neisseria Meningtitidis A" Chem Eur J (2007) vol. 13, pp. 6623-6635.
Toshima, K. Glycosyl fluorides in glycosidations. Carbohydr. Res. 327, 15-26 (2000).
Trinchieri, "Interleukin-12: a proinflammatory cytokine with immunoregulatory functions that bridge innate resistance and antigen-specific adaptive immunity," Annu. Rev. Immunol., 1995, 13:251-276.
Tsai et al., "Design and synthesis of activity probes for glycosidases," Org. Lett., Oct. 17, 2002, 4(21):3607-3610.
Tsai, Charng-sheng et al., Development of Trifunctional Probes for Glycoproteomic Analysis, Chem. Commun. 2010, 46, 5575-5577.
Tseng, Susan Y. et al., Glycan Arrays on Aluminum Coated Glass Slides. Chem. Asian J, 2008, 3, 1395-1405.
Tsuji, et al., "Preparation of glycolipids and analogs as antigens for NKT cells for use in vaccines and immunotherapy," CAPLUS 149:492050 (2008).
Tsukamoto, Hiroshi et al., Photobacterium sp. JT-ISH-224 produces two sialyltransferases, alpha-/beta-galactoside alpha2,3-sialyltransferase and betagalactoside alpha2,6-sialyltransferase. J. Biochem. 143, 187-197, 2008.
Tumpey, Terrence et al., Characterization of the Reconstructed 1918 Spanish Influenza Pandemic Virus, Science, 310:77, 2005.
Tzeng, Y. L. et al, Epidemiology and Pathogenesis of Neisseria Meningitidis, Microbes Infect 2000, 2, 687-700.
Uchida, Tsuyoshi et al., Diphtheria Toxin and Related Proteins, J Biol. Chem. 218; 3838-3844 (1973).
Udommaneethanakit et al., "Dynamic behavior of avain influenza A virus neuraminidase subtype H5N1 in complex with oseltamivir, zanamivir, peramivir, and their phosphonate analogues," J Chem. Inf Model, Oct. 2009, 49(10):2323-2332.
Ulevitch, RJ et al., Receptor-Dependent Mechanisms of Cell Stimulation by Bacterial Endotoxin, 1995, Annu. Rev. Immunol., 13: 437.
Ulrich, G.; Ziessel, R.; Harriman, A. "The chemistry of fluorescent bodipy dyes: Versatility unsurpassed." Angew. Chem. Int. Ed. 2008, 47, 1184-1201.

(56) References Cited

OTHER PUBLICATIONS van der Horst et al., "Photoaffinity labeling of a bacterial sialidase with an aryl azide derivative of sialic acid," *J. Biol. Chem.*, Jul. 5, 1990, 265(19), 10801-10804.
Van Hest, Jan C.M. et al., Efficient Introduction of Alkene Functionality Into Proteins in Vivo (1998) FEES Lett. 428:68.
Vaki, Ajit et al., Symbols Nomenclatures for Glycan Representation, Proteomics. Dec. 2009, 9(24): 5398-5399.
Varki, "Glycan-based interactions involving vertebrate sialic-acid-recognizing proteins," *Nature*, Apr. 26, 2007, 446(7139):1023-1029.
Vasella et al., "Synthesis of a phosphonic acid analogue of N-Acetyl-2,3-didehydro-2-deoxyneuraminic acid, an inhibitor of Vibrio cholerae sialidase," Helv. Chim. Acta, Mar. 13, 1991, 74(2):451-463.
Vavricka, Christopher et al., Influenza Neuraminidase Operates via a Nucleophilic Mechanism and Can Be Targeted by Covalent Inhibitors, Nature Communcations, 4:1491 (2013).
Vinogradova et al., "Molecular mechanism of lysosomal sialidase deficiency in galactosialidosis involves its rapid degradation," *Biochem. J.*, Mar. 1, 1998, 330(Pt 2.):641-650.
Vippagunta, Sudha et al., Crystalline Solids, Advanced Drug Delivery Reviews 48, 3-26 (2001).
Virji, Mumtaz et al., Pathogenic Neisseriae: Surface Modulation, Pathogenesis and Infection Control, Nat Rev, Microbiol 2009, 7, 274-286.
Vitetta, ES et al., Redesigning Nature's Poisons to Create Anti-Tumor Reagents, Science 23(8): 1098 (1987).
Vocadlo et al., "A strategy for functional proteomic analysis of glycosidase activity from cell lysates," *Angew. Chem. Int. Ed. Engl.*, Oct. 11, 2004, 43(40):5338-5342.
Von Itzstein et al., "Rational design of potent sialidase-based inhibitors of influenza virus replication," Nature, Jun. 3, 1993, 363(6428):418-423.
Voskoglou-Nomikos, Clinical predictive value of the in vitro cell line, human xenograft, and mouse allograft preclinical cancer models, Clin Can Res, 9: 4227-4239 (2003).
Wada et al., "A crucial role of plasma membrane-associated sialidase in the survival of human cancer cells," Oncogene, Apr. 12, 2007, 26(17):2483-2490.
Wagner, R et al., "Functional balance between haemagglutinin and neuraminidase in influenza virus infections," Rev. Med Viral., May-Jun. 2002, 12(3): 159-166.
Walls et al., "Activity-based protein profiling of protein tyrosine phosphatases," *Methods Mol. Biol.*, 2009, 519:417-429.
Walker, L. M. et al. Broad neutralization coverage of HIV by multiple highly potent antibodies. Nature 477, 466-470, (2011).
Wang, Chao et al., Tuning the Optical Properties of BODIPY Dye Through Cu(I) Catalyzed Azide-Alkyne Cycloaddition (CuAAC) Reaction, Sci. China Chemistry 2012, 55, 125-130.
Wang, Zhen et al., Multi-Component One-Pot Synthesis of the Tumor-Associated Carbohydrate Antigen Globo-H Based on Preactivation of Thioglycosyl Donors, J Org. Chem. 2007, 72, 6409.
Wang et al., "A continuous colorimetric assay for rhinovirus-14 3C protease using peptide p-nitroanilides as substrates," Anal. Biochem., Oct. 15, 1997, 252(2):238-245.
Wang et al., "Synthesis of Neisseria Meningitidis Serogroup W135 Capsular Oligosaccharides for Immunogenicity Comparison and Vaccine Development" Angew Chem Int Ed (2013) vol. 52, pp. 9157-9161.
Wang, Michael et al., "Mechanism by which mutations at his274 alter sensitivity of influenza A virus NI neuraminidase to oseltamivir carboxylate and zanamivir," Antimicrob. Agents Chemother., Dec. 2002, 46(12):3809-3816.
Wang, D., Liu, S., Trummer, B. J., Deng, C. & Wang, A. Carbohydrate microarrays for the recognition of cross-reactive molecular markers of microbes and host cells. Nat. Biotechnol . 20, 275-281, (2002).
Wang et al., Computational Studies of H5N1 Influenza Virus Resistance to Oseltamivir. Protein Sci. 2009, 18(4): 707-715; p. 713.
Wang, C. C. et al. Glycans on Influenza Hemagglutinin Affect Receptor Binding and Immune Response, Proc. Natl. Acad. Sci. 2009, 106, 18137-18142.
Wang, L. X. Carbohydrate-based vaccines against HIV/AIDS. Acs Sym. Ser. 932, 133-160 (2006).
Wang, L. X. Synthetic carbohydrate antigens for HIV vaccine design. Curr. Opin. Chem. Biol. 17, 997-1005, (2013).
Wang, W. et al. A systematic study of the N-glycosylation sites of HIV-I envelope protein on infectivity and antibody-mediated neutralization. Retrovirology, 10, 14, (2014).
Wang, Zhen et al. A general strategy for the chemoenzymatic synthesis of asymmetrically branched N-glycans. Science 341, 379-383, (2013).
Watts et al., "The Synthesis of Some Mechanistic Probes for Sialic Acid Processing Enzymes and the Labeling of a Sialidase from Trypanosoma Rangeli," Canadian Journal of Chemistry, 82(11), 1581-1588 (2004).
Watts et al., "*Trypanosoma cruzi* trans-sialidase operates through a covalent sialyl-enzyme intermediate: tyrosine is the catalytic nucleophile," *J. Am. Chem. Soc.*, Jun. 25, 2003, 125(25):7532-7533.
Weibel, Robert et al., Tumor-Associated Membrane Sialoglycoprotein on Human Small Cell Lung Carcinoma Identified by the IgG2a Monoclonal Antibody SWA20, (1988) Cancer Res. 48, 4318-4323.
Wen, Wen Hsien et al., "Synergistic effect of zanamivir-porphyrin conjugates on inhibition of neuraminidase and inactivation of influenza virus," J Med Chem., Aug. 13, 2009, 52(15):4903-4910.
White, Clinton et al., "A sialic acid-derived phosphonate analog inhibits different strains of influenza virus neuraminidase with different efficiencies," J Mol. Biol., Feb. 3, 1995, 245(5):623-634.
Wilen et al., "Strategies in optical resolutions," Tetrahedron, 1977, 33(21):2725-2736.
Wiltshire, S. et al. Proc. Natl. Acad. Sci. (2000) 97, 10113-10119.
Wiseman, GA et al., Phase I/II 90Y-Zevalin (yttrium-90 Ibritumomab Tiuxetan, IDEC-Y2B8) Radioimmunotherapy Dosimetry Results in Relapsed or Refractory Non-Hodgkin's Lymphoma, Eur Jour Nucl Med 27(7): 766-77 (2000).
Wiseman, Gregory et al., Ibritumomab Tiuxetan Radioimmunotherapy for Patients with Relapsed or Refractory Non-Hodgkin Lymphoma and Mild Thrombocytopenia: a Phase II Multicenter Trial, Blood 99(12): 4336-42 (2002).
Witte et al., "Ultrasensitive in situ visualization of active glucocerebrosidase molecules," *Nat. Chem. Biol.*, Dec. 2010, 6(12):907-913.
Witzig, Thomas et al., Randomized Controlled Trial of Yttrium-90-Labeled Ibritumomab Tiuxetan Radioimmunotherpay Versus Rituximab Immunotherapy for Patients with Relapsed or Refractory Low-Grade, Follicular, or Transformed B-Cell Non-Hodgkin's Lymphoma, J Clin Oncol 20(10):2453-63 (2002).
Witzig, Thomas et al., Treatment with Ibritumomab Tiuxetan Radioimmunotherapy in Patients with Rituximab-Refractory Follicular Non-Hodgkin's Lymphoma, J Clin Oncol 20(15):3262-69 (2002).
Wong et al., α-Galactosyl Ceramide Analogs and Their use as Therapeutic, 2010:50988, 2 Pages.
Woyke, Tanja et al., Effect of Auristatin PHE on Microtubule Integrity and Nuclear Localization in Cryptococcus Neoformans, Antimicrob. Agents and Chemother. 45(12): 3580-3584 (2001).
Wright et al. Antibody variable region glycosylation: biochemical and clinical effects, Springer Semin Immunopathology, 15:259-273 (1993).
Wu et al., "Avidity of CD1d-ligand-receptor ternary complex contributes to T-helper 1 (Th1) polarization and anticancer efficacy," *Proc. Natl. Acad. Sci. USA*, Oct. 18, 2011, 108(42):17275-17280.
Wu, Xueling et al. Rational design of envelope identifies broadly neutralizing human monoclonal antibodies to HIV-I. Science 329, 856-861, (2010).
Wu, Liangxing et al., Fluorescent Cassettes for Monitoring Three-Component Interactions in Vitro and in Living Cells, Journal of the American Chemical Society (2009), 131(26), 9156-9157.
Wu et al., "Catalytic azide-alkyne cycloaddition: reactivity and applications," Aldrichimica Acta, 2007, 40(1):7-17.
Xie, F.; Sivakumar, K.; Zeng, Q. B.; Bruckman, M. A.; Hodges, B.; Wang, Q. "A fluorogenic 'click' reaction of azidoanthracene derivatives." Tetrahedron 2008, 64, 2906-2914.

(56) References Cited

OTHER PUBLICATIONS

Yamaguchi, Kazunori et al., "Evidence for mitochondrial localization of a novel human sialidase (NEU4)," Biochem. J., Aug. 15, 2005, 390(Pt 1):85-93.
Yamane-Ohnuki, Naoko et al., Production of Therapeutic Antibodies with Controlled Fucosylation, mAbs 2009, 1;3:230-236.
Yamashita et al., CS-8958, a prodrug of the new neuraminidase inhibitor R-125489, shows ong-acting anti-influenza virus activity. Antimicrob Agents Chemother. Jan. 2009;53(1): 186-92.
Yang, JM et al., Alterations of )-Glycan Biosynthesis in Human Colon Cancer Tissues, (1994) Glycobiology 4, 873-884.
Yaniv, Nature 297: 17-18, 1982.
Yates AJ et al., Brain Tumors in Childhood. Childs Brain 5(1), 31-39 (1979).
Yguerabide, Juan et al., Light-Scattering Submicroscopic Particles as Highly Fluorescent Analogs and Their Use as Tracer Labels in Clinical and Biological Applications: II. Experimental Characterization, Anal. Biochem. (1998), 262, 157-176.
Yoshida M, et al. Glycoconjugate J. 1993, 10, 324.
Yoshimoto et al., "$CD4^{pos}$, $NK1.1^{pos}$ T cells promptly produce interleukin 4 in response to in vivo challenge with anti-CD3," J. Exp. Med., Apr. 1, 1994, 179(4):1285-1295.
Zhang et al., "New cerebrosides from Acanthopanax gracilistylus," CAPLUS 156:225776 (2011).
Zhou et al., A fluorogenic probe for the copper(I)-catalyzed azide-alkyne ligation reaction: modulation of the fluorescence emission via $^{3}(n,\pi)$-$^{1}(\pi,\pi^*)$ inversion, J. Am. Chem. Soc., Jul. 28, 2004, 126(29):8862-8863.
Zhu, X et al., Mass spectrometric characterization of the glycosylation pattern of HIV-gp120 expressed in CHO cells. Biochemistry 39, 11194-11204 (2000).
Zou, et al., Chemoenzymatic synthesis and Fc gamma receptor binding of homogenous glycoforms of antibody Fc to FcIIIa receptor. J Am Chem Soc. 2011, 133(46):18975-91.
Chu, Kuo-Chinget al., Efficient and Stereoselective Synthesis of [alpha](2→9) Oligosialic Acids: From Monomers to Dodecamers, Angewandte Chemie International Edition, vol. 50, No. 40, Sep. 2011, 9391-9395.
Frank, Natasha et al., The Therapeutic Promise of the Cancer Stem Cell Concept, Journal of Clinical Investigation, 120(1) 41-50, Jan. 2010.
Hsu, Nien-Yeen et al., Desorption Ionization of Biomolecules on Metals, Anal. Chem., 80, 5203-5210, 2008.
Katagiri, Yohko et al., Laminin Binding Protein, 34/67 Laminin Receptor, Carries Stage-Specific Embryonic Antigen-4 Epitope Defined by Monoclonal Antibody Raft.2, Biochemical and Biophysical Research Communcations, 332, 1004-1011, 2005.
Liang, Yuh-Jin et al., Switching of the Core Structures of Glycosphingolipids From Blobo- and Lacto- to Ganglio-Series Upon Human Embryonic Stem Cell Differentiation, PNAS, 107(52), Dec. 2010, 22564-22569.
Merck, MAB4304, Anti-Stage-Specific Embryonic Antigen-4 Antibody, Clone MC-813-70, 4 Pages, 2017.
Moal, E. Le et al., Enhanced Fluorescence Cell Imaging with Metal-Coated Slides, Biophysical Journal, vol. 92, 2150-2161, Mar. 2007.
Oberli, Matthias et al., A Possible Oligosaccharide-Conjugate Vaccine Candidate for Clostridium Difficile is Antigenic and Immunogenic, Chemistry & Biology, vol. 18, No. 5, May 2011, 580-588.
Pan, Yanbin et al., Synthesis and Immunological Properties of N-Modified GM3 Antigens as Therapeutic Cancer Vaccines, J. Med. Chem., 48(3), 875-883, 2005.
Shevinsky, LH et al., Monoclonal Antibody to Murine Embryos Defines a Stage-Specific Embryonic Antigen Expressed on Mouse Embryos and Human Teratocarinoma Cells., Cell vol. 30, Issue 3, Oct. 1982, pp. 697-705.
Zhang, Hai-Long et al., A Novel Combined Conjugate Vaccine: Enhanced Immunogenicity of bFGF with CRM197 as a Carrier Protein, Molecular Medicine Reports, 4, 857-863, 2011.
Bacteroides Fragilis NCTC 9343, Complete Genome., Mar. 3, 2005, XP002775523, Database Accession No. CR626927, 2 Pages.
Bacteroides Thetaiotaomicron VPI-5482, Section 8 of 21 of the Complete Genome, XP002775522, Jan. 6, 2006, Database Accession No. AE016933, 2 Pages.
Berg, Jan-Olof et al., Purification of Glycoside Hydrolases From Bacteroides Fragilis, Applied and Environmental Microbiology, vol. 40, No. 1, Jul. 1980, p. 40-47.
Dicker, Martina et al., Using Glyco-Engineering to Produce Therapeutic Proteins, Expert Opinion on Biological Therapy, vol. 15, Jan. 1, 2015, pp. 1501-1516.
Extended European Search Report, App. No. 15799789.1, dated Nov. 28, 2017, 10 Pages.
Extended European Search Report, App. No. 158001917, dated Nov. 28, 2017, 12 Pages.
Extended European Search Report, App. No. 15799981.4, dated Nov. 29, 2017, 9 Pages.
Huang, Wei et al., Chemoenzymatic Glycoengineering of Intact lgG Antibodies for Gain of Functions, Journal American Chemical Socirty, vol. 134, No. 9, Jul. 25, 2012, pp. 12308-12318.
Liao, Shih-Fen et al., Immunization of Fucose-Containing Polysaccharides From Reishi Mushroom Induces Antibodies to Tumor-Associated Globo H-Series Epitopes, Proceedings National Academy of Sciences PNAS, vol. 110, No. 34, Aug. 1, 2013, pp. 13809-13814.
Lin, Chin-Wei et al., A Common Glycan Structure on Immunoglobulin G for Enhancement of Effector Functions, vol. 112, No. 34, Aug. 7, 2015, pp. 10611-10616.
Sakurama, Haruko et al., Differences in the Substrate Specificities and Active-Site Structures of Two α-L-Fucosidases (Glycoside Hydrolase Family 29) From Bacteroides Thetaiotaomicron, Bioscience Biotechnology Biochemistry, vol. 76, No. 5, May 23, 2012, pp. 1022-1024.
Tsai, Tsung-I et al., An Effective Bacterial Ducosidase for Glycoprotein Remodeling, ACS Chemical Biology, vol. 12, No. 1, Jan. 20, 2017, pp. 63-72.
Cheung et al., Meeting Info: 23rd International Symposium on Glycoconjugates, GLYCO 23. Split, Croatia. Sep. 15, 2015-Sep. 20, 2015, vol. 32, No. 5, pp. 323.
International Search Report and Written Opinion in International Application No. PCT/US2017/048074, dated Dec. 26, 2017, 17 pages.
Lei, Jianqing et al., Potential antitumor applications of a monoclonal antibody specifically targeting human papilloma virus 16 E749-57 peptide, Microbiology and Immunology, 2012, vol. 56, pp. 456-462.
Tsai, Charng-Sheng et al., Cell-Permeable Probe for Identification and Imaging of Sialidases, PNAS, vol. 110, No. 7, 2013, 2466-2471.
Greene, Theodora et al., Protective Groups in Organic Synthesis, pp. 42-51 and 96-100, 1991.
Schelhaas, Michael et al., Protecting Group Strategies in Organic Synthesis, Angew. Chem. Int. Ed. Engl. 1996, 35, 2056-2083.
Unverzagt, Carlo et al., A Double Regio- and Stereoselective Glycosylation Strategy for the Synthesis of N-Glycans, Chem. Eur. J., 2008, 14, 1304-1311.

\* cited by examiner (A)

(B)

(C)

ENHANCED ANTI-INFLUENZA AGENTS CONJUGATED WITH ANTI-INFLAMMATORY ACTIVITY

RELATED APPLICATION

This application claims priority to U.S. Provisional Application No. 61/624,250 under 35 U.S.C. 119(e), filed on Apr. 14, 2012, the content of which is hereby incorporated by reference in its entirety.

TECHNICAL FIELD OF THE INVENTION

The invention relates to the field of antiviral therapy. Specifically, the invention relates to bifunctional therapeutics directed to influenza virus infection wherein the therapeutic drug comprises an anti-influenza moiety conjugated to an anti-inflammatory agent.

BACKGROUND OF THE INVENTION

Influenza is a respiratory infection that causes severe health problems. The worldwide spread of the A/H5N1 avian flu and the outbreak of the new type A/H1N1 human influenza in 2009 have increased public awareness of the potential for global influenza pandemics. H5N1 influenza virus appears to replicate more rapidly than seasonal influenza and the pandemic H1N1/2009 strain. The H5N1 virus infection of macrophages also causes strong expression of proinflammatory cytokines and chemokines, namely cytokine storm. (Lee, S. M. Y. et al. *J. Infect. Dis.* 2008, 198, 525; Woo, P. C. Y. et al. *J. Infec. Dis.* 2010, 201, 346)

In the patients of H5N1 virus infection, induction of tumor necrosis factor (TNF)-α and interferons (IFN)-β/γ have been observed in alveolar and bronchial epithelial cells. (Yuen, K. Y. et al. *Hong Kong Med. J.* 11, 189 (2005)) Other cytokines, such as interleukins (e.g. IL-6 and IL-10), IFN-induced chemokines (e.g. IP-10, MIG and MIG-1) are also found at high levels in the H5N1 virus infected patients. (de Jong, M. D. et al. *Nat Med* 2005, 11, 189) The high mortality of human infected by influenza H5N1 has been attributed to poor response of virus to neuraminidase (NA) inhibitor, e.g. oseltamivir, and the excessive induction of a severe cytokine storm. (Peiris, J. S. M. et al. *Lancet* 2004, 363, 617; Geiler, J., *Med. Microbiol. Immunol.* 2011, 200, 53) Though treatment of the H5N1 virus infected mice with anti-inflammatory agent alone can inhibit proinflammatory cytokines, (Fedson, D. S. *Influenza Other Resp.* 2009, 3, 129) the mortality of infected mice is not reduced. (Carter, M. J. *A J. Med. Microbiol.* 2007, 56, 875; Salomon, R. et al. *Proc. Natl. Acad. Sci. U.S.A.* 2007, 104, 12479)

Monotherapy with a single antiviral drug for influenza may be limited in efficacy due to the rapidly developed drug-resistance. (Baz, M. et al. *New Engl. J. Med.* 2009, 361, 2296). Moreover, the uncontrolled virus-induced cytokines could cause the high mortality of human infected by H5N1 avian influenza virus.

In a different approach, combination chemotherapy consisting of two or more drugs that target different viral proteins or host immune response may provide additive or synergistic antiviral activities, (Govorkova, E. A. & Webster, R. G. *Viruses* 2010, 2, 1510) and thus reduce the risk of drug-resistance with monotherapy.

Zanamivir (ZA) is a potent influenza virus neuraminidase (NA) inhibitor, known as Relenza™ on market; (Ryan, D. M. et al. *Antimicrob. Agents Chemother.* 1994, 38, 2270) the viral resistance to zanamivir is rare. (Collins, P. J. et al. *Nature* 2008, 453, 1258-1261). Zanamivir combined with triamcinolone, an anti-inflammatory corticosteroid, has been applied to treat H3N2 virus infection. (Ottolini, M. et al. *Pediatr. Pulmonol.* 2003, 36, 290) In another study, (Zheng, B. J. et al. *Proc. Natl. Acad. Sci. USA* 2008, 105, 8091) the mice infected with highly virulent H5N1 virus (1000 $LD_{50}$) receiving a triple combination of zanamivir with immunomodulating drugs (celocoxib and mesalazine) showed better survival rate in comparison with the treatment with zanamivir alone. The enhanced therapeutic effect may be attributable to the synergistic antiviral activity and cytokine suppression.

Therefore, there is a need for newer and synergistically effective bifunctional drugs for the prophylaxis, treatment and therapy of influenza virus infection where the drugs are formed by conjugation of an anti-influenza moiety with a moiety that suppresses pro-inflammatory cytokines.

SUMMARY OF THE INVENTION

The present invention provides compounds with dual-targeted and bifunctional anti-influenza activities. The provided compounds are generally formed by conjugation one or more anti-inflammatory agents with one or more anti-influenza agents. Exemplary compounds according to the invention include caffeic acid (CA)-bearing zanamivir (ZA) conjugates ZA-7-CA (1), ZA-7-CA-amide (7) and ZA-7-Nap (43), for simultaneous inhibition of influenza virus neuraminidase and suppression of proinflammatory cytokines. Preparation of these enhanced anti-influenza conjugate compounds are described herein. The present application also demonstrates that the synthetic bifunctional ZA conjugates act synergistically towards protection of mice lethally infected by H1N1 or H5N1 influenza viruses. Unexpectedly, the efficacy of ZA-7-CA, ZA-7-CA-amide and ZA-7-Nap conjugates was found to be much greater than the combination therapy of ZA with anti-inflammatory agents.

In one aspect, the invention provides chimeric compounds derived from neuraminidase inhibitors and anti-inflammatory agents (see, e.g., those shown in FIG. 2), such as the conjugates 43-51.

In another aspect, the invention provides dual-targeted anti-influenza compounds by conjugating one or more anti-inflamatory agents with one ore more anti-inflammatory agents. In certain embodiments, the anti-inflamatory agent is zanamivir (ZA), phosphono-zanamivir (PZA), oseltamivir (OS), tamiphosphor (TP) or peramivir (PE). In certain embodiments, the anti-inflammatory agents are caffeic acid (CA), mesalazine (ME), naproxen (Nap) and ibuprofen (Ibu). In certain embodiments, the provided compounds simultaneously inhibit influenza virus neuraminidase and suppression of proinflammatory cytokines. These anti-influenza conjugates show synergistic effect to provide remarkable protection of cells and mice against influenza infections. Intranasal administration of low dosage (<1.2 μmol/kg/day) of zanamivir conjugates, in particular ZA-7-CA (1) and ZA-7-CA-amido (7) conjugates, showed greater effect than the combination therapy with ZA and anti-inflammatory agents in protection of the lethally infected mice by H1N1 or H5N1 influenza viruses.

In another aspect, the invention provides chimeric, bifunctional compounds comprising a first moiety and a second moiety. In certain embodiments, the first moiety is an anti-influenza agent. In certain embodiments, the second moiety is an anti-inflammatory agent or an antioxidant moiety. In certain embodiments, the first and second moieties are conjugated via a linker. In certain embodiments, the anti-influenza agent and the anti-inflammatory agent are conjugated via a linker as in Formula (A). In certain embodiments, the linker comprises 2-12 carbon atoms and/or 0-5 heteroatoms selected from N, O and S.

Formula (A)

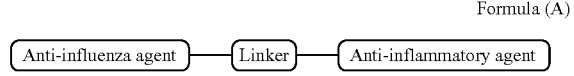

In some embodiments, more than one (e.g., 2) anti-influenza agents can be conjugated with one anti-inflammatory agent via the linker. An example is shown below.

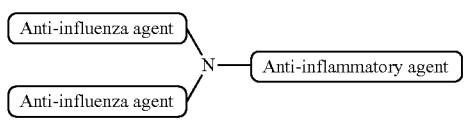

In other embodiments, one anti-influenza agent can be conjugated with one or more anti-inflammatory agents via the linker. An example is shown below.

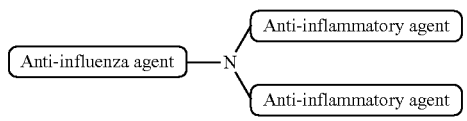

In yet other embodiments, multiple anti-influenza agents are conjugated with multiple anti-inflammatory agents via the linker. Below is an example.

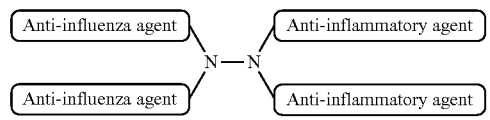

In some embodiments, the anti-inflammatory agent is a non-steroidal anti-inflammatory agent. In particular embodiments, the non-steroidal anti-inflammatory agent is an acid anti-inflammatory agent. In some embodiments, the anti-influenza agent is a derivative of zanamivir (ZA), phosphono-zanamivir (PZA), oseltamivir (OS), tamiphosphor (TP), or peramivir (PE).

In another aspect, a compound of formula (A) is of formula (I) or formula (II):

(I)

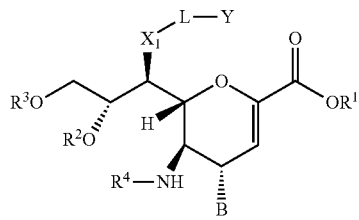

(II)

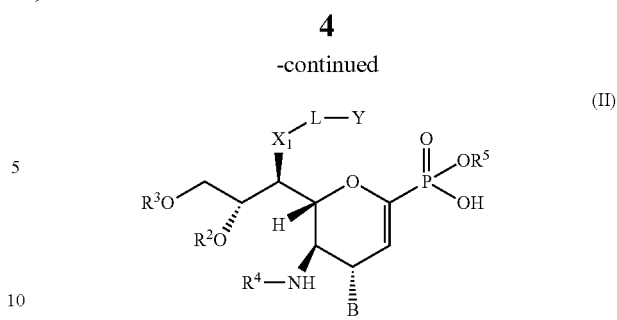

or a pharmaceutically acceptable salt thereof, wherein $X_1$, L, Y, B, $R^1$, $R^2$, $R^3$, $R^4$, and $R^5$ are as defined herein.

In another aspect, a provided compound is of formula (III) or (IV):

(III)

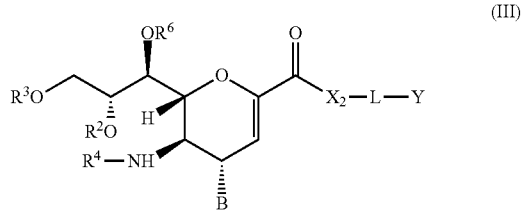

(IV)

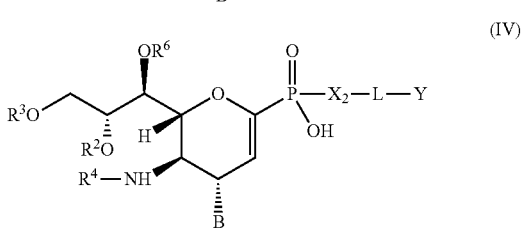

or a pharmaceutically acceptable salt thereof, wherein $X_2$, L, Y, B, $R^2$, $R^3$, $R^4$, and $R^6$ are as defined herein.

In another aspect, a provided compound is of formula (V) or (VI):

(V)

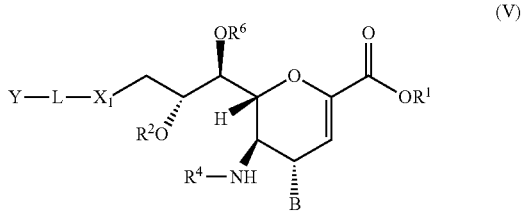

(VI)

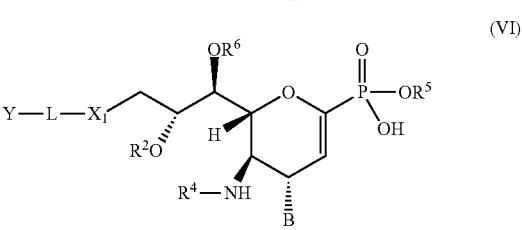

or a pharmaceutically acceptable salt thereof, wherein $X_1$, L, Y, B, $R^2$, $R^4$, and $R^6$ are as defined herein.

In another aspect, a provided compound is of formula (VII) or (VIII):

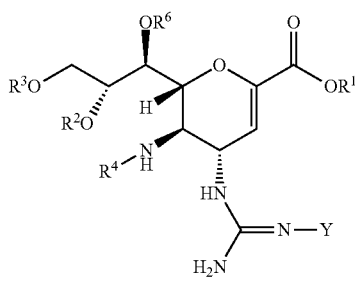

(VII)

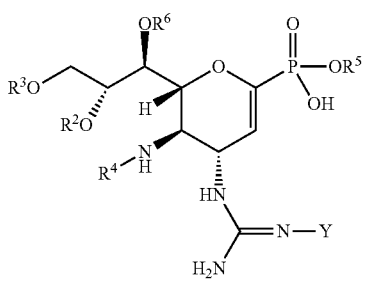

(VIII)

or a pharmaceutically acceptable salt thereof, wherein Y, B, $R^1$, $R^2$, $R^3$, $R^4$, $R^5$, K and $R^6$ are as defined herein.

In another aspect, a provided compound is of formula (IX) or (X):

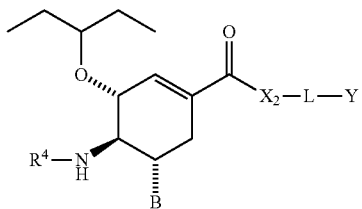

(IX)

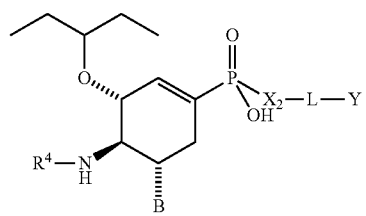

(X)

or a pharmaceutically acceptable salt thereof, wherein $X_2$, L, Y, B, and $R^4$ are as defined herein.

In another aspect, a provided compound is of formula (XI) or (XII):

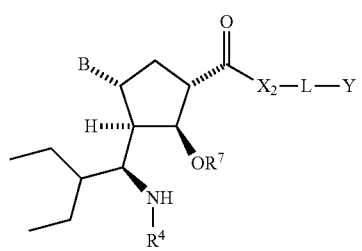

(XI)

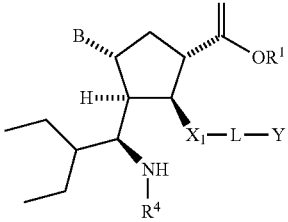

(XII)

or a pharmaceutically acceptable salt thereof, wherein $X_1$, L, Y, B, $R^1$, and $R^4$ are as defined herein.

In some embodiments, a provided compound is any one of the following formulae:

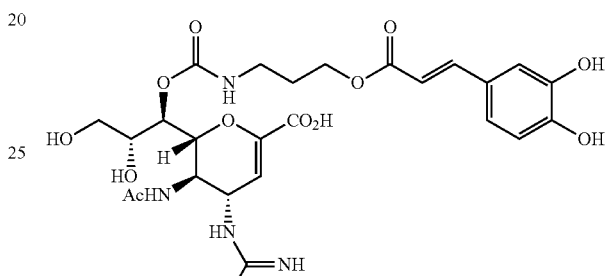

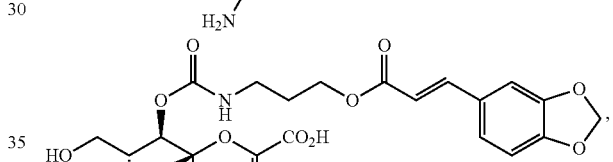

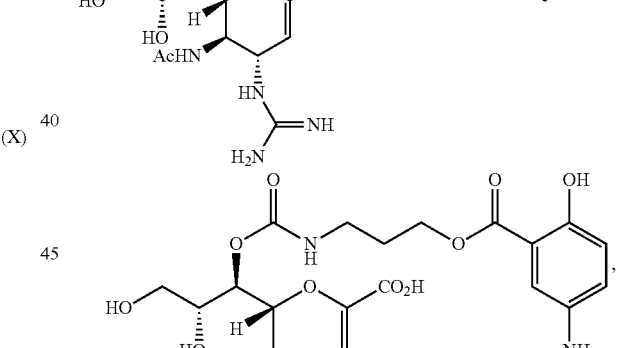

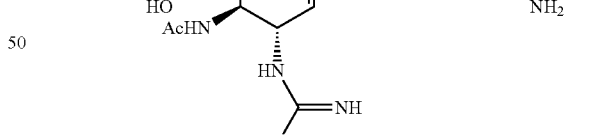

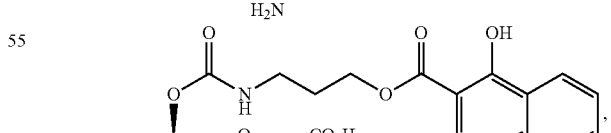

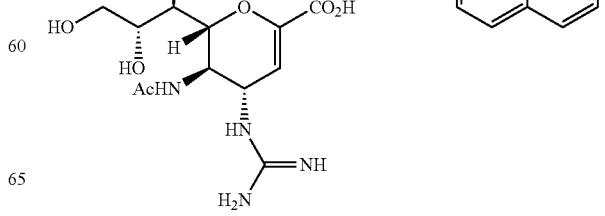

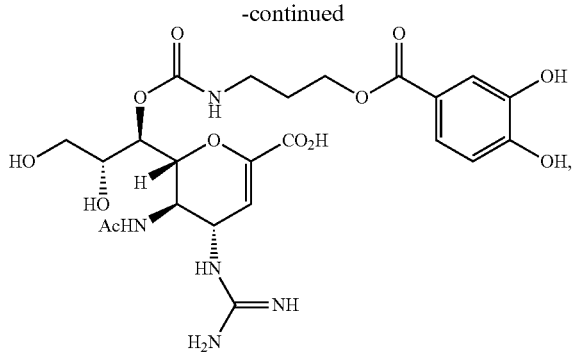
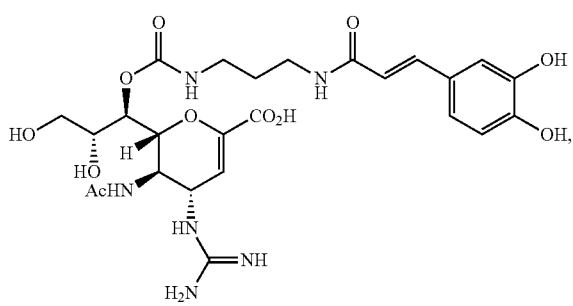
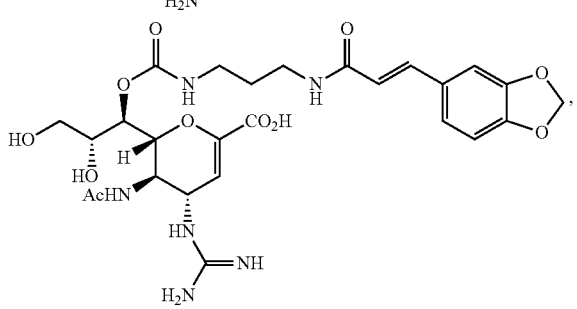
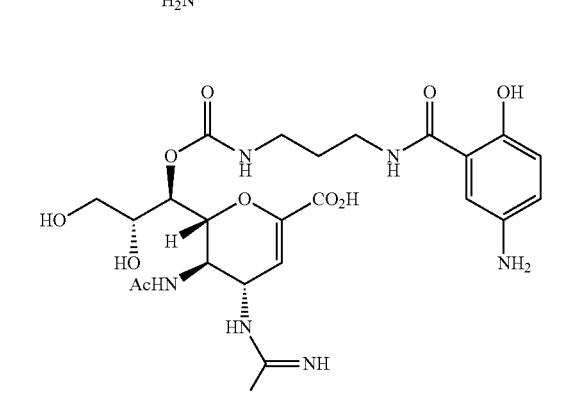
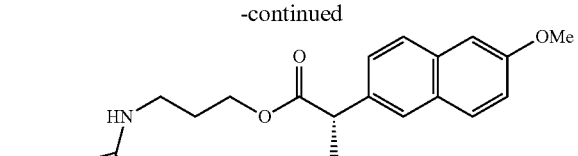
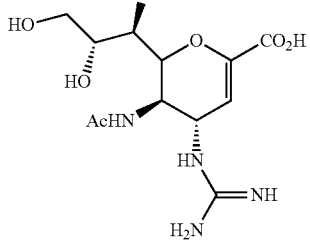
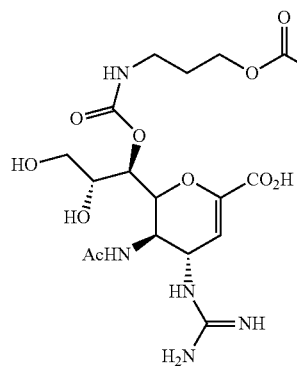
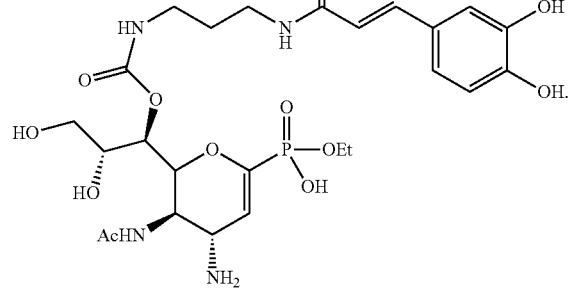
In some embodiments, a provided compound is selected from the group consisting of:
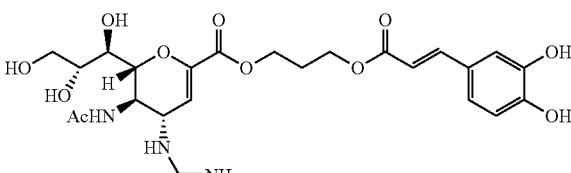
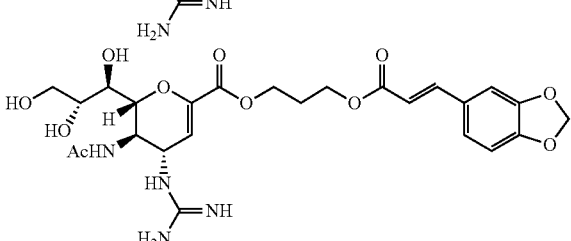

-continued

[Chemical structures shown]

In some embodiments, a provided compound is selected from the group consisting of:

[Chemical structures shown]

In some embodiments, a provided compound is selected from the group consisting of:

[Chemical structures shown]

In some embodiments, a provided compound is selected from the group consisting of:

[Chemical structures shown]

In some embodiments, a provided compound is selected from the group consisting of:

[Chemical structures shown]

In another aspect, the present invention provides pharmaceutical compositions comprising a compound of Formula (A), or a pharmaceutically acceptable salt, solvate, hydrate, polymorph, co-crystal, tautomer, stereoisomer, isotopically labeled derivative, or prodrug thereof, and optionally a pharmaceutically acceptable excipient. In certain embodiments, the pharmaceutical compositions described herein include a therapeutically effective amount of a compound of Formula (A), or a pharmaceutically acceptable salt, solvate, hydrate, polymorph, co-crystal, tautomer, stereoisomer, isotopically labeled derivative, or prodrug thereof. In certain embodiments, the provided pharmaceutical composition simultaneously inhibits influenza virus and inflammation.

In some embodiments, the pharmaceutical composition inhibits influenza virus neuraminidase. In some embodiments, the pharmaceutical composition inhibits pro-inflammatory cytokines. In some embodiments, wherein the pharmaceutical composition inhibits influenza virus neuraminidase and pro-inflammatory cytokines at levels greater than the inhibition observed by a composition comprising equivalent amounts of the unconjugated influenza virus inhibitor and the unconjugated anti-inflammatory agent.

In some embodiments, the compounds of Formula (A), or pharmaceutically acceptable salts thereof, bind both human and avian influenza virus strains. In some embodiments, the compounds of Formula (A), or pharmaceutically acceptable salts thereof, bind at least one of H1N1 and H5N1 strains of influenza virus.

In some embodiments, the compounds of Formula (A), or pharmaceutically acceptable salts thereof, bind the neuraminidase protein of the influenza virus. In some embodiments, the neuraminidase is wild-type. In some embodiments, the neuraminidase is oseltamivir-resistant.

In another aspect, the present invention provides methods of treating or preventing influenza infection by administering to a subject in need thereof a therapeutically effective amount of a compound according to any of Formula (A), or pharmaceutically acceptable salt thereof. In some embodiments, the administration is continued until symptoms of influenza infection are reduced, alleviated or terminated. Also within the scope of the present disclosure are pharmaceutical compositions for use in treating influenza infection, the composition comprising one or more of the compounds of Formula (A) as described herein and a pharmaceutically acceptable carrier, as well as uses of such compounds for manufacturing a medicament for use in treating influenza infection.

In another aspect, the present invention provides kits comprising a compound of Formula (A), or a pharmaceutically acceptable salt, solvate, hydrate, polymorph, co-crystal, tautomer, stereoisomer, isotopically labeled derivative, or prodrug thereof, or a pharmaceutical composition thereof. The kits of the invention may include a single dose or multiple doses of a compound of Formula (A), or a pharmaceutically acceptable salt, solvate, hydrate, polymorph, co-crystal, tautomer, stereoisomer, isotopically labeled derivative, or prodrug thereof, or a pharmaceutical composition thereof. The provided kits may be useful for the treatment and/or prevention of influenza infection. In certain embodiments, the kits described herein further include instructions for administering the compound of Formula (A), or the pharmaceutically acceptable salt, solvate, hydrate, polymorph, co-crystal, tautomer, stereoisomer, isotopically labeled derivative, or prodrug thereof, or the pharmaceutical composition thereof. The kits may also include packaging information describing the use or prescribing information for the subject or a health care professional. Such information may be required by a regulatory agency such as the U.S. Food and Drug Administration (FDA). The kit may also optionally include a device for administration of the compound or composition, for example, a dropper for ocular administration or a syringe for parenteral administration.

The details of certain embodiments of the invention are set forth herein. Other features, objects, and advantages of the invention will be apparent from the Detailed Description, Figures, Examples, and Claims.

Definitions

Chemical Definitions

Definitions of specific functional groups and chemical terms are described in more detail below. The chemical elements are identified in accordance with the Periodic Table of the Elements, CAS version, Handbook of Chemistry and Physics, $75^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, $5^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, $3^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, E. L. Stereochemistry of Carbon Compounds (McGraw-Hill, NY, 1962); and Wilen, S. H. *Tables of Resolving Agents and Optical Resolutions* p. 268 (E. L. Eliel, Ed., Univ. of Notre Dame Press, Notre Dame, Ind. 1972). The invention additionally encompasses compounds as individual isomers substantially free of other isomers, and alternatively, as mixtures of various isomers.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

The term "aliphatic," as used herein, refers to alkyl, alkenyl, alkynyl, and carbocyclic groups. Likewise, the term "heteroaliphatic" as used herein, refers to heteroalkyl, heteroalkenyl, heteroalkynyl, and heterocyclic groups.

As used herein, "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., $CH_3$). In certain embodiments, the alkyl group is a substituted $C_{1-10}$ alkyl.

As used herein, "haloalkyl" is a substituted alkyl group as defined herein wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). In some embodiments, all of the haloalkyl hydrogen atoms are replaced with fluoro to provide a perfluoroalkyl group. In some embodiments, all of the haloalkyl hydrogen atoms are replaced with chloro to provide a "perchloroalkyl" group. Examples of haloalkyl groups include $CF_3$, $CF_2CF_3$, $CF_2CF_2CF_3$, $CCl_3$, $CFCl_2$, $CF_2Cl$, and the like.

As understood from the above, alkyl, alkenyl, alkynyl, heteroalkyl, heteroalkenyl, heteroalkynyl, carbocyclyl, heterocyclyl, aryl, and heteroaryl groups, as defined herein, are, in certain embodiments, optionally substituted. Optionally substituted refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted" means that at least one hydrogen present on a group is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

As used herein, the term "halo" or "halogen" refers to fluorine (fluoro, —F), chlorine (chloro, —Cl), bromine (bromo, —Br), or iodine (iodo, —I).

As used herein, a "counterion" is a negatively charged group associated with a positively charged quarternary amine in order to maintain electronic neutrality. Exemplary counterions include halide ions (e.g., $F^-$, $Cl^-$, $Br^-$, $I^-$), $NO_3^-$, $ClO_4^-$, $OH^-$, $H_2PO_4^-$, $HSO_4^-$, sulfonate ions (e.g., methansulfonate, trifluoromethanesulfonate, p-toluenesulfonate, benzenesulfonate, 10-camphor sulfonate, naphthalene-2-sulfonate, naphthalenelsulfonic acid-5-sulfonate, ethanlsulfonic acid-2-sulfonate, and the like), and carboxylate ions (e.g., acetate, ethanoate, propanoate, benzoate, glycerate, lactate, tartrate, glycolate, and the like).

As used herein, the term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —$OR^{aa}$, —ON($R^{bb}$)$_2$, —OC(=O)$SR^{aa}$, —OC(=O)$R^{aa}$, —$OCO_2R^{aa}$, —OC(=O)N($R^{bb}$)$_2$, —OC(=$NR^{bb}$)$R^{aa}$, —OC(=$NR^{bb}$)$OR^{aa}$, —OC(=$NR^{bb}$)N($R^{bb}$)$_2$, —OS(=O)$R^{aa}$, —$OSO_2R^{aa}$, —OSi($R^{aa}$)$_3$, —OP($R^{cc}$)$_2$, —OP($R^{cc}$)$_3$, —OP(=O)$_2R^{aa}$, —OP(=O)($R^{aa}$)$_2$, —OP(=O)($OR^{cc}$)$_2$, —OP(=O)$_2$N($R^{bb}$)$_2$, and —OP(=O)(N$R^{bb}$)$_2$, wherein $R^{aa}$, $R^{bb}$, and $R^{cc}$ are as defined herein.

As used herein, the term, "amino" refers to the group —$NH_2$. The term "substituted amino," by extension, refers to a monosubstituted amino, a disubstituted amino, or a trisubstituted amino, as defined herein. In certain embodiments, the "substituted amino" is a monosubstituted amino or a disubstituted amino group.

As used herein, the term "monosubstituted amino" refers to an amino group wherein the nitrogen atom directly attached to the parent molecule is substituted with one hydrogen and one group other than hydrogen, and includes groups selected from NH($R^{bb}$), NHC(=O)$R^{aa}$, —$NHCO_2R^{aa}$, NHC(=O)N($R^{bb}$)$_2$, NHC(=$NR^{bb}$)N($R^{bb}$)$_2$, $NHSO_2R^{aa}$, NHP(=O)($OR^{cc}$)$_2$, and —NHP(=O)(N$R^{bb}$)$_2$, wherein $R^{aa}$, $R^{bb}$ and $R^{cc}$ are as defined herein, and wherein $R^{bb}$ of the group NH($R^{bb}$) is not hydrogen.

As used herein, the term "disubstituted amino" refers to an amino group wherein the nitrogen atom directly attached to the parent molecule is substituted with two groups other than hydrogen, and includes groups selected from —N($R^{bb}$)$_2$, —$NR^{bb}$C(=O)$R^{aa}$, —$NR^{bb}CO_2R^{aa}$, —$NR^{bb}$C(=O)N($R^{bb}$)$_2$, —$NR^{bb}$C(=$NR^{bb}$)N($R^{bb}$)$_2$, —$NR^{bb}SO_2R^{aa}$, —$NR^{bb}$P(=O)($OR^{cc}$)$_2$, and —$NR^{bb}$P(=O)(N$R^{bb}$)$_2$, wherein $R^{aa}$, $R^{bb}$, and $R^{cc}$ are as defined herein, with the proviso that the nitrogen atom directly attached to the parent molecule is not substituted with hydrogen.

As used herein, the term "trisubstituted amino" refers to an amino group wherein the nitrogen atom directly attached to the parent molecule is substituted with three groups, and includes groups selected from —N($R^{bb}$)$_3$ and —N($R^{bb}$)$_3^+$ $X^-$, wherein $R^{bb}$ and $X^-$ are as defined herein.

As used herein, the term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —$OR^{aa}$, —ON($R^{bb}$)$_2$—OC(=O)$SR^{aa}$, —OC(=O)$R^{aa}$, —$OCO_2R^{aa}$, —OC(=O)N($R^{bb}$)$_2$, —OC(=$NR^{bb}$)$R^{aa}$, —OC(=$NR^{bb}$)$OR^{aa}$, —OC(=$NR^{bb}$)N($R^{bb}$)$_2$, —OS(=O)$R^{aa}$, —$OSO_2R^{aa}$, —OSi($R^{aa}$)$_3$, —PP($R^{cc}$)$_2$, —OP($R^{cc}$)$_3$, —OP(=O)$_2R^{aa}$, —OP(=O)($R^{aa}$)$_2$, —OP(=O)($OR^{cc}$)$_2$, —OP(=O)$_2$N($R^{bb}$)$_2$, and —OP(=O)(N$R^{bb}$)$_2$, wherein $R^{aa}$, $R^{bb}$, and $R^{cc}$ are as defined herein. In the case wherein "substituted hydroxyl" is a ligand $L_1$ or $L_2$, "substituted hydroxyl" also refers to the group ($R^{aa}$)$_2$O, wherein $R^{aa}$ is as defined herein.

Nitrogen protecting groups such as carbamate groups (e.g., —C(=O)$OR^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-T-moc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)-ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), pnitobenzyl carbamate, pbromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Nitrogen protecting groups such as sulfonamide groups (e.g., $S(=O)_2R^{aa}$) include, but are not limited to, p-toluenesulfonamide (Ts), benzenesulfonamide, 2,3,6,trimethyl-4-methoxybenzenesulfonamide (Mtr), 2,4,6-trimethoxybenzenesulfonamide (Mtb), 2,6-dimethyl 4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl(10) acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STAB ASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2 picolylamino N'-oxide, N-1,1-dimethylthiomethyleneamine, N-benzylideneamine, N-p-methoxybenzylideneamine, N-diphenylmethyleneamine, N-[2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl (pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, onitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

These and other exemplary substituents are described in more detail in the Detailed Description, Examples, and Claims. The invention is not intended to be limited in any manner by the above exemplary listing of substituents.

As used herein, the term "salt" refers to any and all salts. The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al. describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid, or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

As used herein, the term "tautomer" refers to particular isomers of a compound in which a hydrogen and double bond have changed position with respect to the other atoms of the molecule. For a pair of tautomers to exist there must be a mechanism for interconversion. Examples of tautomers include keto-enol forms, imine-enamine forms, amide-imino alcohol forms, amidine-aminidine forms, nitroso-oxime forms, thio ketone-enethiol forms, N-nitroso-hydroxyazo forms, nitro-aci-nitro forms, and pyridone-hydroxypyridine forms.

As used herein, use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

Other Definition

The following definitions are more general terms used throughout the present application:

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid, and perchloric acid or with organic acids such as acetic acid, oxalic acid, maleic acid, tartaric acid, citric acid, succinic acid, or malonic acid or by using other methods known in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. Representative alkali or alkaline earth metal salts include sodium, lithium, potassium, calcium, magnesium, and the like. Further pharmaceutically acceptable salts include, when appropriate, non-toxic ammonium, quaternary ammonium, and amine cations formed using counterions such as halide, hydroxide, carboxylate, sulfate, phosphate, nitrate, loweralkyl sulfonate, and aryl sulfonate.

The term "solvate" refers to forms of the compound that are associated with a solvent, usually by a solvolysis reaction. This physical association may include hydrogen bonding. Conventional solvents include water, methanol, ethanol, acetic acid, DMSO, THF, diethyl ether, and the like. The compounds of Formulae (I)-(II) may be prepared, e.g., in crystalline form, and may be solvated. Suitable solvates include pharmaceutically acceptable solvates and further include both stoichiometric solvates and non-stoichiometric solvates. In certain instances, the solvate will be capable of isolation, for example, when one or more solvent molecules are incorporated in the crystal lattice of a crystalline solid. "Solvate" encompasses both solution-phase and isolable solvates. Representative solvates include hydrates, ethanolates, and methanolates.

The term "hydrate" refers to a compound which is associated with water. Typically, the number of the water molecules contained in a hydrate of a compound is in a definite ratio to the number of the compound molecules in the hydrate. Therefore, a hydrate of a compound may be represented, for example, by the general formula R·x H$_2$O, wherein R is the compound, and x is a number greater than 0. A given compound may form more than one type of hydrates, including, e.g., monohydrates (x is 1), lower hydrates (x is a number greater than 0 and smaller than 1, e.g., hemihydrates (R·0.5 H$_2$O)), and polyhydrates (x is a number greater than 1, e.g., dihydrates (R·2H$_2$O) and hexahydrates (R·6H$_2$O)).

As used herein, the term "tautomer" includes two or more interconvertable forms resulting from at least one formal migration of a hydrogen atom and at least one change in valency (e.g., a single bond to a double bond, a triple bond to a double bond, or vice versa). The exact ratio of the tautomers depends on several factors, including temperature, solvent, and pH. Tautomerizations (i.e., the reaction providing a tautomeric pair) may be catalyzed by acid or base. Exemplary tautomerizations include keto-to-enol; amide-to-imide; lactam-to-lactim; enamine-to-imine; and enamine-to-(a different) enamine tautomerizations.

It is also to be understood that compounds that have the same molecular formula but differ in the nature or sequence of bonding of their atoms or the arrangement of their atoms in space are termed "isomers". Isomers that differ in the arrangement of their atoms in space are termed "stereoisomers".

Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "polymorphs" refers to a crystalline form of a compound (or a salt, hydrate, or solvate thereof) in a particular crystal packing arrangement. All polymorphs have the same elemental composition. Different crystalline forms usually have different X-ray diffraction patterns, infrared spectra, melting points, density, hardness, crystal shape, optical and electrical properties, stability, and/or solubility. Recrystallization solvent, rate of crystallization, storage temperature, and other factors may cause one crystal form to dominate. Various polymorphs of a compound can be prepared by crystallization under different conditions.

The term "prodrugs" refer to compounds, including derivatives of the compounds of Formula (I), which have cleavable groups and become by solvolysis or under physiological conditions the compounds of Formula (I)-(II) which are pharmaceutically active in vivo. Such examples include, but are not limited to, choline ester derivatives and the like, N-alkylmorpholine esters and the like. Other derivatives of the compounds of this invention have activity in both their acid and acid derivative forms, but in the acid sensitive form often offers advantages of solubility, tissue compatibility, or delayed release in the mammalian organism (see, Bundgard, *Design of Prodrugs*, pp. 7-9, 21-24, Elsevier, Amsterdam 1985). Prodrugs include acid derivatives well known to practitioners of the art, such as, for example, esters prepared by reaction of the parent acid with a suitable alcohol, or amides prepared by reaction of the parent acid compound with a substituted or unsubstituted amine, or acid anhydrides, or mixed anhydrides. Simple aliphatic or aromatic esters, amides, and anhydrides derived from acidic groups pendant on the compounds of this invention are particular prodrugs. In some cases it is desirable to prepare double ester type prodrugs such as (acyloxy)alkyl esters or ((alkoxycarbonyl)oxy)alkylesters. $C_1$-$C_8$ alkyl, $C_2$-$C_8$ alkenyl, $C_2$-$C_8$ alkynyl, aryl, $C_7$-$C_{12}$ substituted aryl, and $C_7$-$C_{12}$ arylalkyl esters of the compounds of Formulae (I)-(II) may be preferred in certain instances.

A "subject" to which administration is contemplated includes, but is not limited to, humans (i.e., a male or female of any age group, e.g., a pediatric subject (e.g., infant, child, adolescent) or adult subject (e.g., young adult, middle-aged adult, or senior adult)) and/or other nonhuman animals, for example, mammals (e.g., primates (e.g., cynomolgus monkeys, rhesus monkeys); commercially relevant mammals such as cattle, pigs, horses, sheep, goats, cats, and/or dogs) and birds (e.g., commercially relevant birds such as chickens, ducks, geese, and/or turkeys). In certain embodiments, the animal is a mammal. The animal may be a male or female and at any stage of development. A nonhuman animal may be a transgenic animal.

The terms "administer," "administering," or "administration," as used herein refers to implanting, absorbing, ingesting, injecting, inhaling, or otherwise introducing an inventive compound, or a pharmaceutical composition thereof.

As used herein, the terms "treatment," "treat," and "treating" refer to reversing, alleviating, delaying the onset of, or inhibiting the progress of a "pathological condition" (e.g., a disease, disorder, or condition, or one or more signs or symptoms thereof) described herein. In some embodiments, treatment may be administered after one or more signs or symptoms have developed or have been observed. In other embodiments, treatment may be administered in the absence of signs or symptoms of the disease or condition. For example, treatment may be administered to a susceptible individual prior to the onset of symptoms (e.g., in light of a history of symptoms and/or in light of genetic or other susceptibility factors). Treatment may also be continued after symptoms have resolved, for example, to delay or prevent recurrence, or to reduce the risk for the disease or condition.

As used herein, the terms "condition," "disease," and "disorder" are used interchangeably.

An "effective amount" of a compound of Formulae (A) refers to an amount sufficient to elicit a desired biological response, i.e., treating the condition. As will be appreciated by those of ordinary skill in this art, the effective amount of a compound of Formula (A) may vary depending on such factors as the desired biological endpoint, the pharmacokinetics of the compound, the condition being treated, the mode of administration, and the age and health of the subject. An effective amount encompasses therapeutic and prophylactic treatment. For example, in treating cancer, an effective amount of an inventive compound may reduce the tumor burden or stop the growth or spread of a tumor. In treating macular degeneration, an effective amount of an inventive compound may improve sight, reduce the risk of vision loss, or prevent central vision loss from worsening.

A "therapeutically effective amount" of a compound of Formula (A) is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent.

A "prophylactically effective amount" of a compound of Formula (A) is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

As used herein "inhibition", "inhibiting", "inhibit" and "inhibitor", and the like, refer to the ability of a compound to reduce, slow, halt, or prevent the activity of a particular biological process involving Ras in a cell relative to vehicle.

BRIEF DESCRIPTION OF THE DRAWINGS

The following drawings form part of the present specification and are included to further demonstrate certain aspects of the present disclosure, the inventions of which can be better understood by reference to one or more of these drawings in combination with the detailed description of specific embodiments presented herein.

-continued

Figure 1:
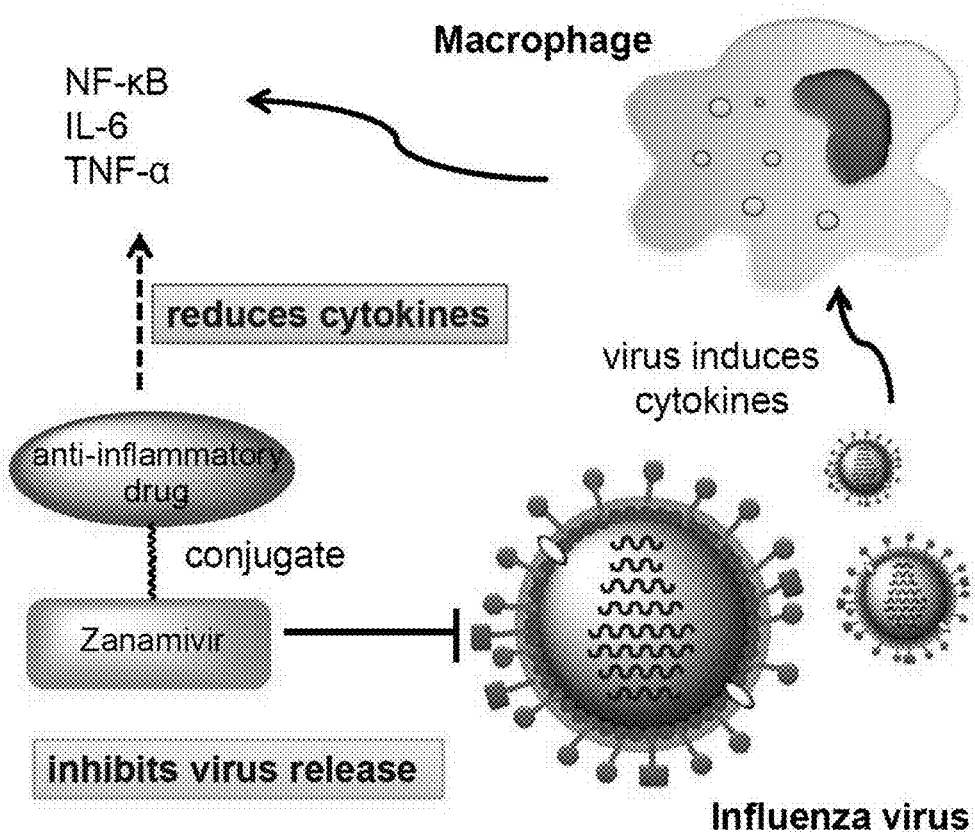
FIG. 1. Working mechanism of the dual-targeted anti-influenza drugs for virus inactivation and cytokine suppression. The conjugate drug is brought to the virus infection sites via strong affinity of the neuraminidase inhibitor (e.g., zanamivir), so that the infection-mediated cytokine induction can be effectively suppressed by the anti-inflammatory component (e.g., caffeic acid) of the conjugate drug.

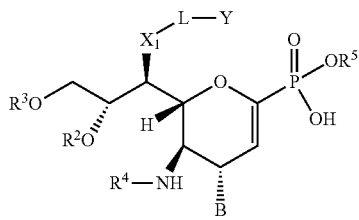
(II)

or a pharmaceutically acceptable salt thereof;
wherein:

$X_1$ is —O—, —O(C=O)—, —NH—, —NHCO—, —O(C=O)NH—, —O(C=S)NH—, —NH(C=O)NH—, or —NH(C=S)NH—;

L is a linker selected from the group consisting of a bond, —(CH$_2$)$_n$—, —(CH$_2$)$_n$O—, —O(CH$_2$)$_n$—, —(CH$_2$)$_n$—C(O)—, —(CH$_2$)$_n$—NH—, —NH—(CH$_2$)$_n$—, —C(O)(CH$_2$)$_n$—, —(CH$_2$)$_n$—NHC(O)—, —C(O)(CH$_2$)$_n$—NHC(O)—, (CH$_2$)$_n$SCH$_2$C(O)—, and —(CH$_2$CH$_2$O)$_m$—;

n is an integer from 1 to 8, inclusive;

m is an integer from 1 to 4, inclusive;

$X_1$ is covalently linked to L;

Y is a non-steroidal anti-inflammatory agent selected from the group consisting of aceclofenac, acemetacin, acetyl-sailcylic acid, 5-aminoacetylsalicylic acid, aldlofenac, amfenac, bendazac, benoxaprofen, bermoprofen, bromfenac, 5-bromosalicylic acid acetate, bucloxic acid, butibufen, caffeic acid, carprofen, chromoglycate, cinmetacin, clindanac, clopirac, sodium diclofenac, diflunisal, 3,4-dihydroxybenzoic acid, enfenamic acid, etodolac, felbinac, fenbufen, fenclozic acid, fendosal, fenoprofen, fentiazac, flufenac, flufenamic acid, flunixin, flunoxaprofen, flurbiprofen, 1-hydroxynaphthoic acid, ibufenac, ibuprofen, indomethacin, indoprofen, isofezolac, isoxepac, ketoprofen, ketorolac, loxoprofen, meclofenamic acid, mefenamic acid, mesalazine, 3,4-methylenedioxycinnamic acid, metiazinic acid, mofezolac, montelukast, mycophenolic acid, naproxen, niflumic acid, olsalazine, oxaceprol, oxaprozin, pyrazolac, pirprofen, pranoprofen, protizinic acid, sulindac, suprofen, suxibutazone, tiaprofenic acid, tinoridine acid, tolfenamic acid, tolmetin, tropesin, xenbucin, ximoprofen, zaltoprofen, and zomepirac;

Y is covalently linked to L via an acid group in the non-steroidal anti-inflammatory agent;

B is an azido, a hydroxyl, an unsubstituted or substituted amino, or an unsubstituted or substituted guanidino, or the corresponding salts with an anionic counterion selected from the group consisting of chloride, bromide, iodide, acetate, trifluoroacetate, phosphate, diphosphate, nitrate, sulfate, benzenesulfonate, benzoate, salicylate, hydroxynaphthoate, fumarate, maleate, lactate, malate, succinate, tartrate, citrate, glutamate, and gluconate; each instance of $R^1$ and $R^5$ is, independently, hydrogen or optionally substituted $C_{1-6}$ alkyl; each instance of $R^2$ and $R^3$ is, independently, hydrogen, optionally substituted alkyl, or optionally substituted acyl group; and $R^4$ is —COCH$_3$, —COCF$_3$, —SO$_2$CH$_3$ or —SO$_2$CF$_3$.

In certain embodiments, a compound of Formula (A) is of Formula (V) or (VI):

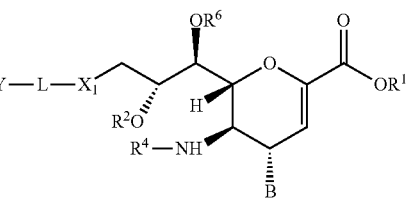
(V)

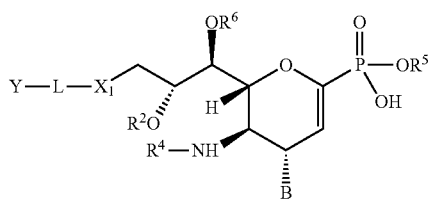
(VI)

or a pharmaceutically acceptable salt thereof;
wherein:

$X_1$ is —O—, —O(C=O)—, —NH—, —NHCO—, —O(C=O)NH—, —O(C=S)NH—, —NH(C=O)NH—, or —NH(C=S)NH—;

L is a linker selected from the group consisting of a bond, —(CH$_2$)$_n$—, —(CH$_2$)$_n$O—, —O(CH$_2$)$_n$—, —(CH$_2$)$_n$—C(O)—, —(CH$_2$)$_n$—NH—, —NH—(CH$_2$)$_n$—, —C(O)(CH$_2$)$_n$—, —(CH$_2$)$_n$—NHC(O)—, —C(O)(CH$_2$)$_n$—NHC(O)—, (CH$_2$)$_n$SCH$_2$C(O)—, and —(CH$_2$CH$_2$O)$_m$—;

n is an integer from 1 to 8;

m is an integer from 1 to 4;

$X_1$ is covalently linked to L;

Y is a non-steroidal anti-inflammatory agent selected from the group consisting of aceclofenac, acemetacin, acetyl-sailcylic acid, 5-aminoacetylsalicylic acid, aldlofenac, amfenac, bendazac, benoxaprofen, bermoprofen, bromfenac, 5-bromosalicylic acid acetate, bucloxic acid, butibufen, caffeic acid, carprofen, chromoglycate, cinmetacin, clindanac, clopirac, sodium diclofenac, diflunisal, 3,4-dihydroxybenzoic acid, enfenamic acid, etodolac, felbinac, fenbufen, fenclozic acid, fendosal, fenoprofen, fentiazac, flufenac, flufenamic acid, flunixin, flunoxaprofen, flurbiprofen, 1-hydroxynaphthoic acid, ibufenac, ibuprofen, indomethacin, indoprofen, isofezolac, isoxepac, ketoprofen, ketorolac, loxoprofen, meclofenamic acid, mefenamic acid, mesalazine, 3,4-methylenedioxycinnamic acid, metiazinic acid, mofezolac, montelukast, mycophenolic acid, naproxen, niflumic acid, olsalazine, oxaceprol, oxaprozin, pyrazolac, pirprofen, pranoprofen, protizinic acid, sulindac, suprofen, suxibutazone, tiaprofenic acid, tinoridine acid, tolfenamic acid, tolmetin, tropesin, xenbucin, ximoprofen, zaltoprofen, and zomepirac;

Y is covalently linked to L via an acid group in the non-steroidal anti-inflammatory agent;

B is an azido, a hydroxyl, an unsubstituted or substituted amino, or an unsubstituted or substituted guanidino, or the corresponding salts with an anionic counterion selected from the group consisting of chloride, bromide, iodide, acetate, trifluoroacetate, phosphate, diphosphate, nitrate, sulfate, benzenesulfonate, benzoate, salicylate, hydroxynaphthoate, fumarate, maleate, lactate, malate, succinate, tartrate, citrate, glutamate, and gluconate;

each instance of $R^1$, $R^5$ and $R^6$ is, independently, hydrogen or optionally substituted $C_{1-6}$ alkyl;

each instance of $R^2$ and $R^3$ is, independently, hydrogen, optionally substituted alkyl, or optionally substituted acyl group; and $R^4$ is —COCH$_3$, —COCF$_3$, —SO$_2$CH$_3$ or —SO$_2$CF$_3$.

As generally defined herein, $X_1$ is —O—, —O(C═O)—, —NH—, —NHCO—, —O(C═O)NH—, —O(C═S)NH—, —NH(C═O)NH—, or —NH(C═S)NH—. In certain embodiments, $X_1$ is —O—. In certain embodiments, $X_1$ is —O(C═O)—. In certain embodiments, $X_1$ is —NH—. In certain embodiments, $X_1$ is —O(C═O)NH—. In certain embodiments, $X_1$ is —O(C═S)NH—. In certain embodiments, $X_1$ is —NH(C═O)NH—. In certain embodiments, $X_1$ is —NH(C═S)NH—.

As generally defined herein, L is a linker selected from the group consisting of —(CH$_2$)$_n$—, —(CH$_2$)$_n$O—, —O(CH$_2$)$_n$—, —(CH$_2$)$_n$C(O)—, —(CH$_2$)$_n$NH—, —NH—(CH$_2$)$_n$—, —C(O)(CH$_2$)$_n$—, —(CH$_2$)$_n$NHC(O)—, —C(O)(CH$_2$)$_n$NHC(O)—, —(CH$_2$)$_n$SCH$_2$C(O)—, and —(CH$_2$CH$_2$O)$_m$—. As used herein, n is an integer from 1 to 8, inclusive. In certain embodiments, n is 1. In certain embodiments, n is 2. In certain embodiments, n is 3. In certain embodiments, n is 4. In certain embodiments, n is 5. In certain embodiments, n is 6. In certain embodiments, n is 7. In certain embodiments, n is 8. As used herein, m is an integer from 1 to 4, inclusive. In certain embodiments, m is 1. In certain embodiments, m is 2. In certain embodiments, m is 3. In certain embodiments, m is 4. In certain embodiments, L is —(CH$_2$)$_n$—. In certain embodiments, L is —(CH$_2$)$_2$—. In certain embodiments, L is —(CH$_2$)$_3$—. In certain embodiments, L is —(CH$_2$)$_4$—. In certain embodiments, L is —(CH$_2$)$_5$—. In certain embodiments, L is —(CH$_2$)$_6$—. In certain embodiments, L is —(CH$_2$)$_7$—. In certain embodiments, L is —(CH$_2$)$_8$—. In certain embodiments, m is 4. In certain embodiments, L is —(CH$_2$)$_n$O—. In certain embodiments, L is —(CH$_2$)$_2$O—. In certain embodiments, L is —(CH$_2$)$_3$O—. In certain embodiments, L is —(CH$_2$)$_4$O—. In certain embodiments, L is —(CH$_2$)$_5$O—. In certain embodiments, L is —(CH$_2$)$_6$O—. In certain embodiments, L is —(CH$_2$)$_7$O—. In certain embodiments, L is —(CH$_2$)$_8$O—. In certain embodiments, L is —(CH$_2$)$_n$NH—. In certain embodiments, L is —(CH$_2$)$_2$NH—. In certain embodiments, L is —(CH$_2$)$_3$NH—. In certain embodiments, L is —(CH$_2$)$_4$NH—. In certain embodiments, L is —(CH$_2$)$_5$NH—. In certain embodiments, L is —(CH$_2$)$_6$NH—. In certain embodiments, L is —(CH$_2$)$_7$NH—. In certain embodiments, L is —(CH$_2$)$_8$NH—.

In certain embodiments, —$X_1$-L- is —O(C═O)NH—(CH$_2$)$_n$O—. In certain embodiments, —$X_1$-L- is —O(C═O)NH—(CH$_2$)$_n$NH—. In certain embodiments, —$X_1$-L- is —(C═O)O—(CH$_2$)$_n$NH—. In certain embodiments, —$X_1$-L- is —(C═O)O—(CH$_2$)$_n$O—. In certain embodiments, —$X_1$-L- is —O—(CH$_2$)$_n$O—. In certain embodiments, —$X_1$-L- is —NH—(CH$_2$)$_n$O—.

As generally defined herein, Y is a non-steroidal anti-inflammatory agent selected from the group consisting of aceclofenac, acemetacin, acetyl-sailcylic acid, 5-aminoacetylsalicylic acid, aldlofenac, amfenac, bendazac, benoxaprofen, bermoprofen, bromfenac, 5-bromosalicylic acid acetate, bucloxic acid, butibufen, caffeic acid, carprofen, chromoglycate, cinmetacin, clindanac, clopirac, sodium diclofenac, diflunisal, 3,4-dihydroxybenzoic acid, enfenamic acid, etodolac, felbinac, fenbufen, fenclozic acid, fendosal, fenoprofen, fentiazac, flufenac, flufenamic acid, flunixin, flunoxaprofen, flurbiprofen, 1-hydroxynaphthoic acid, ibufenac, ibuprofen, indomethacin, indoprofen, isofezolac, isoxepac, ketoprofen, ketorolac, loxoprofen, meclofenamic acid, mefenamic acid, mesalazine, 3,4-methylenedioxycinnamic acid, metiazinic acid, mofezolac, montelukast, mycophenolic acid, naproxen, niflumic acid, olsalazine, oxaceprol, oxaprozin, pyrazolac, pirprofen, pranoprofen, protizinic acid, sulindac, suprofen, suxibutazone, tiaprofenic acid, tinoridine acid, tolfenamic acid, tolmetin, tropesin, xenbucin, ximoprofen, zaltoprofen, and zomepirac. Y is covalently linked to L via an acid group in the non-steroidal anti-inflammatory agent. In certain embodiments, Y is caffeic acid (CA). In certain embodiments, Y is mesalazine (ME). In certain embodiments, Y is naproxen (Nap). In certain embodiments, Y is ibuprofen (Ibu).

As generally defined herein, B is azido, hydroxyl, unsubstituted or substituted amino, or an unsubstituted or substituted guanidino, or the corresponding salts with an anionic counterion selected from the group consisting of chloride, bromide, iodide, acetate, trifluoroacetate, phosphate, diphosphate, nitrate, sulfate, benzenesulfonate, benzoate, salicylate, hydroxynaphthoate, fumarate, maleate, lactate, malate, succinate, tartrate, citrate, glutamate, and gluconate. In certain embodiments, B is azido. In certain embodiments, B is hydroxyl. In certain embodiments, B is substituted amino. In certain embodiments, B is unsubstituted amino. In certain embodiments, B is unsubstituted guanidino. In certain embodiments, B is substituted guanidino.

As generally defined herein, each instance of $R^1$ is independently, hydrogen or optionally substituted C$_{1-6}$ alkyl. In certain embodiments, $R^1$ is hydrogen. In certain embodiments, $R^1$ is substituted C$_{1-6}$ alkyl. In certain embodiments, $R^1$ is unsubstituted C$_{1-6}$ alkyl. In certain embodiments, $R^1$ is methyl. In certain embodiments, $R^1$ is ethyl. In certain embodiments, $R^1$ is propyl, butyl, pentyl, or hexyl. In certain embodiments, $R^1$ is isopropyl, isobutyl, or isoamyl. In certain embodiments, $R^1$ is isobutyl. In certain embodiments, $R^1$ is tert-butyl.

As generally defined herein, each instance of $R^5$ is independently, hydrogen or optionally substituted C$_{1-6}$ alkyl. In certain embodiments, $R^5$ is hydrogen. In certain embodiments, $R^5$ is substituted C$_{1-6}$ alkyl. In certain embodiments, $R^5$ is unsubstituted C$_{1-6}$ alkyl. In certain embodiments, $R^5$ is methyl. In certain embodiments, $R^5$ is ethyl. In certain embodiments, $R^5$ is propyl, butyl, pentyl, or hexyl. In certain embodiments, $R^5$ is isopropyl, isobutyl, or isoamyl. In certain embodiments, $R^5$ is isobutyl. In certain embodiments, $R^5$ is tert-butyl.

As generally defined herein, each instance of $R^6$ is independently, hydrogen or optionally substituted C$_{1-6}$ alkyl. In certain embodiments, $R^6$ is hydrogen. In certain embodiments, $R^6$ is substituted C$_{1-6}$ alkyl. In certain embodiments, $R^6$ is unsubstituted C$_{1-6}$ alkyl. In certain embodiments, $R^6$ is methyl. In certain embodiments, $R^6$ is ethyl. In certain embodiments, $R^6$ is propyl, butyl, pentyl, or hexyl. In certain embodiments, $R^6$ is isopropyl, isobutyl, or isoamyl. In certain embodiments, $R^6$ is isobutyl. In certain embodiments, $R^6$ is tert-butyl.

As generally defined herein, each instance of $R^2$ is, independently, hydrogen, optionally substituted alkyl, or optionally substituted acyl group. In certain embodiments, $R^2$ is hydrogen. In certain embodiments, $R^2$ is substituted C$_{1-6}$ alkyl. In certain embodiments, $R^2$ is unsubstituted C$_{1-6}$ alkyl. In certain embodiments, $R^2$ is methyl, ethyl, propyl, butyl, pentyl, or hexyl. In certain embodiments, $R^2$ is isopropyl, isobutyl, or isoamyl. In certain embodiments, $R^2$ is isobutyl. In certain embodiments, $R^2$ is tert-butyl. In certain embodiments, $R^2$ is acyl. In certain embodiments, $R^2$ is acetyl.

As generally defined herein, each instance of $R^3$ is, independently, hydrogen, optionally substituted alkyl, or optionally substituted acyl group. In certain embodiments, $R^3$ is hydrogen. In certain embodiments, $R^3$ is substituted C$_{1-6}$ alkyl. In certain embodiments, $R^3$ is unsubstituted C$_{1-6}$ alkyl. In certain embodiments, $R^3$ is methyl, ethyl, propyl, butyl, pentyl, or hexyl. In certain embodiments, $R^3$ is isopropyl, isobutyl, or isoamyl. In certain embodiments, $R^3$ is isobutyl. In certain embodiments, $R^3$ is tert-butyl. In certain embodiments, $R^3$ is acyl. In certain embodiments, $R^3$ is acetyl.

As generally defined herein, $R^4$ is —$COCH_3$, —$COCF_3$, —$SO_2CH_3$ or —$SO_2CF_3$. In certain embodiments, $R^4$ is —$COCH_3$. In certain embodiments, $R^4$ is —$COCF_3$. In certain embodiments, $R^4$ is —$SO_2CH_3$. In certain embodiments, $R^4$ is —$SO_2CF_3$.

In certain embodiments, a compound of Formula (A) is of Formula (VII) or (VIII):

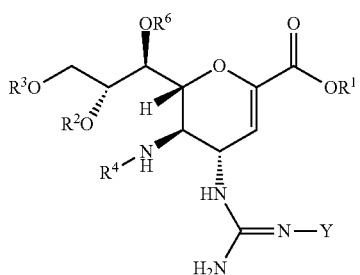

(VII)

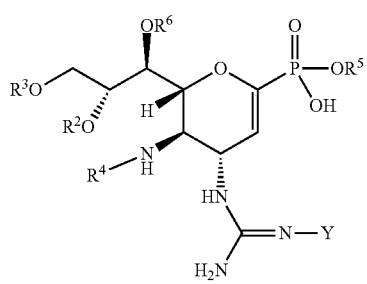

(VIII)

or a pharmaceutically acceptable salt thereof, wherein Y, B, $R^1$, $R^2$, $R^3$, $R^4$, $R^5$, and $R^6$ are as defined herein.

In another aspect, a provided compound is of formula (III) or (IV):

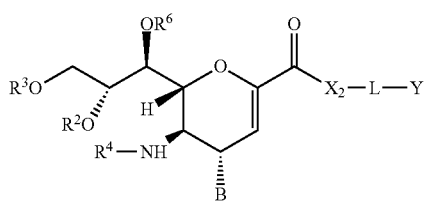

(III)

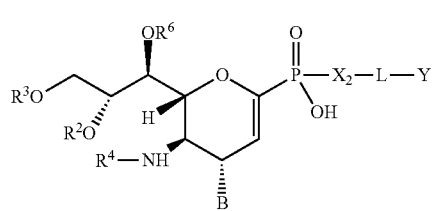

(IV)

or a pharmaceutically acceptable salt thereof,
wherein:
L, Y, B, $R^2$, $R^3$, $R^4$, and $R^6$ are as defined above; and
$X_2$ is —O— or —NH—.

In certain embodiments, a provided compound is of formula (IX) or (X):

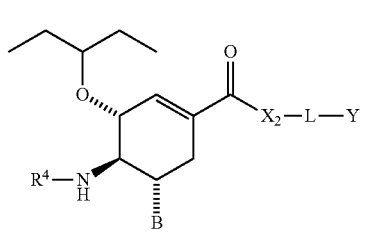

(IX)

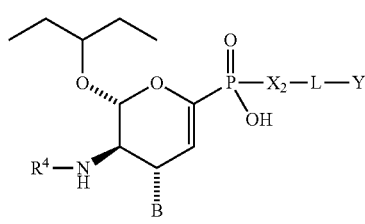

(X)

or a pharmaceutically acceptable salt thereof,
wherein:
L, Y, B, and $R^4$ are as defined above; and
$X_2$ is —O— or —NH—.

In another aspect, a provided compound is of formula (XI) or (XII):

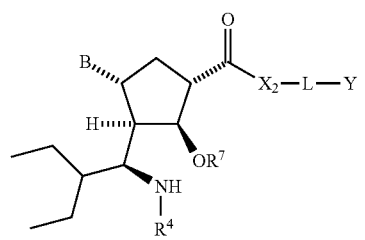

(XI)

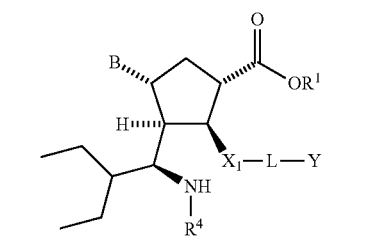

(XII)

or a pharmaceutically acceptable salt thereof,
wherein:
L, Y, B, $X_1$, $R^1$, and $R^4$ are as defined above;
$X_2$ is —O— or —NH—; and
$R^7$ is hydrogen or optionally substituted $C_{1-6}$ alkyl.

As generally defined herein, $X_2$ is —O— or —NH—. In certain embodiments, $X_2$ is —O—. In certain embodiments, $X_2$ is —NH—. In certain embodiments, —$X_2$-L- is —O—$(CH_2)_n$O—. In certain embodiments, —$X_2$-L- is —O—$(CH_2)_n$NH—. In certain embodiments, —$X_2$-L- is —NH—$(CH_2)_n$O—. In certain embodiments, —$X_2$-L- is —NH—$(CH_2)_n$NH—.

As generally defined herein, $R^7$ is independently, hydrogen or optionally substituted $C_{1-6}$ alkyl. In certain embodiments, $R^7$ is hydrogen. In certain embodiments, $R^7$ is substituted $C_{1-6}$ alkyl. In certain embodiments, $R^7$ is unsubstituted $C_{1-6}$ alkyl. In certain embodiments, $R^7$ is methyl. In certain embodiments, $R^7$ is ethyl. In certain embodiments, $R^7$ is propyl, butyl, pentyl, or hexyl. In certain embodiments, $R^7$ is isopropyl, isobutyl, or isoamyl. In certain embodiments, $R^7$ is isobutyl. In certain embodiments, $R^7$ is tert-butyl.

The present invention further provides pharmaceutical compositions comprising a compound of Formula (A), or a pharmaceutically acceptable salt, solvate, hydrate, polymorph, co-crystal, tautomer, stereoisomer, isotopically labeled derivative, or prodrug thereof, as described herein, and optionally a pharmaceutically acceptable excipient. In certain embodiments, the pharmaceutical composition of the invention comprises a compound of Formula (A), or a pharmaceutically acceptable salt thereof, and optionally a pharmaceutically acceptable excipient. In certain embodiments, the compound of Formula (A), or a pharmaceutically acceptable salt, solvate, hydrate, polymorph, co-crystal, tautomer, stereoisomer, isotopically labeled derivative, or prodrug thereof, is provided in an effective amount in the pharmaceutical composition. In certain embodiments, the effective amount is a therapeutically effective amount. In certain embodiments, the effective amount is a prophylactically effective amount.

Pharmaceutical compositions described herein can be prepared by any method known in the art of pharmacology. In general, such preparatory methods include the steps of bringing the compound of Formula (A) into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose, and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite (aluminum silicate) and Veegum (magnesium aluminum silicate)), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60), sorbitan tristearate (Span 65), glyceryl monooleate, sorbitan monooleate (Span 80)), polyoxyethylene esters (e.g. polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g. Cremophor™), polyoxyethylene ethers, (e.g. polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F-68, Poloxamer-188, cetrimonium bromide, cetylpyridinium chloride, benzalkonium chloride, docusate sodium, and/or mixtures thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives. In certain embodiments, the preservative is an antioxidant. In other embodiments, the preservative is a chelating agent.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macadamia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor™, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension, or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or (a) fillers or extenders such as starches, lactose, sucrose, glucose, mannitol, and silicic acid, (b) binders such as, for example, carboxymethylcellulose, alginates, gelatin, polyvinylpyrrolidinone, sucrose, and acacia, (c) humectants such as glycerol, (d) disintegrating agents such as agar, calcium carbonate, potato or tapioca starch, alginic acid, certain silicates, and sodium carbonate, (e) solution retarding agents such as paraffin, (f) absorption accelerators such as quaternary ammonium compounds, (g) wetting agents such as, for example, cetyl alcohol and glycerol monostearate, (h) absorbents such as kaolin and bentonite clay, and (i) lubricants such as talc, calcium stearate, magnesium stearate, solid polyethylene glycols, sodium lauryl sulfate, and mixtures thereof. In the case of capsules, tablets, and pills, the dosage form may include a buffering agent.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the art of pharmacology. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredient can be in a micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets, and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a compound of this invention may include ointments, pastes, creams, lotions, gels, powders, solutions, sprays, inhalants and/or patches. Generally, the active ingredient is admixed under sterile conditions with a pharmaceutically acceptable carrier and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate the compound in powder form through the outer layers of the skin to the dermis are suitable. Alternatively or additionally, conventional syringes can be used in the classical mantoux method of intradermal administration.

Formulations suitable for topical administration include, but are not limited to, liquid and/or semi liquid preparations such as liniments, lotions, oil-in-water and/or water-in-oil emulsions such as creams, ointments, and/or pastes, and/or solutions and/or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition of the invention can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self-propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) to as much as 100% (w/w) of the active ingredient, and may comprise one or more of the additional ingredients described herein. A pharmaceutical composition of the invention can be prepared, packaged, and/or sold in a formulation for buccal administration. Such formulations may, for example, be in the form of tablets, and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds of Formula (I) may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional pharmaceutical agents. The compounds or compositions can be administered in combination with additional pharmaceutical agents that improve their bioavailability, reduce and/or modify their metabolism, inhibit their excretion, and/or modify their distribution within the body. It will also be appreciated that the therapy employed may achieve a desired effect for the same disorder, and/or it may achieve different effects.

The compound or composition can be administered concurrently with, prior to, or subsequent to, one or more additional pharmaceutical agents, which may be useful as, e.g., combination therapies. Pharmaceutical agents include therapeutically active agents. Pharmaceutical agents also include prophylactically active agents. Each additional pharmaceutical agent may be administered at a dose and/or on a time schedule determined for that pharmaceutical agent. The additional pharmaceutical agents may also be administered together with each other and/or with the compound or composition described herein in a single dose or administered separately in different doses. The particular combination to employ in a regimen will take into account compatibility of the inventive compound with the additional pharmaceutical agents and/or the desired therapeutic and/or prophylactic effect to be achieved. In general, it is expected that the additional pharmaceutical agents utilized in combination be utilized at levels that do not exceed the levels at which they are utilized individually. In some embodiments, the levels utilized in combination will be lower than those utilized individually.

Exemplary additional pharmaceutical agents include, but are not limited to, anti-proliferative agents, anti-cancer agents, anti-diabetic agents, anti-inflammatory agents, immunosuppressant agents, and a pain-relieving agent. Pharmaceutical agents include small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells.

Also encompassed by the invention are kits (e.g., pharmaceutical packs). The inventive kits may be useful for preventing and/or treating a influenza infection. The kits provided may comprise an inventive pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or compound. In some embodiments, the inventive pharmaceutical composition or compound provided in the container and the second container are combined to form one unit dosage form.

Thus, in one aspect, provided are kits including a first container comprising a compound described herein, or a pharmaceutically acceptable salt, solvate, hydrate, polymorph, co-crystal, tautomer, stereoisomer, isotopically labeled derivative, and prodrug thereof, or a pharmaceutical composition thereof. In certain embodiments, the kit of the invention includes a first container comprising a compound described herein, or a pharmaceutically acceptable salt thereof, or a pharmaceutical composition thereof. In certain embodiments, the kits are useful in preventing and/or treating influenza infection in a subject. In certain embodiments, the kits further include instructions for administering the compound, or a pharmaceutically acceptable salt, solvate, hydrate, polymorph, co-crystal, tautomer, stereoisomer, isotopically labeled derivative, and prodrug thereof, or a pharmaceutical composition thereof, to a subject to prevent and/or treat an influenza infection.

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. Likewise, the invention is not limited to various embodiments given in this specification.

Unless otherwise defined, all technical and scientific terms used herein have the same meaning as commonly understood by one of ordinary skill in the art to which this invention pertains. In the case of conflict, the present document, including definitions will control.

As used herein, the term therapeutic drug is intended to define a subclass of drugs which have therapeutic (and not just prophylactic) properties. Such drugs may have prophylactic activity in addition to therapeutic potential. They find application in the treatment of existing diseases, infections or conditions.

As used herein, the term co-administration, as used in the context of the administration of the various components of the compositions, vaccines etc. of the invention, is intended to cover the sequential, concurrent or separate administration of the referenced components. Concurrent administration therefore covers the case where the referenced components are physically mixed prior to administration. Sequential administration covers circumstances in which the referenced components are administered separately with some degree of temporal separation (typically from several minutes to several hours, although in some embodiments the administration of the co-administered components may be separated by a period of one or more days).

"Synergism" may be measured by combination index (CI). The combination index method was described by Chou and Talalay. (Chou, T.-C. The median-effect principle and the combination index for quantitation of synergism and antagonism, p. 61-102. In T.-C. Chou and D. C. Rideout (ed.), Synergism and antagonism in chemotherapy. Academic Press, San Diego, Calif. (1991); Chou, T.-C., and P. Talalay. Quantitative analysis of dose-effect relationships: the combined effects of multiple drugs on enzyme inhibitors. Adv. Enzyme Regul. 22:27-55 (1984)). A CI value of 0.90 or less is considered synergistic, with values of 0.85 being moderately synergistic and values below 0.70 being significantly synergistic. CI values of 0.90 to 1.10 are considered to be nearly additive and higher values are antagonistic. Table 1. Synergism/antagonism as a function of CI values

TABLE 1

Synergism/antagonism as a function of CI values

| CI Value | Interpretation |
| --- | --- |
| >10 | Very strong antagonism |
| 3.3-10 | Strong antagonism |
| 1.45-3.3 | Antagonism |
| 1.2-1.45 | Moderate antagonism |
| 1.1-1.2 | Slight antagonism |
| 0.9-1.1 | Additive |
| 0.85-0.9 | Slight synergism |
| 0.7-0.85 | Moderate synergism |
| 0.3-0.7 | Synergism |
| 0.1-0.3 | Strong synergism |
| <0.1 | Very strong synergism |

It is noted that determination of synergy may be affected by biological variability, dosage, experimental conditions (temperature, pH, oxygen tension, etc.), treatment schedule and combination ratio.

Novel bifunctional, dual-targeted conjugates of zanamivir with immuno-modulating drugs that are expected to yield greater synergistic effect than the sum of single components. (Meunier, B. Acc. Chem. Res. 2008, 41, 69) FIG. 1 shows the putative working mechanism of such dual-targeted zanamivir conjugates. Therapy with designed multiple ligands (DMLs) may have advantage of better pharmacological effect and improved safety over combination of individual drugs in treatment of multi-genic and multi-target diseases such as cancer, diabetes and infectious diseases. (Morphy, R. et al. Drug Discov. Today 2004, 9, 641; Morphy, R. & Rankovic, Z. J. Med. Chem. 2006, 49, 4961; Zimmermann, G. R. et al. Drug Discov. Today 2007, 12, 34).

Figure 2:
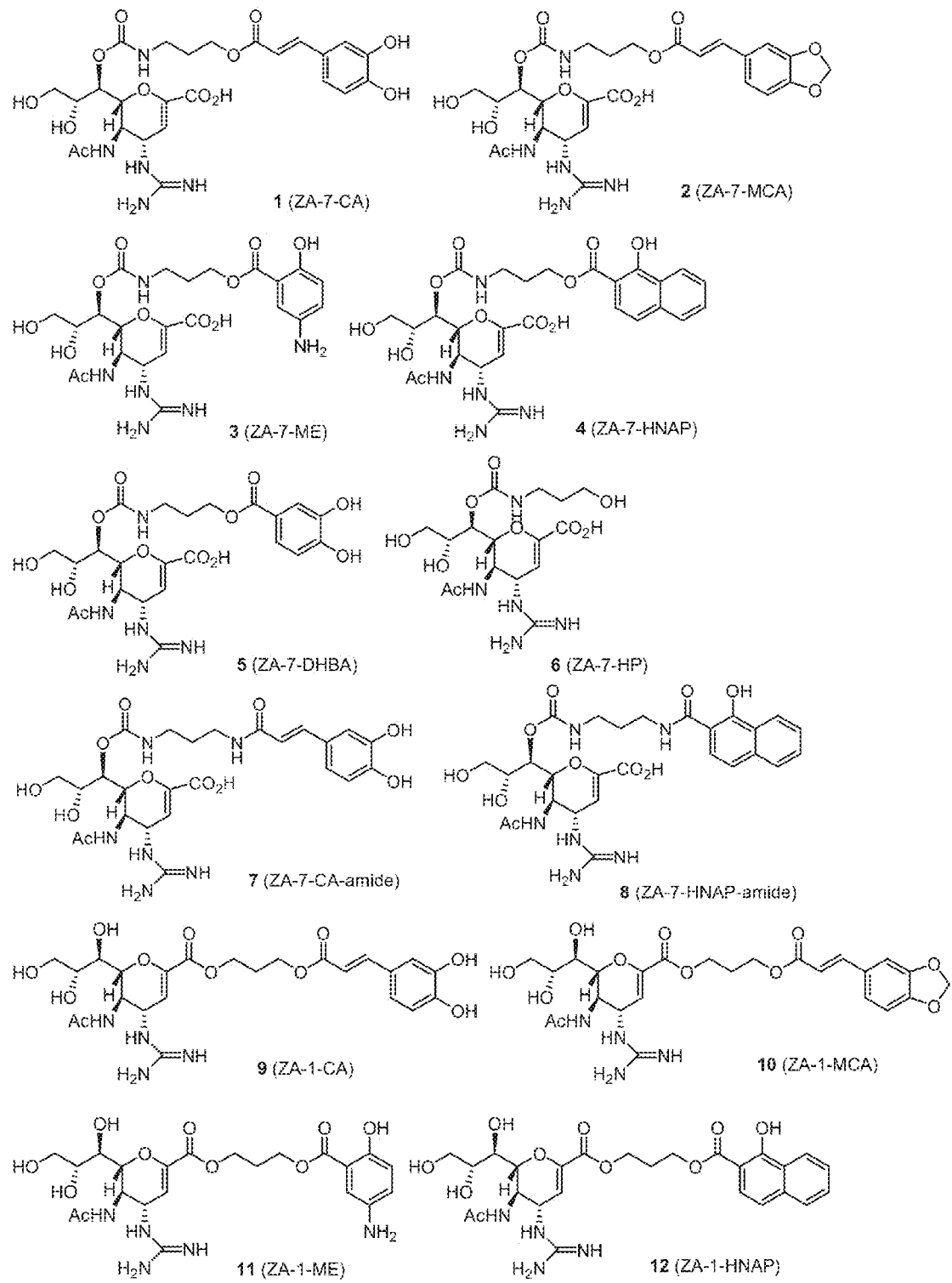
FIG. 2. Chemical structures of exemplary anti-influenza conjugate drugs
Figure 2:
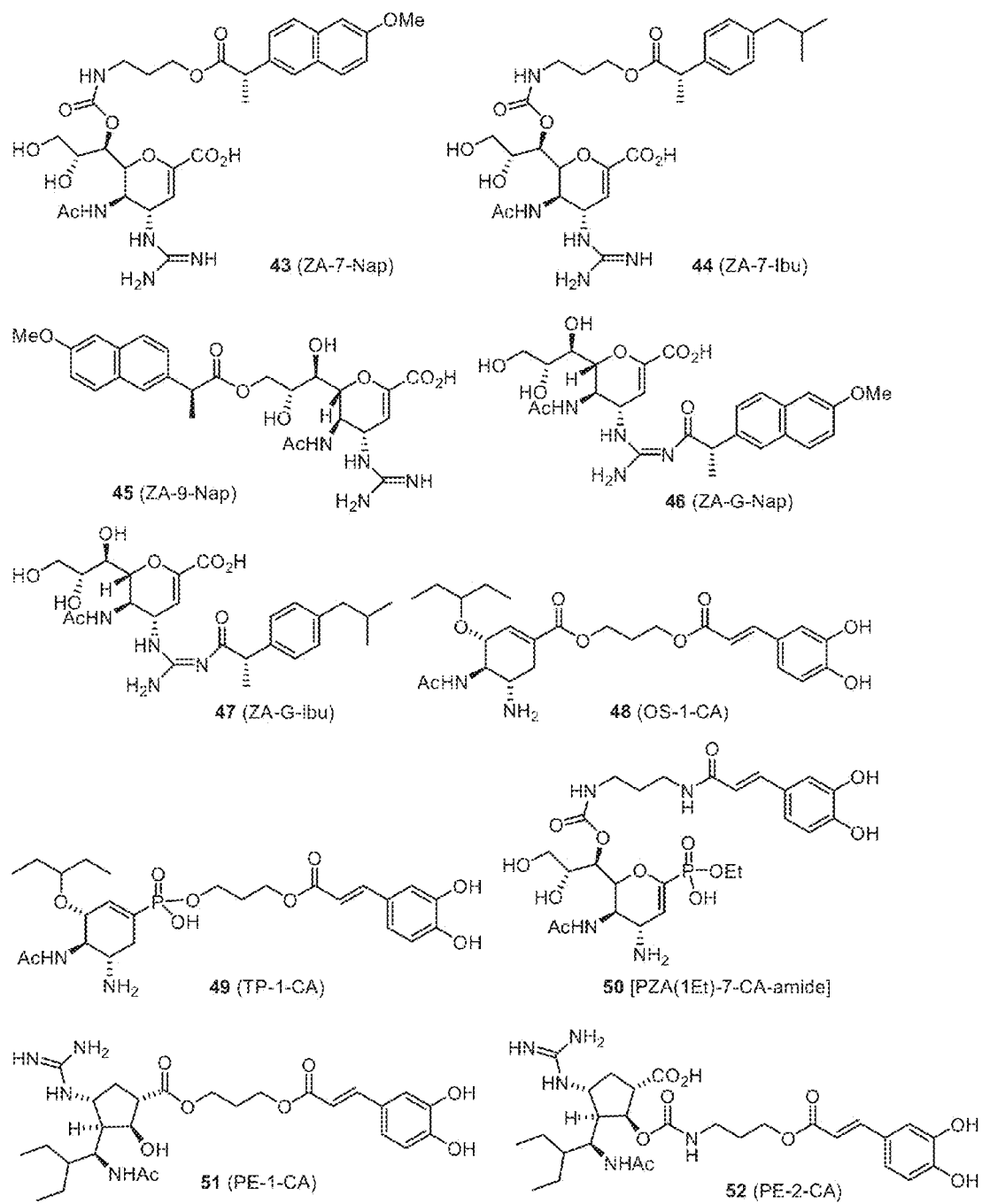

Dual-targeted anti-influenza drugs according to the invention disclosed herein are designed for virus inactivation and cytokine suppression (FIG. 1). Due to high affinity of ZA with NA, the ZA conjugates would be brought to the influenza infected tissues allowing the anti-inflammatory moiety of the conjugates to suppress the induction of proinflammatory cytokines in a highly effective manner. Three zanamivir conjugates ZA-7-CA (1), ZA-7-ME (3) and ZA-7-CA-amido (7) that have the linkage at the C-7 position of zanamivir to caffeic acid (CA) or mesalazine (ME) via ester or amide bonds (FIG. 2) are provided. For comparison, other zanamivir C-7 conjugates ZA-7-MCA (2), ZA-7-HNAP (4), ZA-7-DHBA (5), ZA-7-HP (6) and ZA-7-HNAP-amido (8) as well as zanamivir C-1 conjugates ZA-1-CA (9), ZA-1-MCA (10), ZA-1-ME (11) and ZA-1-HNAP (12) are provided. According to the structural analysis of the ZA-NA complex, (Varghese, J. N. et al. Protein Sci. 1995, 4, 1081) the 7-OH group of ZA exposes to water and makes no direct interaction with the active site of influenza NA protein.

It has been shown that the ZA derivatives with modification at the C7 hydroxyl group retain good NA inhibitory activity. (Andrews, D. M. et al. Eur. J. Med. Chem. 1999, 34, 563; Honda, T. et al. Bioorg. Med. Chem. Lett. 2002, 12, 1921; Honda, T. et al. Bioorg. Med. Chem. Lett. 2002, 12, 1925) Thus, the ZA-7-conjugates 1-8 with improved lipophilicity are expected to exhibit good anti-influenza activity. The ZA-1-conjugates 9-12 with ester linkage would undergo enzymatic hydrolysis in body to give the active ZA drug, so that 9-12 may act as long-acting neuraminidase inhibitors. (Liu, Z.-y. et al. Bioorg. Med. Chem. Lett. 2007, 17, 4851; Yamashita, M. et al. Antimicrob. Agents Chemother. 2009, 53, 186; Kubo, S. et al. Antimicrob. Agents Chemother. 2010, 54, 1256; Ishizuka, H. et al. J. Clin. Pharmacol. 2010, 50, 1319)

Caffeic acid (CA) and its ester derivatives are known to exhibit anti-inflammatory effect in addition to other biological activities. (Michaluart, P. et al. Cancer Res. 1999, 59, 2347; Jung, W. K. et al. Int. J. Biochem. Cell Biol. 2008, 40, 2572; Shin, K.-M. et al. Biochem. Pharmacol. 2004, 68, 2327) Caffeic esters can suppress NF-κB and its downstream mediators, iNOS and COX-2, by inhibiting the formation of NF-κB with DNA complex. (Natarajan, K. et al. Proc. Natl. Acad. Sci. USA 1996, 93, 9090; Chiang, Y. M. et al. Brit. J. Pharmacol. 2005, 146, 352) Mesalazine (ME) is an anti-inflammatory drug used to treat ulcerative colitis and Crohn's disease, which are two major human chronic inflammatory bowel diseases. (Kaiser, G. C. t al. Gastroenterology 1999, 116, 602; Kruis, W. et al. Gut 2001, 49, 783; Sandborn, W. J. et al. Aliment. Pharmacol. Ther. 2007, 26, 987) Mesalazine is also known as an agonist of peroxisome proliferator-activator receptor (PPAR-γ) for induction of anti-inflammatory effects. (Rousseaux, C. et al. J. Exp. Med. 2005, 201, 1205)

Chemical Synthesis of Anti-Influenza Conjugates

Figure 3:
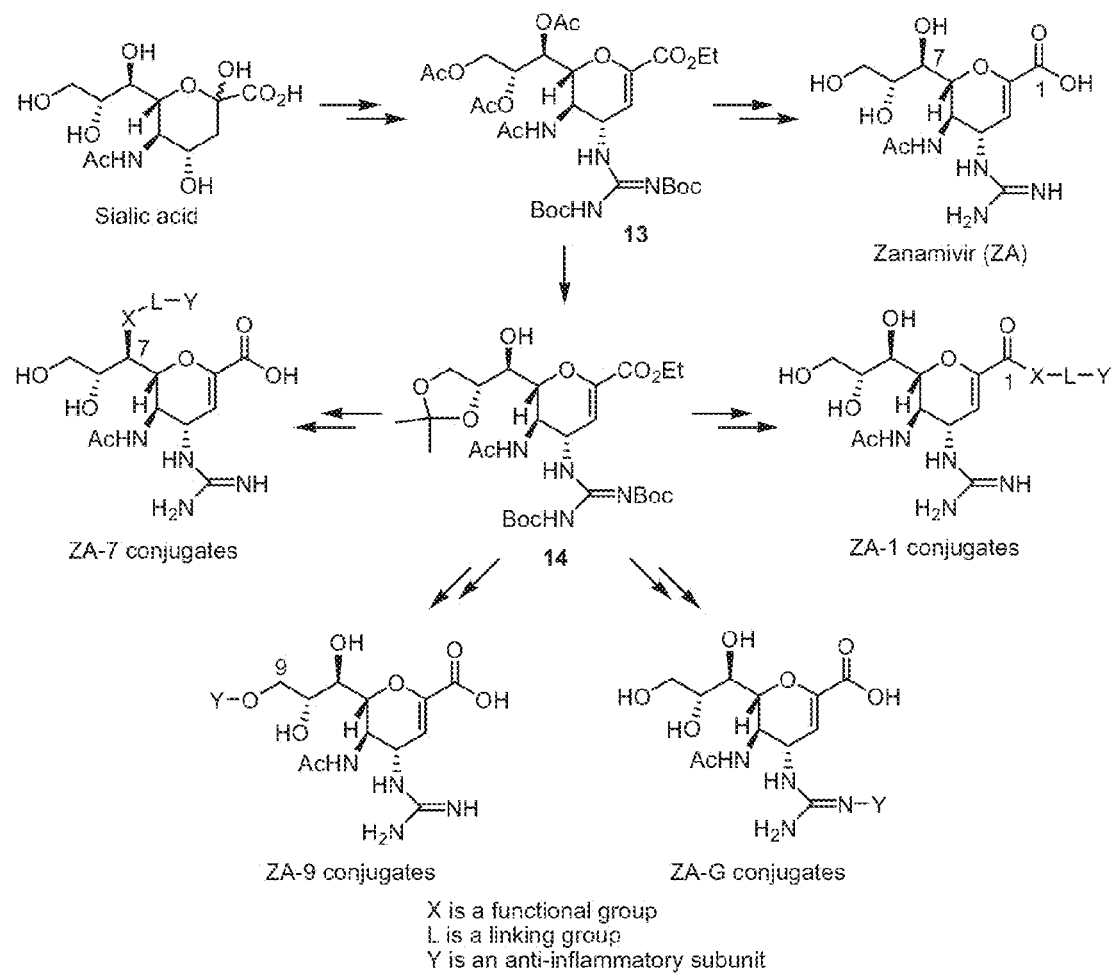
FIG. 3. Synthetic design for the exemplary conjugate compounds of zanamivir with anti-inflammatory agent at 1-, 7-, 9- or guanidine (G)-positions.

FIG. 3 shows the general synthetic strategy for zanamivir conjugates 1-12. Sialic acid was converted to ethyl ester derivative 13 by slight modification of the reported method for the corresponding methyl ester 13a. (Chandler, M. et al. J. Chem. Soc., Perkin Trans. 1 1995, 1173) Compound 13 was then transformed to 14, which has a free hydroxyl group readily for further linkage with appropriate anti-inflammation drugs to form zanamivir-7-conjugates, such as compounds 1-8. Alternatively, ester 14 was hydrolyzed to give the corresponding acid, which could undergo condensation reactions with appropriate alcohols to give zanamivir-1-conjugates, such as compounds 9-12. The synthetic procedures for these conjugates are shown in FIGS. 4-15, FIG. 19 and FIG. 20. Compound 14 also served as the common intermediate for the synthesis of zanamivir conjugates containing anti-inflammatory agents at the 9- or guanidine positions, such as those shown in FIGS. 21-23.

Figure 4:
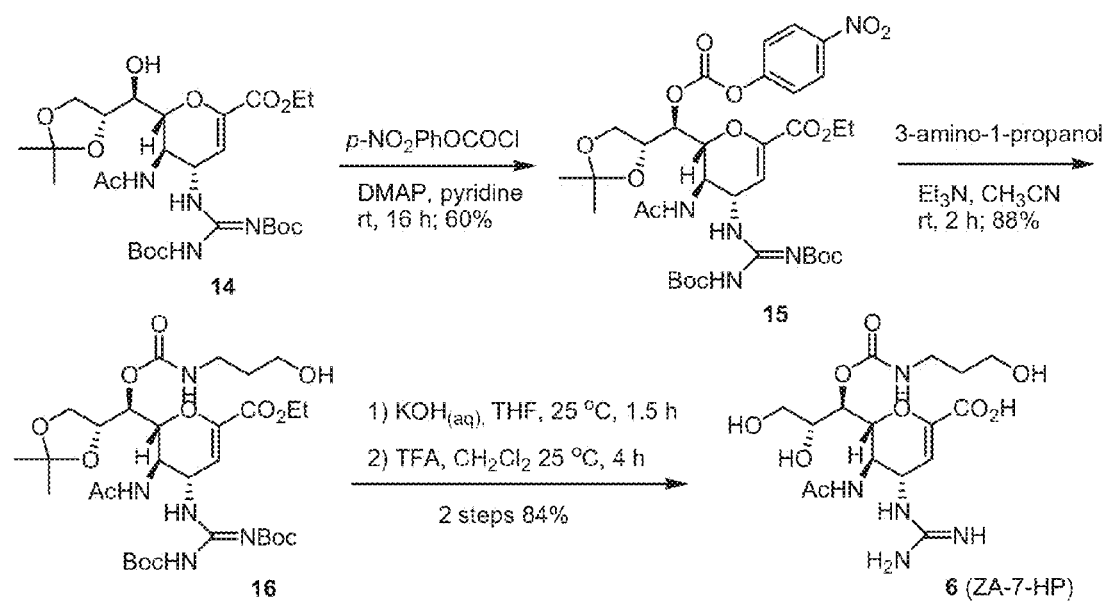
FIG. 4. Synthesis of ZA-7-H

Compound 14 was treated with 4-nitrophenyl chloroformate and DMAP in dry pyridine to afford an active carbonate 15, (Ying, L. & Gervay-Hague, J. ChemBioChem 2005, 6, 1857; Wen, W.-H. et al. J. Med. Chem. 2009, 52, 4903) which was subsequently reacted with 3-amino-1-propanol to give a carbamate derivative 16 (FIG. 4). All the protecting groups in 16 were removed to afford the ZA-7-HP conjugate 6 bearing an N-(3-hydroxypropyl)carmamate moiety at the C-7 position of ZA.

Figure 5:
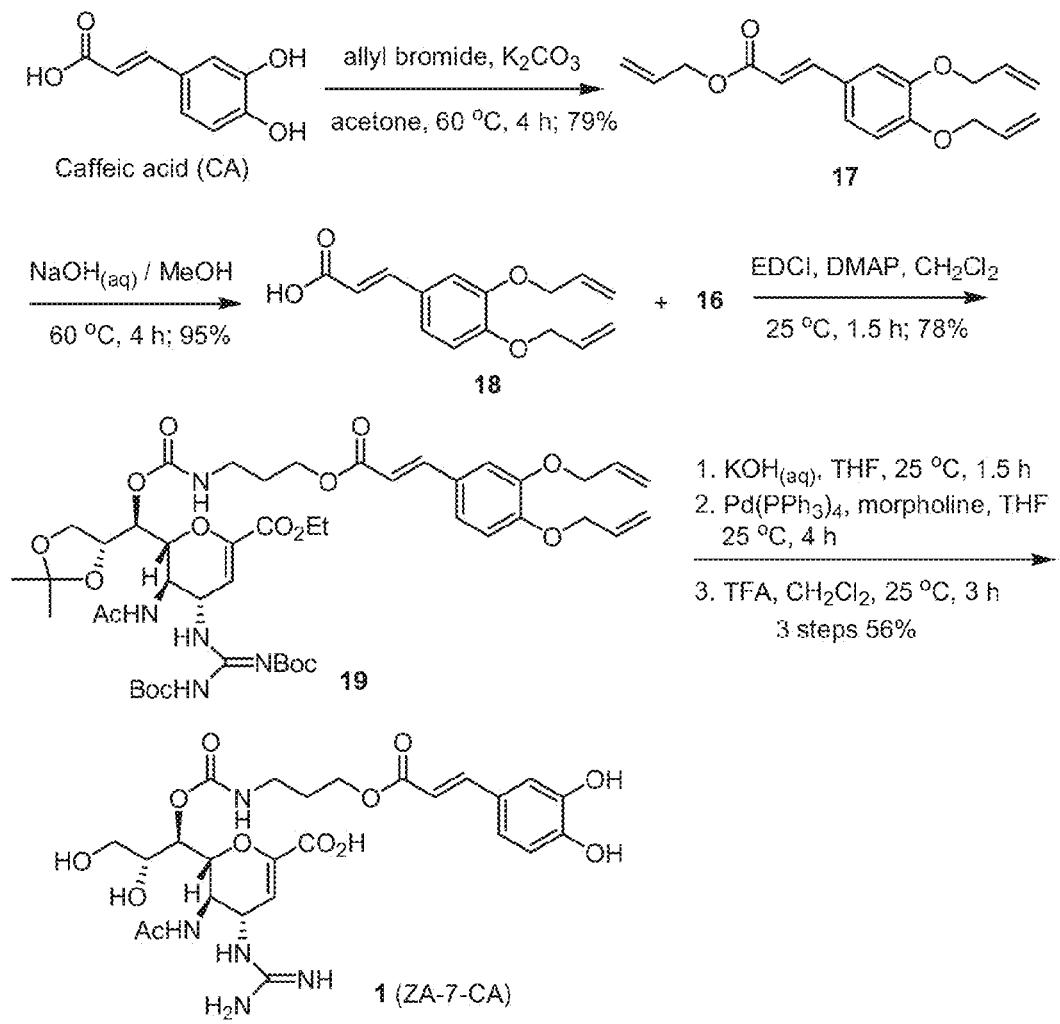

The condensation reaction of 16 with the bis-allyl ether of caffeic acid (18) was carried out by using 1-ethyl-3-(3-dimethylaminopropyl)carbodiimide (EDCI) and 4-dimethylaminopyridine (DMAP) as the promoters to yield the desired coupling product 19 with an ester linkage (FIG. 5). Compound 19 was treated with KOH (1 M aqueous solution) at room temperature for a selective saponification of the ethyl ester at C-1 without cleavage of the ester linkage between zanamivir and the caffeic moiety. Palladium-catalyzed deallylation was effected, and the subsequent treatment with trifluoroacetic acid (TFA) removed the acetonide and tert-butoxycarbonyl (Boc) protecting groups to afford the ZA-7-CA conjugate (1).

By similar procedures, the coupling reactions of 16 with 3,4-(methylenedioxy)cinnamic acid (MCA), mesalazine allyl ether (22), 1-hydroxy-2-naphthoic acid (HNAP) allyl ether (25) and 3,4-dihydroxybenzoic acid (DHBA) bis-allyl ether (28) gave, respectively, compounds 20, 23, 26 and 29, which were elaborated to the ZA-7-MCA (2), ZA-7-ME (3), ZA-7-HNAP (4) and ZA-7-DHBA (5) conjugates after removal of the protecting groups (FIGS. 6-9).

Figure 10:
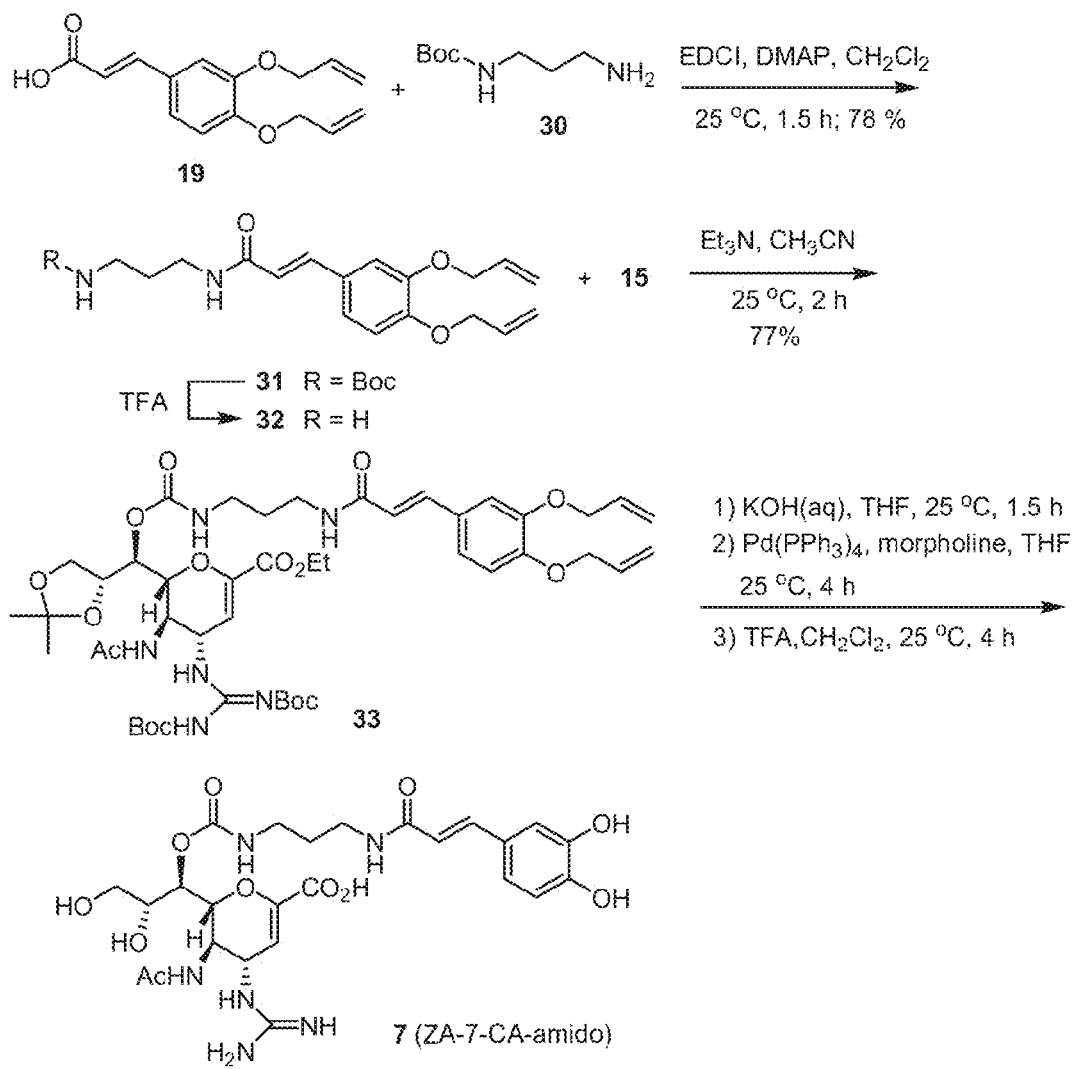
Figure 11:
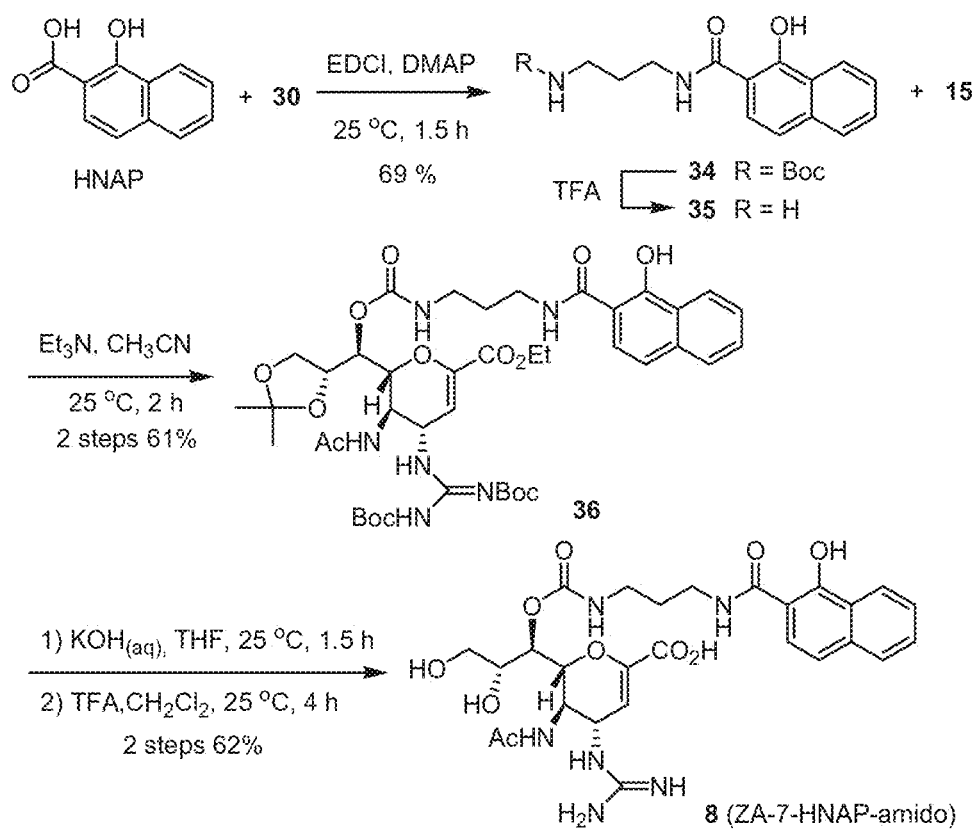

The CA derivative 32 bearing a terminal amino group was prepared, and then reacted with the activated carbonate 15 to give the ZA-7-CA-amide conjugate (7) after removal of the protecting groups (FIG. 10). The ZA-7-HNAP-amido conjugate (8) was similarly synthesized via the coupling reaction of carbonate 15 with the amine-annexed HNAP derivative 35, followed by removal of protecting groups (FIG. 11). The amide linkage in ZA-7-CA-amide and ZA-7-HNAP-amide conjugates is considered more stable than the enzymatically cleavable ester linkage in the conjugates 1-5.

To prepare ZA-1-conjugates, acid 37 was treated with KOH (1 equiv) to afford the carboxylate potassium salt, which reacted with 3-iodo-1-propanol to provide ester 38. The coupling reactions of 38 with CA allyl ether 18, MCA, ME allyl ether 22 and HNAP allyl ether 25 produced the ZA-1-CA (9), ZA-1-MCA (10), ZA-1-ME (11) and ZA-1-HNAP (12) conjugates, respectively, after removal of the protecting groups (FIGS. 12-15).

Figure 19:
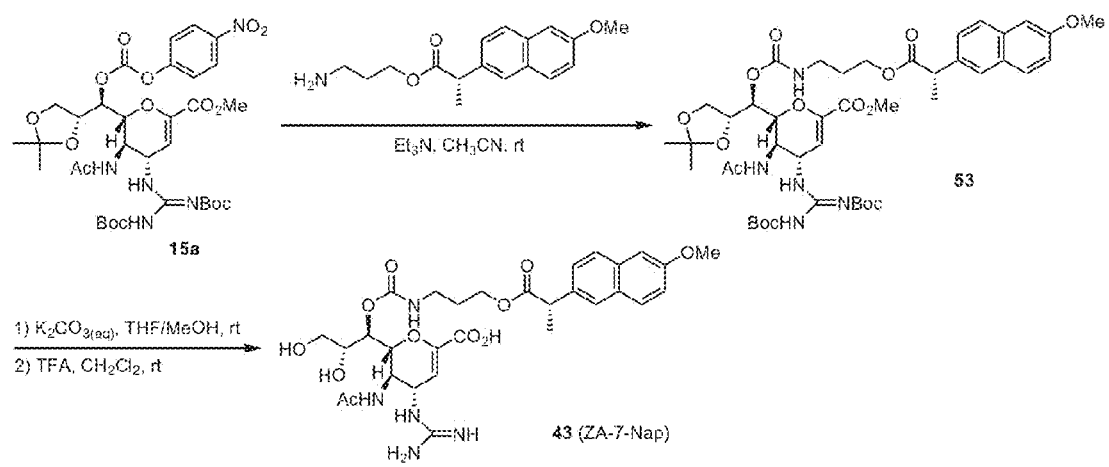
Figure 20:
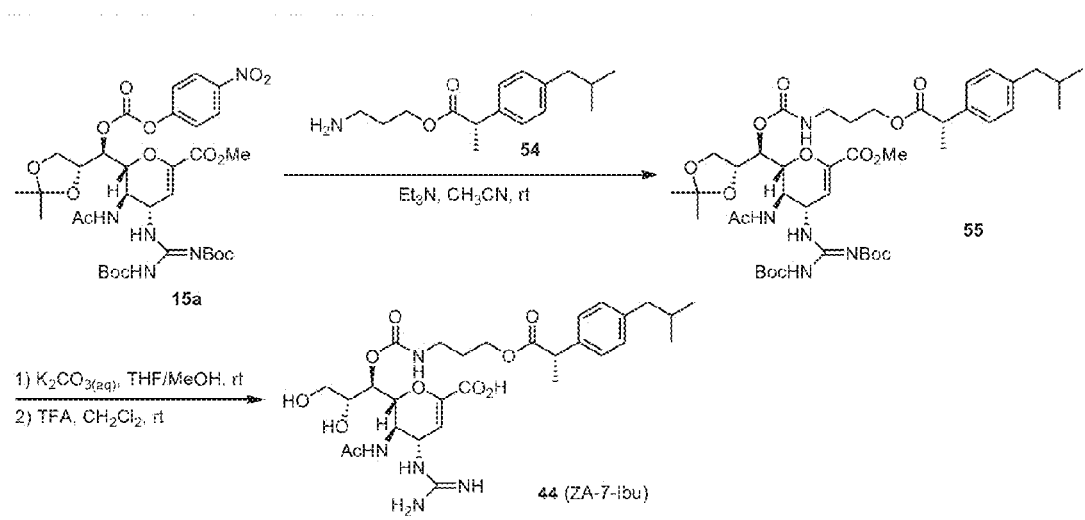

FIGS. 19 and 20 show the syntheses of ZA-7-Nap conjugate (43) and ZA-7-Ibu (44). Methyl ester 13a, a counterpart of the ethyl ester 13, was prepared according to the reported procedure (Chandler, M. et al. *J. Chem. Soc., Perkin Trans.* 11995, 1173). Saponification of 13a with NaOMe in methanol, followed by acid-catalyzed acetalization with 2,2-dimethoxypropane afforded compound 14a, which was treated with 4-nitrophenyl chloroformate and 4-dimethylaminopyridine in anhydrous pyridine to give carbonate 15a. The coupling reaction of 15a with naproxen 3-aminopropyl ester in the presence of 1-ethyl-3-(3-dimethylaminopropyl)carbodiimide (EDCI) and 4-dimethylaminopyridine (DMAP) gave ZA-7-Nap conjugate 43 after removal of the acetal and t-Boc protecting groups. By a similar procedure, the coupling reaction of 15a with ibuprofen 3-aminopropyl ester was carried out, and the protecting groups were removed to afford ZA-7-Ibu conjugate 44.

Figure 21:
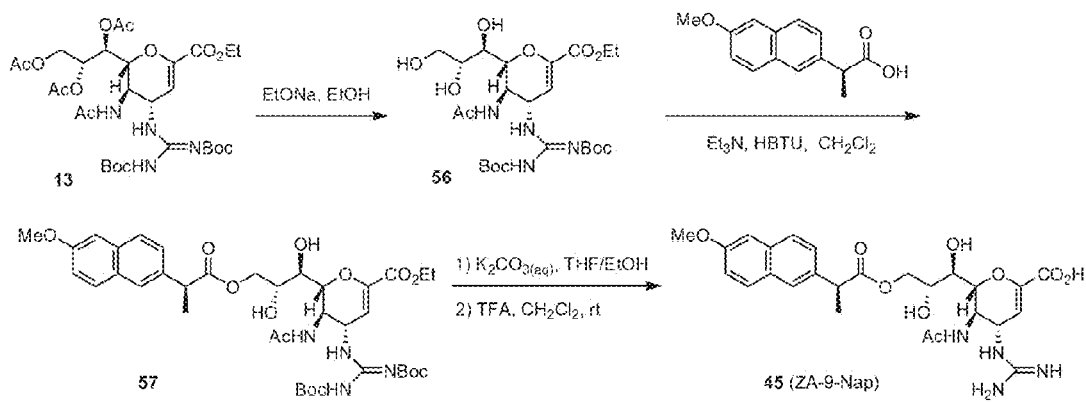

To synthesize zanamivir conjugates at 9-position, the acetyl groups compound 13 was selectively hydrolyzed to give a triol compound 56 (FIG. 21). The coupling reaction of naproxen with 56 occurred regioselectively at the primary alcohol, giving compound 57. The ethyl ester in 57 was selectively saponified under mild alkaline condition, and ZA-9-Nap conjugate 45 was obtained after removal of the t-Boc groups.

Figure 22:
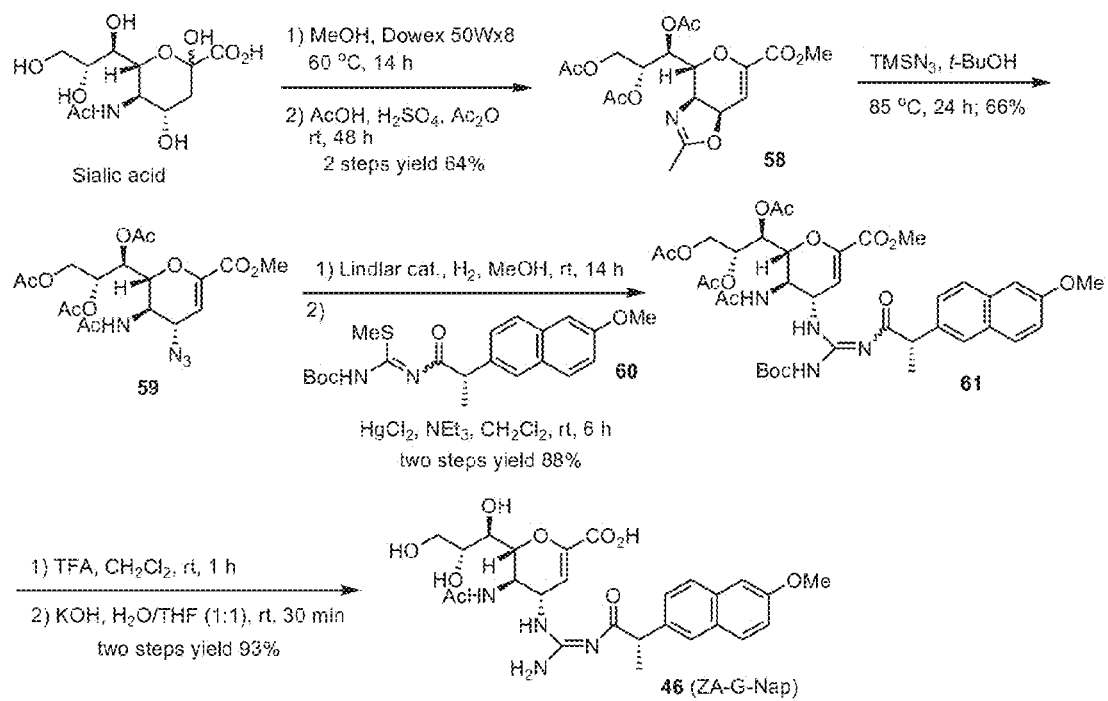
Figure 23:
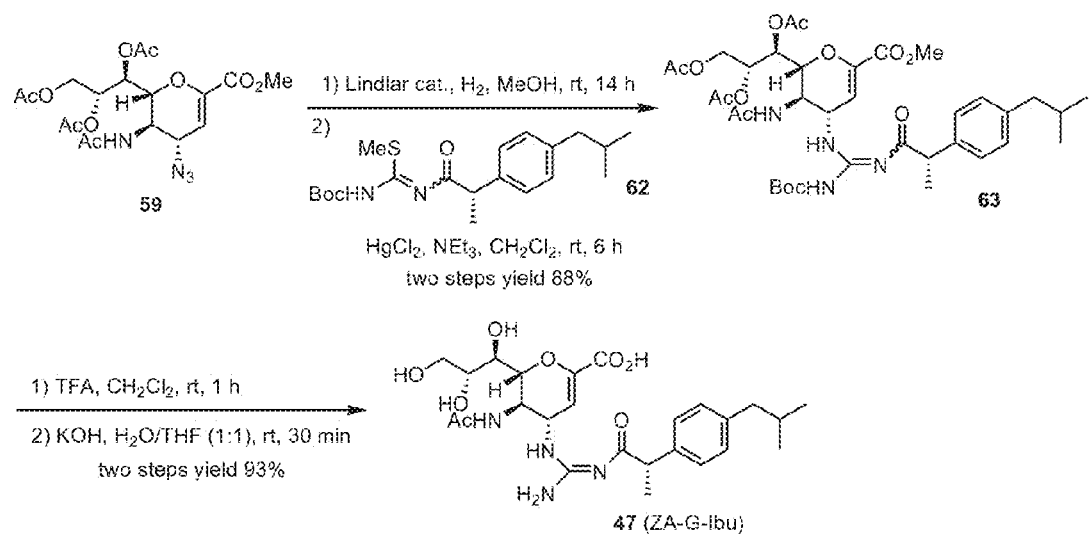

FIGS. 22 and 23 show the syntheses of zanamivir conjugates at the guanidine position. For example, naproxen was condensed with tert-butyl[imino(methylthio)methyl] carbamate to give compound 60. The reaction of 60 with the amine obtained from hydrogenation of azide 59 in the presence of $HgCl_2$ and $Et_3N$ was carried out to give compound 60. Removal the t-Boc group and the subsequent hydrolysis thus yield ZA-G-Nap 46. By a similar procedure using ibuprofen as the starting material, ZA-G-Ibu conjugate 47 was prepared (FIG. 23).

Figure 24:
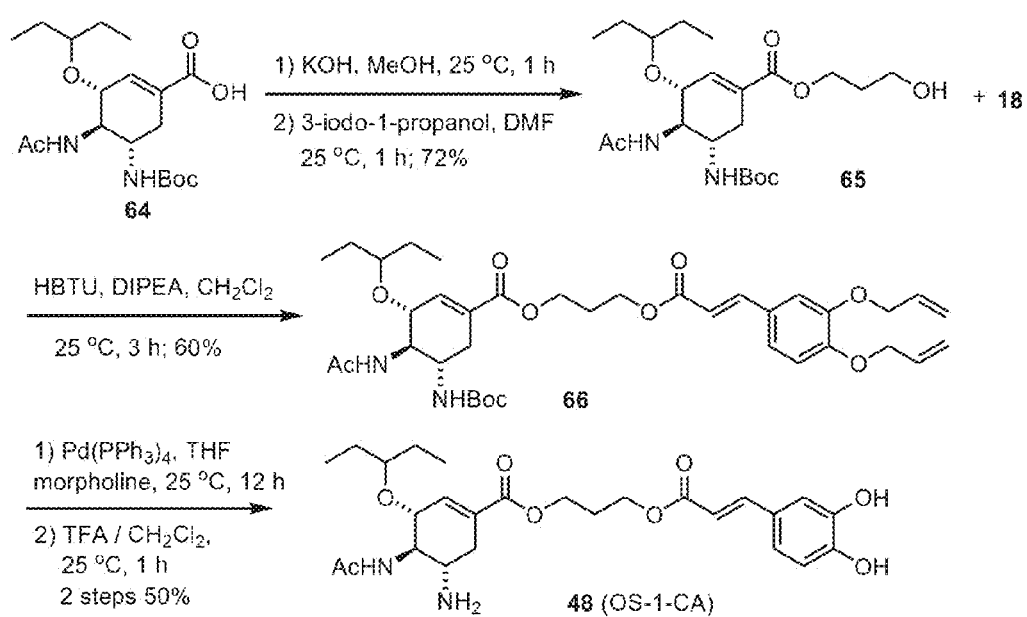

FIG. 24 shows the synthesis of oseltamivir-caffeate conjugate OS-1-CA (48). Oseltamivir N-Boc derivative 64 was treated with 3-iodo-1-propanol in alkaline conditions to afford ester 65, which underwent a condensation reaction with bis-allyl ether of caffeic acid (18) to give the coupling product 66. The desired OS-1-CA conjugate (48) was thus obtained by removal of the allyl and Boc protecting groups.

Figure 25:
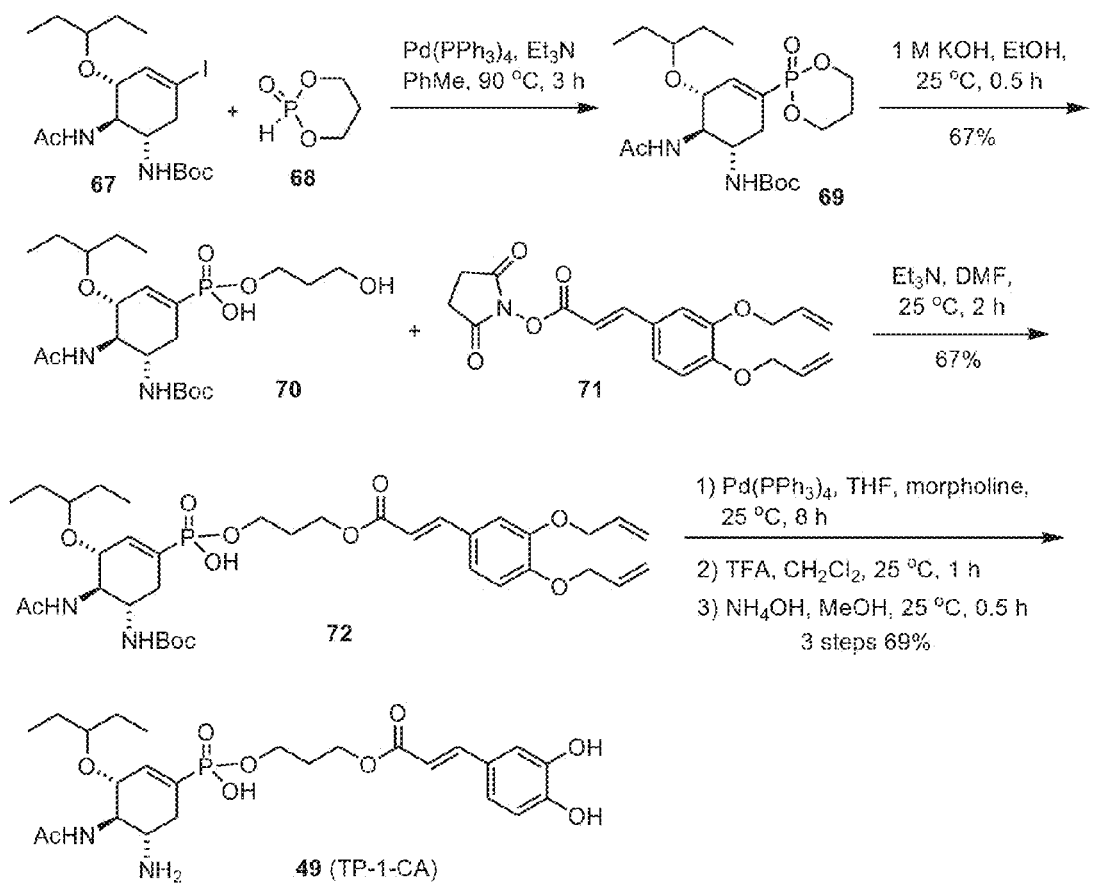

FIG. 25 shows the synthesis of tamiphosphor-caffeate conjugate TP-1-CA (49). The iodine compound 67 was prepared as previously described. (Shie, J.-J. et al. *Angew. Chem. Int. Ed.* 2008, 47, 5788) The reaction of 67 with 2-phosphora-1,3-dioxin-2-one (68) by the catalysis of palladium gave the phosphonate product 69. Saponification of 69 afforded the phosphonate monoester 70, which reacted with the activated caffeic acid O-Su ester (71) to give the coupling product 72. Removal of the allyl and Boc protecting groups in 72 gave the desired TP-1-CA conjugate 49.

Figure 26:
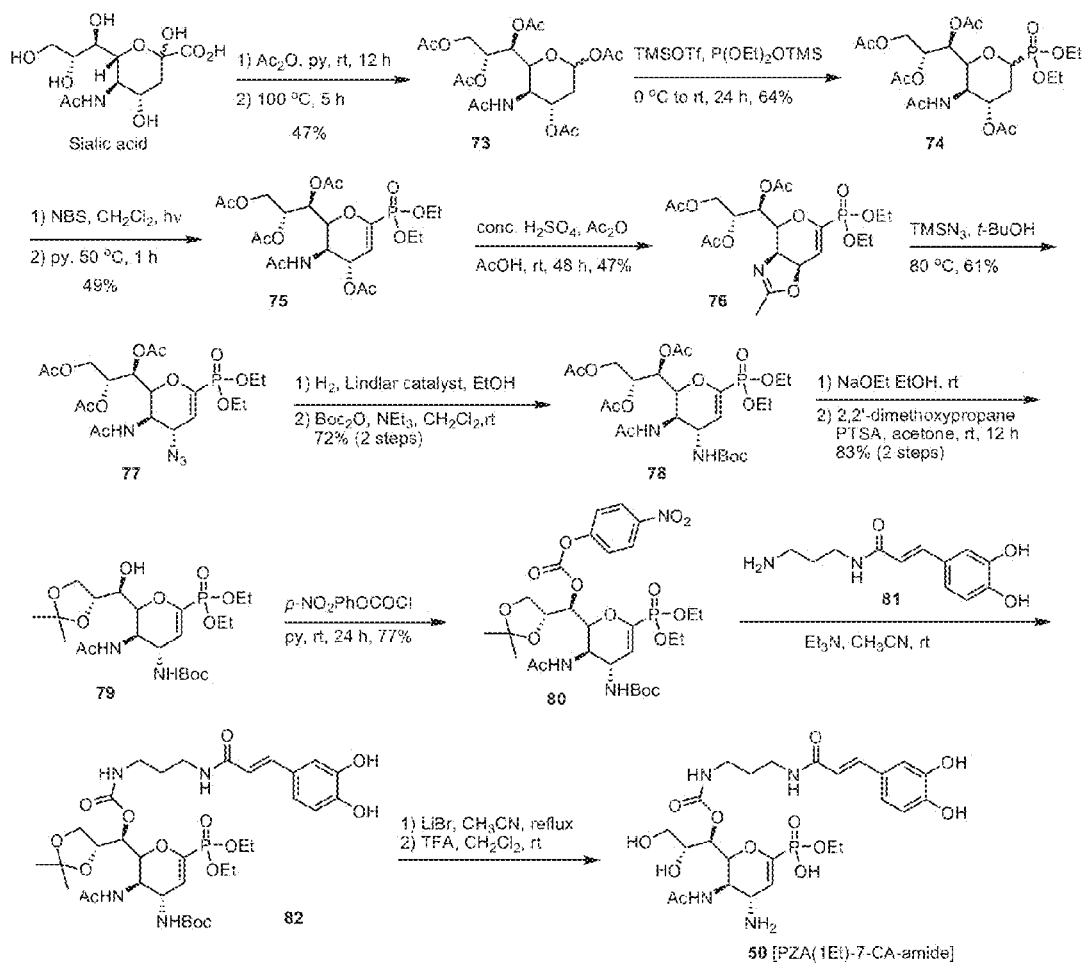

FIG. 26 shows the synthesis of the conjugate 50 derived from phosphono-zanamivir monoethyl ester and caffeic acid. According to the reported procedure, (Horn, E. J. et al. *Carbohydr. Res.* 2008, 343, 936) sialic acid was treated with acetic anhydride in pyridine to afford the peracetylation product, which was heated at 100° C. to induce decarboxylation to furnish compound 73. Using trimethylsilyl diethyl phosphite as an appropriate nucleophile, the substitution reaction of 73 was carried out by the promotion of trimethylsilyl trifluoromethylsulfonate (TMSOTf) to give the phosphonate compound 74 as a mixture of α and β anomers (2:3). These anomers were separated by chromatography and characterized by NMR spectral analyses. For synthetic purpose, the anomeric mixture 74 without further separation was treated with N-bromosuccinimide (NBS) under photochemical conditions to give an α-bromination compound, which was subsequently treated with pyridine to give the conjugated phosphonate 75. Compound 75 was converted into the oxazoline 76 in the presence of acetic anhydride, acetic acid and concentrated $H_2SO_4$. The regio- and stereo-selective ring-opening reaction of oxazoline 76 with azido-trimethylsilane was carried out to afford the azido compound 77. After catalytic hydrogenation, the amine intermediate was protected as the t-Boc derivative 78. Saponification of 78 gave a triol product, which reacted with 2,2'-dimethoxypropane to give acetal 79. The free hydroxyl group at the C-7 position was activated as the p-nitrophenyl carbonate 80, which reacted with the amine 81 derived from caffeic acid to afford carbamate 82. On refluxing with LiBr, the diethyl phosphonate was converted to monoethyl phosphonate. The subsequent treatment with TFA thus culminated the synthesis of PZA(1Et)-7-CA-amide conjugate 50.

Figure 27:
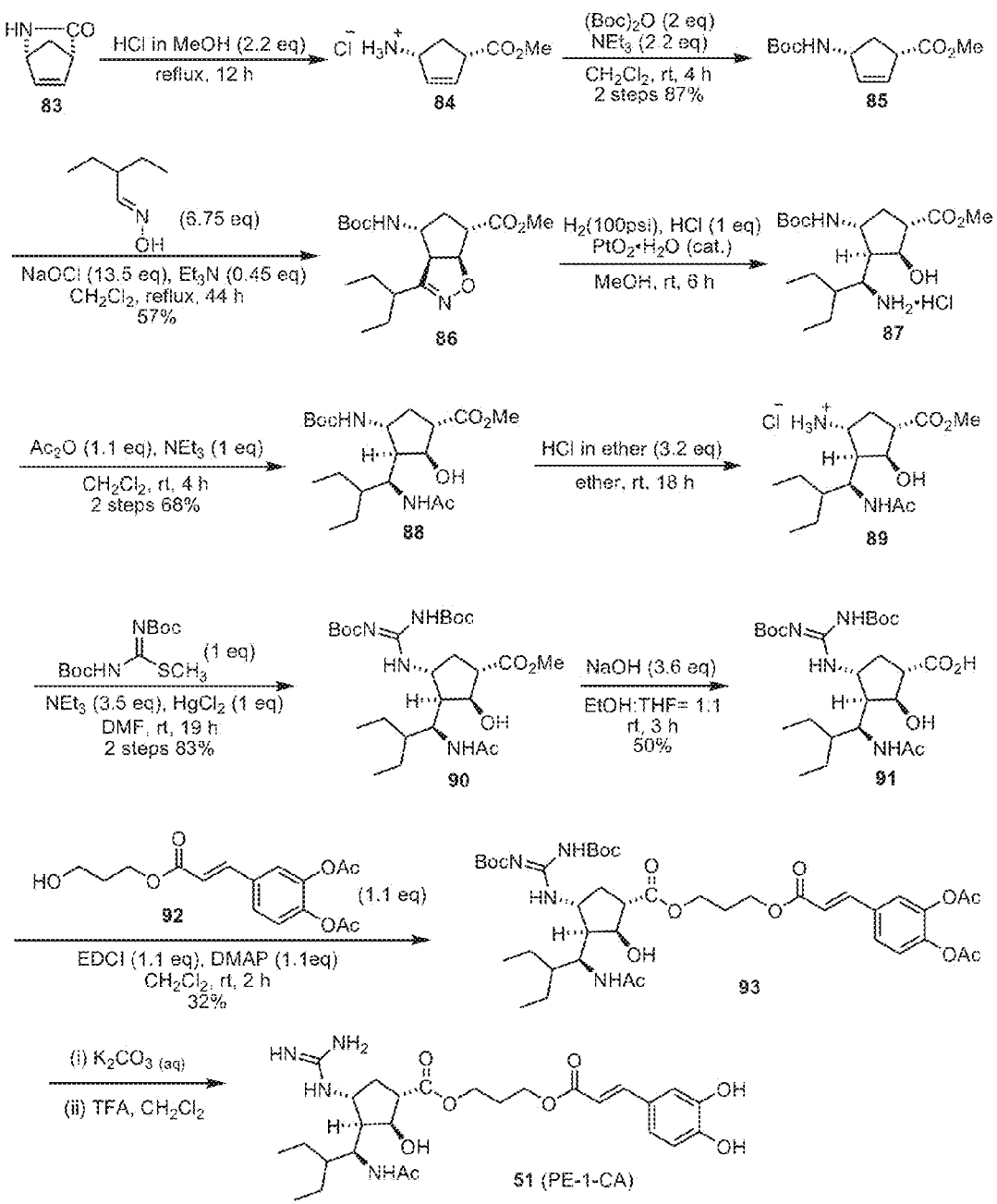

FIG. 27 shows the synthesis of peramivir-caffeate conjugate PE-1-CA (51). According to the reported method, (Mineno, T.; Miller, M. J. *J. Org. Chem.* 2003, 68, 6591.) (1R,4S)-2-azabicyclo[2.2.1]hept-5-en-3-one 83 was treated with HCl in MeOH to give 4-aminocyclopent-2-ene carboxylate 84. The amino group was protected to give 85, which was subject to 1,3-diploar cycloaddition with the nitrile oxide generated from 2-ethylbutanal oxime, giving compound 86. After hydrogenolysis, the newly formed amino group was subject to acetylation. The t-Boc group was removed in acidic conditions, and then treated with 1,3-bis(tert-butoxycarbony)-2-methyl-2-thiopseudourea in the presence of $HgCl_2$ to give compound 90. After saponification, the resulting carboxylic acid underwent condensation reaction with the caffeic acid derivative 92 to give compound 93. Saponification of 93 in mild alkaline conditions, followed by removal of t-Boc group with TFA, gave PE-1-CA (51).

Figure 28:
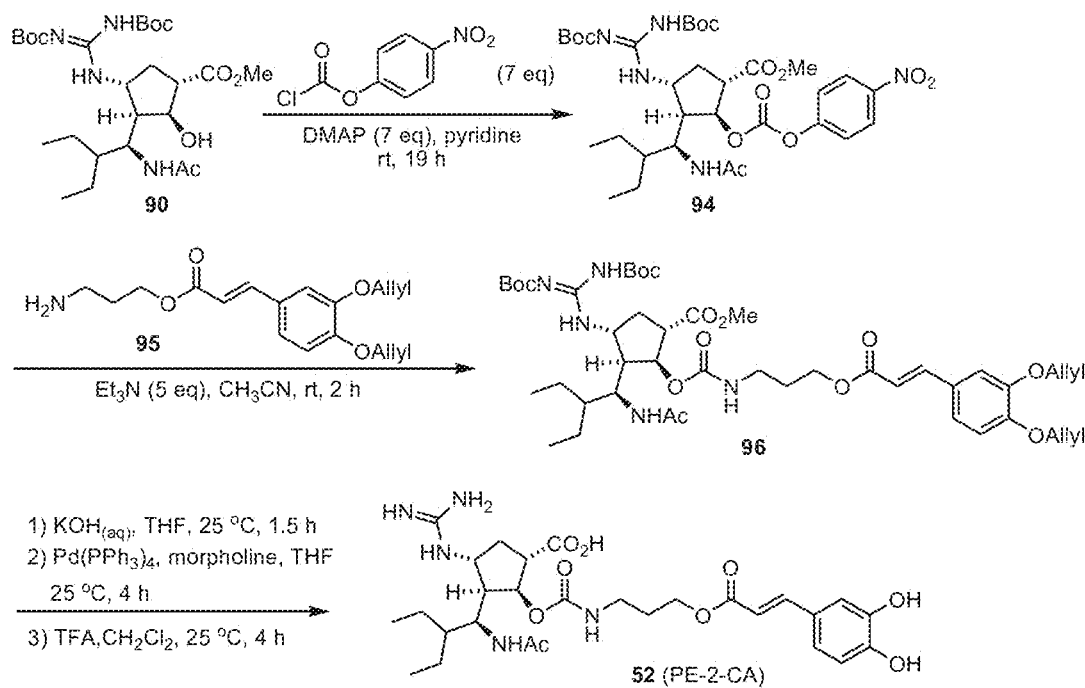

FIG. 28 shows the synthesis of peramivir-caffeate conjugate PE-2-CA (52). Compound 90 was activated with p-nitrophenyl chloroformate, giving a carbonate intermediate, and reacted with the caffeic acid derivative 95 to afford carbamate 96. The desired product PE-2-CA (52) was thus obtained after saponification of the methyl ester and removal of the allyl and t-Boc protecting groups.

Bioactivity of Conjugates

Inhibition of Influenza Virus Neuraminidase A/WSN/1933 (H1N1)

The NA inhibition activities of zanamivir and its conjugates 1-12 were evaluated using a fluorogenic substrate 2'-(4-methyl-umbelliferyl)-α-D-N-acetylneuraminic acid (MUNANA) against influenza A/WSN/1933 (H1N1) viruses (Table 1). The ZA-7-conjugates 1-8 exibited NA inhibitory activities with $IC_{50}$ values in nanomolar range comparable to ZA. In contrast, the ZA-1-conjugates 9-12 lost NA inhibitory activity, supporting that the C-1 group of carboxylic acid played an essential role in electrostatic interactions with the three arginine (Arg118, Arg292 and Arg371) residues in the active site of NA. (Chong, A. K. J. et al. *Eur. J. Biochem.* 1992, 207, 335; von Itzstein, M. et al. *Nature* 1993, 363, 418; Taylor, N. R. & von Itzstein, M. *J. Med. Chem.* 1994, 37, 616; Lew, W. et al. *Curr. Med. Chem.* 2000, 7, 663; Russell, R. J. et al. *Nature* 2006, 443, 45) The anti-inflammation agents CA, MCA, and ME alone did not exhibit any NA inhibitory activity.

Anti-Influenza Activity

The cytopathic prevention assays in Madin-Darby canine kidney (MDCK) cells were conducted to evaluate the anti-influenza activity. To our anticipation, the ZA-7-conjugates were potent inhibitors against human H1N1 virus (Table 2). The ZA-1-conjugates 9-12 also resumed anti-influenza activity in the cell-based assays. In sharp contrast, our assays indicated that 3-hydroxypropyl caffeate, 3-(tert-butoxyamido)propyl caffeate and chlorogenic acid (a caffeic ester formed with L-quinic acid) were inactive to H1N1 influenza viruses. Thus, the observed potent anti-influenza activity of conjugates ZA-1-CA (1) and ZA-7-CA (9) may be related to the enzymatic cleavage of the ester linkages to release the active ZA drug. The anti-influenza activity could not be caused by caffeic esters alone. (Salomon, R. et al. *Proc. Natl. Acad. Sci. U.S.A.* 2007, 104, 12479)

The activity against avian H5N1 influenza virus was also evaluated by the cytopathic prevention assays using the recombinant NIBRG-14 (A/Viet Nam/1194/2004) virus. In particular, the ZA-7-CA conjugate showed very high activity against the avian H5N1 virus with an $EC_{50}$ value of 50 nM, about 13-fold greater potency than zanamivir ($EC_{50}$=680 nM). The ZA-7-ME and ZA-7-HP conjugates showed the inhibitory activities similar to zanamivir against H5N1 virus with $EC_{50}$ of 430 and 820 nM, similar to the potency of ZA.

TABLE 2

Influenza neuraminidase inhibition ($IC_{50}$) and anti-influenza activity ($EC_{50}$) against A/WSN/1933 (H1N1) virus

| Compound[a] | $IC_{50}$ (nM)[b] | $EC_{50}$ (nM)[b] | cLog P[c] |
|---|---|---|---|
| ZA | 2.4-7.0 (8) | 3.5-20.2 (8) | −4.13 |
| CA | >10$^5$ | >10$^5$ | 1.42 |
| MCA | >10$^5$ | >10$^5$ | 2.53 |
| ME | >10$^5$ | >10$^5$ | 0.46 |
| HNAP | >10$^5$ | >10$^5$ | 3.29 |
| ZA-7-CA (1) | 2.9-7.4 (8) | 1.4-10.6 (8) | −1.63 |
| ZA-7-MCA (2) | 5.4-7.9 (3) | 66, 146 | −0.52 |
| ZA-7-ME (3) | 8.6-56.3 (2) | 3.3, 7.9 | −2.26 |
| ZA-7-HNAP (4) | 0.7-3.6 (3) | 50-168 (3) | 0.65 |
| ZA-7-DHBA (5) | 2.9 | 53 | −1.13 |
| ZA-7-HP (6) | 11.7-19.8 (2) | 105, 371 | −3.54 |
| ZA-7-CA-amide (7) | 41.3-60.3 (3) | 5.1, 5.9 | −2.36 |
| ZA-7-HNAP-amide (8) | 3.1 | 6.6 | −0.39 |
| ZA-1-CA (9) | 2853 | 25 | −3.60 |
| ZA-1-MCA (10) | 3986 | 28 | −2.49 |
| ZA-1-ME (11) | 996 | 16 | −3.49 |
| ZA-1-HNAP (12) | 590 | 48 | −0.59 |

[a]All the test compounds are nontoxic to MDCK cells at the highest testing concentrations (100 μM).
[b]$IC_{50}$ and $EC_{50}$ values were determined by nonparametric curve fitting of assay results, and the shown data are ranges of assay results with number of assays in parentheses.
[c]Calculated values of octanol-water partition coefficients using Advanced Chemistry Development (ACD/Labs) Software V12.01.

ZA-7-Nap (43) and ZA-7-Ibu (44) conjugates showed potent inhibitory activity against the neuraminidase of influenza A/WSN/1933 (H1N1) virus with $IC_{50}$ values of 3-6 nM, similar to zanamivir. ZA-7-Nap enhanced activity with $EC_{50}$ value of 0.8 nM in protection of the MDCK cells infected by A/WSN/1933 viruses, whereas ZA-7-Ibu showed the anti-influenza activity similar to zanamivir ($EC_{50}$=14 nM in this experiment).

ZA-G-Nap (46) and ZA-G-Ibu (47) conjugates showed decreased affinity to neuraminidase ($IC_{50}$=44-81 nM). However, they possess the anti-influenza activity ($EC_{50}$=18-20 nM) against A/WSN/1933 virus similar to zanamivir.

OS-1-CA (48) and TP-1-CA (49) conjugates showed mild inhibitory activity against the neuraminidase of influenza A/WSN/1933 (H1N1) virus with $IC_{50}$ values of 2.4 μM and 0.7 μM, respectively. In the cell-based assay, OS-1-CA resumed high activity with $EC_{50}$ value of 73 nM, about 6-fold greater potency than oseltamivir in protection of the MDCK cells infected by A/WSN/1933 viruses.

Animal Experiments

Figure 16:
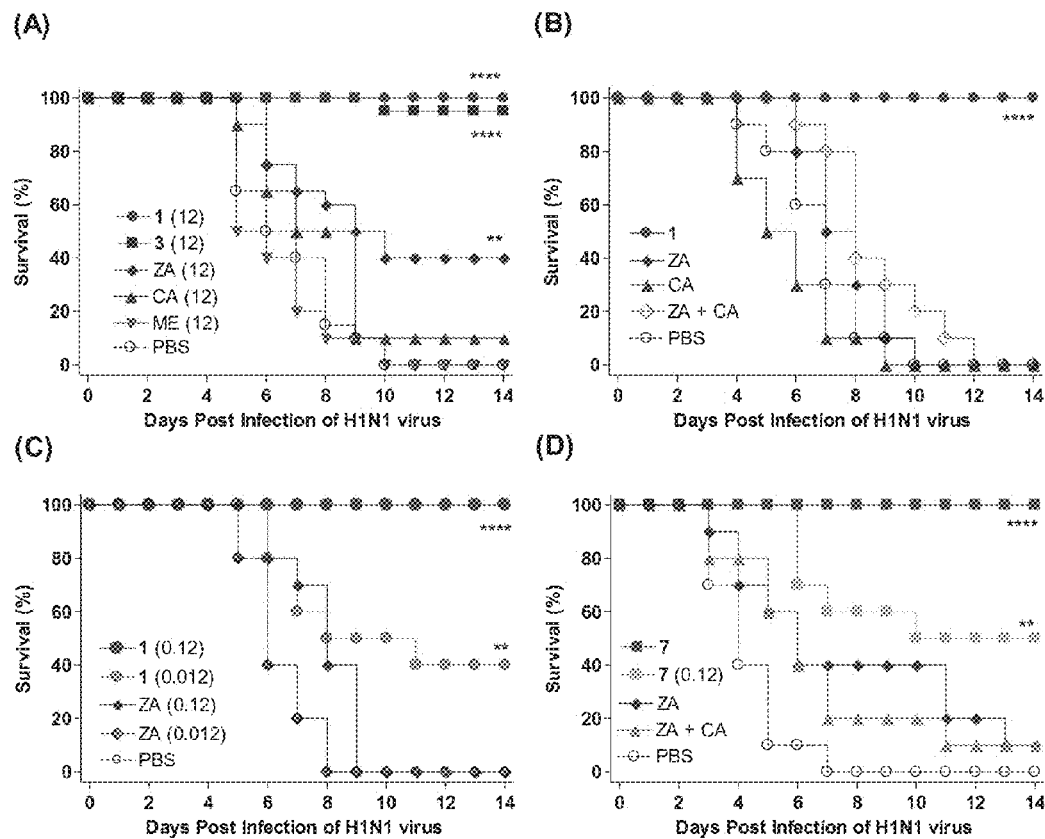

Zanamivir (Relenza™) is an inhaled drug requiring a dose of 20 mg/50 kg/day (1.2 μmol/kg/day) by intranasal administrations twice (with half of the dosage at each administration) for treatment of influenza infected patients. Accordingly, the test compounds at the indicated dosages (12, 1.2, 0.12, 0.012 or 0.0012 μmol/kg/day) were intranasally administered to mice twice-daily on days 1-4, and day 0 before infection with lethal doses (10 $LD_{50}$) of influenza A/Cal/07/2009 H1N1 (FIGS. 16A-D) or NIBRG-14 (A/VietNam/1194/2004) H5N1 (FIGS. 17A and 17B) viruses. The survival of mice was monitored for 14 days. The synthetic conjugates ZA-7-CA (1) and Za-7-ME (3) at a dose of 12 μmol/kg/day showed greater protection than ZA, CA or ME in H1N1 virus infected mice (FIG. 16A). The combination therapy with ZA+CA showed slight increase in survival time compared to those treated with ZA or CA alone at a dose of 1.2 μmol/kg/day, but all the mice died at day 12 except for those treated with conjugate 1 (FIG. 16B). The group of mice treated with conjugate 1 at a low dose of 0.12 μmol/kg/day all survived at day 14 (FIG. 16C). The survival rate of mice decreased to 40% at day 14 on treatment with even less dose (0.012 μmol/kg/day) of 1. However, 0.0012 μmol/kg/day of 1 did not show significant protection of mice from influenza virus infection (data not shown). The ZA-7-CA-amide conjugate (7) with amide linkage at a dose of 1.2

µmol/kg/day also showed 100% protection from virus-induced death, greater protection than ZA or the combination therapy of ZA+CA in treatment of the H1N1 virus infected mice (both showed 10% survival at day 14) (FIG. 16D). Treatment with 0.12 µmol/kg/day of conjugate 7 led to 50% survival at day 14, but treatment with lower dose at 0.012 µmol/kg/day did not improve the survival rate.

Figure 17:
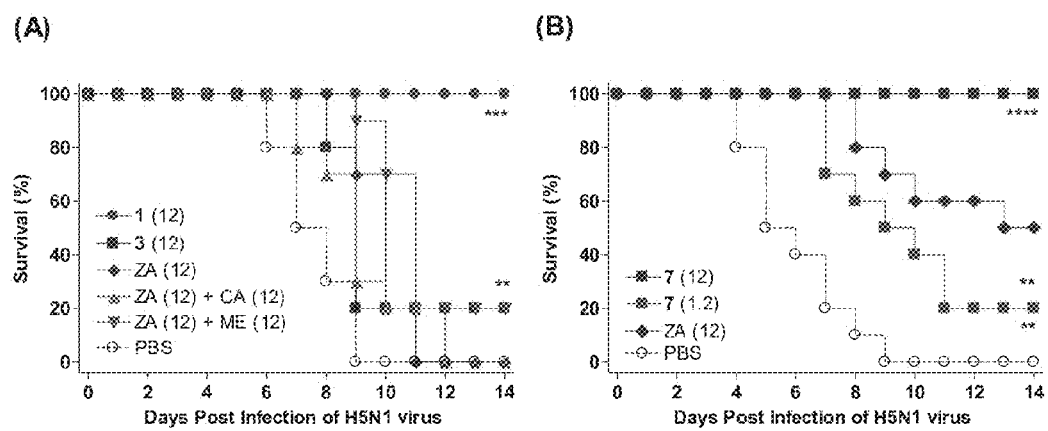

The mice infected by NIBRG-14 H5N1 virus all survived by treatment with intranasal administration of conjugate 1 at 12 µmol/kg/day, whereas the combination therapy ZA+CA or ZA+ME at the same dose did not improve the survival rate, nor did the treatment with ZA alone (FIG. 17A). Conjugate 3 did not provide better protection effect than ZA against avian H5N1 virus (FIG. 17A), though this conjugate showed good activity in treatment of human H1N1 influenza (FIG. 16A). Conjugate 7 at 12 µmol/kg/day showed greater potency against H5N1 virus, in comparison with ZA alone or the combination therapy of ZA+CA (FIG. 17B). On treatment with conjugate 7 at a dose of 1.2 µmol/kg/day, improved survival rate was still noted (FIG. 17B).

Cytokine Suppression

Figure 18:
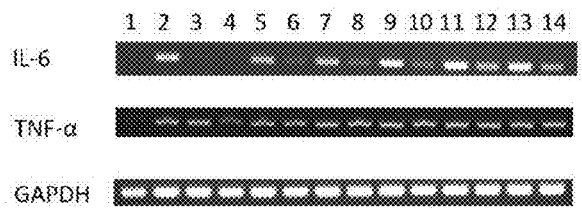
Figure 18:
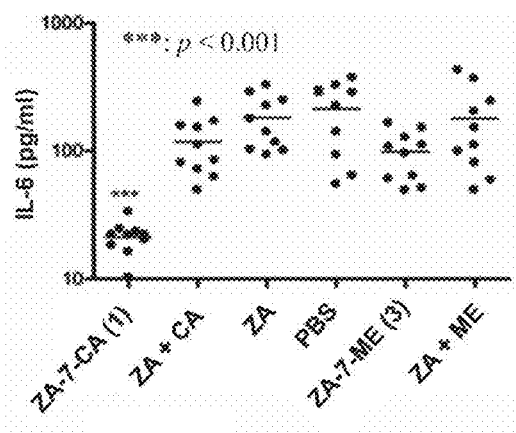
Figure 18:
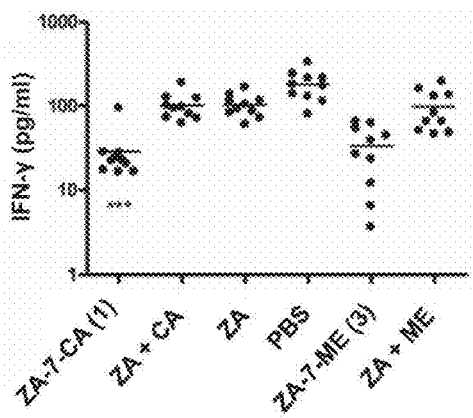

The potential effects of synthetic conjugates on inhibition of the production of pro-inflammatory cytokines were determined in lipopolysaccharide (LPS)-activated RAW264.7 cells (FIG. 18A). Apigenin, a flavone known to possess anti-inflammatory activity, was used as positive control (FIG. 18A, lanes 3 and 4). The anti-inflammatory drugs (CA, MCA and ME in lanes 5, 6, and 11-14) and their ZA conjugates 1 and 3 (lanes 7-10) did cause dose-dependent decreases in the mRNAs encoding IL-6 and TNF-α.

For the H5N1 virus infected mice, the test compounds at 12 µmol/kg/day were intranasally administered, and the serum samples were collected at 72 h to determine the levels of IL-6 and INF-γ. The results indicated that the cytokine levels in the serum were lower in the groups treated respectively with ZA-7-CA and ZA-7-ME conjugates (FIGS. 18B and 18C) by comparison with the groups treated with the combination of ZA+CA and ZA+ME or zanamivir alone. These preliminary results suggested that the ZA-7-CA and ZA-7-ME conjugates acted to prevent the accumulation of pro-inflammatory cytokines at the transcriptional level.

Biologic tests clearly indicated that the survival rates in the mice challenged with H1N1 or H5N1 viruses were tremendously improved by treatment with the zanamivir conjugates, such as ZA-7-CA (1), ZA-7-ME (3) and ZA-7-CA-amide (7), in comparison with the combination treatment with zanamivir and anti-inflammatory drugs. Though the detailed processes for such synergistic effect on influenza treatment is not fully resolved, some observations from our tests may give insights into the working mechanism. These dual-targeted conjugates not only inactivated influenza viruses but also decreased proinflammatory cytokines as shown by the cell-based assays and mice challenge experiments. It was suggested that the zanamivir component in the conjugates might act as a specific binder to influenza virus, and brought the anti-inflammatory component to the location where the virus-induced cytokine storm might be effectively suppressed.

The ester bonds could be hydrolyzed by endogenous esterases in the blood, liver and kidney. (Lavis, L. D. *ACS Chem. Biol.* 2008, 3, 203.] As shown in Table 1, the zanamivir-1-conjugates did not exhibit good NA inhibition; however, they resumed anti-influenza activity ($EC_{50}$=16-48 nM) in the cell-based assays most likely due to enzymatic cleavage of the C-1 ester to release the active zanamivir drug. Indeed, incubation of ZA-1-HNAP conjugate (12, m/z 561, [M+H]$^+$) in rat plasma at 37° C. for 24 h gave the expected degradative products of ZA (m/z 333, [M+H]$^+$) and HNAP (m/z 189, [M+H]$^+$) as evidence by the MALDI-TOFMS and LC-QTOFMS spectrometric analyses. Under the similar incubation conditions, the ester linkages in ZA-1-CA conjugate (9, m/z 561 [M+H]$^+$) were also cleaved by plasma esterases to release the two active components ZA and CA (m/z 181, [M+H]$^+$). The enzymatic cleavage of ZA-7-CA conjugate (1, m/z 596 [M+H]$^+$) in plasma also released a degradation product ZA-7-HP (6) showing the protonation signal at m/z 434. However, the ZA-7-CA-amide conjugate (7, m/z 617 [M+H]$^+$) with amide linkage was relatively stable in plasma. Since both ZA-7-CA and ZA-7-CA-amide conjugates exhibited good anti-influenza activity, enzymatic cleavage of the ester linkage in zanamivir-7-conjugates seemed not to be a prerequisite for the synergistic dual-targeted functions in NA inhibition and cytokine suppression.

In another aspect, zanamivir has poor bioavailability (estimated to be 5% in humans) due to its low lipophilicity and rapid metabolism. (Cass, L. M. R. et al. *Clin. Pharmacokinet.* 1999, 36, 1) Lipophilicity is a key determinant of the pharmacokinetic behavior of drugs. The partition coefficient (P) between octanol and water is usually taken as a suitable measure of lipophilicity. The calculated value clog P for zanamivir is −4.13 (Table 1). The ZA-7-conjugates with CA, MCA, ME and HNAP that contain aromatic moieties would have higher lipophilicity than zanamivir, as shown by the clog P values of these conjugates in the range of −2.36 to 0.65 (Table 2). The zanamivir C-1 ester containing a lipophilic alkoxyalkyl moiety has been shown to exhibit significant protective effect in the mice infected by influenza virus. (Liu, Z.-y. et al. *Bioorg. Med. Chem. Lett.* 2007, 17, 4851) In this study, the ZA-7-conjugates with increased lipophilicity may also improve pharmacokinetic properties for better anti-influenza activity.

To treat influenza infection that is accompanied by the virus-induced cytokine storm, the drug comprising an anti-influenza moiety linked with an anti-inflammatory agent may provide a better therapy. Our study indicated that the dual-targeted ZA conjugates exhibited synergistic anti-influenza activity in comparison with ZA alone or the combination of ZA and anti-inflammatory agent.

EXAMPLES

Without intent to limit the scope of the invention, exemplary instruments, apparatus, methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Example 1: Instrumentation

Melting points were recorded on a Yanaco or Electrothermal MEL-TEMP 1101D apparatus in open capillaries and are not corrected. Optical rotations were measured on digital polarimeter of Japan JASCO Co. DIP-1000. $[\alpha]_D$ values are given in units of $10^{-1}$ deg cm$^2$ g$^{-1}$. Infrared (IR) spectra were recorded on Nicolet Magna 550-II or Thermo Nicolet 380 FT-IR spectrometers. UV-visible spectra were measured on a Perkin Elmer Lambda 35 spectrophotometer. Nuclear magnetic resonance (NMR) spectra were obtained on Bruker Advance-400 (400 MHz) spectrometer. Chemical shifts (δ) are given in parts per million (ppm) relative to $\delta_H$ 7.24/$\delta_C$ 77.0 (central line of t) for CHCl$_3$/CDCl$_3$, $\delta_H$ 4.80 for H$_2$O/D$_2$O, $\delta_H$ 3.31/$\delta_C$ 48.2 for CD$_3$OD, or $\delta_H$ 2.49/$\delta_C$ 39.5 for DMSO-d$_6$. The splitting patterns are reported as s (singlet), d (doublet), t (triplet), q (quartet), m (multiplet), dd (double of doublets) and br (broad). Coupling constants (J) are given in Hz. Distortionless enhancement polarization transfer (DEPT) spectra were taken to determine the types of carbon signals. The ESI-MS experiments were conducted on a Bruker Daltonics BioTOF III high-resolution mass spectrometer. The MALDI-MS measurements were performed on a Bruker Daltonics Ultraflez II MALDI-TOF/TOF 2000 mass spectrometer. The 2,5-dihydroxybenzoic acid (DHB), as MALDI matrix, was photoionized at different irradiances of a UV laser with $\lambda_{max}$ at 337 nm and 355 nm.

Example 2: Chemical Materials

All the reagents and solvents were reagent grade and were used without further purification unless otherwise specified. All solvents were anhydrous grade unless indicated otherwise. CH$_2$Cl$_2$ was distilled from CaH$_2$. All non-aqueous reactions were carried out in oven-dried glassware under a slight positive pressure of argon unless otherwise noted. Reactions were magnetically stirred and monitored by thin-layer chromatography on silica gel using aqueous p-anisaldehyde as visualizing agent. Silica gel (0.040-0.063 mm particle sizes) and LiChroprep® RP-18 (0.040-0.063 mm particle sizes) were used for column chromatography. Flash chromatography was performed on silica gel of 60-200 m particle size. Molecular sieves were activated under high vacuum at 220° C. over 6 hours. Purity of compounds 1-12 was assessed to be ≥95% by HPLC (Agilent HP-1100) with detection at 254 or 360 nm wavelength.

Example 3: Biological Materials

Influenza virus A/Vietnam/1194/2004 RG14 (H5N1) and A/California/7/2009 (H1N1) were from the Center for Disease Control and Prevention in Taiwan and influenza A/WSN/1933 (H1N1) was from Dr. Shin-Ru Shih in Chang Gung University in Taiwan. All Viruses were cultured in the allantoic cavities of 10-day-old embryonated chicken eggs for 72 h, and purified by sucrose gradient centrifugation. Madin-Darby canine kidney (MDCK) cells were obtained from American Type Culture Collection (Manassas, Va.), and were grown in DMEM (Dulbecco's modified Eagle medium, GibcoBRL) containing 10% fetal bovine serum (GibcoBRL) and penicillin-streptomycin (GibcoBRL) at 37° C. under 5% $CO_2$.

Example 4: Determination of Influenza Virus $TCID_{50}$

The $TCID_{50}$ (50% tissue culture infectious dose) was determined by serial dilution of the influenza virus stock onto 100 μL MDCK cells at $1\times10^5$ cells/mL in 96-well microplates. The infected cells were incubated at 37° C. under 5.0% $CO_2$ for 48 h and added to each wells with 100 μL per well of CellTiter 96® AQueous Non-Radioactive Cell Proliferation Assay reagent (Promega). After incubation at 37° C. for 15 min, absorbance at 490 nm was read on a plate reader. Influenza virus $TCID_{50}$ was determined using Reed-Muench method. (Reed, L. J.; Muench, H. *Am. J. Epidemiol.* 1938, 27, 493; Burleson, F. G. et al. *Virology, a Laboratory Manual,* 1992)

Example 5: Determination of NA Activity by Fluorescent Assay

The neuraminidase (NA) activity was measured using diluted allantoic fluid harvested from influenza A/WSN/1933 (H1N1) infected embryonated eggs. A fluorometric assay was used to determine the NA activity with the fluorogenic substrate 2'-(4-methylumbelliferyl)-α-D-N-acetylneuraminic acid (MUNANA; Sigma). The fluorescence of the released 4-methylumbelliferone was measured in Envision plate reader (Perkin-Elmer, Wellesley, Mass.) using excitation and emission wavelengths of 365 and 460 nm, respectively. Neuraminidase activity was determined at 200 μM of MUNANA. Enzyme activity was expressed as the fluorescence increase during 15 min incubation at room temperature.

Example 6: Determination of $IC_{50}$ of NA Inhibitor

NA inhibition was determined by mixing inhibitor and neuraminidase for 10 min at room temperature followed by the addition of 200 μM of substrate. Inhibitor $IC_{50}$ value were determined from the dose-response curves by plotting the percent inhibition of NA activity versus inhibitor concentrations using Graph Pad Prism 4.

Example 7: Determination of $EC_{50}$ of NA Inhibitor

The anti-flu activities of neuraminidase inhibitors were measured by the $EC_{50}$ values that were the concentrations of NA inhibitor for 50% protection of the H1N1 CPE activities. Fifty μL diluted H1N1 at 100 $TCID_{50}$ were mixed with equal volumes of NA inhibitors at varied concentrations. The mixtures were used to infect 100 μL of MDCK cells at $1\times10^5$ cells/mL in 96-wells. After 48 h incubation at 37° C. under 5.0% $CO_2$, the cytopathic effects (CPE) were determined with CellTiter 96® AQueous Non-Radioactive Cell Proliferation Assay reagent as described above. Inhibitor $EC_{50}$ value were determined by fitting the curve of percent CPE versus the concentrations of NA inhibitor using Graph Pad Prism 4.

Example 8: Animal Experiments

Female BALB/c mice (4-5 weeks old) were anesthetized with zoletil and inoculated intranasally with 25 μL of infectious influenza virus. Synthetic compounds and zanamivir were administered to groups of 10 mice at dosages of 0.0012, 0.012, 0.12, 1.2 and 12 μmol per kg of body weight per day by intranasal instillation twice daily for 5 days. Control (placebo) mice received PBS on the same schedule. Four hours after the first dose of drug, mice were inoculated with 10 $MLD_{50}$ of influenza virus [A/Cal/07/2009 (H1N1) or NIBRG-14 (A/Vietnam/1194/2004 (H5N1)]. Mice were observed daily for 14 days for survival.

Example 9: RNA Isolation and Real-Time Polymerase Chain Reaction (RT-PCR)

Raw264.7 cells were cultured in 6-well plates at $3\times10^6$ cells per well for 24 h and treated with test compounds for 30 min followed by addition of 100 ng mL LPS for another 6 h. The cells were collected and stored at −80° C. until use.

Total RNA was extracted using Trizol® (Invitrogen) and processed for RT-PCR as described previously. (Hsieh, Y. S. Y. et al. *Bioorg. Med. Chem. Lett.* 2008, 16, 6054-6068)

Example 10: Cytokine Determination by ELISA

The concentrations of IL-6 and IFN-γ in the mice serum were assayed using the Quantikine® mouse ELISA kits (R&D Systems, Minneapolis, Minn.) according to the manufacturer's protocol.

Example 11: Incubation of Zanamivir Conjugates in Plasma and Mass Spectrometric Analyses Sprague Dawley® rat plasma (550 μL) and 50 μL of analyte were mixed to yield a final concentration of 1 mM. The mixture was incubated at 37° C. for 24 h, extracted with methanol (3.6 mL) by vortex mixing at 4° C. for 2H, and then subjected to centrifugation at 10,000 rpm for 20 min. The precipitate was removed by filtration. The filtrate was concentrated under reduced pressure, and the content of enzymatic cleavage products was analyzed by MALDI-TOFMS.

Alternatively, the mixture resulted from incubation was subjected to LC-QTOF MS analysis. The sample was loaded onto a Sep-Pak® Plus tC18 cartridge (Waters Corp), and flushed with deionized water (2×2 mL) to remove excess salts and proteins, followed by elution with MeOH/$H_2O$ (1:1, 4×2 mL) to collect analyte. The analyte was evaporated to dryness, and re-dissolved in $CH_3CN/H_2O$ (1:9, 100 μL) for LC-QTOF MS analysis on a nano Acquity UPLC BEH C18 column (1.7 μm, 75 μm×250 mm, Waters Corp). The injection volume was 2-5 μL and the total run time was 50 min. A mixture of 0.1% formic acid in water (mobile phase A) and 0.1% formic acid in acetonitrile (mobile phase B) was used with a gradient program at a flow rate of 0.3 μL/min at ambient temperature. To analyze the product mixture formed by incubation of ZA-1-HNAP in plasma, the gradient program of mobile phase was set: a linear increase from 10:90 to 85:15 B/A in 25 min, and kept at 85:15 B/A for 10 min. The column was washed for 15 min before returning to original conditions.

Example 12: Determination of Octanol-Buffer Partition Coefficients

Solutions of each compound (100 μg/mL) were prepared in octanol saturated phosphate buffered saline (0.01 M, pH 7.4). These aqueous solutions were then equilibrated at 37° C. with an equivalent volume (0.5 mL) of buffer saturated octanol using magnetic stirring at 1200 rpm for 24 hours. Five replicates of each determination were carried out to assess reproducibility. The octanol and aqueous phases were then separated by centrifugation at 3000 rpm for 15 min. Each sample (300 μL) of aqueous layer was diluted with PBS to 3 mL, and organic layer was diluted with MeOH to 3 mL. The concentration of drug was measured UV spectrophotometry at $\lambda_{max}$ (MeOH) 290 nm (ε=14440) and $\lambda_{max}$ (PBS) 290 nm (ε=4610) at pH 7.4 for the chromophore of 1-hydroxy-2-naphthoic acid. From these data, the apparent octanol/buffer (pH 7.4) partition coefficient, DB=[Bt]oct/[Bt]aq, is determined, where [Bt]oct and [Bt]aq are the concentrations of the drug in organic and aqueous phases, respectively.

Example 13: Synthesis of Zanamivir (FIG. 3)

Zanamivir (ZA) was prepared from sialic acid by a procedure similar to the previous report (Chandler, M. et al. *J. Chem. Soc., Perkin Trans.* 1 1995, 1173) through the ethyl ester 13 instead of the corresponding methyl ester.

Example 14: Synthesis of ZA-7-HP Conjugate 6 (FIG. 4)

5-Acetylamino-4-[2,3-bis(tert-butoxycarbonyl) guanidino]-6-[(2,2-dimethyl-[1,3]dioxolan-4-yl)-hydroxy-methyl]-5,6-dihydro-4H-pyran-2-carboxylic acid ethyl ester (14)

To a solution of 13 (1100 mg, 1.60 mmol) in anhydrous ethanol (10 mL) was added NaOEt (54.4 mg, 0.80 mmol). The mixture was stirred at room temperature for 1 h, neutralized by Dowex 50 W×8 ($H^+$), filtered, and concentrated under reduced pressure to afford yellow solids. The residue was dissolved in anhydrous acetone (10 mL), and p-toluene sulfonic acid and 2,2-dimethoxypropane were added. The mixture was stirred at room temperature for 12 h. After concentration, the residue was purified by silica gel column chromatography (EtOAc/hexane=2:3) to afford compound 14 (635 mg, 66%). $C_{27}H_{44}N_4O_{11}$; white solid, mp 118-120° C.; TLC (EtOAc/hexane=2:3) $R_f$=0.22; $[\alpha]^{20}_D$ −33.4 (c=1.0, $CHCl_3$); IR $\nu_{max}$ (neat) 3309, 2981, 1725, 1647, 1609, 1559, 1369, 1251, 1151 $cm^{-1}$; $^1$H NMR (400 MHz, $CDCl_3$) δ 11.30 (1H, s), 8.54 (1H, d, J=7.2 Hz), 7.91 (1H, d, J=4.4 Hz), 5.71 (1H, d, J=2.4 Hz), 5.21 (1H, br s), 5.08-5.05 (1H, m), 4.33-4.30 (1H, m), 4.19-4.13 (2H, m), 4.11-4.00 (2H, m), 3.98-3.88 (1H, m), 3.45 (1H, d, J=3.6 Hz), 1.93 (3H, s), 1.44 (9H, s), 1.41 (9H, s), 1.34 (3H, s), 1.28-1.22 (6H, m); $^{13}$C NMR (100 MHz, $CDCl_3$) δ 173.8, 162.2, 161.3, 157.5, 152.5, 147.0, 108.9, 106.3, 84.2, 79.9, 78.5, 74.1, 69.6, 67.3, 61.4, 51.9, 48.3, 28.1 (3×), 27.9 (3×), 26.9, 25.1, 22.8, 13.9; ESI-HRMS (negative mode) calcd for $C_{27}H_{43}N_4O_{11}$: 599.2928, found: m/z 599.2926 [M−H]$^-$.

5-Acetylamino-4-[2,3-bis(tert-butoxycarbonyl) guanidino]-6-[(2,2-dimethyl-[1,3]dioxolan-4-yl)-(4-nitrophenoxy)carbonyloxy)methyl]-5,6-dihydro-4H-pyran-2-carboxylic acid ethyl ester (15)

A solution of compound 14 (540 mg, 0.8 mmol), 4-nitrophenyl chloroformate (1131 mg, 5.6 mmol) and 4-dimethylaminopyridine (327 mg, 5.6 mmol) in anhydrous pyridine (12 mL) was stirred at room temperature for 16 h. After concentration, the mixture was added EtOAc, and then filtered. The filtrate was concentrated under reduced pressure, and purified by silica gel column chromatography (EtOAc/hexane=1:2) to give carbonate 15 (360 mg, 60%). $C_{34}H_{47}N_5O_{15}$; white solid, mp 127-128° C.; TLC (EtOAc/hexane=2:3) $R_f$=0.35; $[\alpha]^{20}_D$ −45.7 (c=1.0, $CHCl_3$); IR $\nu_{max}$ (neat) 2981, 1777, 1729, 1645, 1612, 1527, 1369, 1253, 1221, 1149 $cm^{-1}$; $^1$H NMR (400 MHz, $CDCl_3$) δ 11.29 (1H, s), 8.44 (1H, d, J=8.8 Hz), 8.16 (2H, d, J=9.2 Hz), 7.44 (2H, d, J=9.2 Hz), 6.54 (1H, d, J=8.8 Hz), 5.81 (1H, d, J=2.0 Hz), 5.25 (1H, dd, J=5.6, 1.6 Hz), 5.13-5.08 (1H, m), 4.38-4.31 (2H, m), 4.19-4.14 (4H, m), 4.09-3.99 (1H, m), 1.82 (3H, s). 1.39 (18H, s), 1.31 (3H, s), 1.28-1.22 (6H, m); $^{13}$C NMR (100 MHz, $CDCl_3$) δ 171.2, 162.5, 160.9, 157.0, 155.7, 152.4, 152.3, 145.3, 125.0 (2×), 122.2 (2×), 108.9, 108.5, 83.8, 79.6, 77.3, 75.2, 73.9, 65.3, 61.5, 60.2, 48.5, 48.0, 28.0 (3×), 27.8 (3×), 26.1, 25.3, 22.8, 13.9; ESI-HRMS calcd for $C_{34}H_{48}N_5O_{15}$: 766.3147, found: m/z 766.3146 [M+H]$^+$.

5-Acetylamino-6-[(2,2-dimethyl-[1,3]dioxolan-4-yl)-3-[(hydroxypropyl)carbamoyloxy]methyl-4-[2,3-bis(tert-butoxycarbonyl)guanidino]-5,6-dihydro-4H-pyran-2-carboxylic acid ethyl ester (16)

To a solution of carbonate 15 (400 mg, 0.52 mmol) in $CH_3CN$ (7 mL) was added 3-amino-1-propanol (0.084 mL, 1.1 mmol) and Et$_3$N (0.153 mL, 1.1 mmol). The mixture was stirred at room temperature for 2H, and then concentrated under reduced pressure. The residue was partitioned between EtOAc and 1 M HCl. The organic layer was washed with saturated NaHCO$_3$ and brine, dried over MgSO$_4$, filtered, and concentrated by rotary evaporation under reduced pressure. The crude material was purified by silica gel column chromatography (EtOAc/hexane=3:1) to yield carbamate 16 (320 mg, 88%). C$_{31}$H$_{51}$N$_5$O$_{13}$; white solid, mp 135-137° C.; TLC (EtOAc/hexane=4:1) R$_f$=0.38; [α]$^{20}_D$ −24.2 (c=1.0, CHCl$_3$); IR ν$_{max}$ (neat) 3315, 2981, 1731, 1643, 1613, 1250, 1144, 1057 cm$^{-1}$; $^1$H NMR (400 MHz, CDCl$_3$) δ 11.28 (1H, s), 8.34 (1H, d, J=8.8 Hz), 6.55 (1H, d, J=9.6 Hz), 5.79 (1H, d, J=1.2 Hz), 5.22-5.14 (2H, m), 5.04-5.00 (1H, m), 4.29-4.20 (2H, m), 4.17-4.06 (4H, m), 4.04-3.89 (2H, m), 3.60 (2H, s), 3.39-3.30 (1H, m), 3.10-3.03 (1H, m), 1.82 (3H, s), 1.72-1.60 (1H, m), 1.59-1.50 (1H, m), 1.39 (9H, s), 1.37 (9H, s), 1.27 (3H, s), 1.25-1.20 (6H, m); $^{13}$C NMR (100 MHz, CDCl$_3$) δ 171.1, 162.9, 161.4, 157.0, 156.0, 152.7, 145.4, 109.5, 108.7, 83.7, 79.6, 77.7, 74.9, 69.7, 65.8, 61.5, 59.5, 49.2, 47.9, 38.3, 31.7, 28.2 (3×), 28.0 (3×), 26.4, 25.3, 23.0, 14.1; ESI-HRMS calcd for C$_{31}$H$_{52}$N$_5$O$_{13}$: 702.3562, found: m/z 702.3560 [M+H]$^+$.

5-Acetylamino-6-[2,3-dihydroxy-1-(3-hydroxypropylcarbamoyloxy)propyl]-4-guanidino-5,6-dihydro-4H-pyran-2-carboxylic acid (6)

To a solution of carbamate 16 (100 mg, 0.14 mmol) in THF (2 mL) was added 1 M KOH (2 mL). The solution was stirred at room temperature for 1.5 h, neutralized by Dowex 50 W×8 (H$^+$), filtered and concentrated under reduced pressure. The residue was dissolved in CH$_2$Cl$_2$ (2 mL) and TFA (2 mL). After stirring at room temperature for 3H, the mixture was evaporated under reduced pressure. The residue was triturated with Et$_2$O, and centrifuged to give the ZA-7-HP conjugate 6 (51 mg, 84%). C$_{16}$H$_{27}$N$_5$O$_9$; colorless solid, mp 265-267° C.; [α]$^{20}_D$ −218.7 (c=1.0, H$_2$O); IR ν$_{max}$ (neat) 3410, 1674, 1544, 1263, 1140 cm$^{-1}$; $^1$H NMR (400 MHz, D$_2$O) δ 6.05 (1H, d, J=2.4 Hz), 4.99 (1H, dd, J=8.8, 2.0 Hz), 4.60 (1H, dd, J=10.0, 2.0 Hz), 4.48 (1H, dd, J=10.0, 2.0 Hz), 4.18 (1H, dd, J=9.6, 9.2 Hz), 4.08-4.03 (1H, m), 3.72-3.63 (3H, m), 3.56-3.51 (1H, m), 3.17 (1H, dd, J=6.8, 6.8 Hz), 2.00 (3H, s), 1.78-1.71 (3H, m); $^{13}$C NMR (100 MHz, D$_2$O) δ 173.9, 164.8, 157.0, 156.6, 145.0, 109.1, 75.8, 69.5, 68.8, 62.3, 59.1, 51.1, 47.1, 37.5, 31.2, 21.8; ESI-HRMS (negative mode) calcd for C$_{16}$H$_{26}$N$_5$O$_9$: 432.1731, found: m/z 432.1727 [M−H]$^-$.

Example 15: Synthesis of ZA-7-CA Conjugate 1 (FIG. 5)

3-(3,4-Bis-allyloxyphenyl)acrylic acid allyl ester (17)

To a solution of caffeic acid (1000 mg, 5.56 mmol) and ally bromide (2 mL, 22.2 mmol) in anhydrous acetone (15 ml) was added finely powdered K$_2$CO$_3$ (3069 mg, 22.2 mmol). The mixture was stirred for 4 h at 60° C., and then concentrated under reduced pressure. The residue was partitioned between EtOAc and 1 M HCl. The organic layer was washed with saturated NaHCO$_3$ and brine, dried over MgSO$_4$, filtered, and concentrated by rotary evaporation under reduced pressure. The crude material was purified by silica gel column chromatography (EtOAc/hexane=1:9) to yield a fully allylation product 17 (1320 mg, 79%). C$_{18}$H$_{20}$O$_4$; TLC (EtOAc/hexane=1:9) R$_f$=0.80; $^1$H NMR (400 MHz, CDCl$_3$) δ 7.60 (1H, d, J=16.0 Hz), 7.05 (2H, m), 6.84 (1H, d, J=8.8 Hz), 6.27 (1H, d, J=16.0 Hz), 6.12-5.90 (3H, m), 5.42-5.25 (6H, m), 4.65 (2H, dd, J=5.6, 1.0 Hz), 4.60 (4H, dd, J=3.6, 1.8 Hz).

3-(3,4-Bis-allyloxyphenyl)acrylic acid (18)

To a solution of the fully allylation derivative of caffeic acid 17 (845 mg, 2.82 mmol) in MeOH (20 mL) was added 1M NaOH (2 mL). The mixture was stirred for 4 h at 60° C., and then concentrated under reduced pressure. H$_2$O (20 mL) was added and washed with ether, acidified with 1M HCl, then extracted with CH$_2$Cl$_2$. The organic layer was dried over MgSO$_4$, filtered, and concentrated by rotary evaporation under reduced pressure. The crude material was purified by silica gel column chromatography (EtOAc/hexane=3:7) to yield the bis-allyl ether 18 (695 mg, 95%). C$_{15}$H$_{16}$O$_4$; yellow solid; TLC (EtOAc/hexane=3:7); $^1$H NMR (400 MHz, CDCl$_3$) δ 7.68 (1H, d, J=16.0 Hz), 7.08 (2H, m), 6.86 (1H, d, J=8.0 Hz), 6.26 (1H, d, J=16.0 Hz), 6.09-6.03 (2H, m), 5.44-5.27 (4H, m), 4.63 (4H, dd, J=3.2, 1.6 Hz); $^{13}$C NMR (100 MHz, CDCl$_3$) 172.5, 151.0, 148.5, 146.9, 133.0, 132.8, 127.2, 123.1, 118.0, 117.9, 114.9, 113.3, 112.8, 69.9, 69.7; ESI-HRMS (negative mode) calcd for C$_{15}$H$_{15}$O$_4$: 259.0970, found: m/z 259.0957 [M−H]$^-$.

Compound 19

To a solution of ZA-7-HP derivative 16 (210 mg, 0.30 mmol) in CH$_2$Cl$_2$ (10 mL) was added the allyl ether of caffeic acid 18 (86 mg, 0.33 mmol), 1-ethyl-3-(3-dimethylaminopropyl)carbodiimide (EDCI, 63 mg, 0.33 mmol) and 4-dimethylaminopyridine (DMAP, 37 mg, 0.33 mmol). The mixture was stirred at room temperature for 1.5 h. The resulting solution was extracted with 1 M HCl, saturated NaHCO$_3$ and brine, dried over MgSO$_4$, concentrated under reduced pressure, and purified by flash silica gel column chromatography (EtOAc/hexane=2:3 to EtOAc/hexane=3:2) to afford ester 19 (240 mg, 85%). C$_{46}$H$_{65}$N$_5$O$_{16}$; colorless solid, mp 98-100° C.; TLC (EtOAc/hexane=3:2) R$_f$=0.30; [α]$^{24}_D$ −20.3 (c=1.0, CHCl$_3$); IR ν$_{max}$ (neat) 3316, 2980, 1728, 1638, 1609, 1510, 1306, 1253, 1142 cm$^{-1}$; $^1$H NMR (400 MHz, CDCl$_3$) δ 11.36 (1H, s), 8.37 (1H, d, J=8.4 Hz), 7.54 (1H, d, J=16.0 Hz), 7.03 (2H, m), 6.82 (1H, d, J=8.8 Hz), 6.21 (1H, d, J=16.0 Hz), 6.16 (1H, d, J=9.6 Hz), 6.08-5.96 (2H, m), 5.83 (1H, d, J=2.0 Hz), 5.40-5.38 (1H, m), 5.36-5.34 (1H, m), 5.26-5.16 (4H, m), 5.10-5.06 (1H, m), 4.59 (4H, dd, J=2.8, 2.4 Hz), 4.36-4.28 (2H, m), 4.24-4.16 (3H, m), 4.09-3.95 (4H, m), 3.28-3.19 (2H, m), 1.84 (5H, s), 1.42 (9H, s), 1.41 (9H, s), 1.34 (3H, s), 1.30-1.18 (6H, m); $^{13}$C NMR (100 MHz, CDCl$_3$) δ 170.8, 167.3, 163.0, 161.4, 157.0, 155.6, 152.7, 150.6, 148.5, 145.4, 144.8, 133.0, 132.8, 127.5, 122.7, 117.9, 117.8, 115.6, 113.4, 112.6, 109.5, 108.7, 83.6, 79.6, 77.5, 74.9, 69.9, 69.7, 65.9, 61.6, 61.5, 48.7, 48.4, 37.9, 36.6, 29.6, 29.0, 28.2 (3×), 28.0 (3×), 25.3, 23.0, 14.1; ESI-HRMS calcd for C$_{46}$H$_{66}$N$_5$O$_{16}$: 944.4505, found: m/z 944.4518 [M+H]$^+$.

ZA-7-CA Conjugate 1

To a solution of compound 19 (215 mg, 0.23 mmol) in THF (4 mL) was added 1 M KOH (4 mL). The solution was stirred at room temperature for 1.5 h, neutralized by Dowex 50 W×8 (H$^+$), filtered and concentrated under reduced pressure. The residue was dissolved in anhydrous THF (5 mL), then added Pd(PPh$_3$)$_4$ (26 mg, 0.02 mmol) and morpholine (0.4 mL, 4.5 mmol). The mixture was stirred at room temperature for 4 h. The resulting solution was extracted with 1 M HCl and brine, dried over MgSO$_4$, concentrated under reduced pressure, and purified by flash silica gel column chromatography (MeOH/CH$_2$Cl$_2$=1:9 to MeOH/CH$_2$Cl$_2$=1:4). The residue was dissolved in CH$_2$Cl$_2$ (2 mL) and TFA (2 mL). After stirring at room temperature for 3H, the mixture was evaporated under reduced pressure. The residue was triturated with Et$_2$O, and centrifuged to give ZA-7-CA conjugate 1 (75 mg, 56%). C$_{25}$H$_{33}$N$_5$O$_{12}$; yellow solid, mp 217-219° C.; [α]$^{24}{}_D$ +144.9 (c=0.33, H$_2$O); IR $\nu_{max}$ (neat) 3403, 1702, 1628, 1404, 1262 cm$^{-1}$; $^1$H NMR (400 MHz, CD$_3$OD) δ 7.55 (1H, d, J=16.0 Hz), 7.04 (1H, d, J=1.6 Hz), 6.94 (1H, dd, J=8.4, 2.0 Hz), 6.78 (1H, d, J=8.4 Hz), 6.26 (1H, d, J=16.0 Hz), 5.84 (1H, d, J=2.4 Hz), 5.00 (1H, dd, J=8.8, 2.0 Hz), 4.57 (1H, dd, J=10.0, 2.0 Hz), 4.43 (1H, dd, J=6.8, 1.6 Hz), 4.25-4.16 (2H, m), 4.04-3.99 (1H, m), 3.89-3.86 (1H, m), 3.66 (1H, dd, J=12.0, 3.2 Hz), 3.53-3.47 (1H, m), 3.23-3.19 (2H, m), 1.95 (3H, s), 1.92-1.86 (2H, m); $^{13}$C NMR (100 MHz, CD$_3$OD) δ 172.3, 168.0, 163.7, 157.5, 156.6, 148.2, 145.8, 145.5, 145.4, 126.3, 121.6, 115.1, 113.7 (2×), 107.1, 75.9, 69.5, 69.1, 62.9, 61.6, 51.1, 48.5, 37.3, 28.6, 21.4; ESI-HRMS (negative mode) calcd for C$_{25}$H$_{32}$N$_5$O$_{12}$: 594.2047, found: m/z 594.2051 [M−H]$^-$.

Figure 6:
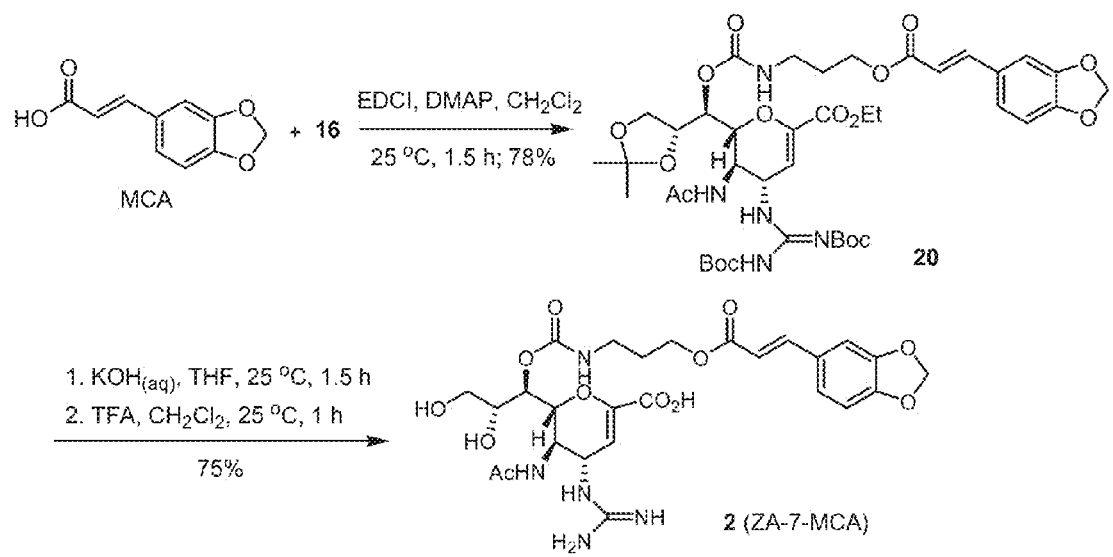

Example 16: Synthesis of ZA-7-MCA Conjugate 2 (FIG. 6)

Compound 20

To a solution of ZA-7-HP derivative 16 (90 mg, 0.13 mmol) in CH$_2$Cl$_2$ (5 mL) were added 3,4-(methylenedioxy) cinnamic acid (MCA, 27 mg, 0.14 mmol), EDCI (27 mg, 0.14 mmol) and 4-dimethylaminopyridine (17 mg, 0.14 mmol). The mixture was stirred at room temperature for 1.5 h, and then was extracted with 1 M HCl, saturated NaHCO$_3$ and brine. The organic phase was dried over MgSO$_4$, concentrated under reduced pressure, and purified by flash silica gel column chromatography (EtOAc/hexane=3:7 to EtOAc/hexane=1:1) to afford ester 20 (98 mg, 86%). C$_{41}$H$_{57}$N$_5$O$_{16}$; colorless solid, mp 112-114° C.; TLC (EtOAc/hexane=3:2) R$_f$=0.18; [α]$^{25}{}_D$ −19.2 (c=1.0, CH$_3$Cl); IR $\nu_{max}$ (neat) 3316, 2980, 2931, 1729, 1639, 1609, 1250, 1152 cm$^{-1}$; $^1$H NMR (400 MHz, CDCl$_3$) δ 11.34 (1H, s), 8.34 (1H, d, J=8.4 Hz), 7.51 (1H, d, J=16.0 Hz), 6.97 (1H, s), 6.94 (1H, d, J=8.0 Hz), 6.73 (1H, d, J=8.0 Hz), 6.30 (1H, d, J=9.2 Hz), 6.19 (1H, d, J=16.0 Hz), 5.94 (2H, s), 5.82 (1H, d, J=2.4 Hz), 5.24-5.11 (3H, m), 4.33-4.72 (2H, m), 4.22-4.16 (4H, m), 4.14-4.04 (2H, m), 4.02-3.95 (1H, m), 3.22-3.19 (2H, m), 1.84 (5H, s), 1.41 (9H, s), 1.40 (9H, s), 1.31 (3H, s), 1.28-1.23 (6H, m); $^{13}$C NMR (100 MHz, CDCl$_3$) δ 170.6, 167.1, 162.9, 161.3, 156.8, 155.5, 152.4, 149.5, 148.2, 145.3, 144.5, 128.6, 124.4, 115.7, 109.6, 108.6, 108.4, 106.4, 101.4, 83.4, 79.4, 77.5, 74.9, 69.6, 65.7, 61.6, 61.4, 48.7, 48.1, 37.8, 28.9, 28.1 (3×), 27.9 (3×), 26.3, 25.2, 22.9, 14.0; ESI-HRMS calcd for C$_{41}$H$_{58}$N$_5$O$_{16}$: 876.3879, found: m/z 876.3876 [M+H]$^+$.

ZA-7-MCA Conjugate 2

To a solution of compound 20 (98 mg, 0.11 mmol) in THF (2 mL) was added 1 M KOH (2 mL). The solution was stirred at room temperature for 1.5 h, neutralized by Dowex 50 W×8 (H$^+$), filtered and concentrated under reduced pressure. The residue was dissolved in CH$_2$Cl$_2$ (2 mL) and TFA (2 mL). After stirring at room temperature for 3H, the mixture was evaporated under reduced pressure. The residue was triturated with Et$_2$O, and centrifuged to give the ZA-7-MCA conjugate 2 (48 mg, 71%). C$_{26}$H$_{33}$N$_5$O$_{12}$; white solid, mp 218-220° C.; [α]$^{20}{}_D$+11.4 (c=0.33, H$_2$O); IR $\nu_{max}$ (neat) 3369, 2920, 1686, 1629, 1449, 1252, 1038 cm$^{-1}$; $^1$H NMR (400 MHz, CD$_3$OD) δ 7.60 (1H, d, J=16.0 Hz), 7.14 (1H, s), 7.10 (1H, d, J=8.0 Hz), 6.87 (1H, d, J=8.0 Hz), 6.35 (1H, d, J=16.0 Hz), 6.01 (2H, s), 5.59 (1H, d, J=2.0 Hz), 4.93 (1H, dd, J=7.6, 1.6 Hz), 4.48 (1H, dd, J=10.4, 1.6 Hz), 4.36 (1H, dd, J=9.2, 2.0 Hz), 4.26-4.14 (3H, m), 4.08-4.03 (1H, m), 3.63 (1H, dd, J=12.0, 2.8 Hz), 3.51-3.46 (1H, m), 3.21 (2H, t, J=6.4 Hz), 1.95 (3H, s), 1.90 (2H, t, J=6.8 Hz); $^{13}$C NMR (100 MHz, CD$_3$OD) δ 174.0, 169.7, 158.7, 158.1, 151.4, 151.3, 149.8, 146.6, 146.4, 130.0, 126.1, 126.0, 116.5, 109.7, 107.5, 103.2, 103.1, 76.9, 71.2, 70.2, 64.4, 63.5, 53.4, 38.8, 29.8, 23.1; ESI-HRMS (negative mode) calcd for C$_{26}$H$_{32}$N$_5$O$_{12}$: 606.2047, found: m/z 606.2044 [M−H]$^-$.

Figure 7:
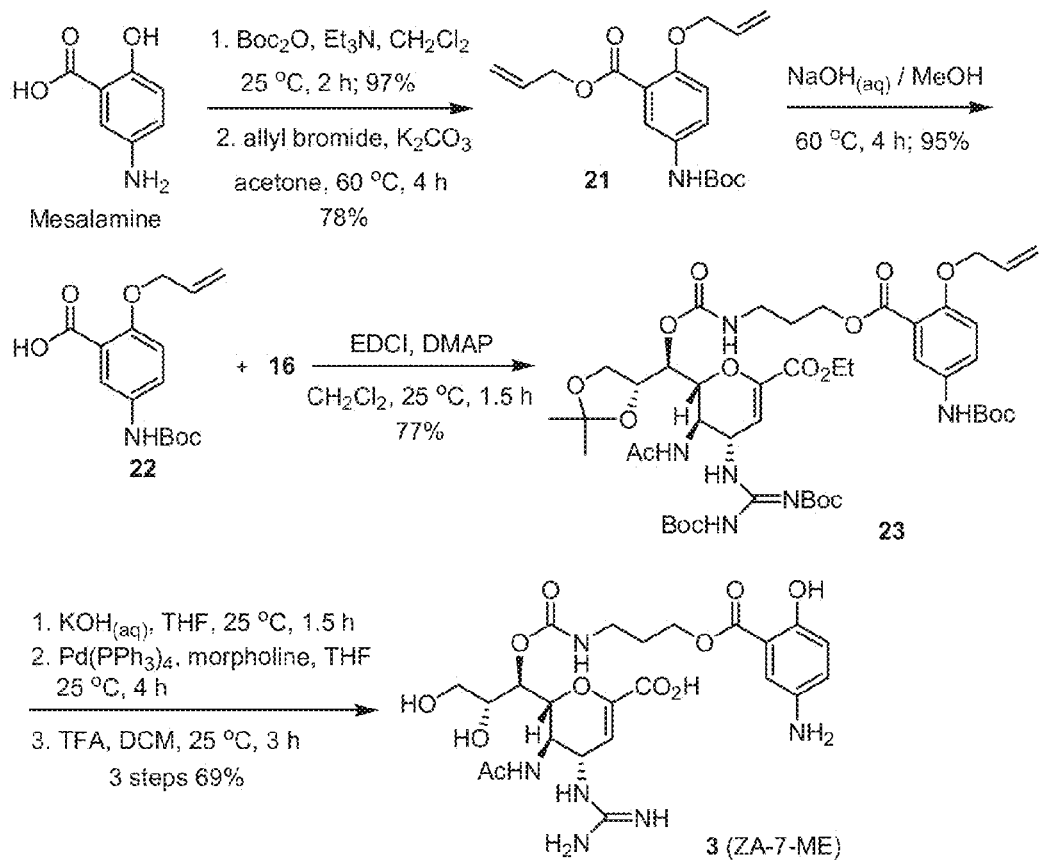

Example 17: Synthesis of ZA-7-ME Conjugate 3 (FIG. 7)

2-Allyloxy-5-tert-butoxycarbonylamino-benzoic acid allyl ester (21)

To a stirred solution of mesalazine (500 mg, 3.27 mmol) in CH$_2$Cl$_2$ (10 ml) was added Et$_3$N (0.9 mL, 6.54 mmol), followed by Boc$_2$O (784 mg, 3.60 mmol). The mixture was stirred at room temperature for 2H, and then quenched by adding saturated NaHCO$_3$. The mixture was poured into water and extracted with EtOAc (3×). The combined organic layer was dried over MgSO$_4$, filtered, and concentrated under reduced pressure to give the N-Boc protected derivative, 5-tert-butoxycarbonylamino-2-hydroxybenzoic acid (803 mg, 97%). The crude product was used in the next reaction without further purification. Pale yellow solid; C$_{12}$H$_{15}$NO$_5$; $^1$H NMR (400 MHz, CD$_3$OD) δ 7.92 (1H, d, J=2.0 Hz), 7.44 (1H, d, J=8.8 Hz), 6.84 (1H, d, J=8.8 Hz), 1.51 (9H, s); $^{13}$C NMR (100 MHz, CD$_3$OD) δ 172.6, 158.3, 155.0, 131.3, 128.0, 121.2, 117.5, 112.8, 80.2, 28.0 (3×); ESI-HRMS (negative mode) calcd for C$_{12}$H$_{14}$NO$_5$: 252.0872, found: m/z 252.0862 [M−H]$^-$.

To a solution of the above-prepared N-Boc protected derivative (605 mg, 2.39 mmol) in anhydrous acetone (10 mL) were added ally bromide (0.6 mL, 7.17 mmol) and finely powdered K$_2$CO$_3$ (990 mg, 7.17 mmol). The mixture was stirred for 4 h at 60° C., and then concentrated under reduced pressure. The residue was partitioned between EtOAc and 1 M HCl. The organic layer was washed with saturated NaHCO$_3$ and brine, dried over MgSO$_4$, filtered, and concentrated by rotary evaporation under reduced pressure. The crude material was purified by silica gel column chromatography (EtOAc/hexane=2:8) to yield an allylation product 21 (620 mg, 78%). C$_{18}$H$_{23}$NO$_5$; white solid, mp 77-78° C.; $^1$H NMR (400 MHz, CDCl$_3$) δ 7.72 (1H, d, J=2.8 Hz), 7.50 (1H, br), 7.18 (1H, s), 6.76 (1H, d, J=9.2 Hz), 5.94-5.85 (2H, m), 5.37-5.27 (2H, m), 5.18-5.11 (2H, m), 4.68 (2H, m), 4.34 (2H, m), 1.38 (9H, s); $^{13}$C NMR (100 MHz, CDCl$_3$) δ 165.4, 153.6, 153.0, 132.6, 131.9, 131.5, 124.1, 122.1, 120.2, 117.8, 117.0, 114.3, 79.8, 69.7, 65.2, 28.0 (3×); ESI-HRMS (negative mode) calcd for C$_{18}$H$_{22}$NO$_5$: 332.1498 found: m/z 332.1499 [M−H]$^-$.

2-Allyloxy-5-tert-butoxycarbonylamino-benzoic acid (22)

To a solution of compound 21 (500 mg, 1.50 mmol) in MeOH (20 mL) was added 1 M NaOH (2 mL). The mixture was stirred for 4 h at 60° C., and then concentrated under reduced pressure. H$_2$O (20 mL) was added and washed with ether, acidified with 1 M HCl, then extracted with CH$_2$Cl$_2$. The organic layer was dried over MgSO$_4$, filtered, and concentrated by rotary evaporation under reduced pressure. The crude material was purified by silica gel column chromatography (EtOAc/hexane=2:3) to yield the allyl ether 22 (405 mg, 92%). C$_{15}$H$_{19}$NO$_5$; yellow solid; [α]$^{22}_D$ +2.1 (c=0.5, CHCl$_3$); IR ν$_{max}$ (neat) 3347, 1694, 1589, 1523, 1416, 1260, 1239, 1163 cm$^{-1}$; $^1$H NMR (400 MHz, CDCl$_3$) δ 7.71 (1H, d, J=2.8 Hz), 7.50 (1H, s), 7.18 (1H, s), 6.86 (1H, d, J=8.8 Hz), 6.05-5.96 (2H, m), 6.76 (1H, d, J=9.2 Hz), 5.43 (1H, dt, J=17.2, 1.6 Hz), 5.23 (1H, dt, J=10.4, 1.6 Hz), 4.54 (2H, m), 1.47 (9H, s); $^{13}$C NMR (100 MHz, CDCl$_3$) 165.9, 152.8, 133.0, 131.1, 125.5, 123.2, 119.6, 117.8, 113.7, 80.2, 77.2, 70.7, 28.0 (3×); ESI-HRMS (negative mode) calculated for C$_{15}$H$_{18}$NO$_5$: 292.1185 found: m/z 292.1179 [M−H]$^-$.

Compound 23

To a solution of ZA-7-HP derivative 16 (70 mg, 0.10 mmol) in CH$_2$Cl$_2$ (5 mL) was added the mesalamine derivative 22 (33 mg, 0.11 mmol), EDCI (21 mg, 0.11 mmol) and 4-dimethylaminopyridine (13 mg, 0.11 mmol). The mixture was stirred at room temperature for 1.5 h. The resulting solution was extracted with 1 M HCl, saturated NaHCO$_3$ and brine, dried over MgSO$_4$, concentrated under reduced pressure, and purified by flash silica gel column chromatography (EtOAc/hexane=3:7 to EtOAc/hexane=1:1) to afford ester 23 (75 mg, 77%). C$_{46}$H$_{68}$N$_6$O$_{17}$; light yellow solid, mp 114-116° C.; TLC (EtOAc/hexane=7:3) R$_f$=0.33; [α]$^{20}_D$−11.5 (c=1.0, CH$_3$Cl); IR ν$_{max}$ (neat) 3319, 2979, 1728, 1610, 1248, 1154 cm$^{-1}$; $^1$H NMR (400 MHz, CDCl$_3$) δ 11.32 (1H, s), 8.29 (1H, d, J=8.8 Hz), 7.70 (1H, br), 7.57 (1H, d, J=2.4 Hz), 7.00 (1H, br), 6.87 (1H, d, J=9.2 Hz), 6.15 (1H, d, J=9.2 Hz), 6.07-5.97 (1H, m), 5.79 (1H, d, J=2.0 Hz), 5.42 (1H, s), 5.38 (1H, s), 5.26-5.16 (2H, m), 4.56 (1H, d, J=4.8 Hz), 4.42-4.19 (7H, m), 4.09-3.89 (4H, m), 3.35-3.24 (2H, m), 1.98-1.92 (2H, m), 1.85 (3H, s), 1.46 (9H, s), 1.43 (9H, s), 1.42 (9H, s), 1.32 (3H, s), 1.31-1.25 (6H, m); $^{13}$C NMR (100 MHz, CDCl$_3$) δ 170.8, 166.2, 163.1, 161.5, 156.9, 155.6, 153.8, 153.1, 152.8, 145.4, 132.9, 131.8, 124.4, 122.3, 120.4, 117.9, 114.6, 109.6, 108.8, 83.7, 80.3, 79.6, 74.9, 70.1, 69.6, 65.8, 63.1, 61.5, 48.7, 48.4, 38.7, 29.7, 28.5, 28.3 (3×), 28.2 (3×), 28.0 (3×), 26.5, 25.4, 23.0, 14.1; ESI-HRMS calcd for C$_{46}$H$_{69}$N$_6$O$_{17}$: 977.4719, found: m/z 977.4716 [M+H]$^+$.

ZA-7-ME Conjugate 3

To a solution of compound 23 (70 mg, 0.07 mmol) in THF (4 mL) was added 1 M KOH (4 mL). The solution was stirred at room temperature for 1.5 h, neutralized by Dowex® 50 W×8 (H$^+$), filtered and concentrated under reduced pressure. The residue was dissolved in anhydrous THF (5 mL), then added Pd(PPh$_3$)$_4$ (12 mg, 0.01 mmol) and morpholine (0.1 mL, 1.4 mmol). The mixture was stirred at room temperature for 4 h. The resulting solution was extracted with 1 M HCl and brine, dried over MgSO$_4$, concentrated under reduced pressure, and purified by flash silica gel column chromatography (MeOH/CH$_2$Cl$_2$=1:20 to MeOH/CH$_2$Cl$_2$=1:9). The residue was dissolved in CH$_2$Cl$_2$ (2 mL) and TFA (2 mL). After stirring at room temperature for 3H, the mixture was evaporated under reduced pressure. The residue was triturated with Et$_2$O, and centrifuged to give ZA-7-ME conjugate 3 (28 mg, 69%). C$_{23}$H$_{32}$N$_6$O$_{11}$; orange solid, mp 210-212° C.; [α]$^{22}_D$ −53.0 (c=0.5, MeOH); IR ν$_{max}$ (neat) 3351, 1673, 1622, 1493, 1403, 1228 cm$^{-1}$; $^1$H NMR (400 MHz, D$_2$O) δ 7.38 (1H, d, J=2.8 Hz), 7.10 (1H, dd, J=8.8, 2.8 Hz), 6.88 (1H, d, J=8.8 Hz), 5.67 (1H, d, J=2.0 Hz), 4.93 (1H, dd, J=9.2, 1.6 Hz), 4.50 (1H, dd, J=10.4, 1.6 Hz), 4.47-4.38 (3H, m), 4.09-4.01 (2H, m), 3.64 (1H, dd, J=12.0, 2.8 Hz), 3.48-3.43 (1H, m), 3.32-3.28 (2H, m), 2.00-1.96 (5H, m); $^{13}$C NMR (100 MHz, D$_2$O) δ 173.6, 169.8, 168.6, 157.0, 156.6, 153.6, 149.4, 136.9, 125.8, 117.8, 117.3, 112.9, 104.5, 75.2, 69.8, 68.5, 63.6, 62.5, 51.9, 47.3, 37.8, 27.8, 21.9; ESI-HRMS calcd for C$_{23}$H$_{33}$N$_6$O$_{11}$: 569.2207, found: m/z 569.2215 [M+H]$^+$.

Figure 8:
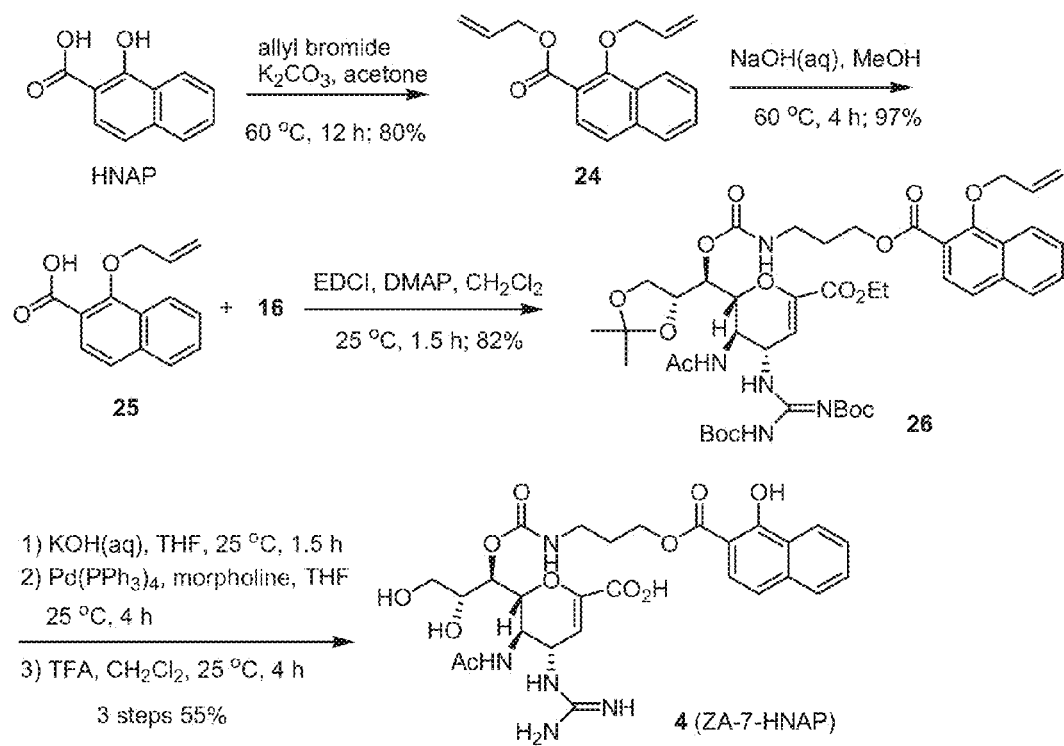

Example 18: Synthesis of ZA-7-HNAP Conjugate 4 (FIG. 8)

Allyl ether allyl ester of 1-hydroxy-2-naphthoic acid (24)

To a solution of 1-hydroxy-2-napthoic acid (HNAP, 1.04 g, 5.51 mmol) in anhydrous acetone (12 mL) were added ally bromide (1.4 mL, 16.53 mmol) and finely powdered K$_2$CO$_3$ (2.28 g, 16.53 mmol). The mixture was stirred for 4 h at 60° C., and then concentrated under reduced pressure. The residue was partitioned between EtOAc and 1 M HCl. The organic layer was washed with saturated NaHCO$_3$ and brine, dried over MgSO$_4$, filtered, and concentrated by rotary evaporation under reduced pressure. The crude material was purified by silica gel column chromatography (EtOAc/hexane=1:9) to yield the bis-allylation product 24 (1180 mg, 80%). C$_{17}$H$_{16}$O$_3$; TLC (EtOAc/hexane=1:9) R$_f$=0.65; IR ν$_{max}$ (neat) 1722, 1334, 1274, 1233, 1131 cm$^{-1}$; $^1$H NMR (400 MHz, CDCl$_3$) δ 8.27-8.24 (1H, m), 7.87 (1H, d, J=8.4 Hz), 7.77-7.27 (1H, m), 7.53 (1H, d, J=8.4 Hz), 7.51-7.47 (2H, m), 6.24-6.17 (1H, m), 6.09-6.02 (1H, m), 5.50-5.40 (2H, m), 5.30-5.25 (2H, m), 4.87-4.84 (2H, m), 4.61-4.62 (2H, m); $^{13}$C NMR (100 MHz, CDCl$_3$) δ 165.4, 156.7, 136.4, 133.5, 131.9, 128.5, 128.0, 127.5, 126.3, 126.2, 123.4, 123.3, 119.3, 118.2, 117.4, 76.3, 65.4; ESI-HRMS calcd for C$_{17}$H$_{17}$O$_3$: 269.1178, found: m/z 269.1184 [M+H]$^+$.

Allyl ether of 1-hydroxy-2-naphthoic acid (25)

To a solution of the allyl ester 24 (350 mg, 1.31 mmol) in MeOH (10 mL) was added 1 M NaOH (1 mL). The mixture was stirred for 4 h at 60° C., and then concentrated under reduced pressure. H$_2$O (20 mL) was added and washed with ether, acidified with 1 M HCl, then extracted with CH$_2$Cl$_2$. The organic layer was dried over MgSO$_4$, filtered, and concentrated by rotary evaporation under reduced pressure. The crude material was purified by silica gel column chromatography (EtOAc/hexane=3:7) to yield the allyl ether 25 of HNAP (289 mg, 97%). C$_{14}$H$_{12}$O$_3$; yellow solid, mp 99-101° C.; TLC (EtOAc/hexane=3:7) R$_f$=0.18; IR ν$_{max}$ (neat) 3455, 1738, 1365, 1232, 1228 cm$^{-1}$; $^1$H NMR (400 MHz, CDCl$_3$) δ 8.21 (1H, d, J=9.6 Hz), 8.03 (1H, d, J=8.4 Hz), 7.83 (1H, dd, J=8.4, 1.2 Hz), 7.63 (1H, d, J=8.8 Hz), 7.60-7.52 (2H, m), 6.28-6.17 (1H, m), 5.50 (1H, dd, J=17.2, 1.2 Hz), 5.37 (1H, dd, J=10.4, 0.8 Hz), 4.71 (1H, d, J=6.0 Hz); $^{13}$C NMR (100 MHz, CDCl$_3$) δ 169.2, 157.1, 137.2, 132.5, 128.8, 128.0, 127.8, 126.7, 126.6, 124.3, 119.2, 118.2, 77.4; ESI-HRMS (negative mode) calcd for C$_{14}$H$_{11}$O$_3$: 227.0708, found: m/z 227.0715 [M−H]$^-$.

Compound 26

To a solution of ZA-7-HP derivative 16 (96 mg, 0.14 mmol) in CH$_2$Cl$_2$ (5 mL) was added mesalamine derivative 25 (34 mg, 0.15 mmol), EDCI (29 mg, 0.15 mmol) and 4-dimethylaminopyridine (18 mg, 0.15 mmol). The mixture was stirred at room temperature for 1.5 h. The resulting solution was extracted successively with 1 M HCl, saturated $NaHCO_3$ and brine, dried over $MgSO_4$, concentrated under reduced pressure, and purified by flash silica gel column chromatography (EtOAc/hexane=1:4 to EtOAc/hexane=1:1) to afford compound 26 (101 mg, 82%). $C_{45}H_{61}N_5O_{15}$; white solid, mp 95-97° C.; TLC (EtOAc/hexane=1:1) $R_f$=0.62; $[\alpha]^{20}_D$ −17.0 (c=1.0, $CHCl_3$); IR $\nu_{max}$ (neat) 3316, 2979, 2930, 1724, 1641, 1610, 1369, 1249, 1141 $cm^{-1}$; ESI-HRMS calcd for $C_{45}H_{62}N_5O_{15}$: 912.4242, found: m/z 912.4249 $[M+H]^+$.

ZA-7-HNAP Conjugate 4

To a solution of compound 26 (84 mg, 0.09 mmol) in THF (3 mL) was added 1 M KOH (3 mL). The solution was stirred at room temperature for 1.5 h, neutralized by Dowex 50 W×8 ($H^+$), filtered and concentrated under reduced pressure. The residue was dissolved in anhydrous THF (5 mL), then added $Pd(PPh_3)_4$ (12 mg, 0.01 mmol) and morpholine (0.24 mL, 2.3 mmol). The mixture was stirred at room temperature for 4 h. The resulting solution was extracted with 1 M HCl and brine, dried over $MgSO_4$, concentrated under reduced pressure, and purified by flash silica gel column chromatography (MeOH/$CH_2Cl_2$=1:9 to MeOH/$CH_2Cl_2$=1:4). The residue was dissolved in $CH_2Cl_2$ (2 mL) and TFA (2 mL). After stirring at room temperature for 3H, the mixture was evaporated under reduced pressure. The residue was triturated with $Et_2O$, and centrifuged to give ZA-7-HNAP conjugate 4 (30 mg, 55%). $C_{27}H_{33}N_5O_{11}$; colorless solid, mp 230-232° C.; $[\alpha]^{24}_D$ −5.0 (c=0.5, $CH_3OH$); IR $\nu_{max}$ (neat) 3402, 1740, 1655, 1596, 1406, 1369, 1256, 1163 $cm^{-1}$; $^1H$ NMR (400 MHz, $CD_3OD$) δ 8.34 (1H, d, J=8.4 Hz), 7.80 (2H, d, J=8.8 Hz), 7.61 (1H, m), 7.51 (1H, t, J=7.6 Hz), 7.31 (1H, d, J=8.8 Hz), 5.58 (1H, d, J=2.0 Hz), 4.97 (1H, m), 4.49-4.44 (3H, m), 4.34 (1H, d, J=8.8 Hz), 4.23-4.18 (1H, m), 4.07-4.02 (1H, m), 3.64 (1H, dd, J=12.0, 2.4 Hz), 3.51-3.46 (1H, m), 3.30-3.27 (2H, m), 2.04-1.97 (2H, m), 1.93 (3H, s); $^{13}C$ NMR (100 MHz, $CD_3OD$) δ 172.1, 170.9, 160.4, 157.5, 156.8, 137.3, 129.1, 127.3, 125.5, 124.5, 124.0, 123.1, 118.4, 105.5, 103.3, 75.7, 69.8, 68.8, 63.1, 62.8, 52.0, 47.8, 37.3, 29.3, 28.5, 21.5; ESI-HRMS (negative mode) calcd for $C_{27}H_{32}N_5O_{11}$: 602.2098, found: m/z 602.2087 $[M-H]^-$.

Figure 9:
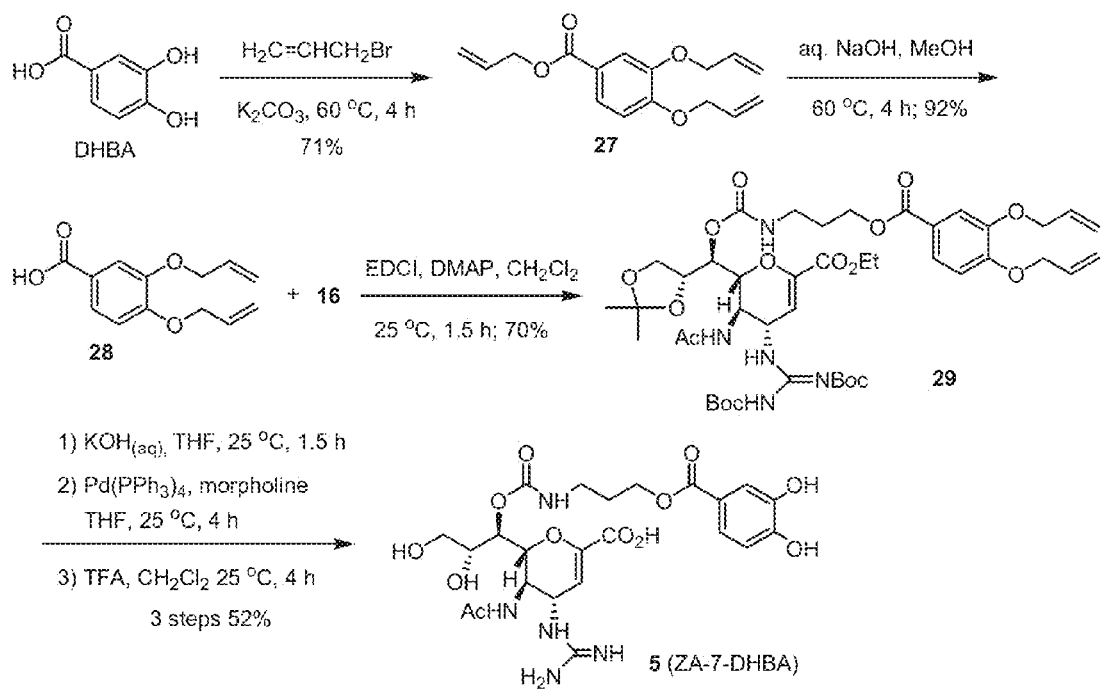

Example 19: Synthesis of ZA-7-DHBA Conjugate 5 (FIG. 9)

3,4-(Bis-allyloxy)benzoic acid allyl ester (27)

To a solution of 3,4-dihydroxybenzoic acid (DHBA, 676 mg, 4.39 mmol) in anhydrous acetone (10 ml) were added ally bromide (1.5 mL, 17.56 mmol) and finely powdered $K_2CO_3$ (2426 mg, 17.56 mmol). The mixture was stirred for 4 h at 60° C., and then concentrated under reduced pressure. The residue was partitioned between EtOAc and 1 M HCl. The organic layer was washed with saturated $NaHCO_3$ and brine, dried over $MgSO_4$, filtered, and concentrated by rotary evaporation under reduced pressure. The crude material was purified by silica gel column chromatography (EtOAc/hexane=1:9) to yield a fully allylation product 27 (852 mg, 71%). $C_{16}H_{18}O_4$; yellow oil; TLC (EtOAc/hexane=1:9) $R_f$=0.52; $^1H$ NMR (400 MHz, $CDCl_3$) δ 7.63 (1H, dd, J=8.4, 1.6 Hz), 7.55 (1H, d, J=1.6 Hz), 6.84 (1H, d, J=8.4 Hz), 6.01-5.92 (3H, m), 5.43-5.33 (3H, m), 5.27-5.21 (3H, m), 4.75 (2H, d, J=5.6 Hz), 4.62-4.60 (4H, m); $^{13}C$ NMR (100 MHz, $CDCl_3$) δ 165.2, 152.5, 147.9, 133.0, 132.7, 132.4, 123.8, 122.7, 118.0 (2×), 117.9, 114.6, 112.4, 69.8, 69.6, 65.3; ESI-HRMS calcd for $C_{16}H_{19}O_4$: 275.1283, found: m/z 275.1293 $[M+H]^+$.

3,4-(Bis-allyloxy)benzoic acid (28)

To a solution of the allyl ester 27 (300 mg, 1.09 mmol) in MeOH (5 mL) was added 1 M NaOH (0.5 mL). The mixture was stirred for 4 h at 60° C., and then concentrated under reduced pressure. $H_2O$ (15 mL) was added and washed with ether, acidified with 1 M HCl, then extracted with $CH_2Cl_2$. The organic layer was dried over $MgSO_4$, filtered, and concentrated by rotary evaporation under reduced pressure. The crude material was purified by silica gel column chromatography (EtOAc/hexane=3:7) to yield acid 28 (235 mg, 92%). $C_{13}H_{14}O_4$; colorless solid; TLC (EtOAc/hexane=3:7) $R_f$=0.35; $^1H$ NMR (400 MHz, $CDCl_3$) δ 7.71 (1H, dd, J=8.8, 1.0 Hz), 7.59 (1H, d, J=2.0 Hz), 6.89 (1H, d, J=8.8 Hz), 6.12-6.01 (2H, m), 5.45-5.39 (2H, m), 5.31-5.27 (2H, m), 4.66-4.63 (4H, m); $^{13}C$ NMR (100 MHz, $CDCl_3$) δ172.0, 153.1, 147.8, 132.8, 132.5, 124.6, 121.8, 118.1, 118.0, 114.8, 112.3, 69.8, 69.6; ESI-HRMS (negative mode) calcd for $C_{13}H_{13}O_4$: 233.0814, found: m/z 233.0812 $[M-H]^-$.

Compound 29

To a solution of ZA-7-HP derivative 16 (100 mg, 0.14 mmol) in $CH_2Cl_2$ (5 mL) was added 3,4-(bis-allyloxy) benzoic acid 28 (37 mg, 0.16 mmol), EDCI (30 mg, 0.16 mmol) and 4-dimethylaminopyridine (20 mg, 0.16 mmol). The mixture was stirred at room temperature for 1.5 h. The resulting solution was extracted with 1 M HCl, saturated $NaHCO_3$ and brine, dried over $MgSO_4$, concentrated under reduced pressure, and purified by flash silica gel column chromatography (EtOAc/hexane=3:7 to EtOAc/hexane=3:2) to afford compound 29 (90 mg, 70%). $C_{44}H_{63}N_5O_{16}$; white solid, mp 102-104° C.; $[\alpha]^{20}_D$ −26.5 (c=0.5, $CHCl_3$); IR $\nu_{max}$ (neat) 3315, 2980, 2931, 1729, 1641, 1608, 1267, 1141 $cm^{-1}$; $^1H$ NMR (400 MHz, $CDCl_3$) δ 11.36 (1H, s), 8.40 (1H, d, J=8.8 Hz), 7.59 (1H, d, J=8.4 Hz), 7.52 (1H, s), 6.85 (1H, d, J=8.8 Hz), 6.11 (1H, d, J=5.2 Hz), 6.08-5.98 (2H, m), 5.84 (1H, d, J=2.0 Hz), 5.40 (2H, dd, J=17.2, 4.8 Hz), 5.27-5.16 (5H, m), 5.10-5.07 (1H, m), 4.61 (1H, t, J=5.6 Hz), 4.33-4.31 (5H, m), 4.23-3.97 (6H, m), 3.28-3.25 (2H, m), 1.95-1.92 (2H, m), 1.86 (3H, s), 1.44 (9H, s), 1.42 (9H, s), 1.34 (3H, s), 1.30-1.26 (6H, m); $^{13}C$ NMR (100 MHz, $CDCl_3$) δ 170.7, 166.3, 163.0, 161.4, 157.0, 155.6, 152.7, 152.5, 147.9, 145.5, 133.0, 132.7, 123.7, 122.7, 118.0, 117.9, 114.6, 112.5, 109.5, 108.7, 83.6, 79.5, 77.6, 74.9, 69.8, 69.6, 65.9, 62.0, 61.5, 48.9, 48.4, 38.0, 29.6, 29.1, 28.2 (3×), 28.0 (3×), 26.4, 25.3, 23.0, 14.1; ESI-HRMS (negative mode) calcd for $C_{44}H_{62}N_5O_{16}$: 916.4192, found: m/z 916.4194 $[M-H]^-$.

ZA-7-DHBA Conjugate 5

To a solution of compound 29 (80 mg, 0.09 mmol) in THF (3 mL) was added 1 M KOH (3 mL). The solution was stirred at room temperature for 1.5 h, neutralized by Dowex 50 W×8 ($H^+$), filtered and concentrated under reduced pressure. The residue was dissolved in anhydrous THF (5 mL), then added $Pd(PPh_3)_4$ (23 mg, 0.02 mmol) and morpholine (0.4 mL, 4.5 mmol). The mixture was stirred at room temperature for 4 h. The resulting solution was extracted with 1 M HCl and brine, dried over $MgSO_4$, concentrated under reduced pressure, and purified by flash silica gel column chromatography (MeOH/CH$_2$Cl$_2$=1:9 to MeOH/CH$_2$Cl$_2$=1:4). The residue was dissolved in CH$_2$Cl$_2$ (2 mL) and TFA (2 mL). After stirring at room temperature for 3H, the mixture was evaporated under reduced pressure. The residue was triturated with Et$_2$O, and centrifuged to give ZA-7-DHBA conjugate 5 (26 mg, 52%). C$_{23}$H$_{31}$N$_5$O$_{12}$; yellow solid, mp 223-225° C.; [α]$^{25}_D$ −6.5 (c=0.33, H$_2$O); IR ν$_{max}$ (neat) 3376, 1674, 1618, 1405, 1296, 1234, 1119 cm$^{-1}$; $^1$H NMR (400 MHz, CD$_3$OD) δ 7.44 (1H, s), 7.42 (1H, d, J=8.0 Hz), 6.80 (1H, dd, J=8.0 Hz), 5.58 (1H, d, J=2.0 Hz), 4.95 (1H, m), 4.46 (1H, dd, J=10.4, 2.0 Hz), 4.36-4.29 (3H, m), 4.20-4.15 (1H, m), 4.06-4.01 (1H, m), 3.62 (1H, dd, J=12.0, 2.8 Hz), 3.49-3.45 (1H, m), 3.30-3.22 (2H, m), 1.94 (3H, s), 1.93-1.91 (2H, m); $^{13}$C NMR (100 MHz, CD$_3$OD) δ 173.7, 169.3, 168.5, 159.0, 158.3, 151.8, 151.7, 146.3, 123.8, 122.9, 117.6, 116.1, 104.6, 77.1, 71.3, 70.4, 64.6, 63.5, 39.0, 30.2, 23.0; ESI-HRMS (negative mode) calcd for C$_{23}$H$_{30}$N$_5$O$_{12}$: 568.1891, found: m/z 568.1893 [M−H]$^-$.

Example 20: Synthesis of ZA-7-CA-Amide Conjugate 7 (FIG. 10)

Tert-Butyl 3-aminopropyl carbamate (30)

A solution of Boc$_2$O (500 mg, 2.29 mmol) in 1,4-dioxane (10 mL) was added over 3 h to a stirring solution of 1,3-diaminopropane (2.5 mL, 11.45 mmol) in 1,4-dioxane (10 mL) at room temperature. After stirring for 16 h, the solvent was removed under reduced pressure. Water (20 mL) was added to the residue, and the insoluble side product was collected by filtration. The filtrate was extracted with CH$_2$Cl$_2$. The organic extract was dried over MgSO$_4$, filtered and concentrated under reduced pressure to afford carbamate 30 (358 mg, 90%). C$_8$H$_{18}$N$_2$O$_2$; colorless oil; $^1$H NMR (400 MHz, CDCl$_3$) δ 5.32 (1H, br), 2.95 (2H, m), 2.51 (2H, t, J=6.4 Hz), 1.48 (1H, br), 1.38 (2H, t, J=6.4 Hz), 1.20 (9H, s); $^{13}$C NMR (100 MHz, CDCl$_3$) δ 155.9, 78.2, 39.0, 37.7, 32.9, 28.0; ESI-HRMS calcd for C$_8$H$_{19}$N$_2$O$_2$: 175.1447, found: m/z 175.1445 [M+H]$^+$.

Tert-Butyl 3-[(3,4-Bis-allyloxyphenyl)acryloylamino]propyl carbamate (31)

To a solution of allyl ether of caffeic acid 18 (134 mg, 0.51 mmol) in CH$_2$Cl$_2$ (5 mL) was added amine 30 (98 mg, 0.56 mmol), EDCI (108 mg, 0.56 mmol) and 4-dimethylaminopyridine (68 mg, 0.56 mmol). The mixture was stirred at room temperature for 1.5 h. The resulting solution was extracted successively with 1 M HCl, saturated NaHCO$_3$ and brine, dried over MgSO$_4$, concentrated under reduced pressure, and purified by flash silica gel column chromatography (EtOAc/hexane=1:3 to EtOAc/hexane=2:3) to afford the coupling product 31 (154 mg, 73%). C$_{23}$H$_{32}$N$_2$O$_5$; colorless solid, mp 115-117° C.; [α]$^{24}_D$ −3.7 (c=0.25, CHCl$_3$); IR ν$_{max}$ (neat) 3306, 2925, 1694, 1658, 1510, 1257 cm$^{-1}$; $^1$H NMR (400 MHz, CDCl$_3$) δ 7.46 (1H, d, J=15.6 Hz), 6.97 (2H, m), 6.82 (1H, br), 6.76 (1H, d, J=8.0 Hz), 6.28 (1H, d, J=15.6 Hz), 6.03-5.95 (2H, m), 5.35 (2H, d, J=17.2 Hz), 5.23-5.20 (3H, m), 4.53 (4H, s), 3.35 (2H, t, J=5.6 Hz), 3.12 (2H, t, J=5.2 Hz), 1.61 (2H, s), 1.38 (9H, s); $^{13}$C NMR (100 MHz, CDCl$_3$) δ 166.5, 156.6, 149.8, 148.3, 140.3, 133.0, 132.8, 128.0, 121.8, 118.8, 117.7, 117.6, 113.4, 112.7, 79.1, 69.8, 69.6, 36.9, 35.9, 30.1, 28.2 (3×); ESI-HRMS calcd for C$_{23}$H$_{33}$N$_2$O$_5$: 417.2389, found: m/z 417.2388 [M+H]$^+$.

Compound 33

To a solution of the above-prepared N-Boc compound 31 (150 mg, 0.36 mmol) in CH$_2$Cl$_2$ (2 mL) was added TFA (2 mL). After stirring at room temperature for 1 h, the mixture was evaporated under reduced pressure to give the corresponding amine 32. The crude amine product was dissolved in CH$_3$CN (7 mL), and added carbonate 15 (260 mL, 0.34 mmol) and Et$_3$N (0.075 mL, 0.50 mmol). The mixture was stirred at room temperature for 2H, and then concentrated under reduced pressure. The residue was partitioned between CH$_2$Cl$_2$ and saturated NaHCO$_3$. The organic layer was dried over MgSO$_4$, filtered, and concentrated by rotary evaporation under reduced pressure. The crude material was purified by silica gel column chromatography (EtOAc/hexane=4:1) to yield carbamate 33 (224 mg, 70%). C$_{46}$H$_{66}$N$_6$O$_{15}$; TLC (EtOAc/hexane=4:1) R$_f$=0.15; white solid, mp 113-115° C.; [α]$^{24}_D$+13.5 (c=1.0, CHCl$_3$); IR ν$_{max}$ (neat) 3308, 2979, 2930, 1728, 1641, 1611, 1511, 1253, 1140 cm$^{-1}$; $^1$H NMR (400 MHz, CDCl$_3$) δ 11.36 (1H, s), 8.45 (1H, d, J=8.4 Hz), 7.44 (1H, d, J=15.6 Hz), 7.32 (1H, t, J=2.0 Hz), 6.98 (2H, d, J=6.8 Hz), 6.79 (1H, d, J=8.8 Hz), 6.50 (1H, d, J=9.2 Hz), 6.31 (1H, d, J=15.6 Hz), 6.05-5.95 (2H, m), 5.84 (1H, d, J=1.2 Hz), 5.34 (1H, d, J=17.2 Hz), 5.26-5.18 (3H, m), 5.12-5.05 (2H, m), 4.56-4.52 (4H, m), 4.30-4.25 (2H, m), 4.22-4.12 (3H, m), 4.08-4.01 (3H, m), 3.98-3.94 (1H, m), 3.50-3.45 (1H, m), 3.38-3.32 (3H, m), 3.05-3.00 (1H, m), 1.97 (3H, s), 1.41 (9H, s), 1.33 (9H, s), 1.30-1.18 (9H, m); $^{13}$C NMR (100 MHz, CDCl$_3$) δ 171.0, 166.5, 163.0, 161.2, 156.9, 155.6, 152.6, 149.7, 148.3, 145.1, 139.9, 133.0, 133.0, 128.2, 121.4, 119.2, 117.6, 113.5, 113.1, 109.4, 108.6, 83.5, 79.4, 75.0, 69.6, 69.5, 65.6, 61.4, 60.2, 49.2, 47.8, 38.1, 36.1, 29.5, 28.5, 28.1 (3×), 27.8 (3×), 26.3, 25.2, 23.0, 14.0; ESI-HRMS calcd for C$_{46}$H$_{67}$N$_6$O$_{15}$: 943.4664, found: m/z 943.4662 [M+H]$^+$.

ZA-7-CA-Amide Conjugate 7

To a solution of compound 33 (100 mg, 0.11 mmol) in THF (4 mL) was added 1 M KOH (2 mL). The solution was stirred at room temperature for 1.5 h, neutralized by Dowex 50 W×8 (H$^+$), filtered and concentrated under reduced pressure. The residue was dissolved in anhydrous THF (5 mL), then added Pd(PPh$_3$)$_4$ (23 mg, 0.02 mmol) and morpholine (0.4 mL, 4.5 mmol). The mixture was stirred at room temperature for 4 h. The resulting solution was extracted with 1 M HCl and brine, dried over MgSO$_4$, concentrated under reduced pressure, and purified by flash silica gel column chromatography (MeOH/CH$_2$Cl$_2$=1:9 to MeOH/CH$_2$Cl$_2$=1:4). The residue was dissolved in CH$_2$Cl$_2$ (2 mL) and TFA (2 mL). After stirring at room temperature for 3H, the mixture was evaporated under reduced pressure. The residue was triturated with Et$_2$O, and centrifuged to give ZA-7-CA-amide conjugate 7 (35 mg, 56%). C$_{25}$H$_{34}$N$_6$O$_{11}$; yellow solid, mp 288-290° C.; [α]$^{19}_D$+220.1 (c=0.50, H$_2$O); IR ν$_{max}$ (neat) 3422, 1702, 1655, 1545, 1259, 1202, 1131, 1064 cm$^{-1}$; $^1$H NMR (400 MHz, D$_2$O) δ 7.36 (1H, d, J=15.6 Hz), 7.13 (1H, s), 7.06 (1H, d, J=7.6 Hz), 6.94 (1H, d, J=8.0 Hz), 6.40 (1H, dd, J=16.0 Hz), 5.74 (1H, d, J=2.0 Hz), 4.99 (1H, dd, J=9.2, 2.0 Hz), 4.46 (1H, dd, J=8.4, 3.2 Hz), 4.45 (1H, d, J=7.2 Hz), 4.18-4.11 (2H, m), 3.72 (1H, dd, J=12.0, 2.0 Hz), 3.57-3.52 (1H, m), 3.35 (2H, t, J=6.0 Hz), 3.18 (2H, t, J=6.4 Hz), 2.02 (3H, s), 1.78 (2H, m); $^{13}$C NMR (100 MHz, D$_2$O) δ 173.8, 169.0, 168.5, 157.0, 156.7, 149.2, 146.3, 144.2, 140.7, 127.4, 121.9, 117.8, 116.2, 114.8, 104.8, 75.3, 69.8, 68.6, 62.5, 51.8, 47.4, 38.2, 37.0, 28.4, 21.9;

ESI-HRMS (negative mode) calcd for $C_{25}H_{33}N_6O_{11}$: 593.2207, found: m/z 593.2222 [M–H]$^-$.

Example 21: Synthesis of ZA-7-HNAP-Amide Conjugate 8 (FIG. 11)

N-3-(Tert-butoxycarbonylamino)propyl 1-hydroxynaphthene-2-carboxamide (34)

To a solution of HNAP (300 mg, 1.60 mmol) in $CH_2Cl_2$ (5 mL) was added amine 30 (306 mg, 1.76 mmol), EDCI (334 mg, 1.76 mmol) and 4-dimethylaminopyridine (215 mg, 1.76 mmol). The mixture was stirred at room temperature for 12 h. The resulting solution was washed with 1 M HCl, dried over $MgSO_4$, concentrated under reduced pressure, and purified by flash silica gel column chromatography (hexane to EtOAc/hexane=1:4) to afford the coupling product 34 (378 mg, 69%). $C_{19}H_{24}N_2O_4$; TLC (EtOAc/hexane=3:7) R=0.31; red foam; IR $v_{max}$ (neat) 3356, 2976, 1692, 1619, 1609, 1538, 1392, 1365, 1282 cm$^{-1}$; $^1$H NMR (400 MHz, CDCl$_3$) δ 14.16 (1H, s), 8.43 (1H, d, J=8.4 Hz), 7.94 (1H, s), 7.73 (1H, d, J=8.0 Hz), 7.53 (3H, m), 7.25 (1H, d, J=8.8 Hz), 5.22 (1H, s), 3.51 (2H, m), 3.23 (2H, t, J=6.0 Hz), 1.71 (2H, t, J=5.2 Hz), 1.49 (9H, s); $^{13}$C NMR (100 MHz, CDCl$_3$) δ 170.7, 160.2, 157.1, 136.0, 128.5, 127.1, 125.4, 123.5, 121.3, 118.0, 106.8, 79.5, 77.0, 36.9, 35.5, 29.8, 28.2 (3×); ESI-HRMS (negative mode) calcd for $C_{19}H_{23}N_2O_4$: 343.1658, found: m/z 343.1648 [M–H]$^-$.

Compound 36

To a solution of N-Boc compound 34 (189 mg, 0.55 mmol) in $CH_2Cl_2$ (2 mL) was added TFA (2 mL). After stirring at room temperature for 1 h, the mixture was evaporated under reduced pressure to give the corresponding amine 35. The crude amine product was dissolved in $CH_3CN$ (7 mL), and added carbonate 15 (236 mL, 0.31 mmol) and $Et_3N$ (0.05 mL, 0.34 mmol). The mixture was stirred at room temperature for 2H, and then concentrated under reduced pressure. The residue was partitioned between $CH_2Cl_2$ and saturated $NaHCO_3$. The organic layer was dried over $MgSO_4$, filtered, and concentrated by rotary evaporation under reduced pressure. The crude material was purified by silica gel column chromatography (EtOAc/hexane=1:4 to EtOAc/hexane=2:3) to yield carbamate 36 (165 mg, 61%). $C_{42}H_{58}N_6O_{14}$; TLC (EtOAc/hexane=1:1) R$_f$=0.55; white solid, mp 157-160° C.; [α]$^{24}_D$+14.6 (c=0.5, CHCl$_3$); IR $v_{max}$ (neat) 3413, 1641, 1634, 1252, 1142 cm$^{-1}$; $^1$H NMR (400 MHz, CDCl$_3$) δ 14.08 (1H, s), 11.36 (1H, s), 8.56 (1H, d, J=8.4 Hz), 8.46 (1H, s), 8.35 (1H, d, J=8.0 Hz), 7.66 (1H, t, J=8.0 Hz), 7.60 (1H, t, J=8.8 Hz), 7.50-7.41 (2H, m), 7.16 (1H, d, J=8.8 Hz), 6.62 (1H, d, J=8.4 Hz), 5.88 (1H, d, J=2.0 Hz), 5.30 (1H, d, J=5.2 Hz), 5.13-5.08 (2H, m), 4.35-4.15 (6H, m), 4.11-3.95 (3H, m), 3.71-3.66 (1H, m), 3.41 (2H, br), 3.04 (1H, br), 1.92 (3H, s), 1.46 (9H, s), 1.43 (9H, s), 1.34-1.25 (9H, m); $^{13}$C NMR (100 MHz, CDCl$_3$) δ 171.4, 171.0, 162.5, 161.2, 160.3, 156.9, 155.6, 152.6, 145.3, 136.1, 128.3, 127.1, 125.5, 125.3, 123.6, 122.0, 117.7, 109.2, 108.8, 107.2, 83.8, 79.9, 77.3, 74.9, 69.6, 65.7, 61.5, 49.4, 47.5, 38.0, 35.9, 28.3, 28.1 (3×), 27.6 (3×), 26.3, 25.2, 23.0, 14.0; ESI-HRMS (negative mode) alcd for $C_{42}H_{57}N_6O_{14}$: 869.3933, found: m/z 869.3932 [M–H]$^-$.

ZA-7-HNAP-Amide Conjugate 8

To a solution of compound 36 (95 mg, 0.11 mmol) in THF (3 mL) was added 1 M KOH (1 mL). The solution was stirred at room temperature for 1.5 h, neutralized by Dowex 50 W×8 (H$^+$), filtered and concentrated under reduced pressure. The residue was dissolved in $CH_2Cl_2$ (2 mL) and treated with TFA (2 mL). After stirring at room temperature for 3H, the mixture was evaporated under reduced pressure. The residue was triturated with $Et_2O$, and centrifuged to give ZA-7-HNAP-amide conjugate 8 (41 mg, 62%). $C_{27}H_{34}N_6O_{10}$; light yellow solid, mp 230-232° C.; [α]$^{24}_D$+17.1 (c=1.0, CH$_3$OH); IR $v_{max}$ (neat) 3423, 1637, 1405, 1261, 1145 cm$^{-1}$; $^1$H NMR (400 MHz, CD$_3$OD) δ 8.33 (1H, d, J=8.0 Hz), 7.78 (1H, d, J=8.0 Hz), 7.72 (1H, d, J=8.8 Hz), 7.57 (1H, t, J=9.2 Hz), 7.49 (1H, t, J=8.0 Hz), 7.30 (1H, d, J=8.8 Hz), 5.55 (1H, d, J=2.4 Hz), 4.93 (1H, dd, J=9.2, 6.4 Hz), 4.46 (1H, dd, J=10.4, 6.0 Hz), 4.32 (1H, dd, J=9.2, 2.0 Hz), 4.22 (1H, d, J=10.0 Hz), 4.07-4.02 (1H, m), 3.66-3.61 (1H, m), 3.60-3.43 (3H, m), 3.27-3.20 (1H, m), 3.17-3.10 (1H, m), 1.97 (3H, s), 1.89-1.75 (2H, m); $^{13}$C NMR (100 MHz, CD$_3$OD) δ 172.6, 171.5, 169.2, 160.2, 157.9, 157.2, 150.9, 136.7, 128.7, 127.4, 125.7, 125.6, 123.4, 122.2, 118.1 (2×), 107.5, 103.0, 76.0, 70.2, 69.2, 63.6, 52.6, 38.2, 36.6, 29.3, 21.9; ESI-HRMS calcd for $C_{27}H_{35}N_6O_{10}$: 603.2415, found: m/z 603.2405 [M+H]$^+$.

Figure 12:
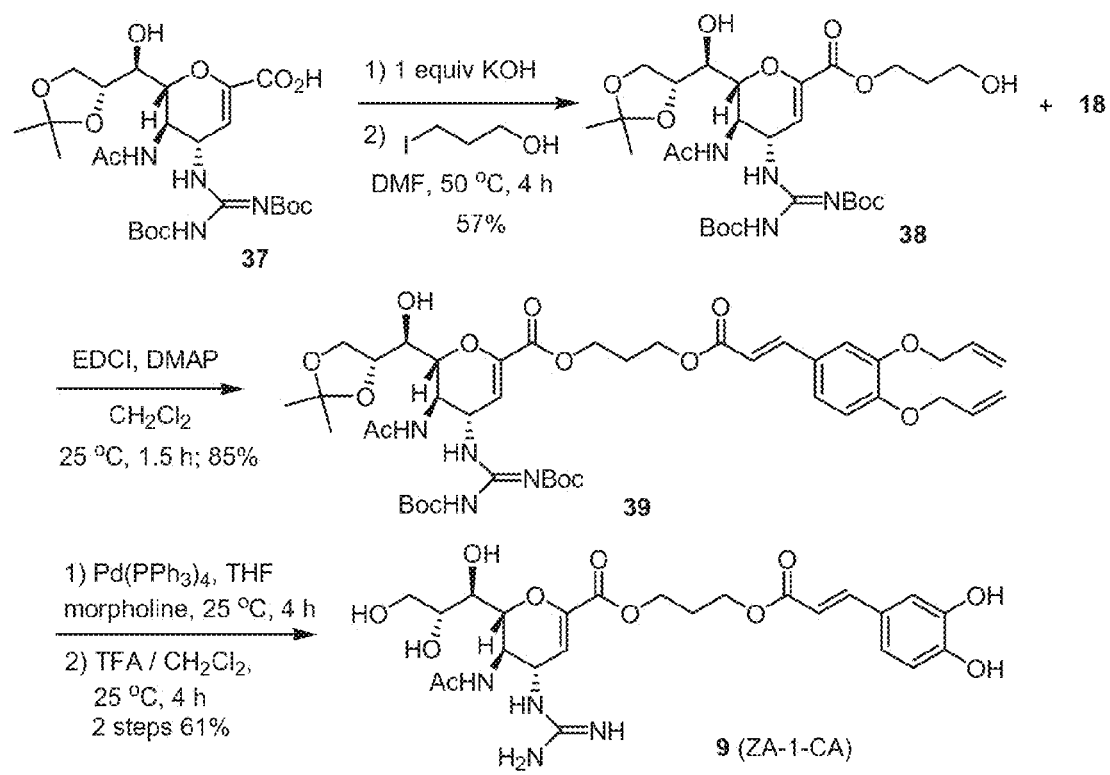

Example 22: Synthesis of ZA-1-CA Conjugate 9 (FIG. 12)

5-Acetylamino-4-[2,3-bis(tert-butoxycarbonyl) guanidino]-6-[2,2-dimethyl-[1,3]dioxolan-4-yl)-hydroxymethyl]-5,6-dihydro-4H-pyran-2-carboxylic acid (37)

To a solution of ester 14 (500 mg, 0.83 mmol) in THF (10 mL) was added 1 M KOH (5 mL). The solution was stirred at room temperature for 1.5 h, neutralized by Dowex 50 W×8 (H$^+$), filtered and concentrated under reduced pressure. The residue was dissolved in $CH_2Cl_2$ (20 mL) and extracted with 1 M HCl and brine, dried over $MgSO_4$, concentrated under reduced pressure, and purified by flash silica gel column chromatography (MeOH/CH$_2$Cl$_2$=1:9) to afford acid 37 (428 mg, 90%). $C_{25}H_{40}N_4O_{11}$; white solid, mp 118-120° C.; $^1$H NMR (400 MHz, CDCl$_3$) δ 11.28 (1H, s), 8.57 (1H, d, J=7.6 Hz), 8.00 (1H, d, J=4.4 Hz), 5.74 (1H, d, J=2.4 Hz), 5.08-5.03 (1H, m), 4.32 (1H, d, J=5.6 Hz), 4.09-3.89 (4H, m), 3.41 (1H, d, J=8.8 Hz), 1.95 (3H, s), 1.41 (9H, s), 1.39 (9H, s), 1.33 (3H, s), 1.26 (3H, s); $^{13}$C NMR (100 MHz, CDCl$_3$) 174.1, 171.2, 162.0, 157.3, 152.3, 146.7, 109.2, 106.9, 84.1, 79.9, 77.9, 73.6, 69.6, 67.2, 51.6, 48.3, 28.0 (3×), 27.8 (3×), 26.9, 24.9, 22.7; ESI-HRMS (negative mode) calcd for $C_{25}H_{39}N_4O_{11}$: 571.2615, found: m/z 571.2615 [M–H]$^-$.

5-Acetylamino-4-[2,3-bis(tert-butoxycarbonyl) guanidino]-6-[(2,2-dimethyl-[1,3]dioxolan-4-yl)-hydroxymethyl]-5,6-dihydro-4H-pyran-2-carboxylic acid 3-hydroxypropyl ester (38)

To a solution of acid 37 (402 mg, 0.80 mmol) in MeOH (5 mL) was added KOH (45 mg, 0.80 mmol). The mixture was stirred at room temperature for 30 min, and then concentrated under reduced pressure to give the corresponding potassium salt. The salt was dissolved in DMF (5 mL), and then added 3-iodo-1-propanol (93 μL, 1.00 mmol). After stirring at 50° C. for 4 h, the mixture was evaporated under reduced pressure. The residue was dissolved in $CH_2Cl_2$ (20 mL) and extracted with 1M HCl and brine, dried over $MgSO_4$, concentrated under reduced pressure, and purified by flash silica gel column chromatography (EtOAc/ hexane=1:1 to EtOAc/hexane=4:1) to afford ester 38 (285 mg, 57%). $C_{28}H_{46}N_4O_{12}$; colorless solid, mp 86-88° C.; TLC (EtOAc/hexane=4:1) $R_f$=0.48; $[\alpha]^{21}_D$ −23.1 (c=1.0, CHCl$_3$); IR $\nu_{max}$ (neat) 3275, 2931, 1727, 1646, 1611, 1558, 1150 cm$^{-1}$; $^1$H NMR (400 MHz, CDCl$_3$) δ 11.32 (1H, s), 8.58 (1H, d, J=7.6 Hz), 7.96 (1H, d, J=0.8 Hz), 5.76 (1H, d, J=2.0 Hz), 5.26 (1H, d, J=4.4 Hz), 5.12-5.08 (1H, m), 4.34-4.28 (2H, m), 4.14-4.10 (1H, m), 4.07-3.91 (3H, m), 3.68 (2H, t, J=6.0 Hz), 3.47-3.44 (1H, m), 1.96 (3H, s), 1.90-1.87 (2H, m), 1.46 (9H, s), 1.44 (9H, s), 1.37 (3H, s), 1.31 (3H, s); $^{13}$C NMR (100 MHz, CDCl$_3$) δ 173.9, 162.2, 161.6, 157.5, 152.6, 146.7, 109.1, 107.0, 84.3, 80.0, 78.5, 74.0, 69.7, 67.4, 62.7, 59.1, 51.7, 48.3, 31.4, 28.1 (3×), 27.9 (3×), 26.9, 25.1, 22.9; ESI-HRMS calcd for $C_{28}H_{47}N_4O_{12}$: 631.3190, found: m/z 631.3187 [M+H]$^+$.

Compound 39

To a solution of 38 (86 mg, 0.14 mmol) in CH$_2$Cl$_2$ (5 mL) was added the allyl ether of caffeic acid 18 (39 mg, 0.15 mmol), EDCI (29 mg, 0.15 mmol) and 4-dimethylaminopyridine (18 mg, 0.15 mmol). The mixture was stirred at room temperature for 1.5 h. The resulting solution was extracted with 1 M HCl, saturated NaHCO$_3$ and brine, dried over MgSO$_4$, concentrated under reduced pressure, and purified by flash silica gel column chromatography (EtOAc/hexane=1:4 to EtOAc/hexane=2:3) to afford compound 39 (101 mg, 85%). $C_{43}H_{60}N_4O_{15}$; light yellow solid, mp 70-72° C.; TLC (EtOAc/hexane=2:3) $R_f$=0.24; $[\alpha]^{20}_D$−18.7 (c=1.0, CHCl$_3$); IR $\nu_{max}$ (neat) 3311, 2979, 2930, 1724, 1646, 1607, 1253, 1153 cm$^{-1}$; $^1$H NMR (400 MHz, CDCl$_3$) δ 11.34 (1H, s), 8.60 (1H, d, J=8.0 Hz), 7.96 (1H, d, J=5.2 Hz), 7.56 (1H, d, J=16.0 Hz), 7.03 (2H, s), 6.83 (1H, d, J=8.8 Hz), 6.22 (1H, d, J=16.0 Hz), 6.21-5.98 (2H, m), 5.77 (1H, d, J=2.0 Hz), 5.39 (2H, dd, J=17.2, 5.2 Hz), 5.28-5.44 (2H, m), 5.14-5.10 (1H, m), 4.61-4.55 (4H, m), 4.37-4.33 (1H, m), 4.30-4.24 (4H, m), 4.16-4.12 (2H, m), 4.06-3.93 (3H, m), 2.09-2.05 (2H, m), 1.98 (3H, s), 1.47 (9H, s), 1.45 (9H, s), 1.38 (3H, s), 1.32 (3H, s); $^{13}$C NMR (100 MHz, CDCl$_3$) δ 173.9, 166.9, 162.2, 161.3, 157.5, 152.6, 150.6, 148.5, 146.7, 144.8, 133.0, 132.8, 127.4, 122.7, 117.8, 117.7, 115.4, 113.3, 112.6, 109.0, 106.9, 84.2, 80.0, 78.5, 77.2, 73.9, 69.8, 69.7, 67.4, 62.1, 60.6, 51.8, 48.3, 29.6, 28.1 (3×), 27.9 (3×), 26.9, 25.0, 22.8; ESI-HRMS (negative mode) calcd for $C_{43}H_{59}N_4O_{15}$: 803.3351, found: m/z 803.3351 [M−H]$^-$.

ZA-1-CA Conjugate 9

To a solution of compound 39 (60 mg, 0.07 mmol) in anhydrous THF (4 mL) was added Pd(PPh$_3$)$_4$ (12 mg, 0.01 mmol) and morpholine (0.1 mL, 1.4 mmol). The mixture was stirred at room temperature for 4 h. The resulting solution was extracted with 1 M HCl and brine, dried over MgSO$_4$, concentrated under reduced pressure, and purified by flash silica gel column chromatography (MeOH/CH$_2$Cl$_2$=1:20 to MeOH/CH$_2$Cl$_2$=1:9). The residue was dissolved in CH$_2$Cl$_2$ (2 mL) and TFA (2 mL). After stirring at room temperature for 3 h, the mixture was evaporated under reduced pressure. The residue was triturated with Et$_2$O, and centrifuged to give ZA-1-CA conjugate 9 (23 mg, 61%). $C_{24}H_{32}N_4O_{11}$; orange solid, mp 135-137° C.; $[\alpha]^{20}_D$+6.6 (c=1.0, H$_2$O); IR $\nu_{max}$ (neat) 3414, 1675, 1636, 1276, 1203, 1185, 1141 cm$^{-1}$; $^1$H NMR (400 MHz, CD$_3$OD) δ 7.55 (1H, d, J=16.0 Hz), 7.04 (1H, d, J=2.0 Hz), 6.95 (1H, dd, J=8.0, 2.0 Hz), 6.79 (1H, d, J=8.0 Hz), 6.25 (1H, d, J=15.6 Hz), 5.90 (1H, d, J=2.4 Hz), 4.35-4.19 (6H, m), 3.88-3.81 (2H, m), 3.71-3.67 (3H, m), 2.11-2.07 (2H, m), 1.99 (3H, s); $^{13}$C NMR (100 MHz, CD$_3$OD) δ 174.6, 169.3, 163.4, 159.0, 149.8, 147.3, 147.0, 146.6, 127.8, 123.2, 116.7, 115.3, 115.0, 109.0, 78.1, 71.5, 70.3, 64.8, 63.5, 62.1, 51.5, 50.0, 29.2, 22.8; ESI-HRMS calcd for $C_{24}H_{33}N_4O_{11}$: 553.2146, found: m/z 553.2150 [M+H]$^+$.

Figure 13:
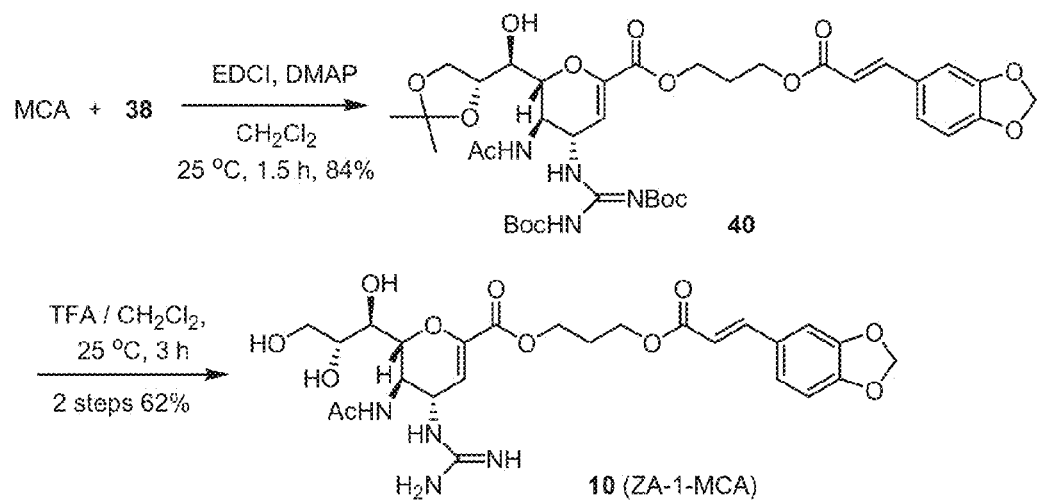

Example 23: Synthesis of ZA-1-MCA Conjugate 10 (FIG. 13)

Compound 40

To a solution of alcohol 38 (40 mg, 0.06 mmol) in CH$_2$Cl$_2$ (3 mL) was added (3,4-methylenedioxy)cinnamic acid (MCA, 13 mg, 0.07 mmol), EDCI (13 mg, 0.07 mmol) and 4-dimethylaminopyridine (9 mg, 0.07 mmol). The mixture was stirred at room temperature for 1.5 h. The resulting solution was extracted with 1 M HCl, saturated NaHCO$_3$ and brine, dried over MgSO$_4$, concentrated under reduced pressure, and purified by flash silica gel column chromatography (EtOAc/hexane=1:4 to EtOAc/hexane=2:3) to afford compound 40 (43 mg, 84%). $C_{38}H_{52}N_4O_{15}$; pale yellow solid, mp 73-75° C.; TLC (EtOAc/hexane=1:1) $R_f$=0.20; $[\alpha]^{20}_D$ −17.3 (c=1.0, CHCl$_3$); IR $\nu_{max}$ (neat) 2924, 1723, 1646, 1607, 1250, 1154, 1127 cm$^{-1}$; $^1$H NMR (400 MHz, CDCl$_3$) δ 11.34 (1H, s), 8.59 (1H, d, J=7.9 Hz), 7.95 (1H, d, J=5.2 Hz), 7.55 (1H, d, J=16.0 Hz), 7.00 (1H, s), 6.98 (1H, d, J=8.0 Hz), 6.78 (1H, d, J=8.0 Hz), 6.22 (1H, d, J=15.6 Hz), 5.97 (2H, s), 5.77 (1H, d, J=1.6 Hz), 5.27 (1H, br), 5.13-5.09 (1H, m), 4.38-4.32 (1H, m), 4.29-4.25 (3H, m), 4.21-4.13 (2H, m), 4.06-3.90 (3H, m), 2.09-2.05 (2H, m), 1.98 (3H, s), 1.48 (9H, s), 1.46 (9H, s), 1.39 (3H, s), 1.33 (3H, s); $^{13}$C NMR (100 MHz, CDCl$_3$) δ 174.0, 166.9, 162.3, 161.4, 157.6, 152.6, 149.6, 148.3, 146.8, 144.7, 128.7, 124.4, 115.7, 109.1, 108.5, 106.9, 106.5, 101.5, 84.3, 80.1, 78.6, 74.0, 69.8, 67.5, 62.2, 60.8, 51.9, 48.4, 29.7, 28.2 (3×), 28.0 (3×), 27.0, 25.1, 22.9; ESI-HRMS (negative mode) calcd for $C_{38}H_{51}N_4O_{15}$: 803.3351, found: m/z 803.3351 [M−H]$^-$.

ZA-1-MCA Conjugate 10

To a solution of compound 40 (48 mg, 0.06 mmol) in CH$_2$Cl$_2$ (2 mL) was added TFA (2 mL). After stirring at room temperature for 3H, the mixture was evaporated under reduced pressure. The residue was triturated with Et$_2$O, and centrifuged to give ZA-1-MCA conjugate 10 (21 mg, 62%). $C_{25}H_{32}N_4O_{11}$; white solid, mp 130-132° C.; $[\alpha]^{19}_D$+17.2 (c=0.5, CH$_3$OH); IR $\nu_{max}$ (neat) 3395, 1682, 1634, 1253, 1203, 1040 cm$^{-1}$; $^1$H NMR (400 MHz, CD$_3$OD) δ 7.61 (1H, d, J=16.0 Hz), 7.17 (1H, d, J=1.2 Hz), 7.09 (1H, dd, J=8.0, 2.0 Hz), 6.85 (1H, d, J=8.0 Hz), 6.37 (1H, d, J=16.0 Hz), 6.00 (2H, s), 5.89 (1H, d, J=2.8 Hz), 4.47-4.19 (7H, m), 3.90-3.81 (2H, m), 3.71-3.67 (2H, m), 2.11 (2H, t, J=6.4 Hz), 2.01 (3H, s); $^{13}$C NMR (100 MHz, CD$_3$OD) δ 173.6, 168.1, 162.5, 158.1, 150.6, 149.2, 145.7, 145.6, 131.5, 129.3, 125.1, 115.6, 108.7, 107.9, 106.7, 102.3, 77.2, 70.5, 69.5, 63.9, 62.5, 61.2, 50.6, 28.3, 21.8; ESI-HRMS calcd for $C_{25}H_{33}N_4O_{11}$: 565.2146, found: m/z 565.2144 [M+H]$^+$.

Figure 14:
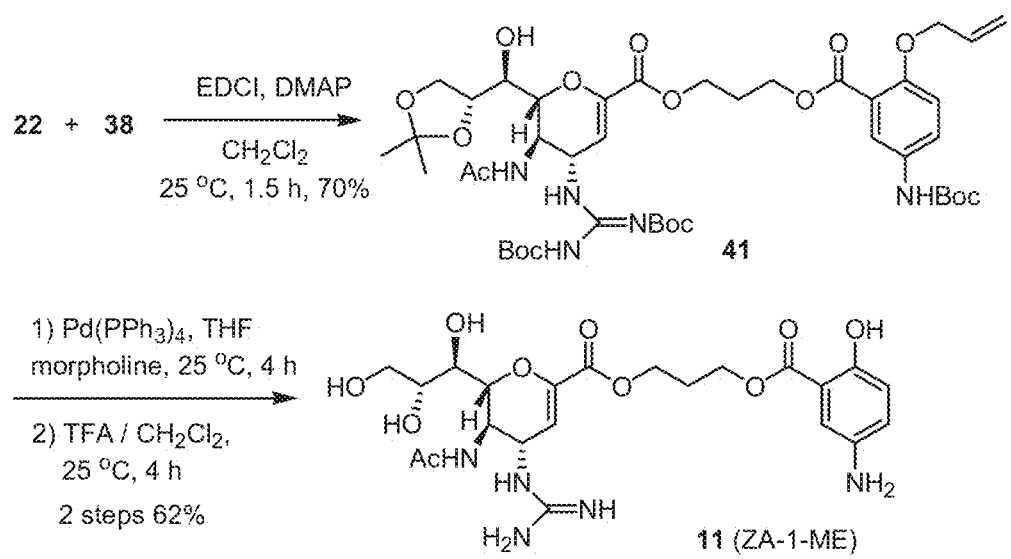

Example 24: Synthesis of ZA-1-ME Conjugate 11 (FIG. 14)

Compound 41

To a solution of 38 (100 mg, 0.16 mmol) in CH$_2$Cl$_2$ (5 mL) was added the allyl ether of mesalazine 22 (47 mg, 0.16 mmol), EDCI (31 mg, 0.16 mmol) and 4-dimethylaminopyridine (18 mg, 0.16 mmol). The mixture was stirred at room temperature for 1.5 h. The resulting solution was extracted with 1M HCl, saturated NaHCO$_3$ and brine, dried over MgSO$_4$, concentrated under reduced pressure, and purified by flash silica gel column chromatography (EtOAc/hexane=1:4 to EtOAc/hexane=2:3) to afford ester 41 (98 mg, 70%). C$_{43}$H$_{63}$N$_5$O$_{16}$; light yellow solid, mp 82-84° C.; TLC (EtOAc/hexane=1:1) R=0.18; [α]$^{20}_D$ −21.0 (c=1.0, CHCl$_3$); IR ν$_{max}$ (neat) 3312, 2978, 2927, 1725, 1646, 1248, 1231, 1155 cm$^{-1}$; $^1$H NMR (400 MHz, CDCl$_3$) δ 11.32 (1H, s), 8.55 (1H, d, J=8.0 Hz), 7.90 (1H, d, J=3.6 Hz), 7.61 (1H, s), 7.58 (1H, d, J=2.8 Hz), 6.87 (1H, d, J=9.2 Hz), 6.69 (1H, s), 6.07-5.95 (1H, m), 5.73 (1H, d, J=2.4 Hz), 5.41 (2H, dd, J=16.8, 1.0 Hz), 5.25-5.21 (2H, m), 5.10-5.01 (1H, m), 4.54 (2H, d, J=5.2 Hz), 4.38-4.29 (4H, m), 4.16-3.91 (2H, m), 3.48-3.44 (2H, m), 2.14-2.07 (2H, m), 1.98 (3H, s), 1.47 (9H, s), 1.46 (18H, s), 1.39 (3H, s), 1.32 (3H, s); $^{13}$C NMR (100 MHz, CDCl$_3$) 173.9, 165.7, 162.3, 161.3, 157.5, 154.1, 153.2, 152.6, 146.5, 132.9, 131.4, 131.0, 120.6, 117.7, 114.6, 114.0, 109.1, 107.1, 84.3, 80.1, 78.5, 77.2, 74.0, 71.2, 70.1, 69.8, 67.4, 62.4, 61.5, 51.5, 48.3, 36.6, 29.6, 28.3 (3×), 28.2 (3×), 28.0 (3×), 27.0, 25.1, 22.9; ESI-HRMS (negative mode) calcd for C$_{43}$H$_{62}$N$_5$O$_{16}$: 904.4192, found: m/z 904.4214 [M−H]$^-$.

ZA-1-ME Conjugate 11

To a solution of compound 41 (34 mg, 0.04 mmol) in anhydrous THF (3 mL) was added Pd(PPh$_3$)$_4$ (12 mg, 0.01 mmol) and morpholine (0.1 mL, 1.4 mmol). The mixture was stirred at room temperature for 4 h. The resulting solution was extracted with 1M HCl and brine, dried over MgSO$_4$, concentrated under reduced pressure, and purified by flash silica gel column chromatography (MeOH/CH$_2$Cl$_2$=1:20 to MeOH/CH$_2$Cl$_2$=1:9). The residue was dissolved in CH$_2$Cl$_2$ (2 mL) and TFA (2 mL). After stirring at room temperature for 3H, the mixture was evaporated under reduced pressure. The residue was triturated with Et$_2$O, and centrifuged to give ZA-1-ME conjugate 11 (23 mg, 62%). C$_{22}$H$_{31}$N$_5$O$_{10}$; yellow solid, mp 126-128° C.; [α]$^{18}_D$+18.6 (c=0.25, CH$_3$OH); IR ν$_{max}$ (neat) 3422, 1677, 1493, 1204, 1137 cm$^{-1}$; $^1$H NMR (400 MHz, CD$_3$OD) δ 7.73 (1H, d, J=2.8 Hz), 7.38 (1H, dd, J=9.2, 2.8 Hz), 5.86 (1H, d, J=2.8 Hz), 4.53-4.38 (6H, m), 4.20-4.16 (1H, m), 3.89-3.80 (2H, m), 3.71-3.66 (3H, m), 2.21 (2H, t, J=6.4 Hz), 2.00 (3H, s); $^{13}$C NMR (100 MHz, CD$_3$OD) δ 173.7, 172.1, 169.5, 162.4, 160.0, 158.1, 145.7, 129.1, 122.2, 119.3, 113.4, 108.1, 77.3, 70.6, 69.4, 64.1, 63.9, 62.8, 62.5, 50.6, 28.1, 21.8; ESI-HRMS calcd for C$_{22}$H$_{32}$N$_5$O$_{10}$: 526.2149, found: m/z 526.2146 [M+H]$^+$.

Figure 15:
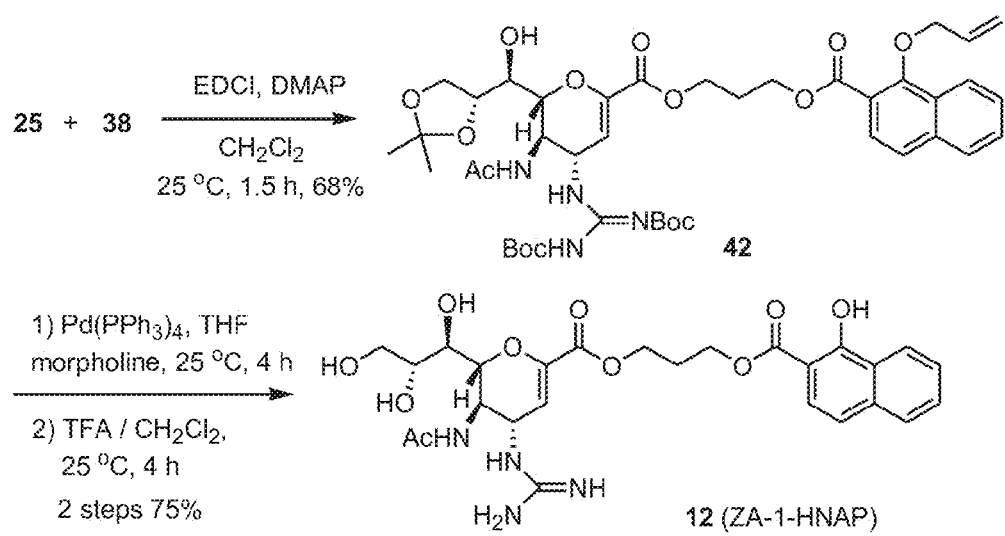

Example 25: Synthesis of ZA-1-HNAP Conjugate 12 (FIG. 15)

Compound 42

To a solution of alcohol 38 (117 mg, 0.19 mmol) in CH$_2$Cl$_2$ (3 mL) was added the allyl ether of 1-hydroxy-2-naphthoic acid 25 (43 mg, 0.19 mmol), EDCI (36 mg, 0.19 mmol) and 4-dimethylaminopyridine (21 mg, 0.19 mmol). The mixture was stirred at room temperature for 1.5 h. The resulting solution was extracted with 1 M HCl, saturated NaHCO$_3$ and brine, dried over MgSO$_4$, concentrated under reduced pressure, and purified by flash silica gel column chromatography (EtOAc/hexane=1:4 to EtOAc/hexane=2:3) to afford compound 42 (105 mg, 68%). C$_{42}$H$_{56}$N$_4$O$_{14}$; light yellow foam; TLC (EtOAc/hexane=2:3) R$_f$=0.22; [α]$^{19}_D$ −25.5 (c=1.0, CHCl$_3$); IR ν$_{max}$ (neat) 2980, 2930, 1726, 1647, 1607, 1565, 1369, 1250, 1152, 1129 cm$^{-1}$; $^1$H NMR (400 MHz, CDCl$_3$) δ 11.32 (1H, s), 8.57 (1H, d, J=7.6 Hz), 8.22 (1H, d, J=8.0 Hz), 7.94 (1H, d, J=4.8 Hz), 7.81 (1H, d, J=8.8 Hz), 7.58-7.47 (3H, m), 6.21-6.11 (1H, m), 5.75 (1H, d, J=2.0 Hz), 5.45 (1H, dd, J=17.2, 1.2 Hz), 5.27 (2H, d, J=11.6 Hz), 5.09-5.04 (1H, m), 4.61 (1H, d, J=5.6 Hz), 4.45-4.42 (2H, m), 4.38-4.33 (3H, m), 4.16-4.01 (3H, m), 3.97-3.91 (2H, m), 3.47-3.44 (1H, m), 2.18-2.14 (2H, m), 1.97 (3H, s), 1.46 (9H, s), 1.45 (9H, s), 1.37 (3H, s), 1.31 (3H, s); $^{13}$C NMR (100 MHz, CDCl$_3$) δ 173.9, 165.9, 162.2, 161.2, 157.5, 156.9, 152.6, 146.7, 136.6, 133.6, 128.7, 128.3, 127.8, 126.5, 126.4, 123.6, 119.5, 117.6, 109.0, 106.8, 84.2, 80.0, 78.5, 76.5, 73.9, 69.7, 67.4, 62.3, 61.5, 60.3, 51.9, 48.3, 28.1 (3×), 27.9 (3×), 26.9, 25.0, 22.9, 14.1; ESI-HRMS calcd for C$_{42}$H$_{57}$N$_4$O$_{14}$: 841.3871, found: m/z 841.3907 [M+H]$^+$.

ZA-1-HNAP Conjugate 12

To a solution of compound 42 (65 mg, 0.08 mmol) in anhydrous THF (4 mL) was added Pd(PPh$_3$)$_4$ (12 mg, 0.01 mmol) and morpholine (0.1 mL, 1.4 mmol). The mixture was stirred at room temperature for 4 h. The resulting solution was extracted with 1 M HCl and brine, dried over MgSO$_4$, concentrated under reduced pressure, and purified by flash silica gel column chromatography (EtOAc/hexane=1:4 to EtOAc/hexane=1:1). The residue was dissolved in CH$_2$Cl$_2$ (2 mL) and TFA (2 mL). After stirring at room temperature for 3H, the mixture was evaporated under reduced pressure. The residue was triturated with Et$_2$O, and centrifuged to give ZA-1-HNAP conjugate 12 (33 mg, 75%). C$_{26}$H$_{32}$N$_4$O$_{10}$; pale yellow solid, mp 120-122° C.; [α]$^{21}_D$+ 19.3 (c=1.0, MeOH); UV-vis (MeOH) λ$_{max}$ 316 nm (ε=5340), 260 nm (ε=28990); UV-vis (PBS) λ$_{max}$ 316 nm (ε=4180), 260 nm (ε=4420); IR ν$_{max}$ (neat) 3422, 1719, 1663, 1638, 1253, 1203, 1139, 1090 cm$^{-1}$; $^1$H NMR (400 MHz, CD$_3$OD) δ 8.35 (1H, d, J=8.4 Hz), 7.81 (1H, d, J=8.4 Hz), 7.77 (1H, d, J=8.8 Hz), 7.63 (1H, m), 7.53 (1H, m), 7.33 (1H, d, J=8.8 Hz), 5.89 (1H, d, J=2.8 Hz), 4.54-4.51 (2H, m), 4.46-4.41 (4H, m), 4.23-4.18 (1H, m), 3.89-3.81 (2H, m), 3.72-3.67 (2H, m), 2.26-2.20 (2H, m), 2.00 (3H, s); $^{13}$C NMR (100 MHz, CD$_3$OD) δ 173.5, 171.3, 162.4, 161.0, 158.0, 145.6, 137.8, 129.8, 127.8, 126.1, 125.0, 124.3, 123.6, 119.0, 108.0, 105.7, 77.1, 70.5, 69.3, 63.8, 62.5, 62.3, 50.4, 47.9, 28.1, 21.7; ESI-HRMS calcd for C$_{26}$H$_{33}$N$_4$O$_{10}$: 561.2197, found: m/z 561.2194 [M+H]$^+$.

Example 26: Synthesis of ZA-7-Nap Conjugate 43 (FIG. 19)

5-Acetylamino-4-[2,3-bis(tert-butoxycarbonyl) guanidino]-6-[(2,2-dimethyl-[1,3]dioxolan-4-yl)-(4-nitrophenoxy)carbonyloxy)methyl]-5,6-dihydro-4H-pyran-2-carboxylic acid ethyl ester (15a)

Methyl ester 13a, a counterpart of the ethyl ester 13, was prepared according to the reported procedure (Chandler, M. et al. *J. Chem. Soc., Perkin Trans.* 11995, 1173). Saponification of 13a with NaOMe in methanol, followed by acid-catalyzed acetalization with 2,2-dimethoxypropane afforded compound 14a, which was treated with 4-nitrophenyl chloroformate and 4-dimethylaminopyridine in anhydrous pyridine to give carbonate 15a in 36% overall yield.

Carbamate Compound 53

To a solution of naproxen (100 mg, 0.43 mmol) in CH$_2$Cl$_2$ (2 mL) was added EDCI (92 mg, 0.48 mmol) and DMAP (63 mg, 0.52 mmol). After 5 min, 3-(tert-butoxycarbonyl)amino-1-propanol (91 mg, 0.52 mmol) was added. The mixture was stirred at room temperature for 1.5 h. The mixture was extracted with 1 M HCl, saturated NaHCO$_3$ and brine, dried over MgSO$_4$, filtered, and concentrated under reduced pressure. The residue was purified by silica gel column chromatography (EtOAc/hexane, 1:2) to afford an ester product (93 mg, 55%). C$_{22}$H$_{29}$NO$_5$; TLC (EtOAc/hexane, 1:2) R$_f$=0.38; $^1$H NMR (400 MHz, CDCl$_3$) δ 7.68 (2H, d, J=8.1 Hz), 7.64 (1H, s), 7.38 (1H, dd, J=8.6, 1.6 Hz), 7.12 (1H, dd, J=8.5, 2.1 Hz), 7.09 (2H, d, J=2.1 Hz), 4.62 (1H, br, NH), 4.13-4.09 (2H, m), 3.89 (3H, s), 3.83 (1H, q, J=7.32 Hz), 3.04 (2H, m), 1.76-1.69 (2H, m), 1.56 (3H, d, J=7.1 Hz), 1.40 (9H, s); $^{13}$C NMR (100 MHz, CDCl$_3$) δ 174.7, 157.6, 155.8, 135.6, 133.7, 129.2, 128.9, 127.1, 126.1, 125.8, 119.0, 105.6, 79.1, 62.2, 55.2, 45.4, 37.2, 29.0, 28.3, 18.4; HRMS calcd for C$_{22}$H$_{30}$NO$_5$: 388.2124, found: m/z 388.2125 [M+H]$^+$.

The above-prepared product (69 mg, 0.18 mmol) was treated with trifluoroacetic acid (1.5 mL) in CH$_2$Cl$_2$ (4 mL) for 15 min, and then concentrated under reduced pressure to give naproxen 3-aminopropyl ester. This compound was dissolved in CH$_3$CN (7 mL), and 15a (112 mg, 0.15 mmol) and Et$_3$N (0.080 mL, 0.59 mmol) were added. The mixture was stirred at room temperature for 12 h, and then concentrated under reduced pressure. The residue was purified by silica gel column chromatography (EtOAc/hexane, 1:2 to 2:1) to afford the carbamate product 53 (119 mg, 90%). C$_{44}$H$_{61}$N$_5$O$_{15}$; yellow oil; TLC (EtOAc:Hexane=2:1) R$_f$=0.38; $^1$H NMR (400 MHz, CDCl$_3$) δ 11.36 (1H, s), 8.41 (1H, d, J=8.4 Hz), 7.68 (2H, dd, J=8.7, 3.4 Hz), 7.63 (1H, s), 7.36 (1H, d, J=8.7 Hz), 7.11-7.09 (2H, m), 6.11 (1H, d, J=9.4 Hz), 5.85 (1H, d, J=1.6 Hz), 5.21-5.14 (2H, m), 4.91 (1H, t, J=6.4 Hz), 4.34-4.30 (2H, m), 4.14-4.08 (3H, m), 4.06-4.02 (1H, m), 3.97-3.94 (1H, m), 3.88 (3H, s), 3.82 (1H, q, J=7.0 Hz), 3.75 (3H, s), 3.13-3.01 (2H, m), 1.84 (3H, s), 1.79-1.71 (2H, m), 1.53 (3H, d, J=7.1 Hz), 1.45 (18H, s), 1.33 (3H, s), 1.32 (3H, s); $^{13}$C NMR (100 MHz, CDCl$_3$) δ 174.7, 170.7, 162.9, 161.9, 157.6, 157.0, 155.5, 152.7, 145.3, 135.6, 133.6, 129.3, 128.9, 127.2, 126.1, 125.9, 118.9, 109.8, 108.9, 105.6, 83.7, 79.6, 77.5, 74.6, 69.7, 65.9, 62.2, 55.3, 52.3, 48.8, 48.3, 45.4, 37.9, 28.7, 28.2, 28.0, 26.5, 25.4, 23.0, 18.4; HRMS calcd for C$_{44}$H$_{62}$N$_5$O$_{15}$: 900.4242, found: m/z 900.4245 [M+H]$^+$.

ZA-7-Nap 43

A solution of compound 53 (101 mg, 0.112 mmol) in THF/MeOH (1:1, 6 mL) and 1 M aqueous K$_2$CO$_3$ (6 mL) was stirred at room temperature for 7 h. The mixture was neutralized by Dowex 50 W×8, filtered and concentrated under reduced pressure. The residue was dissolved in CH$_2$Cl$_2$ (2.5 mL), and TFA (0.5 mL) was added. After stirring at room temperature for 30 min, the mixture was concentrated under reduced pressure. The residue was purified by RP-18 reversed-phase column chromatography (MeOH/H$_2$O, 20:80 to 80:20) and subjected to lyophilization to afford ZA-7-Nap 43 (72 mg, 72%). The purity of product was 96% as shown by HPLC on an HC—C18 column (Agilent, 4.6×250 mm, 5 μm), t$_R$=18.5 min (gradients of MeOH/H$_2$O, 40% to 100% in 30 min, 1 mL/min). C$_{30}$H$_{39}$N$_5$O$_{11}$; White solid; $^1$H NMR (400 MHz, CD$_3$OD) δ 7.74-7.71 (2H, m), 7.66 (1H, s), 7.39 (1H, dd, J=8.6, 1.5 Hz), 7.20 (1H, d, J=2.3 Hz), 7.11 (1H, dd, J=9.0, 2.5 Hz), 5.88 (1H, d, J=2.5 Hz), 4.97 (1H, dd, J=9.3, 2.5 Hz), 4.55 (1H, dd, J=9.9, 2.2 Hz), 4.39 (1H, dd, J=8.8, 2.2 Hz), 4.19-4.10 (3H, m), 4.02-3.97 (1H, m), 3.92-3.87 (4H, m), 3.62 (1H, dd, J=11.9, 2.8 Hz), 3.47 (1H, dd, J=11.9, 5.9 Hz), 3.12-3.00 (2H, m), 1.90 (3H, s), 1.79-1.72 (2H, m), 1.54 (3H, d, J=7.1 Hz); $^{13}$C NMR (100 MHz, D$_2$O) δ 176.7, 173.7, 166.0, 157.2, 156.6, 146.4, 135.8, 133.6, 129.4, 128.8, 127.4, 126.3, 125.9, 118.7, 108.1, 106.0, 75.8, 69.8, 68.9, 63.1, 62.6, 57.4, 55.1, 51.6, 47.3, 45.2, 37.5, 28.0, 22.0, 17.7; HRMS calcd for C$_{30}$H$_{40}$N$_5$O$_{11}$: 646.2724, found: m/z 646.2722 [M+H]$^+$.

Example 27: Synthesis of ZA-7-Ibu Conjugate 44 (FIG. 20)

Carbamate Compound 55

To a solution of (S)-(+)-ibuprofen (102 mg, 0.49 mmol) in CH$_2$Cl$_2$ (2.5 mL) was added EDCI (124 mg, 0.65 mmol) and DMAP (79 mg, 0.65 mmol). After 5 min, 3-(tert-butoxycarbonyl)amino-1-propanol (93 mg, 0.53 mmol) was added. The mixture was stirred at room temperature for 1.5 h. The mixture was extracted with 1 M HCl, saturated NaHCO$_3$ and brine, dried over MgSO$_4$, filtered, and concentrated under reduced pressure. The residue was purified by silica gel column chromatography (EtOAc/Hexane=3:1) to afford an ester product (127 mg, 72%). C$_{21}$H$_{33}$NO$_4$; TLC (EtOAc:Hexane=1:3) R$_f$=0.63; $^1$H NMR (400 MHz, CDCl$_3$) δ 7.16 (2H, d, J=8.4 Hz), 7.05 (2H, d, J=8.4 Hz), 4.67 (1H, br), 4.08 (2H, t, J=6.6 Hz), 3.65 (1H, q, J=7.4 Hz), 3.01-3.00 (2H, m), 2.41 (2H, d, J=7.1 Hz), 1.84-1.77 (1H, m), 1.74-1.68 (2H, m), 1.45 (3H, d, J=7.1 Hz), 1.40 (9H, s), 0.86 (6H, d, J=7.1 Hz); $^{13}$C NMR (100 MHz, CDCl$_3$) 174.7, 155.8, 140.5, 137.6, 129.3, 127.0, 79.0, 62.1, 45.0, 44.9, 37.2, 30.1, 28.9, 28.3, 22.3, 18.2.

The above-prepared product (123.4 mg, 0.34 mmol) was treated with trifluoroacetic acid (1 mL) in CH$_2$Cl$_2$ (4 mL) for 20 min, and then concentrated under reduced pressure to give ibuprofen derivative 54.

ZA-7-Ibu Conjugate 44

Compound 54 was dissolved in CH$_3$CN (10 mL), and 15a (232 mg, 0.31 mmol) and Et$_3$N (0.180 mL, 1.34 mmol) were added. The mixture was stirred at room temperature for 12 h, and then concentrated under reduced pressure. The residue was purified by silica gel column chromatography (EtOAc/hexane, 2:3 to 1:1) to afford the carbamate product 55 (160 mg, 60%). C$_{43}$H$_{65}$N$_5$O$_{14}$; White foam; TLC (EtOAc:hexane, 1:1) R$_f$=0.37; $^1$H NMR (400 MHz, CDCl$_3$) δ 11.34 (1H, s), 8.39 (1H, d, J=9.1 Hz), 7.14 (2H, d, J=7.8 Hz), 7.04 (2H, d, J=9.1 Hz), 6.14 (1H, d, J=9.1 Hz), 5.85 (1H, d, J=2.1 Hz), 5.19-5.13 (2H, m), 4.93 (1H, t, J=5.8 Hz), 4.33-4.28 (2H, m), 4.13-4.04 (4H, m), 3.98-3.94 (1H, m), 3.74 (3H, s), 3.64 (1H, q, J=7.4 Hz), 3.11-2.99 (2H, m), 2.39 (2H, d, J=7.9 Hz), 1.84 (3H, s), 1.82-1.69 (3H, m), 1.43-1.42 (21H, m), 1.32 (3H, s), 1.30 (3H, s), 0.84 (6H, d, J=6.6 Hz); $^{13}$C NMR (100 MHz, CDCl$_3$) δ 174.8, 170.6, 162.9, 161.9, 156.9, 155.4, 152.6, 145.2, 140.4, 137.6, 129.3, 127.0, 109.8, 108.8, 83.6, 79.5, 77.5, 74.6, 69.6, 65.9, 62.0, 52.3, 48.8, 48.2, 45.0, 44.9, 37.8, 30.1, 28.6, 28.2, 28.0, 26.5, 25.3, 23.0, 22.3, 18.3; HRMS calcd for C$_{43}$H$_{66}$N$_5$O$_{14}$: 876.4606, found: m/z 876.4605 [M+H]$^+$.

Example 28: Synthesis of ZA-9-Nap Conjugate 45 (FIG. 21)

Compound 13 (2455 mg, 3.58 mmol) was treated with NaOEt (194.5 mg, 2.86 mmol) in anhydrous EtOH (15 mL) at room temperature for 1 h. The mixture was neutralized by Dowex 50 W×8 (H⁺), filtered, and concentrated under reduced pressure to afford solids of deacetylation product 56.

Et$_3$N (17.3 mg, 0.17 mmol) and HBTU (81.2 mg, 0.21 mmol) were added to a solution of naproxen (32 mg, 0.13 mmol) in anhydrous CH$_2$Cl$_2$ (7 mL). After 5 min, a solution of the above-prepared compound 56 (96 mg, 0.17 mmol) and Et$_3$N (17.3 mg, 0.17 mmol) in anhydrous CH$_2$Cl$_2$ (3 mL) was added. The mixture was stirred at room temperature for 2H, and then concentrated under reduced pressure. The residue was partitioned between EtOAc and saturated NaHCO$_{3(aq)}$. The organic layer was washed with saturated NaHCO$_{3(aq)}$, dried over MgSO$_4$, filtered, and concentrated by rotary evaporation under reduced pressure. The crude material was purified by silica gel column chromatography (hexane/EtOAc=1:1) to yield compound 57. C$_{38}$H$_{52}$N$_4$O$_{13}$; white solid; $^1$H NMR (400 MHz, CDCl$_3$) δ 11.29 (1H, s), 8.55 (1H, d, J=3.8 Hz), 7.98 (1H, d, J=2.8 Hz), 7.70-7.64 (3H, m), 7.39-7.36 (1H, m), 7.13-7.08 (2H, m), 5.72 (1H, d, J=1.2 Hz), 5.26 (1H, d, J=2.2 Hz), 5.08-5.03 (1H, m), 4.50 (1H, d, J=5.8 Hz), 4.27-4.04 (5H, m), 3.93-3.81 (6H, m), 3.47-3.44 (1H, m), 1.92 (3H, s), 1.62-1.57 (3H, m), 1.53-1.47 (18H, m), 1.27-1.20 (3H, m); $^{13}$C NMR (100 MHz, CDCl$_3$) δ 175.2, 173.9, 162.3, 161.4, 157.7, 157.5, 152.6, 146.7, 135.6, 133.7, 129.3, 128.9, 127.2, 127.2, 126.0, 125.9, 119.0, 106.7, 105.6, 84.3, 79.9, 78.1, 68.8, 68.6, 67.5, 61.6, 55.3, 51.8, 48.4, 45.4, 29.7, 28.2, 28.0, 22.8, 18.6, 18.3, 16.4, 14.0; ESI-HRMS calcd for C$_{38}$H$_{53}$N$_4$O$_{13}$: 773.3609, found: m/z 773.3594 [M+H]⁺.

By a procedure similar to that for preparation of ZA-7-Nap 43, a solution of compound 53 in THF was treated with 1 M aqueous K$_2$CO$_3$ at room temperature to give ZA-9-Nap 45.

Example 29: Synthesis of ZA-G-Nap Conjugate 46 (FIG. 22)

Compound 60

To a solution of S-methylisothiourea hemisulfate salt (1085 mg, 7.80 mmol) and NaHCO$_3$ (655 mg, 7.80 mmol) in H$_2$O (15 mL) and THF (15 mL) was added (Boc)$_2$O (1283 mg, 5.88 mmol) dropwise. The mixture was stirred at room temperature under argon for 14 h, and then concentrated under reduced pressure. The residue was partitioned between EtOAc and H$_2$O. The organic phase was dried over MgSO$_4$, filtered, and purified by silica gel chromatography (EtOAc/hexane=1:4) to afford the product of tert-butyl [imino(methylthio)methyl]carbamate (1104 mg, 99%). C$_7$H$_{14}$N$_2$O$_2$S; white solid; $^1$H NMR (CDCl$_3$, 400 MHz) δ 2.39 (3H, s), 1.45 (9H, s); $^{13}$C NMR (CDCl$_3$, 100 MHz) δ 172.3, 160.4, 79.1, 27.5, 12.7; HRMS (ESI) calcd for C$_7$H$_{15}$N$_2$O$_2$S: 191.0854, found: m/z 191.0848 [M+H]⁺.

To a solution of naproxen (115 mg, 0.50 mmol) in anhydrous DMF (5 mL) was added the above-prepared compound (114 mg, 0.6 mmol), HBTU (247 mg, 0.65 mmol) and diisopropylethylamine (130 μL, 0.75 mmol). The mixture was stirred at room temperature under argon for 14 h, and then concentrated under reduced pressure. The residue was diluted with EtOAc and washed with 1 M HCl$_{(aq)}$, saturated NaHCO$_{3(aq)}$, and brine. The organic phase was dried over MgSO$_4$, filtered, and purified by silica gel chromatography (EtOAc/hexane=1:9) to afford the desired product 60 (169 mg, 84%). C$_{21}$H$_{26}$N$_2$O$_4$S; colorless oil; $^1$H NMR (CDCl$_3$, 400 MHz) δ 12.31 (0.55 H, s), 12.19 (0.45 H, s), 7.69 (3H, m), 7.38 (1H, br), 7.15-7.07 (2H, m), 4.02-3.90 (1H, br), 3.87 (3H, s), 2.30 (3H, s), 1.62 (3H, d, J=6.8 Hz), 1.37 (9H, br); HRMS (ESI) calcd for C$_{21}$H$_{27}$N$_2$O$_4$S: 403.1692, found: m/z 403.1700 [M+H]⁺.

Compound 61

To a solution of azide 59 (192 mg, 0.42 mmol) in MeOH (10 mL) was added Lindlar catalyst (96 mg). The mixture was stirred at room temperature under an atmosphere of hydrogen for 14 h. The mixture was filtered through a pad of Celite, and the filtrate was concentrated under reduced pressure. The residue was dissolved in CH$_2$Cl$_2$ (5 mL) and compound 60 (169 mg, 0.42 mmol), HgCl$_2$ (125 mg, 0.46 mmol) and Et$_3$N (64 μL, 0.46 mmol) were added. The mixture was stirred at room temperature under argon for 6 h, filtered through a pad of Celite, and concentrated under reduced pressure. The residue was diluted with EtOAc and washed with 1 M HCl$_{(aq)}$, saturated NaHCO$_{3(aq)}$, and brine. The organic phase was dried over MgSO$_4$, filtered, and purified by silica gel chromatography (EtOAc/hexane, 1:1 to 7:3) to afford the product 61 (293 mg, 88%). C$_{38}$H$_{48}$N$_4$O$_{14}$; colorless oil; $^1$H NMR (CDCl$_3$, 400 MHz) δ 12.24 (0.6H, s), 11.97 (0.4H, s), 8.98 (0.6H, d, J=8.4 Hz), 8.39 (0.4H, d, J=7.2 Hz), 7.77-7.62 (3H, m), 7.46 (0.4H, d, J=8.4 Hz), 7.33 (0.6H, d, J=8.4 Hz), 7.18-7.07 (2H, m), 6.12 (0.6H, d, J=8.8 Hz), 5.87-5.78 (0.4H, m), 5.42-5.37 (0.6H, m), 5.30-5.23 (1H, m), 5.23-5.18 (0.4H, m), 5.09-4.97 (1H, m), 4.69-4.59 (1H, m), 4.29-4.05 (3H, m), 3.95-3.82 (3H, m), 3.82-3.66 (4H, m), 2.18-1.97 (9H, m), 1.89-1.78 (3H, m), 1.62-1.52 (3H, m), 1.43-1.28 (9H, m); HRMS (ESI) calcd for C$_{38}$H$_{49}$N$_4$O$_{14}$: 785.3245, found: m/z 782.3236 [M+H]⁺.

ZA-G-Nap 46

To a solution of compound 61 (33 mg, 0.042 mmol) in CH$_2$Cl$_2$ (1 mL) was added TFA (1 mL). The mixture was stirred at room temperature for 1 h, and then concentrated under reduced pressure. The residue was dissolved in THF (2 mL), and 1 M KOH$_{(aq)}$ (2 mL) was added. The mixture was stirred at room temperature for 30 min, acidified by addition of TFA, and concentrated under reduced pressure. The residue was purified by reversed-phase chromatography (RP-18; 0-100% MeOH in H$_2$O) to afford ZA-G-Nap 46 (21 mg, 93%). C$_{26}$H$_{32}$N$_4$O$_9$; white solid; $^1$H NMR (D$_2$O, 400 MHz) δ 7.69 (3H, m), 7.36 (1H, br), 7.21-7.05 (2H, m), 5.52 (1H, m), 4.56-4.46 (1H, m), 4.40-4.31 (1H, m), 4.31-4.21 (1H, m), 4.02-3.76 (6H, m), 3.68-3.55 (2H, m), 1.87 (3H, s), 1.51 (3H, d, J=5.2 Hz); HRMS (ESI) calcd for C$_{26}$H$_{33}$N$_4$O$_9$: 545.2248, found: m/z 545.2249 [M+H]⁺.

Example 30: Synthesis of ZA-G-Ibu Conjugate 47 (FIG. 23)

Compound 62

To a solution of (S)-ibuprofen (103 mg, 0.50 mmol) in anhydrous DMF (5 mL) was added HBTU (247 mg, 0.65 mmol), DIEA (130 μL, 0.75 mmol), and compound tert-butyl[imino(methylthio)methyl]carbamate (114 mg, 0.6 mmol). The mixture was stirred at room temperature under argon for 14 h and then concentrated under reduced pressure. The residue was diluted with EtOAc and washed with 1 M HCl$_{(aq)}$, saturated NaHCO$_{3(aq)}$, and brine. The organic phase was dried over MgSO$_4$, filtered, and purified by silica gel chromatography (EtOAc/hexane=1:49) to afford the desired product 62 (153 mg, 80%). C$_{20}$H$_{30}$N$_2$O$_3$S; colorless oil; $^1$H NMR (CDCl$_3$, 400 MHz) δ 12.20 (1H, s), 7.19 (2H, d, J=7.6 Hz), 7.08 (2H, d, J=6.0 Hz), 3.69 (1H, br), 4.41 (2H, d, J=7.2 Hz), 2.29 (3H, s), 1.81 (1H, sep, J=6.8 Hz), 1.50 (3H, d, J=7.2 Hz), 1.42 (9H, s), 0.86 (6H, d, J=6.4 Hz); HRMS (ESI) calcd for $C_{20}H_{31}N_2O_3S$: 379.2055, found: m/z 379.2060 [M+H]$^+$.

Compound 63

To a solution of azide 59 (183 mg, 0.40 mmol) in MeOH (5 mL) was added Lindlar catalyst (91 mg). The mixture was stirred at room temperature under an atmosphere of hydrogen for 14 h. The resulting mixture was filtered through a pad of Celite, and the filtrate was concentrated under reduced pressure. The residue was dissolved in $CH_2Cl_2$ (5 mL), compound 62 (153 mg, 0.40 mmol), $HgCl_2$ (119 mg, 0.44 mmol), and $Et_3N$ (61 µL, 0.44 mmol) were added. The mixture was stirred at room temperature under argon for 6H, filtered through a pad of Celite, and concentrated under reduced pressure. The residue was diluted with EtOAc, and washed with 1 M $HCl_{(aq)}$, saturated $NaHCO_{3(aq)}$, and brine. The organic phase was dried over $MgSO_4$, filtered, and purified by silica gel chromatography (EtOAc/hexane, 1:1 to 7:3) to afford the product 63 (259 mg, 85%). $C_{37}H_{52}N_4O_{13}$; colorless oil; $^1$H NMR (CDCl$_3$, 400 MHz) δ 12.12 (0.6H, s), δ 11.97 (0.4 H, s), 9.01 (0.6H, d, J=8.4 Hz), 8.40 (0.4 H, d, J=8.4 Hz), 7.22 (0.4H, d, J=8.4 Hz), 7.16 (0.6H, d, J=8.0 Hz), 7.09 (1H, d, J=8.0 Hz), 6.00 (0.6H, d, J=8.4 Hz), 5.88-5.82 (0.4H, m), 5.42-5.37 (0.6H, m), 5.32-5.22 (1.4H, m), 5.13-4.97 (1H, m), 4.67-4.58 (1H, m), 4.27-4.08 (3H, m), 3.80-3.71 (3H, m), 3.67-3.55 (1H, m), 2.50-2.35 (2H, m), 2.02-1.98 (9H, m), 1.88-1.75 (3H, m), 1.55-1.31 (13H, m), 0.92-0.78 (6H, m); HRMS (ESI) calcd for $C_{37}H_{53}N_4O_{13}$: 761.3609, found: m/z 761.3613 [M+H]$^+$.

ZA-G-Ibu 47

To a solution of compound 63 (28 mg, 0.037 mmol) in $CH_2Cl_2$ (1 mL) was added TFA (1 mL). The mixture was stirred at room temperature for 1 h, and then concentrated under reduced pressure. The residue was dissolved in THF (2 mL), and 1 M $KOH_{(aq)}$ (2 mL) was added. The mixture was stirred at room temperature for 30 min, acidified by addition of TFA, and concentrated under reduced pressure. The residue was purified by reversed-phase chromatography (RP-18; 0-100% MeOH in $H_2O$) to afford ZA-G-Ibu 47 (18 mg, 95%). $C_{25}H_{36}N_4O_8$; colorless oil; $^1$H NMR (CD$_3$OD, 400 MHz) δ 7.25 (2H, d, J=8.4 Hz), 7.12 (2H, d, J=7.6 Hz), 5.59 (1H, m), 4.62-4.52 (1H, m), 4.41-4.32 (1H, m), 4.32-4.20 (1H, m), 3.92-3.75 (3H, m), 3.71-3.58 (2H, m), 2.44 (2H, d, J=7.2 Hz), 1.93 (3H, s), 1.89-1.79 (1H, m), 1.46 (3H, d, J=6.8 Hz), 0.88 (6H, d, J=6.8 Hz); HRMS (ESI) calcd for $C_{25}H_{37}N_4O_8$: 521.2611, found: m/z 521.2612 [M+H]$^+$.

Example 31: Synthesis of OS-1-CA Conjugate 48 (FIG. 24)

Compound 46

To a solution of oseltamivir carboxylic acid N-Boc derivative (64, 60 mg, 0.16 mmol) in MeOH (0.5 mL) was added KOH (6.87 mg, 0.17 mmol). The mixture was stirred at room temperature for 30 min, and then concentrated under reduced pressure. The residue was dissolved in DMF (0.5 mL), and then added 3-iodo-1-propanol (17 mL, 0.19 mmol). After stirring at 50° C. for 4 h, the mixture was evaporated under reduced pressure. The residues was dissolved in $CH_2Cl_2$ (10 mL) and extracted with 1 M HCl and brine, dried over $MgSO_4$, concentrated under reduced pressure, and purified by flash silica gel column chromatography (EtOAc/hexane, 2:1) to afford compound 65 (50 mg, 72%). $C_{22}H_{38}N_2O_7$; white solid; mp 93-95° C.; TLC (EtOAc/n-hexane, 2:1) R$_f$=0.31; $[α]_D^{22}$=−81.9 (c=1.0, $CH_2Cl_2$); IR (film) 3309, 2964, 2935, 2878, 1686, 1536, 1458, 1392, 1368, 1295, 1255, 1172, 1057 cm; $^1$H NMR (400 MHz, CDCl$_3$) δ 6.77 (1H, s), 5.88 (1H, d, J=8.8 Hz), 5.11 (1H, d, J=9.6 Hz), 4.28-4.31 (2H, m), 4.01-4.08 (1H, m), 3.95 (1H, d, J=7.2 Hz), 3.73-3.82 (1H, m), 3.70 (2H, t, J=6.0 Hz), 3.30-3.34 (1H, m), 2.72 (1H, dd, J=17.6, 5.2 Hz), 2.26 (1H, dd, J=18.0, 10.0 Hz), 1.97 (3H, s), 1.87-1.93 (2H, m), 1.47-1.57 (4H, m), 1.41 (9H, s), 0.85-0.91 (6H, m); $^{13}$C NMR (100 MHz, CDCl$_3$) δ 170.9, 165.9, 156.2, 138.1, 128.8, 82.3, 79.5, 75.8, 61.8, 58.6, 54.6, 49.3, 31.5, 30.9, 28.4 (3×), 26.2, 25.7, 23.3, 9.7, 9.3; HRMS calcd for $C_{22}H_{39}N_2O_7$: 443.2757, found: m/z 443.2753 [M+H]$^+$.

Compound 66

To a solution of the allyl ether of caffeic acid 18 (70 mg g, 0.27 mmol) in anhydrous $CH_2Cl_2$ (2.3 mL) were added $NEt_3$ (1.0 mL, 0.69 mmol), O-benzotriazole-N,N,N',N'-tetramethyluronium hexafluorophosphate (HBTU, 103 mg, 0.27 mmol), and DMAP (catalytic amount). The mixture was stirred at room temperature for 30 min, and alcohol compound 46 (100 mg, 0.23 mmol) was added. The mixture was stirred for another 3 h at room temperature, and concentrated under reduced pressure. The residue was purified by flash chromatography on a silica gel column (EtOAc/hexane, 3:1) to afford the coupling product 47 (93 mg, 60%). $C_{37}H_{52}N_2O_{10}$; pale-yellow solid; TLC (EtOAc/hexane, 3:1) R$_f$=0.57; $[α]_D^{25}$=−87.2 (c=1, $CH_2Cl_2$); IR (film) 3443, 2966, 1876, 1714, 1658, 1514, 1458, 1426, 1368, 1295, 1257, 1167, 1016 cm$^1$; $^1$H NMR (400 MHz, CDCl$_3$) δ 7.58 (1H, d, J=16.0 Hz), 7.07 (2H, s), 6.86 (1H, d, J=8.8 Hz), 6.79 (2H, s), 6.24 (1H, d, J=16.0 Hz), 6.00-6.10 (2H, m), 5.39-5.44 (2H, m), 5.29 (2H, d, J=10.8 Hz), 5.04 (1H, d, J=8.8 Hz), 4.59-4.63 (4H, m), 4.27 (4H, t, J=6.4 Hz), 4.02-4.09 (1H, m), 3.83 (1H, br), 3.77-3.83 (1H, m), 3.31-3.34 (1H, m), 2.74 (1H, dd, J=18.4, 6.0 Hz), 2.25-2.32 (1H, m), 2.08 (2H, t, J=6.0 Hz), 1.97 (3H, s), 1.47-1.54 (4H, m), 1.41 (9H, s), 0.85-0.91 (6H, m); $^{13}$C NMR (100 MHz, CDCl$_3$) δ 170.5, 166.7, 165.5, 156.1, 150.4, 148.2, 144.7, 138.0, 132.8, 132.6, 128.8, 127.2, 122.5, 117.8, 117.7, 115.3, 113.2, 112.4, 82.1, 79.4, 75.7, 69.8, 69.6, 61.5, 60.8, 54.4, 49.1, 30.9, 28.3 (3×), 28.1, 26.1, 25.7, 23.3, 9.6, 9.3; HRMS calcd for $C_{37}H_{53}N_2O_{10}$: 685.3700, found: m/z 685.3725 [M+H]$^+$.

OS-1-CA Conjugate 48

To a solution of compound 66 (50 mg, 0.07 mmol) in anhydrous THF (2 mL) were added Pd(PPh$_3$)$_4$ (23 mg, 0.02 mmol) and morpholine (2 mL). The mixture was stirred at room temperature for 4 h, and then extracted with 1 M HCl and brine. The organic phase was dried over $MgSO_4$, concentrated under reduced pressure, and purified by flash chromatography on a silica gel column (EtOAc/hexane, 2:1). The residue was dissolved in $CH_2Cl_2$ (2 mL) and TFA (2 mL). After stirred at room temperature for 3 h, the mixture was concentrated under reduced pressure. The residue was purified by reverse-phase silica gel chromatography (MeOH/$H_2O$, 0:10 to 10:0) to afford OS-1-CA conjugate 48 (25 mg, 70%). $C_{26}H_{36}N_2O_8$; white powder; TLC (2-propanol/$H_2O$/$NH_4OH$, 10:2:3) R$_f$=0.78; $[α]_D^{24}$=−28.0 (c=1, MeOH); IR (film) 3263, 2966, 2936, 2878, 1679, 1600, 1523, 1443, 1374, 1272, 1249, 1201, 1182, 1135 cm$^1$; $^1$H NMR (400 MHz, CD$_3$OD) δ 8.26 (1H, d, J=8.8 Hz), 7.53

(1H, d, J=15.6 Hz), 7.03 (1H, d, J=2.0 Hz), 6.94 (1H, dd, J=8.0, 2.0 Hz), 6.86 (1H, d, J=2.0 Hz), 6.78 (1H, d, J=8.0 Hz), 6.25 (1H, d, J=15.6 Hz), 4.24-4.35 (4H, m), 4.21 (1H, d, J=8.0 Hz), 3.94-3.99 (1H, m), 3.49-3.56 (1H, m), 3.39-3.44 (1H, m), 2.94 (1H, dd, J=17.6, 5.6 Hz), 2.47 (1H, tt, J=10.4, 2.8 Hz), 2.07-2.13 (2H, m), 2.04 (3H, s), 1.47-1.57 (4H, m), 0.92 (3H, t, J=6.4 Hz), 0.88 (3H, t, J=7.6 Hz); $^{13}$C NMR (100 MHz, CDCl$_3$) δ 175.0, 169.3, 166.9, 149.8, 147.3, 147.0, 139.5, 128.4, 127.8, 123.2, 116.7, 115.4, 115.0, 83.9, 75.8, 63.3, 62.3, 54.4, 50.8, 29.6, 29.3, 27.3, 26.8, 23.3, 10.0, 9.7; HRMS calcd for $C_{26}H_{36}N_2O_8$: 505.2550, found: m/z 505.2553 [M+H]$^+$.

Example 32: Synthesis of TP-1-CA Conjugate 49 (FIG. 25)

Compound 68

To a solution of phosphorus trichloride (1.57 g, 11.4 mmol) in CH$_2$Cl$_2$ (114 mL) was added 1,3-propandiol (0.9 g, 12 mmol) dropwise at 0° C. The mixture was stirred for 8 h, and then washed twice with brine. The organic layer was dried over MgSO$_4$, and concentrated under reduced pressure to give 2-oxo-1,3,2-dioxaphosphorinane (68, 0.93 g, 66%). $C_3H_7O_3P$; colorless oil; $^1$H NMR (400 MHz, CDCl$_3$) δ 6.87 (1H, d, J=675.6 Hz), 4.20-4.49 (2H, m), 2.20-2.31 (1H, m), 1.75-1.82 (1H, m); $^{13}$C NMR (100 MHz, CDCl$_3$) δ 67.1 (2×, d, $J_{c-p}$=6.8 Hz), 25.5 (d, $J_{c-p}$=8.4 Hz); $^{33}$P NMR (162 MHz, CDCl$_3$) δ 3.47.

Compound 69

A mixture of iodine compound 67 (50 mg, 0.11 mmol), phosphorinane 68 (20 mg, 0.22 mmol) and Et$_3$N (46 µL, 0.32 mmol) in anhydrous toluene (1.0 mL) was deoxygenated by bubbling with nitrogen for 10 min, and then added to tetrakis(triphenylphosphine)palladium(0) (10 mg, 8.6 mmol) that was placed in a round-bottomed flask under nitrogen atmosphere. The mixture was gradually heated to 90° C. and maintained at this temperature for 12 h. The mixture was filtered through a pad of Celite, and the filtrate was concentrated under reduced pressure to give yellow foam (98 mg), which was purified by flash column chromatography on a silica gel column (EtOAc/hexane, 1:1) to afford a crude product of phosphonate 69 (77 mg).

Compound 51

The crude product 69 was dissolved in ethanol (1.1 mL), and treated with KOH (1.1 mL of 1 M aqueous solution) at 25° C. for 0.5 h. The mixture was neutralized with Dowex 50 W×8, filtered, and concentrated under reduced pressure. The residue was purified on a C-18 column. The product was dissolved in NH$_4$OH, stirred at room temperature for 0.5 h, and then lyophilized to afford compound 70 as the ammonium salt (43 mg, 83%). $C_{21}H_{39}N_2O_8P$; white solid; mp 174-178° C.; TLC (MeOH/CH$_2$Cl$_2$, 1:10) R$_f$=0.10; [α]$_D^{19}$=−46.9 (c=0.9, MeOH); IR (film) 3325, 2965, 2937, 1660, 1541, 1458, 1369, 1296, 1256, 1184 cm$^1$; $^1$H NMR (400 MHz, CD$_3$OD) δ 6.52 (1H, J=21.2 Hz), 4.03-4.08 (3H, m), 3.86 (1H, t, J=11.2 Hz), 3.69-3.76 (1H, m), 3.67 (2H, t, J=6.8 Hz), 3.39-3.42 (1H, m), 2.54-2.58 (1H, s), 2.22-2.28 (1H, s), 1.96 (3H, s), 1.84-1.90 (2H, m), 1.48-1.56 (4H, m), 1.43 (9H, s), 0.86-0.94 (6H, s); $^{13}$C NMR (100 MHz, CD$_3$OD) δ 174.8, 173.8, 158.2, 137.8 (C-1, d, $J_{c-p}$=118 Hz), 83.6, 80.2, 76.5 (d, $J_{c-p}$=18.7 Hz), 63.4 (d, $J_{c-p}$=5.3 Hz), 54.7, 50.8 (d, $J_{c-p}$=12.0 Hz), 34.9, 34.86, 34.3 (d, $J_{c-p}$=6.7 Hz), 28.9 (3×), 26.8, 23.3, 10.02, 10.0; $^{31}$P NMR (162 MHz, CD$_3$OD) δ 15.6; HRMS calcd for $C_{21}H_{38}N_2O_8P$ (M−H): 477.2366, found: m/z 477.2368.

Compound 71

To a solution of the allyl ether of caffeic acid 18 (160 mg, 0.61 mmol) in anhydrous CH$_2$Cl$_2$ were added N-hydroxysuccinimide (84 mg, 0.74 mmol), HBTU (280 mg, 0.74 mmol), DMAP (16 mg, 10% w/w) and diisopropylethylamine (0.4 mL, 1.8 mmol). The mixture was stirred at room temperature for 2H, concentrated, and washed with H$_2$O. The residue was purified by silica gel chromatography (EtOAc/hexane=1:3) to give compound 71 (164 mg, 75%). $C_{19}H_{19}NO_6$; TLC (EtOAc/hexane=1:2) R$_f$=0.26; $^1$H NMR (400 MHz, CDCl$_3$) δ 7.80 (1H, d, J=16.0 Hz), 7.10 (2H, td, J=8.4, 2.0 Hz), 6.87 (1H, d, J=8.4 Hz), 6.38 (1H, d, J=16.0 Hz), 6.00-6.10 (2H, m), 5.41 (2H, dt, J=17.2, 1.2 Hz), 5.29 (2H, dd, J=10.8, 1.2 Hz), 4.61-4.64 (4H, m), 2.85 (4H, s); $^{13}$C NMR (100 MHz, CDCl$_3$) δ 168.7 (2×), 161.6, 151.1, 149.4, 148.0, 132.4, 132.1, 126.1, 123.5, 117.8, 117.7, 112.8, 112.4, 108.5, 69.9, 69.6, 26.0 (2×).

Compound 72

A solution of alcohol compound 70 (65 mg, 0.14 mmol) and caffeic acid activated ester 71 in anhydrous DMF (2.4 mL) was stirred at room temperature for 16 h. The mixture was concentrated, and the residue was purified on an RP-18 reverse-phase column (H$_2$O/MeOH=6:4 to 5:5) to give the coupling product 72 (66 mg, 67%). $C_{36}H_{53}N_2O_{11}P$; TLC (MeOH/CH$_2$Cl$_2$=1:10) R$_f$=0.17; $^1$H NMR (400 MHz, CD$_3$OD) δ 7.43 (1H, d, J=16.0 Hz), 7.14 (1H, s), 7.09 (1H, d, J=8.4 Hz), 6.94 (1H, d, J=8.4 Hz), 6.50 (1H, d, J=19.2 Hz), 6.41 (1H, d, J=16.0 Hz), 6.02-6.11 (2H, m), 5.42 (2H, d, J=17.2 Hz), 5.25 (2H, d, J=10.8 Hz), 4.59 (4H, d, J=4.8 Hz), 4.18-4.23 (1H, m), 4.12-4.14 (1H, m), 3.96-4.01 (3H, m), 3.66-3.74 (2H, m), 3.41-3.44 (1H, m), 2.62-2.66 (1H, m), 2.35-2.37 (1H, m), 1.89 (3H, s), 1.81-1.87 (2H, m), 1.46-1.56 (4H, m), 1.30-1.37 (4H, m), 0.92 (3H, t, J=7.6 Hz), 0.87 (3H, t, J=7.6 Hz); $^{13}$C NMR (100 MHz, CD$_3$OD) δ 173.7, 168.6, 163.7, 150.7 (C-1, d, $^1J_{C-P}$=172.5 Hz), 141.8, 134.8, 134.7, 134.5, 129.4, 125.0, 123.5, 119.7, 117.9, 117.3, 115.0, 114.0, 83.6, 77.8, 71.1 (d, $^2J_{C-P}$=6.8 Hz), 70.8, 62.8, 59.4, 56.5, 47.9 (3×), 34.9, 32.8, 29.0, 27.6, 27.0, 23.1, 10.2, 9.9, 9.4; $^{31}$P NMR (162 MHz, CD$_3$OD) δ 13.4.

TP-1-CA Conjugate 49

A solution of 72 (100 mg, 0.14 mmol) in anhydrous toluene (1.0 mL) was deoxygenated by bubbling with nitrogen for 10 min, and then added to tetrakis(triphenylphosphine)palladium(0) (10 mg, 8.6 µmol) that was placed in a round-bottomed flask under nitrogen atmosphere. The mixture was stirred at 25° C. for 8 h, and then filtered through Celite. The filtrate was concentrated under reduced pressure to give yellow foam, which was dissolved in CH$_2$Cl$_2$ (0.50 mL) and treated with TFA (0.10 mL, 1.4 mmol). After stirring for 3H, the mixture was concentrated under reduced pressure. The residue was dissolved in NH$_4$OH, stirred at room temperature for 0.5 h, and purified on a C-18 column, followed by lyophilization, to afford TP-1-CA conjugate 49 (48 mg, 64%). $C_{25}H_{37}N_2O_9P$; $^1$H NMR (400 MHz, CD$_3$OD) δ 7.36 (1H, d, J=15.6 Hz), 7.00 (1H, d, J=2.0 Hz), 6.89 (1H, dd, J=8.0, 1.6 Hz), 6.76 (1H, d, J=8.4 Hz), 6.45 (1H, br), 6.31 (1H, d, J=15.6 Hz), 4.19-4.27 (1H, m), 4.10-4.12 (1H, m), 3.78-3.89 (2H, m), 3.42-3.45 (1H, m), 3.21 (2H, t, J=4.8

Hz), 2.63 (1H, br), 2.35 (1H, br), 1.90 (3H, s), 1.75 (2H, m, J=6.8 Hz), 1.43-1.58 (4H, m), 0.93 (3H, t, J=7.6 Hz), 0.88 (3H, t, J=7.6 Hz); $^{13}$C NMR (100 MHz, CD$_3$OD) δ 174.0, 168.9, 150.9 (C-1, d, $J_{C-P}$=172.8 Hz), 138.9, 134.8 (d, $J_{C-P}$=18.3 Hz), 129.6, 123.6, 119.9, 115.2, 114.2, 83.7 (d, $J_{C-P}$=7.8 Hz), 62.8, 59.4, 56.5, 34.8, 32.7, 28.9, 27.5, 26.9, 23.1, 10.1, 9.8, 9.3; $^{31}$P NMR (162 MHz, CD$_3$OD) δ 14.3; HRMS calcd for C$_{25}$H$_{36}$N$_2$O$_9$P (M−H): 539.2158, found: m/z 539.2147.

Example 33: Synthesis of PZA(1Et)-7-CA-Amide Conjugate 50 (FIG. 26)

3-Acetamido-4,6-diacetoxy-2-(1,2,3-triacetoxy)propyl-3,4,5,6-tetrahydro-2H-pyran (73)

Under an atmosphere of nitrogen, a suspension of N-acetylneuraminic acid (5 g, 16.2 mmol) in pyridine (75 mL) and acetic anhydride (75 mL) was stirred at room temperature for 12 h, and then heated at 100° C. for 5 h. The reaction mixture was cooled to room temperature, and concentrated under reduced pressure. The residual brownish glassy oil was dissolved in CH$_2$Cl$_2$ (150 mL), and washed successively with saturated aqueous NaHCO$_3$ (100 mL), aqueous 1 M HCl (100 mL) and brine (100 mL). The organic layer was dried over MgSO$_4$, filtered and concentrated. The brownish residue was purified by column chromatography on silica gel (EtOAc/hexane, 67:33 to 100:0) to afford 73 as a pale yellow foam (3.8 g, 50%), which contained inseparable mixture of anomers (α/β=1:5). The anomeric mixture of 73 was used in the next step without further separation. C$_{20}$H$_{29}$NO$_{12}$; TLC (EtOAc) R$_f$=0.35; $^1$H NMR (600 MHz, CDCl$_3$) δ 6.26 (0.83 H, d, J=2.5 Hz, H-1β), 5.62 (0.17 H, dd, J=10.3, 2.1 Hz, H-1a), 5.43 (0.17 H, ddd, J=6.1, 4.4, 1.9 Hz), 5.29-5.27 (1.66 H, m), 5.22 (0.83 H, td, J=10.6, 4.9 Hz), 5.17 (0.83 H, td, J=6.5, 2.7 Hz), 5.11-5.07 (0.34 H, m), 5.03 (0.17 H, dd, J=6.5, 2.7 Hz), 4.36 (0.17 H, dd, J=12.5, 2.6 Hz), 4.31 (0.83 H, dd, J=12.5, 2.8 Hz), 4.08-3.98 (2.83 H, m), 3.74 (0.17 H, dd, J=10.5, 2.5 Hz), 2.17-2.15 (0.17 H, m), 2.15-2.13 (0.83 H, m), 2.11 (2.49 H, s), 2.10 (0.51H, s), 2.09 (0.51 H, s), 2.08 (2.49 H, s), 2.07 (0.51 H, s), 2.04 (2.49 H, s), 2.03 (0.51 H, s), 2.017 (2.49H, s), 2.013 (0.51 H, s), 2.00 (2.49 H, s), 2.00-1.98 (0.83 H, m), 1.98-1.96 (0.17 H, m), 1.88 (2.49 H, s), 1.87 (0.51 H, s); HRMS calcd for C$_{20}$H$_{29}$NO$_{12}$Na: 498.1587, found: m/z 498.1557 [M+Na]$^+$.

Diethyl [5-acetamido-4-acetoxy-6-(1,2,3-triacetoxy)propyl-3,4,5,6-tetrahydro-2H-pyran-2-yl]phosphonate (74)

The anomeric mixture of 73 (2.15 g, 4.52 mmol) and diethyl trimethylsilyl phosphite (3.11 mL, 13.65 mmol) in anhydrous CH$_2$Cl$_2$ (30 mL) was treated with trimethylsilyl trifluoromethylsulfonate (TMSOTf, 1.23 mL, 6.78 mmol) at 0° C. After 30 min, the mixture was warmed to room temperature, and stirred for 24 h. The mixture was poured into ice water (20 mL), and the aqueous layer was extracted with CH$_2$Cl$_2$ (20 mL, 2×). The combined extracts were washed successively with saturated aqueous NaHCO$_3$ (50 mL) and brine (50 mL), dried over MgSO$_4$, filtered and concentrated. The residue was purified by column chromatography on silica gel (acetone/EtOAc, 1:9) to afford 74 as a colorless syrup (1.55 g, 62%), which contained a mixture of the α- and β-anomers (2:3). The anomeric mixture of phosphonate 74 was used in the next step without further separation. The analytical samples of pure α- and β-anomers (74α and 74β) were obtained by flash column chromatography on silica gel (EtOAc/acetone, 100:0 to 90:10). α-Anomer 74a: C$_{22}$H$_{36}$NO$_{13}$P; colorless foam; TLC (EtOAc/acetone, 9:1) R$_f$=0.25; [α]$_D^{20}$=+39.4 (c=4.6, CH$_2$Cl$_2$); $^1$H NMR (600 MHz, CDCl$_3$) δ 5.30 (1H, dd, J=5.7, 1.7 Hz), 5.24 (1H, d, J=9.9 Hz, NH), 5.18 (1H, td, J=6.6, 2.5 Hz), 4.98 (1H, td, J=10.6, 5.0 Hz), 4.40 (1H, dd, J=12.3, 5.0 Hz), 4.22-4.09 (5H, m), 3.97 (1H, q, J=10.1 Hz), 3.74 (1H, td, J=12.5, 2.4 Hz), 3.62 (1H, dd, J=10.3, 2.0 Hz), 2.27 (1H, dd, J=12.8, 4.9 Hz), 2.09 (3H, s), 2.05 (3H, s), 2.02 (3H, s), 2.01 (3H, s), 1.98-1.92 (1H, m), 1.87 (3H, s), 1.35-1.31 (6H, m); $^{13}$C NMR (150 MHz, CDCl$_3$) δ 170.9 (C), 170.5 (C), 170.3 (C), 170.2 (C), 170.1 (C), 79.0 (CH, d, $^3J_{c-p}$=17.3 Hz), 71.8 (CH, d, $J_{c-p}$=174.6 Hz, C-1), 71.6 (CH, d, $^3J_{c-p}$=20.9 Hz), 71.0 (CH), 67.9 (CH), 63.4 (CH$_2$, d, $^2J_{c-p}$=6.9 Hz, POCH$_2$), 62.8 (CH$_2$, d, $^2J_{c-p}$=6.2 Hz, POCH$_2$), 62.2 (CH$_2$, C-8), 49.6 (CH, C-4), 31.3 (CH$_2$, C-2), 23.1 (CH$_3$), 20.9 (CH$_3$), 20.8 (CH$_3$), 20.7 (CH$_3$, 2×), 16.5 (CH$_3$, d, $^3J_{c-p}$=5.4 Hz, POCH$_2$CH$_3$), 16.3 (CH$_3$, d, $^3J_{c-p}$=5.4 Hz, POCH$_2$CH$_3$); $^{31}$P NMR (202 MHz, CDCl$_3$) δ 18.5; HRMS calcd for C$_{22}$H$_{35}$NO$_{13}$P: 552.1846, found: m/z 552.1921 [M−H]. β-Anomer 74β: C$_{22}$H$_{36}$NO$_{13}$P; colorless foam; TLC (EtOAc/acetone, 9:1) R$_f$=0.28; [α]$_D^{20}$=−40.1 (c=3.0, CH$_2$Cl$_2$); $^1$H NMR (600 MHz, CDCl$_3$) δ 5.45 (1H, d, J=10.1 Hz, NH), 5.35 (1H, dd, J=7.3, 2.3 Hz), 5.32 (1H, td, J=15.0, 4.8 Hz), 5.21-5.18 (1H, m), 4.45 (1H, d, J=10.0 Hz), 4.33 (1H, dd, J=12.4, 2.8 Hz), 4.30 (1H, dd, J=12.3, 7.1 Hz), 4.19-4.13 (2H, m), 4.12-4.04 (4H, m), 2.35-2.31 (1H, m), 2.11 (3H, s), 2.08 (3H, s), 2.017 (3H, s), 2.011 (3H, s), 2.09-2.03 (1H, m), 1.88 (3H, s), 1.34 (3H, t, J=7.0 Hz), 1.33 (3H, t, J=7.0 Hz); $^{13}$C NMR (150 MHz, CDCl$_3$) δ 170.8 (C), 170.6 (C), 170.2 (C), 170.1 (C), 169.8 (C), 74.0 (CH), 69.7 (CH), 69.5 (CH), 67.9 (CH, d, $^1J_{c-p}$=157.2 Hz, C-1), 67.7 (CH), 63.0 (CH$_2$, d, $^2J_{c-p}$=7.2 Hz, POCH$_2$), 62.7 (CH$_2$, d, $^2J_{c-p}$=6.6 Hz, POCH$_2$), 62.0 (CH$_2$, C-8), 49.0 (CH, C-4), 29.5 (CH$_2$, d, $^2J_{c-p}$=3.2 Hz, C-2), 23.1 (CH$_3$), 21.0 (CH$_3$), 20.9 (CH$_3$), 20.7 (CH$_3$, 2×), 16.2 (CH$_3$, d, $^3J_{c-p}$=5.1 Hz, POCH$_2$CH$_3$), 16.3 (CH$_3$, d, $^3J_{c-p}$=5.1 Hz, POCH$_2$CH$_3$); $^{31}$P NMR (202 MHz, CDCl$_3$) δ 21.4; HRMS calcd for C$_{22}$H$_{35}$NO$_{13}$P: 552.1846, found: m/z 552.1879 [M−H].

Diethyl [5-acetamido-4-acetoxy-6-(1,2,3-triacetoxy)propyl-4,5,6-trihydropyran-2-yl]phosphonate (75)

The anomeric mixture of phosphonate 74 (1.1 g, 2 mmol) and N-bromosuccinimide (885 mg, 5 mmol) in anhydrous CH$_2$Cl$_2$ (20 mL) was heated to reflux under irradiation from a 100 W tungsten lamp. The progress of reaction was monitored by TLC. On completion (~6 h) the mixture was cooled to room temperature, and the precipitate succinimide was filtered off. The filtrate was evaporated under reduced pressure to give a crude 2-bromo derivative as yellow syrup, which was used in the next step without further purification.

A solution of the above-prepared bromine compound in anhydrous pyridine (10 mL) was stirred at 50° C. for 2 h. The solution was concentrated under reduced pressure, and the brown residue was purified by column chromatography on silica gel (EtOAc/acetone, 100:0 to 90:10) to afford conjugated phosphonate 75 as colorless foam (827 mg, 75% for two steps). C$_{22}$H$_{34}$NO$_{13}$P; TLC (EtOAc/acetone, 9:1) R$_f$=0.28; [α]$_D^{20}$=+43.8 (c=0.59, CH$_2$Cl$_2$); $^1$H NMR (600 MHz, CDCl$_3$) δ 5.74 (1H, dd, J=10.7, 2.2 Hz), 5.54 (1H, d, J=8.2 Hz, NH), 5.42-5.40 (2H, m), 5.26 (1H, td, J=6.4, 2.9 Hz), 4.39-4.34 (2H, m), 4.29 (1H, q, J=9.1 Hz), 4.17-4.09 (5H, m), 2.09 (3H, s), 2.05 (3H, s), 2.04 (3H, s), 2.02 (3H, s), 1.91 (3H, s), 1.35 (3H, t, J=7.0 Hz), 1.31 (3H, t, J=7.0 Hz); $^{13}$C NMR (150 MHz, CDCl$_3$) δ 170.8 (C), 170.4 (C), 170.3 (C), 169.8 (C), 169.7 (C), 147.8 (C, d, $J_{c-p}$=225 Hz, C-1), 113.0 (CH, d, $^2J_{c-p}$=22.8 Hz, C-2), 76.5 (CH, d, $^3J_{c-p}$=9.3 Hz), 69.9 (CH), 68.4 (CH, d, $^3J_{c-p}$=15.2 Hz), 67.2 (CH), 63.2 (CH$_2$, d, $^2J_{c-p}$=5.4 Hz, POCH$_2$), 63.0 (CH$_2$, d, $^2J_{c-p}$=5.7 Hz, POCH$_2$), 61.8 (CH$_2$, C-8), 46.4 (CH, C-4), 23.0 (CH$_3$), 20.78 (CH$_3$), 20.73 (CH$_3$), 20.63 (CH$_3$), 20.60 (CH$_3$), 16.16 (CH$_3$, d, $^3J_{c-p}$=4.8 Hz, POCH$_2$CH$_3$), 16.12 (CH$_3$, d, $^3J_{c-p}$=4.8 Hz, POCH$_2$CH$_3$); $^{31}$P NMR (202 MHz, CDCl$_3$) δ 6.4; HRMS calcd for C$_{22}$H$_{33}$NO$_{13}$P: 550.1690, found: m/z 550.1684 [M−H].

Diethyl [4-(1,2,3-triacetoxy)propyl-2-methyl-3a,7a-dihydro-4H-pyrano[3,4-d]oxazol-6-yl]phosphonate (76)

To a solution of phosphonate 75 (550 mg, 1 mmol) in a mixture of acetic acid (2 mL) and acetic anhydride (2 mL) was treated with conc. H$_2$SO$_4$ (0.2 mL). The mixture was stirred for 48 h at room temperature, poured into cold (0° C.) saturated aqueous NaHCO$_3$ (pH 9), and stirred for 30 min before extraction with EtOAc (30 mL, 5×). The combined extracts were dried over MgSO$_4$, filtered and concentrated under reduced pressure. The residual oil was purified by column chromatography on silica gel (acetone/EtOAc, 1:9) to afford 76 as pale yellow syrup (394 mg, 80% for two steps). C$_{20}$H$_{30}$NO$_{11}$P; TLC (EtOAc/acetone, 9:1) R$_f$=0.30; $[α]_D^{20}$=−11.6 (c=0.50, CH$_2$Cl$_2$); $^1$H NMR (600 MHz, CDCl$_3$) δ 6.20 (1H, dd, J=10.3, 4.0 Hz), 5.58 (1H, ddd, J=6.6, 2.9, 1.1 Hz), 5.38 (1H, td, J=7.7, 2.5 Hz), 4.71 (1H, ddd, J=8.6, 4.0, 2.0 Hz), 4.40 (1H, dd, J=12.4, 2.5 Hz), 4.19 (1H, dd, J=12.5, 5.9 Hz), 4.18-4.07 (4H, m), 3.93 (1H, td, J=9.2, 0.6 Hz), 3.34 (1H, dd, J=10.1, 2.7 Hz), 2.11 (3H, s), 2.04 (3H, s), 2.03 (3H, s), 1.98 (3H, s), 1.34 (3H, t, J=7.0 Hz), 1.32 (3H, t, J=7.0 Hz); $^{13}$C NMR (150 MHz, CDCl$_3$) δ 170.5 (C), 169.7 (C), 169.4 (C), 167.2 (C, N=CCH$_3$), 150.1 (C, d, $^1J_{c-p}$=225 Hz, C-1), 111.9 (CH, d, $^2J_{c-p}$=23.4 Hz, C-2), 76.1 (CH, d, $^3J_{c-p}$=6.3 Hz), 71.2 (CH, d, $^3J_{c-p}$=15.3 Hz), 69.6 (CH), 68.8 (CH), 63.1 (CH$_2$, d, $^2J_{c-p}$=5.9 Hz, POCH$_2$), 62.9 (CH$_2$, d, $^2J_{c-p}$=5.7 Hz, POCH$_2$), 61.8 (CH, C-4), 61.6 (CH$_2$, C-8), 20.7 (CH$_3$), 20.6 (CH$_3$), 20.5 (CH$_3$), 16.2 (CH$_3$, d, $^3J_{c-p}$=5.1 Hz, POCH$_2$CH$_3$), 16.1 (CH$_3$, d, $^3J_{c-p}$=5.1 Hz, POCH$_2$CH$_3$), 14.0 (CH$_3$, N=CCH$_3$); $^{31}$P NMR (202 MHz, CDCl$_3$) δ 6.4; HRMS calcd for C$_{20}$H$_{29}$NO$_{11}$: 490.1478, found: m/z 490.1374 [M−H]$^-$.

Diethyl [5-acetamido-4-azido-6-(1,2,3-triacetoxy)propyl-4,5,6-trihydropyran-2-yl]phosphonate (77)

To a solution of oxazoline 76 (393 mg, 0.8 mmol) in t-BuOH (10 mL) was treated with azidotrimethylsilane (0.53 mL, 4 mmol) at 80° C. for 24 h. The solution was poured into saturated aqueous NaHCO$_3$, and extracted with EtOAc (30 mL, 3×). The combined extracts were dried over MgSO$_4$, filtered and concentrated to afford the azido compound 77 as a colorless syrup (371 mg, 87%), which was practically pure to be used in the next step. An analytical sample was obtained by flash column chromatography on silica gel (10% acetone in EtOAc). C$_{20}$H$_{31}$N$_4$O$_{11}$P; TLC (EtOAc/acetone, 9:1) R$_f$=0.30; $[α]_D^{20}$=+82.7 (c=0.58, CH$_2$Cl$_2$); $^1$H NMR (600 MHz, CDCl$_3$) δ 5.75 (1H, dd, J=10.3, 2.4 Hz), 5.73 (1H, d, J=8.6 Hz), 5.38 (1H, dt, J=7.1, 1.5 Hz), 5.26 (1H, ddd, J=8.5, 5.8, 2.6 Hz), 4.53-4.50 (2H, m), 4.36 (1H, dd, J=12.5, 2.6 Hz), 4.17-4.08 (5H, m), 3.67 (1H, q, J=9.2 Hz), 2.10 (3H, s), 2.05 (3H, s), 2.02 (3H, s), 1.99 (3H, s), 1.34 (3H, t, J=7.1 Hz), 1.32 (3H, t, J=7.1 Hz); $^{13}$C NMR (150 MHz, CDCl$_3$) δ 170.8 (C), 170.5 (C), 170.1 (C), 169.7 (C), 147.7 (C, d, $^1J_{c-p}$=224 Hz, C-1), 112.4 (CH, d, $^2J_{c-p}$=22.9 Hz, C-2), 75.9 (CH, d, $^3J_{c-p}$=9.2 Hz), 69.7 (CH), 67.3 (CH), 63.5 (CH$_2$, d, $^2J_{c-p}$=5.7 Hz, POCH$_2$), 63.3 (CH$_2$, d, $^2J_{c-p}$=5.9 Hz, POCH$_2$), 61.9 (CH$_2$, C-8), 57.8 (CH, d, $^3J_{c-p}$=14.7 Hz), 48.5 (CH, C-4), 23.2 (CH$_3$), 20.8 (CH$_3$), 20.77 (CH$_3$), 20.71 (CH$_3$), 16.27 (CH$_3$, d, $^3J_{c-p}$=5.7 Hz, POCH$_2$CH$_3$), 16.23 (CH$_3$, d, $^3J_{c-p}$=5.7 Hz, POCH$_2$CH$_3$); $^{31}$P NMR (202 MHz, CDCl$_3$) δ 6.2; HRMS calcd for C$_{20}$H$_{30}$N$_4$O$_{11}$P: 533.1649, found: m/z 533.1540 [M−H].

[5-acetamido-4-tert-butoxycarbonylamino-6-(1,2,3-triacetoxy)propyl-4,5,6-trihydropyran-2-yl]phosphonate (78)

To a solution of azide 77 (249 mg, 0.47 mmol) in ethanol (21 mL) was hydrogenated with Lindlar catalyst (110 mg) under an atmosphere of hydrogen. The mixture was stirred for 12 h, filtered through a pad of Celite, and washed with methanol. The filtrate was concentrated under reduced pressure to give a colorless foam (240 mg). The crude amine product was dissolved in CH$_2$Cl$_2$ (20 mL) and treated with Boc$_2$O (171 mg, 0.78 mmol) and Et$_3$N (191 μL, 1.42 mmol). The reaction was stirred at room temperature for 12 h, and then washed with 1 M HCl (aq) and brine, dried over MgSO$_4$, filtered and concentrated. The residue was purified by flash column chromatography (EtOAc) to afford 78 as a white foam (204 mg, 72%). C$_{25}$H$_{41}$N$_2$O$_{13}$P; TLC (EtOAc) R$_f$=0.25; $^1$H NMR (400 MHz, CDCl$_3$) δ 5.75 (1H, d, J=9.3 Hz), 5.69 (1H, dd, J=10.5, 1.7 Hz), 5.40 (1H, d, J=6.4 Hz), 5.22 (1H, td, J=6.4, 2.6 Hz), 4.71 (1H, d, J=9.5 Hz), 4.42-4.36 (2H, m), 4.21-4.07 (7H, m), 2.07 (3H, s), 2.06 (3H, s), 2.02 (3H, s), 1.90 (3H, s), 1.38 (9H, s), 1.35-1.32 (6H, m); $^{13}$C NMR (100 MHz, CDCl$_3$) δ 171.0, 170.5, 169.9, 169.8, 156.2, 147.1 (d, $^1J_{c-p}$=225 Hz), 115.2 (d, $^2J_{c-p}$=22.8 Hz), 80.3, 77.6 (d, $^3J_{c-p}$=9.9 Hz), 70.2, 67.5, 63.2 (d, $^2J_{c-p}$=5.4 Hz), 63.0 (d, $^2J_{c-p}$=6.1 Hz), 62.0, 49.9 (d, $^3J_{c-p}$=14.4 Hz), 48.0, 28.2, 23.2, 20.9, 20.7, 20.6, 16.3, 16.2; 3P NMR (162 MHz, CDCl$_3$) δ 6.1; HRMS calcd for C$_{25}$H$_{40}$N$_2$O$_{13}$P: 607.2268, found: m/z 607.2269 [M−H]$^-$.

[5-acetamido-4-tert-butoxycarbonylamino-6-[(2,2-dimethyl-[1,3]dioxolan-4-yl)-hydroxy-methyl]-5,6-dihydropyran-2-yl]phosphonate (79)

To a solution of 78 (181 mg, 0.30 mmol) in ethanol (9 mL) was added NaOEt (20 mg, 0.29 mmol). The mixture was stirred at room temperature for 0.5 h, neutralizes by Dowex 50 W×8 (H$^+$), filtered, and concentrated under reduced pressure to afford white solids. The residue was dissolved in acetone (4 mL), and p-toluenesulfonic acid and 2,2-dimethoxypropane were added. The mixture was stirred at room temperature for 16 h and then quenched the reaction with Et$_3$N. After concentration, the residue was purified by silica gel column chromatography (EtOAc) to afford 79 (129 mg, 83%). C$_{22}$H$_{39}$N$_2$O$_{10}$P; Colorless foam; TLC (EtOAc) R$_f$=0.33; $^1$H NMR (400 MHz, CDCl$_3$) δ 6.65 (1H, d, J=6.5 Hz), 5.62 (1H, d, J=10.0 Hz), 5.01 (1H, br), 4.82 (1H, d, J=8.6 Hz), 4.54 (1H, br), 4.24-4.19 (1H, m), 4.17-4.11 (5H, m), 4.01-3.95 (2H, m), 3.87 (1H, m), 3.45 (1H, d, J=7.6 Hz), 2.02 (3H, s), 1.42 (9H, s), 1.37-1.30 (12H, m); $^{13}$C NMR (100 MHz, CDCl$_3$) δ 173.8, 157.3, 147.9 (d, $^1J_{c-p}$=220 Hz), 113.7 (d, $^2J_{c-p}$=24.0 Hz), 109.0, 80.5, 78.8 (d, $^3J_{c-p}$=9.0 Hz), 73.9, 70.0, 67.7, 63.3 (d, $^2J_{c-p}$=6.0 Hz), 63.1 (d, $^2J_{c-p}$=6.0 Hz), 51.8, 48.7 (d, $^3J_{c-p}$=15.0 Hz), 28.2, 26.9, 25.2, 22.9, 16.2-16.1 (2×); $^{31}$P NMR (162 MHz, CDCl$_3$) δ 5.1; HRMS calcd for C$_{22}$H$_{38}$N$_2$O$_{10}$P: 521.2264, found: m/z 521.2267 [M−H]$^-$.

Diethyl [5-acetamido-4-tert-butoxycarbonylamino-6-[(2,2-dimethyl-[1,3]dioxolan-4-yl)-(4-nitro-phenoxycarbonyloxy)-methyl]-5,6-dihydropyran-2-yl] phosphonate (80)

A solution of 79 (129 mg, 0.25 mmol), 4-nitrophenyl chloroformate (127 mg, 0.63 mmol) in pyridine (4 mL) was stirred at room temperature for 18 h. After concentration, the residue was purified by silica gel column chromatography (EtOAc/hexane=1:3 to EtOAc) to afford 80 (130 mg, 77%). $C_{29}H_{42}N_3O_{14}P$; TLC (EtOAc:acetone=9:1) $R_f$=0.48; Colorless solid; $^1$H NMR (400 MHz, CDCl$_3$) δ 8.25 (2H, d, J=9.2 Hz), 7.49 (2H, d, J=9.0 Hz), 5.96 (1H, d, J=9.5 Hz), 5.71 (1H, dd, J=10.4, 1.9 Hz), 5.23 (1H, d, J=5.2 Hz), 4.76 (1H, m), 4.51-4.46 (1H, m), 4.37-4.29 (2H, m), 4.21 (1H, d, J=10.1 Hz), 4.18-4.07 (5H, m), 4.02 (1H, dd, J=9.0, 6.8 Hz), 1.94 (3H, s), 1.39 (9H, s), 1.39-1.32 (12H, m); $^{13}$C NMR (100 MHz, CDCl$_3$) δ 171.1, 156.3, 155.7, 152.4, 146.6 (d, $J_{c-p}$=220 Hz), 145.5, 125.2, 122.3, 115.7 (d, $^2J_{c-p}$=23.0 Hz), 108.8, 80.3, 77.7 (d, $^3J_{c-p}$=9.7 Hz), 74.9, 74.3, 65.5, 63.1 (d, $^2J_{c-p}$=5.0 Hz), 62.9 (d, $^2J_{c-p}$=6.0 Hz), 60.3, 49.7 (d, $^3J_{c-p}$=15.0 Hz), 28.1, 26.2, 25.3, 23.1, 16.2 (d, $^3J_{c-p}$=6.7 Hz), 16.2 (d, $^3J_{c-p}$=6.2 Hz); $^{31}$P NMR (162 MHz, CDCl$_3$) δ 6.3; HRMS calcd for $C_{29}H_{43}N_3O_{14}P$: 688.2483, found: m/z 688.2482 [M+H]$^+$.

Compound 82

To a solution of compound 81 (47 mg, 0.20 mmol) in CH$_3$CN (5 mL) were added compound 80 (120 mg, 0.17 mmol) and Et$_3$N (0.094 mL, 0.70 mmol). The mixture was stirred at room temperature for 12 h, and then concentrated under reduced pressure. The residue was purified by silica gel column chromatography (MeOH/CH$_2$Cl$_2$=1:9) to afford product 82 (98 mg, 72%). $C_{35}H_{53}N_4O_{14}P$; White solid; TLC (MeOH/CH$_2$Cl$_2$=1:9) $R_f$=0.25; $^1$H NMR (400 MHz, CD$_3$OD) δ 7.39 (1H, d, J=16.2 Hz), 7.00 (1H, d, J=1.7 Hz), 6.90 (1H, dd, J=8.5, 2.1 Hz), 6.77 (1H, d, J=8.5 Hz), 6.37 (1H, d, J=15.8 Hz), 5.66 (1H, d, J=9.4 Hz), 5.20 (1H, d, J=6.4 Hz), 4.39-4.36 (2H, m), 4.30 (1H, q, J=6.1 Hz), 4.20-4.10 (4H, m), 4.08-4.04 (2H, m), 3.96 (1H, dd, J=8.6, 6.4 Hz), 3.39-3.33 (3H, m), 3.20-3.06 (2H, m), 1.94 (3H, s), 1.80-1.67 (2H, m), 1.41 (9H, s), 1.38-1.29 (12H, m); $^{13}$C NMR (100 MHz, CD$_3$OD) δ 173.3, 169.3, 158.1, 157.7, 147.7 (d, $^1J_{c-p}$=201 Hz), 142.1, 128.3, 122.1, 118.5, 116.5, 115.0, 110.2, 80.5, 79.3, 76.0, 71.1, 67.1, 64.7-64.6 (2×), 51.5, 39.3, 37.8, 30.2, 28.7, 26.9, 25.7, 23.1, 16.7-16.6 (2×); $^{31}$P NMR (162 MHz, CD$_3$OD) δ 7.7; HRMS calcd for $C_{35}H_{54}N_4O_{14}P$: 785.3374, found: m/z 785.3364 [M+H]$^+$.

PZA(1Et)-7-CA-Amide 50

To a solution of 82 (52 mg, 0.066 mmol) in CH$_3$CN (15 mL) was added LiBr (23 mg, 0.26 mmol). After stirring under reflux for 12 h, the mixture was concentrated under reduced pressure. The residue was dissolved in CH$_2$Cl$_2$ (15 mL), and TFA (2 mL) was added. After stirring at room temperature for 3H, the mixture was concentrated under reduced pressure. The residue was purified by RP-18 reversed-phase column chromatography (MeOH/H$_2$O=5:95 to 40:60) and subjected to lyophilization to afford PZA(1Et)-7-CA-amide conjugate 50 (20 mg, 50%). $C_{25}H_{37}N_4O_{12}P$; Yellow solid; TLC (n-PrOH/H$_2$O=7:3) $R_f$=0.77; $^1$H NMR (400 MHz, CD$_3$OD) δ 7.38 (1H, d, J=12.0 Hz), 7.01 (1H, s), 6.90 (1H, d, J=8.6 Hz), 6.76 (1H, d, J=8.1 Hz), 6.36 (1H, d, J=15.5 Hz), 5.44 (1H, d, J=8.6 Hz), 4.98 (1H, d, J=9.8 Hz), 4.41 (1H, d, J=10.4 Hz), 4.24 (1H, t, J=10.4 Hz), 4.08 (1H, q, J=7.1 Hz), 4.03-3.96 (2H, m), 3.92-3.87 (1H, m), 3.61-3.57 (1H, m), 3.49-3.44 (1H, m), 3.35 (2H, m), 3.18-3.08 (2H, m), 2.00 (3H, s), 1.79-1.68 (2H, m), 1.29 (3H, t, J=6.8 Hz); $^{13}$C NMR (100 MHz, CD$_3$OD) δ 174.3, 169.5, 158.1, 147.9 (d, $^1J_{c-p}$=202 Hz), 142.3, 128.5, 122.2, 118.6, 116.6, 115.2, 105.3, 76.8, 71.1, 70.1, 64.7, 62.8, 53.2, 47.4, 39.4, 37.9, 30.5, 23.3, 17.4 (d, $^3J_{c-p}$=6.3 Hz); $^{31}$P NMR (162 MHz, CD$_3$OD) δ 2.3; HRMS calcd for $C_{25}H_{36}N_4O_{12}P$: 615.2067, found: m/z 615.2066 [M−H].

Example 34: Synthesis of PE-1-CA Conjugate 51 (FIG. 27)

(−)-Methyl (1S,4R)-4-[(tert-butoxycarbonyl)amino] cyclopent-2-ene-1-carboxylate (85)

A mixture of (−)-(1R,4S)-2-azabicyclo[2.2.1]hept-5-en-3-one 83 (3.0 g, 27.5 mmol) and 1.25 M HCl in MeOH (59.0 mL, 73.8 mmol) was heated at reflux for 12 h. The mixture was concentrated under reduced pressure, and the residue was stirred with Et$_2$O (42 mL). The solids obtained were collected, washed with Et$_2$O, and dried under in vacuo to give 4.2 g (85%) of (1S,4R)-(−)-methyl-4-aminocyclopent-2-en-1-carboxylate hydrochloride (84). To a mixture of compound 84 (4.2 g, 23.6 mmol) and di-tert-butyl dicarbonate (10.86 mL, 47.3 mmol) in CH$_2$Cl$_2$ (120 mL) was added triethylamine (9.9 mL, 70.9 mmol) at 0° C. over a period of 2.5 h. The mixture was stirred for 1 h, and purified by flash column chromatography on silica gel (EtOAc/hexane, 1:6) to afford compound 85 (4.9 g, 86%). $C_{12}H_{19}NO_4$; white solid; $^1$H NMR (400 MHz, CDCl$_3$) δ 5.87-5.82 (2H, m), 4.88 (1H, br s), 4.76 (1H, br s), 3.70 (3H, s), 3.48-3.45 (1H, m), 2.50 (1H, ddd, J=13.6, 8.4, 8.4 Hz), 1.86 (1H, ddd, J=13.6, 4.0, 4.0 Hz), 1.43 (9H, s); ESI-HRMS calcd. for $C_{12}H_{20}NO_4$: 242.1392, found: m/z 242.1395 [M+H]$^+$.

(+)-Methyl (3aR,4R,6S,6aS)-4-[(tert-butoxycarbonyl)-amino]-3-(1-ethylpropyl)-4,5,6,6a-tetrahydro-3aH-cyclopenta[d]isoxazole-6-carboxylate (86)

To a mixture of olefin 85 (1.3 g, 5.4 mmol), 2-ethylbutanal oxime (4.2 g, 36.5 mmol), and Et$_3$N (0.34 mL, 2.4 mmol) in CH$_2$Cl$_2$ (12 mL) was added bleach (34.7 mL of 13% NaOCl aqueous solution, 72.7 mmol). The mixture was heated at reflux for 44 h, and monitored for completion by TLC. The mixture was extracted with CH$_2$Cl$_2$ (3×45 mL). The combined organic layers were washed with water and brine, dried over anhydrous Mg$_2$SO$_4$, filtered, and concentrated by rotary evaporation. The residue was purified by silica gel flash column chromatography (EtOAc/hexane gradients, 1:12 to 1:9 to 1:6) to give compound 86 (1.1 g, 57%). $C_{18}H_{30}N_2O_5$; pale yellow oil; $^1$H NMR (400 MHz, CDCl$_3$) δ 5.57 (1H, d, J=7.2 Hz), 5.17 (1H, d, J=9.2 Hz), 4.19 (1H, br s), 3.73 (3H, s), 3.56 (1H, d, J=9.6 Hz), 3.16 (1H, d, J=7.6 Hz), 2.50-2.46 (1H, m), 2.12-2.05 (1H, m), 2.02-1.97 (1H, m), 1.74-1.55 (4H, m), 1.41 (9H, s), 0.92-0.84 (6H, m); $^{13}$C NMR (100 MHz, CDCl$_3$) δ 174.4, 160.5, 154.3, 87.0, 79.5, 63.6, 55.7, 52.7, 52.3, 40.7, 33.6, 28.7, 26.0, 24.3, 12.5, 11.2; ESI-HRMS calcd. for $C_{18}H_{31}N_2O_5$: 355.2233, found: m/z 355.2233 [M+H]$^+$.

(−)-Methyl(1S,2S,3R,4R)-3-[(1S)-1-(Acetylamino)-2-ethylbutyl]-4-[(tert-butoxycarbonyl)amino]-2-hydroxycyclopentanecarboxylate (88)

To a solution of 86 (951.1 mg, 2.7 mmol) in MeOH (20 mL) were added concentrated HCl (0.2 mL, 2.7 mmol) and PtO$_2$·H$_2$O (92.1 mg, 0.4 mmol). The mixture was stirred very vigorously at 100 psi hydrogen pressure for 8 h. The catalyst was removed by filtration, and the filtrate was concentrated to give (−)-methyl (1S,2S,3R,4R)-3-[(1S)-1-(amino)-2-ethylbutyl]-4-[(tert-butoxy-carbonyl)amino]-2-hydroxycyclopentanecarboxylate hydrochloride (87), which was used for acetylation. A solution of 87 (1.1 g, 2.7 mmol) in CH$_2$Cl$_2$ (10 mL) were added Et$_3$N (0.37 mL, 2.7 mmol) and Ac$_2$O (0.28 mL, 3.0 mmol) at room temperature. The mixture was stirred for 12 h, and then washed with water (10 mL). The water layer was back-extracted with CH$_2$Cl$_2$ (4 mL). The combined organic layers were washed with water and brine, dried over anhydrous Mg$_2$SO$_4$, and filtered. The filtrate was concentrated, and purified by silica gel flash column chromatography (EtOAc/hexane gradient, 1:3 to 1:1) to give compound 88 (730.8 mg, 68% from 86). C$_{20}$H$_{36}$N$_2$O$_6$; white solid; $^1$H NMR (400 MHz, CDCl$_3$) δ 7.52 (1H, d, J=10 Hz), 4.76 (1H, d, J=9.2 Hz), 4.21 (1H, d, J=4.8 Hz), 4.13-4.09 (1H, m), 4.02-3.97 (1H, m), 3.68 (3H, s), 2.82-2.78 (1H, m), 2.50-2.42 (1H, m), 2.04 (3H, s), 1.98-1.95 (1H, m), 1.67 (1H, ddd, J=14.0, 8.4, 5.6 Hz), 1.42-1.19 (15H, m), 0.89-0.75 (6H, m); $^{13}$C NMR (100 MHz, CDCl$_3$) 174.7, 170.8, 155.4, 79.9, 77.6, 52.2, 52.0, 50.5, 49.1, 48.2, 43.6, 33.5, 28.7, 23.6, 22.2, 21.6, 11.0, 10.5; ESI-HRMS calcd. for C$_{20}$H$_{37}$N$_2$O$_6$: 401.2652, found: m/z 401.2648 [M+H]$^+$.

(−)-Methyl(1S,2S,3R,4R)-3-[(1S)-1-(Acetylamino)-2-ethylbutyl]-4-({[(tert-butoxycarbonyl)amino][(tert-butoxycarbonyl)imino]methyl}amino)-2-hydroxycyclopentanecarboxylate (90)

A solution of 88 (818.9 mg, 2.04 mmol) in Et$_2$O (8.0 mL) was treated with 2 M HCl in Et$_2$O (3.3 mL, 6.54 mmol). The mixture was stirred at room temperature for 18 h. The solid obtained was collected, washed with Et$_2$O, and dried in vacuo to give 726.5 mg of 89, which used in the next step without further purification. A solution of 89 (726.5 mg, 2.16 mmol) in DMF (7.7 mL) was treated successively with Et$_3$N (1.1 mL, 7.55 mmol), 1,3-bis(tert-butoxycarbony)-2-methyl-2-thiopseudourea (626.3 mg, 2.16 mmol), and HgCl$_2$ (585.6 mg, 2.16 mmol). The mixture was stirred at room temperature for 19 h, diluted with EtOAc (200 mL), and filtered through a pad of Celite. The filtrate was washed with water and brine, dried over anhydrous Mg$_2$SO$_4$, and filtered. The filtrate was concentrated, and purified by silica gel flash column chromatography (EtOAc/hexane gradient, 1:2 to 2:3) to give compound 90 (730.8 mg, 83% from 88). C$_{26}$H$_{46}$N$_4$O$_8$; white foam; $^1$H NMR (400 MHz, CDCl$_3$) δ 11.36 (1H, s), 8.69 (1H, d, J=10 Hz), 8.57 (1H, d, J=8.4 Hz), 4.48-4.39 (1H, m), 4.28-4.26 (1H, m), 4.22 (1H, s), 3.95 (1H, t, J=10 Hz), 3.70 (3H, s), 2.83-2.79 (1H, m), 2.52 (1H, ddd, J=13.6, 8.8, 8.8 Hz), 2.09 (3H, s), 2.08-2.07 (1H, m), 1.83 (1H, ddd, J=13.6, 8.4, 6.0 Hz), 1.48 (9H, s), 1.46 (9H, s), 1.42-1.21 (5H, m), 0.79 (3H, t, J=6.8 Hz), 0.74 (3H, t, J=7.2 Hz); $^{13}$C NMR (100 MHz, CDCl3) 174.8, 171.4, 162.4, 155.5, 152.8, 83.7, 79.8, 78.0, 52.2, 51.9, 50.8, 49.2, 48.5, 43.3, 33.8, 28.4, 28.1, 23.4, 22.5, 21.6, 10.7, 10.1; ESI-HRMS calcd. for C$_{26}$H$_{47}$N$_4$O$_8$: 543.3394, found: m/z 543.3399 [M+H]$^+$.

(−)-(1S,2S,3R,4R)-3-[(1S)-1-(Acetylamino)-2-ethylbutyl]-4-({[(tert-butoxycarbonyl)amino][(tert-butoxycarbonyl)-imino]methyl}amino)-2-hydroxycyclopentanecarboxylic Acid (91)

A solution of 90 (921.7 mg, 1.70 mmol) in EtOH/THF (1:1, 6.2 mL) was treated with 1 M sodium hydroxide (6.1 mL, 6.11 mmol) at room temperature for 3 h. The mixture was concentrated. The residue was dissolved in water (12.3 mL), and acidified with acetic acid. The precipitate thus obtained was collected by filtration to give compound 91 (448.9 mg, 50%). C$_{25}$H$_{44}$N$_4$O$_8$; white solid; $^1$H NMR (400 MHz, CDCl$_3$) δ 11.37 (1H, s), 8.80 (1H, d, J=10.4 Hz), 8.58 (1H, d, J=8.4 Hz), 4.47-4.36 (2H, m), 4.00 (1H, t, J=9.6 Hz), 2.82 (1H, t, J=6.8 Hz), 2.51 (1H, ddd, J=13.6, 8.8, 8.8 Hz), 2.12 (3H, s), 2.09-2.06 (1H, m), 1.94-1.85 (1H, m), 1.49 (9H, s), 1.47 (9H, s), 1.42-1.21 (6H, m), 0.80 (3H, t, J=6.8 Hz), 0.76 (3H, t, J=7.2 Hz); $^{13}$C NMR (100 MHz, CDCl$_3$) δ 177.5, 171.7, 162.4, 155.5, 152.8, 83.8, 79.8, 77.8, 51.6, 50.9, 49.7, 48.7, 43.4, 33.7, 28.4, 28.1, 23.3, 22.5, 21.6, 10.8, 10.3; ESI-HRMS calcd. for C$_{25}$H$_{45}$N$_4$O$_8$: 529.3237, found: m/z 529.3243 [M+H]$^+$.

4-((1E)-3-(3-(((1S,2S,3R,4R)-3-((S)-1-acetamido-2-ethylbutyl)-4-(2,3-bis(tert-butoxycarbonyl)guanidino)-2-hydroxycyclopentanecarbonyl)oxy)propoxy)-3-oxoprop-1-en-1-yl)-1,2-phenylene diacetate (93)

A solution of 91 (88.9 mg, 0.17 mmol), 92 (59.6 mg, 0.18 mmol), EDCI (35.5 mg, 0.18 mmol) and 4-dimethylaminopyridine (22.6 mg, 0.18 mmol) in CH$_2$Cl$_2$ (5.0 mL) was stirred at room temperature for 2 h. The mixture was extracted with 1 M HCl, saturated NaHCO$_3$ and brine, dried over MgSO$_4$, concentrated under reduced pressure, and purified by silica gel flash column chromatography (EtOAc/hexane gradient, 1:2 to 2:1) to give compound 93 (45.2 mg, 32%). C$_{41}$H$_{60}$N$_4$O$_{14}$; transparent oil; $^1$H NMR (400 MHz, CDCl$_3$) δ 11.37 (1H, s), 8.71 (1H, d, J=10.0 Hz), 8.58 (1H, d, J=8.4 Hz), 7.59 (1H, d, J=16.0 Hz), 7.38 (1H, dd, J=8.4, 2.4 Hz), 7.33 (1H, d, J=2.4 Hz), 7.20 (1H, d, J=8.4 Hz), 6.35 (1H, d, J=16.0 Hz), 4.48-4.43 (1H, m), 4.29-4.21 (5H, m), 3.97 (1H, t, J=9.6 Hz), 2.83 (1H, t, J=6.8 Hz), 2.55 (1H, ddd, J=13.6, 8.8, 8.8 Hz), 2.29 (6H, s), 2.13-2.08 (4H, m), 2.07-2.03 (2H, m), 1.89-1.82 (2H, m), 1.49 (9H, s), 1.47 (9H, s), 1.33-1.20 (4H, m), 0.80 (3H, t, J=7.2 Hz), 0.75 (3H, t, J=7.2 Hz); $^{13}$C NMR (100 MHz, CDCl$_3$) δ 174.3, 171.5, 167.8, 167.7, 166.1, 162.4, 155.5, 152.8, 143.3, 142.9, 142.2, 133.0, 126.3, 123.8, 122.6, 118.8, 83.8, 79.8, 78.0, 61.7, 61.1, 51.9, 50.8, 49.4, 48.6, 43.2, 33.8, 29.8, 28.4, 28.1, 23.4, 22.5, 21.6, 20.8, 10.7, 10.1; ESI-HRMS calcd. for C$_{41}$H$_{61}$N$_4$O$_{14}$: 833.4184, found: m/z 833.4185 [M+H]$^+$.

PE-1-CA (51)

By a procedure similar to that for 43, saponification of 93 in aqueous K$_2$CO$_3$, followed by removal of t-Boc group with TFA, gave PE-1-CA (51).

Example 35: Synthesis of PE-2-CA Conjugate 52 (FIG. 28)

(1S,2S,3R,4R)-Methyl-3-((S)-1-acetamido-2-ethylbutyl)-4-(2,3-bis(tert-butoxycarbony)guanidino)-2-(((4-nitrophenoxy)carbonyl)oxy)cyclopentanecarboxylate (94)

A solution of 90 (114.4 mg, 0.21 mmol), 4-nitrophenyl chloroformate (297.4 mg, 1.48 mmol) and 4-dimethylaminopyridine (297.4 mg, 1.48 mmol) in anhydrous pyridine (180.3 mg, 1.48 mmol) was stirred at room temperature for 19 h. After concentration, the mixture was added EtOAc, and then filtered. The filtrate was concentrated under reduced pressure, and purified by silica gel flash column chromatography (EtOAc/hexane gradient, 1:5 to 1:4) to give compound 94 (61.0 mg, 41%). $C_{33}H_{49}N_5O_{12}$; transparent oil; $^1$H NMR (400 MHz, CDCl$_3$) δ 11.46 (1H, s), 8.56 (1H, d, J=8.4 Hz), 8.22 (2H, d, J=9.2 Hz), 8.13 (1H, d, J=10.4 Hz), 7.51 (2H, d, J=8.8 Hz), 5.49 (1H, d, J=5.6 Hz), 4.66 (1H, qui, J=8.8 Hz), 4.31-4.27 (1H, m), 3.72 (3H, s), 2.99-2.96 (1H, m), 2.59 (1H, ddd, J=13.6, 8.8, 8.8 Hz), 2.00 (3H, s), 1.93-1.80 (2H, m), 1.48 (9H, s), 1.45 (9H, s), 1.41-1.25 (5H, m), 0.83 (3H, t, J=7.2 Hz), 0.78 (3H, t, J=7.2 Hz); ESI-HRMS calcd. for $C_{33}H_{50}N_5O_{12}$: 708.3451, found: m/z 708.3450 [M+H]$^+$.

(1S,2S,3R,4R)-Methyl-3-((S)-1-acetamido-2-ethyl-butyl)-4-(2,3-bis(tert-butoxycarbonyl)guanidino)-2-(((3-(((E)-3-(3,4-bis(allyloxy)phenyl)acryloyl)oxy)propyl)carbamoyl)oxy)cyclopentanecarboxylate (96)

To a solution of caffeic acid derivative 95 (47.4 mg, 0.11 mmol) in CH$_2$Cl$_2$ (0.63 mL) was added TFA (0.63 mL, 8.22 mmol). After stirring at room temperature for 1 h, the mixture was concentrated under reduced pressure. The residue was dissolved in CH$_3$CN (0.91 mL), and then 1,3-bis(tert-butoxycarbony)-2-methyl-2-thiopseudourea (31.3 mg, 0.04 mmol) and Et$_3$N (0.03 mL, 0.22 mmol) were added. The mixture was stirred at room temperature for 2H, and then concentrated under reduced pressure. The residue was partitioned between CH$_2$Cl$_2$ and saturated NaHCO$_3$. The organic layer was dried over MgSO$_4$, filtered, and concentrated by rotary evaporation under reduced pressure. The crude material was purified by silica gel flash column chromatography (EtOAc/hexane gradient, 1:1 to 2:1) to give carbamate 96 (25.8 mg, 66%). $C_{45}H_{67}N_5O_{13}$; transparent oil; $^1$H NMR (400 MHz, CDCl$_3$) δ 11.44 (1H, s), 8.57 (1H, d, J=8.0 Hz), 8.27 (1H, d, J=10.0 Hz), 7.56 (1H, d, J=15.6 Hz), 7.06-7.04 (2H, m), 6.84 (1H, d, J=8.8 Hz), 6.25 (1H, d, J=16.0 Hz), 6.11-6.00 (2H, m), 5.82 (1H, t, J=5.6 Hz), 5.43 (1H, dd, J=6.4, 1.6 Hz), 5.39 (1H, dd, J=6.4, 1.6 Hz), 5.27 (2H, dd, J=10.4, 1.6 Hz), 5.05-5.03 (1H, m), 4.62-4.61 (4H, m), 4.49 (1H, qui, J=8.4 Hz), 4.25-4.18 (2H, m), 4.17-4.09 (1H, m), 3.71 (3H, s), 3.26-3.23 (2H, m), 2.97-2.92 (1H, m), 2.44 (1H, ddd, J=12.8, 8.0, 8.0 Hz), 2.30-2.26 (1H, m), 2.07 (3H, s), 1.90-1.87 (2H, m), 1.82-1.75 (1H, m), 1.48 (9H, s), 1.45 (9H, s), 1.39-1.12 (5H, m), 0.84-0.77 (6H, m); ESI-HRMS calcd. for $C_{45}H_{68}N_5O_{13}$: 886.4814, found: m/z 886.4813 [M+H]$^+$.

PE-2-CA (52)

By a procedure similar to that for 7, compound 96 was subject to saponification in aqueous KOH, followed by removal of the allyl and t-Boc groups respectively with Pd(PPh$_3$)$_4$ and TFA, to give PE-2-CA (52).

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claim.

REFERENCES

Andrews, D. M.; Chemy, P. C.; Humber, D. C.; Jones, P. S.; Keeling, S. P.; Martin, P. F.; Shaw, C. D.; Swanson, S. Synthesis and influenza virus sialidase inhibitory activity of analogues of 4-Guanidino-Neu5Ac2en (Zanamivir) modified in the glycerol side-chain. *Eur. J. Med. Chem.* 1999, 34, 563-574.

Baz, M.; Abed, Y.; Papenburg, J.; Bouhy, X.; Hamelin, M.-É.; Boivin, G. Emergence of Oseltamivir-Resistant Pandemic H1N1 Virus during Prophylaxis. *N. Engl. J. Med.* 2009, 361, 2296-2297.

Burleson, F. G.; Chambers, T. M.; Wiedbrauk, D. L. *Virology, a Laboratory Manual*; Academic Press: San Diego, Calif., 1992.

Carter, M. J. A rationale for using steroids in the treatment of severe cases of H5N1 avian influenza. *J. Med. Microbiol.* 2007, 56, 875-883.

Cass, L. M. R.; Efthymiopoulos, C.; Bye, A. Pharmacokinetics of zanamivir after intravenous, oral, inhaled or intranasal administration to healthy volunteers. *Clin. Pharmacokinet.* 1999, 36, 1-11.

Chandler, M.; Bamford, M. J.; Conroy, R.; Lamont, B.; Patel, B.; Patel, V. K.; Steeples, I. P.; Storer, R.; Weir, N. G.; Wright, M.; Williamson, C. Synthesis of the potent influenza neuraminidase inhibitor 4-guanidino Neu5Ac2en. X-Ray molecular structure of 5-acetamido-4-amino-2,6-anhydro-3,4,5-trideoxy-D-erythro-L-gluconononic acid. *J. Chem. Soc., Perkin Trans.* 1 1995, 1173-1180.

Chiang, Y. M.; Lo, C. P.; Chen, Y. P.; Wang, S. Y.; Yang, N. S.; Kuo, Y. H.; Shyur, L. F. Ethyl caffeate suppresses NF-κB activation and its downstream inflammatory mediators, iNOS, COX-2, and PGE2 in vitro or in mouse skin. *Brit. J. Pharmacol.* 2005, 146, 352-363.

Chong, A. K. J.; Pegg, M. S.; Taylor, N. R.; von Itzstein, M. Evidence for a sialosyl cation transition-state complex in the reaction of sialidase from influenza virus. *Eur. J. Biochem.* 1992, 207, 335-343.

Collins, P. J.; Haire, L. F.; Lin, Y. P.; Liu, J. F.; Russell, R. J.; Walker, P. A.; Skehel, J. J.; Martin, S. R.; Hay, A. J.; Gamblin, S. J. Crystal structures of oseltamivir-resistant influenza virus neuraminidase mutants. *Nature* 2008, 453, 1258-1261.

de Jong, M. D.; Simmons, C. P.; Thanh, T. T.; Hien, V. M.; Smith, G. J. D.; Chau, T. N. B.; Hoang, D. M.; Chau, N. V. V.; Khanh, T. H.; Dong, V. C.; Qui, P. T.; Cam, B. V.; Ha, D. Q.; Guan, Y.; Peiris, J. S. M.; Chinh, N. T.; Hien, T. T.; Farrar, J. Fatal outcome of human influenza A (H5N1) is associated with high viral load and hypercytokinemia. *Nature Med.* 2006, 12, 1203-1207.

Fedson, D. S. Confronting the next influenza pandemic with anti-inflammatory and immunomodulatory agents: why they are needed and how they might work. *Influenza Other Resp.* 2009, 3, 129-142.

Geiler, J.; Michaelis, M.; Sithisarn, P.; Cinatl, J. Comparison of pro-inflammatory cytokine expression and cellular signal transduction in human macrophages infected with different influenza A viruses. *Med. Microbiol. Immunol.* 2011, 200, 53-60.

Govorkova, E. A.; Webster, R. G. Combination chemotherapy for influenza. *Viruses* 2010, 2, 1510-1529.

Honda, T.; Masuda, T.; Yoshida, S.; Arai, M.; Kobayashi, Y.; Yamashita, M. Synthesis and anti-influenza virus activity of 4-guanidino-7-substituted Neu5Ac2en derivatives. *Bioorg. Med. Chem. Lett.* 2002, 12, 1921-1924.

Honda, T.; Masuda, T.; Yoshida, S.; Arai, M.; Kaneko, S.; Yamashita, M. Synthesis and anti-Influenza virus activity of 7-O-Alkylated derivatives related to zanamivir. *Bioorg. Med. Chem. Lett.* 2002, 12, 1925-1928.

Horn, E. J.; Saludes, J. P.; Gervay-Hague, J. Investigation into an efficient synthesis of 2,3-dehydro-N-acetyl neuraminic acid leads to three decarboxylated sialic acid dimers. *Carbohydr. Res.* 2008, 343, 936-940.

Hsieh, Y. S. Y.; Chien, C.; Liao, S. K. S.; Liao, S.-F.; Hung, W.-T.; Yang, W.-B.; Lin, C.-C.; Cheng, T.-J. R.; Chang, C.-C.; Fang, J.-M.; Wong, C.-H. Structure and bioactivity of the polysaccharides in medicinal plant Dendrobium huoshanense. *Bioorg. Med. Chem. Lett.* 2008, 16, 6054-6068.

Ishizuka, H.; Yoshiba, S.; Okabe, H.; Yoshihara, K. Clinical pharmacokinetics of laninamivir, a novel long-acting neuraminidase inhibitor, after single and multiple inhaled doses of its prodrug, CS-8958, in healthy male volunteers. *J. Clin. Pharmacol.* 2010, 50, 1319-1329.

Jung, W. K.; Choi, I.; Lee, D. Y.; Yea, S. S.; Choi, Y. H.; Kim, M. M.; Park, S. G.; Seo, S. K.; Lee, S. W.; Lee, C. M.; Park, Y. M.; Choi, I. W. Caffeic acid phenethyl ester protects mice from lethal endotoxin shock and inhibits lipopolysaccharide-induced cyclooxygenase-2 and inducible nitric oxide synthase expression in RAW 264.7 macrophages via the p38/ERK and NF-kappaB pathways. *Int. J. Biochem. Cell Biol.* 2008, 40, 2572-2582.

Kaiser, G. C.; Yan, F.; Polk, D. B. Mesalamine blocks tumor necrosis factor growth inhibition and nuclear factor KB activation in mouse colonocytes. *Gastroenterology* 1999, 116, 602-609.

Kruis, W.; Schreiber, S.; Theuer, D.; Brandes, J.-W.; Schtütz, E.; Howaldt, S.; Krakamp, B.; Hamling, J.; Mönnikes, H.; Koop, I.; Stolte, M.; Pallant, D.; Ewald, U. Low dose balsalazide (1.5 g twice daily) and mesalazine (0.5 g three times daily) maintained remission of ulcerative colitis but high dose balsalazide (3.0 g twice daily) was superior in preventing relapses. *Gut* 2001, 49, 783-789.

Kubo, S.; Tomozawa, T.; Kakuta, M.; Tokumitsu, A.; Yamashita, M. Laninamivir prodrug CS-8958, a long-acting neuraminidase inhibitor, shows superior anti-influenza virus activity after a single administration. *Antimicrob. Agents Chemother.* 2010, 54, 1256-1264.

Lavis, L. D. Ester bonds in prodrugs. *ACS Chem. Biol.* 2008, 3, 203-206.

Lee, S. M. Y.; Cheung, C. Y.; Nicholls, J. M.; Hui, K. P. Y.; Leung, C. Y. H.; Uiprasertkul, M.; Tipoe, G. L.; Lau, Y. L.; Poon, L. L. M.; Ip, N. Y.; Guan, Y.; Peiris, J. S. M. Hyperinduction of cyclooxygenase-2-mediated proinflammatory cascade: A mechanism for the pathogenesis of avian influenza H5N1 infection. *J. Infect. Dis.* 2008, 198, 525-535.

Lew, W.; Chen, X.; Kim, C. U. Discovery and development of GS-4104 (oseltamivir): an orally active influenza neuraminidase inhibitor. *Curr. Med. Chem.* 2000, 7, 663-672.

Liu, Z.-y.; Wang, B.; Zhao, L.-x.; Li, Y.-h.; Shao, H.-y.; Yi, H.; You, X.-f.; $L_1$, Z.-r. Synthesis and anti-influenza activities of carboxyl alkoxyalkyl esters of 4-guanidino-Neu5Ac2en (zanamivir). *Bioorg. Med. Chem. Lett.* 2007, 17, 4851-4854.

Meunier, B. Hybrid molecules with a dual mode of action: Dream or reality? *Acc. Chem. Res.* 2008, 41, 69-77.

Michaluart, P.; Masferrer, J. L.; Carothers, A. M.; Subbaramaiah, K.; Zweifel, B. S.; Koboldt, C.; Mestre, J. R.; Grunberger, D.; Sacks, P. G.; Tanabe, T.; Dannenberg, A. J. Inhibitory effects of caffeic acid phenethyl ester on the activity and expression of cyclooxygenase-2 in human oral epithelial cells and in a rat model of inflammation. *Cancer Res.* 1999, 59, 2347-2352.

Mineno, T.; Miller, M. J. Stereoselective total synthesis of racemic BCX-1812 (RWJ-270201) for the development of neuraminidase inhibitors as anti-influenza agents. *J. Org. Chem.* 2003, 68, 6591-6596.

Morphy, R.; Kay, C.; Rankovic, Z. From magic bullets to designed multiple ligands. *Drug Discov. Today* 2004, 9, 641-651.

Morphy, R.; Rankovic, Z. The physicochemical challenges of designing multiple ligands. *J. Med. Chem.* 2006, 49, 4961-4970.

Natarajan, K.; Singh, S.; Burke, T. R.; Grunberger, D.; Aggarwal, B. B. Caffeic acid phenethyl ester is a potent and specific inhibitor of activation of nuclear transcription factor NF-kappa B. *Proc. Natl. Acad. Sci. USA* 1996, 93, 9090-9095.

Ottolini, M.; Blanco, J.; Porter, D.; Peterson, L.; Curtis, S.; Prince, G. Combination anti-inflammatory and antiviral therapy of influenza in a cotton rat model. *Pediatr. Pulmonol.* 2003, 36, 290-4.

Peiris, J. S. M.; Yu, W. C.; Leung, C. W.; Cheung, C. Y.; Ng, W. F.; Nicholls, J. M.; Ng, T. K.; Chan, K. H.; Lai, S. T.; Lim, W. L.; Yuen, K. Y.; Guan, Y. Re-emergence of fatal human influenza A subtype H5N1 disease. *Lancet* 2004, 363, 617-619.

Reed, L. J.; Muench, H. *Am. J. Epidemiol.* 1938, 27, 493.

Rousseaux, C.; Lefebvre, B.; Dubuquoy, L.; Lefebvre, P.; Romano, O.; Auwerx, J.; Metzger, D.; Wahli, W.; Desvergne, B.; Naccari, G. C.; Chavatte, P.; Farce, A.; Bulois, P.; Cortot, A.; Colombel, J. F.; Desreumaux, P. Intestinal antiinflammatory effect of 5-aminosalicylic acid is dependent on peroxisome proliferator-activated receptor-γ. *J. Exp. Med.* 2005, 201, 1205-1215.

Russell, R. J.; Haire, L. F.; Stevens, D. J.; Collins, P. J.; Lin, Y. P.; Blackburn, G. M.; Hay, A. J.; Camblin, S. J.; Skehel, J. J. *Nature* 2006, 443, 45-47.

Ryan, D. M.; Ticehurst, J.; Dempsey, M. H.; Penn, C. R. Inhibition of influenza virus replication in mice by GG167 (4-guanidino-2,4-dideoxy-2,3-dehydro-N-acetyl-neuraminic acid) is consistent with extracellular activity of viral neuraminidase (sialidase). *Antimicrob. Agents Chemother.* 1994, 38, 2270-2275.

Salomon, R.; Hoffmann, E.; Webster, R. G. Inhibition of the cytokine response does not protect against lethal H5N1 influenza infection. *Proc. Natl. Acad. Sci. U.S.A.* 2007, 104, 12479-12481.

Sandborn, W. J.; Feagan, B. G.; Lichtenstein, G. R. Medical management of mild to moderate Crohn's disease: evidence-based treatment algorithms for induction and maintenance of remission. *Aliment. Pharmacol. Ther.* 2007, 26, 987-1003.

Shie, J.-J.; Fang, J.-M.; Wong, C.-H. A concise and flexible synthesis of the potent anti-influenza agents tamiflu and tamiphosphor. *Angew. Chem. Int. Ed.* 2008, 47, 5788-5791.

Shin, K.-M.; Kim, I.-T.; Park, Y.-M.; Ha, J.; Choi, J.-W.; Park, H.-J.; Lee, Y. S.; Lee, K.-T. Anti-inflammatory effect of caffeic acid methyl ester and its mode of action through the inhibition of prostaglandin E2, nitric oxide and tumor necrosis factor-α production. *Biochem. Pharmacol.* 2004, 68, 2327-2336.

Taylor, N. R.; von Itzstein, M. Molecular Modeling Studies on Ligand Binding to Sialidase from Influenza Virus and the Mechanism of Catalysis. *J. Med. Chem.* 1994, 37, 616-624.

Varghese, J. N.; Epa, V. C.; Colman, P. M. Three-dimensional structure of the complex of 4-guanidino-Neu5Ac2en and influenza virus neuraminidase. *Protein Sci.* 1995, 4, 1081-1087.

von Itzstein, M.; Wu, W.-Y.; Kok, G. B.; Pegg, M. S.; Dyason, J. C.; Jin, B.; Phan, T. V.; Smythe, M. L.; White, H. F.; Oliver, S. W.; Colman, P. M.; Varghese, J. N.; Ryan, D. M.; Woods, J. M.; Bethell, R. C.; Hotham, V. J.; Cameron, J. M.; Penn, C. R. Rational design of potent sialidase-based inhibitors of influenza virus replication. *Nature* 1993, 363, 418-423.

Wen, W.-H.; Lin, M.; Su, C.-Y.; Wang, S.-Y.; Cheng, Y.-S. E.; Fang, J.-M.; Wong, C.-H. Synergistic effect of zanamivir-porphyrin conjugates on inhibition of neuraminidase and inactivation of influenza virus. *J. Med. Chem.* 2009, 52, 4903-4910.

Woo, P. C. Y.; Tung, E. T. K.; Chan, K.-H.; Lau, C. C. Y.; Lau, S. K. P.; Yuen, K.-Y. Cytokine profiles induced by the novel swine-origin influenza A/H1N1 virus: Implications for treatment strategies. *J. Infect. Dis.* 2010, 201, 346-353.

Yamashita, M.; Tomozawa, T.; Kakuta, M.; Tokumitsu, A.; Nasu, H.; Kubo, S. CS-8958, a prodrug of the new neuraminidase inhibitor R-125489, shows long-acting anti-influenza virus activity. *Antimicrob. Agents Chemother.* 2009, 53, 186-192.

Ying, L.; Gervay-Hague, J. One-bead-one-inhibitor-one-substrate screening of neuraminidase activity. *ChemBioChem* 2005, 6, 1857-1865.

Yuen, K. Y.; Wong, S. S. Human infection by avian influenza A H5N1. *Hong Kong Med. J.* 2005, 11, 189-199.

Zheng, B. J.; Chan, K. W.; Lin, Y. P.; Zhao, G. Y.; Chan, C.; Zhang, H. J.; Chen, H. L.; Wong, S. S.; Lau, S. K.; Woo, P. C.; Chan, K. H.; Jin, D. Y.; Yuen, K. Y. Delayed antiviral plus immunomodulator treatment still reduces mortality in mice infected by high inoculum of influenza A/H5N1 virus. *Proc. Natl. Acad. Sci. USA* 2008, 105, 8091-8096.

Zimmermann, G. R.; Lehár, J.; Keith, C. T. Multi-target therapeutics: when the whole is greater than the sum of the parts. *Drug Discov. Today* 2007, 12, 34-42.

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed:

1. A dual anti-influenza and anti-inflammatory compound selected from the group consisting of:

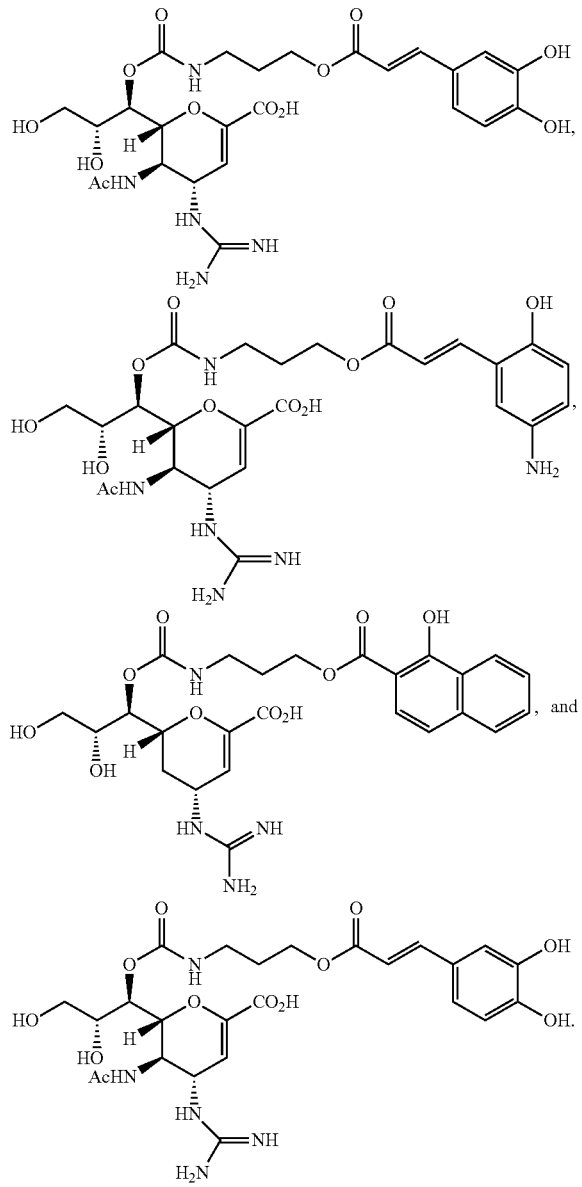

2. A dual-active pharmaceutical composition for simultaneously inhibiting influenza virus and inflammation, the composition comprising:
   a compound of claim 1,
   or a pharmaceutically acceptable salt thereof; and
   a pharmaceutically acceptable excipient.

3. The pharmaceutical composition of claim 2, wherein the compound inhibits both human and avian influenza virus.

4. The pharmaceutical composition of claim 2, wherein the compound inhibits at least one of H1N1 and H5N1 strains of influenza virus.

5. A method for treating influenza infection in a subject, the method comprising: administering to a subject in need thereof a therapeutically effective amount of the pharmaceutical composition of claim 2.

6. The method of claim 5, wherein the subject has, is suspected of having, or is at risk for influenza virus infection.

* * * * *